US011773392B2

(12) United States Patent
Mueller et al.

(10) Patent No.: US 11,773,392 B2
(45) Date of Patent: Oct. 3, 2023

(54) AAV TREATMENT OF HUNTINGTON'S DISEASE

(71) Applicant: University of Massachusetts, Boston, MA (US)

(72) Inventors: Christian Mueller, Concord, MA (US); Neil Aronin, Newtonville, MA (US); Edith L. Pfister, Boxborough, MA (US)

(73) Assignee: University of Massachusetts, Boston, MA (US)

( * ) Notice: Subject to any disclaimer, the term of this patent is extended or adjusted under 35 U.S.C. 154(b) by 214 days.

(21) Appl. No.: 17/326,400

(22) Filed: May 21, 2021

(65) Prior Publication Data

US 2022/0010312 A1  Jan. 13, 2022

Related U.S. Application Data

(63) Continuation of application No. 16/573,412, filed on Sep. 17, 2019, now Pat. No. 11,046,957, which is a continuation of application No. 15/705,909, filed on Sep. 15, 2017, now Pat. No. 10,457,940.

(60) Provisional application No. 62/398,487, filed on Sep. 22, 2016.

(51) Int. Cl.
| | |
|---|---|
| *C12N 15/113* | (2010.01) |
| *A61P 25/28* | (2006.01) |
| *C12N 7/00* | (2006.01) |
| *C12N 15/86* | (2006.01) |

(52) U.S. Cl.
CPC ............ *C12N 15/113* (2013.01); *A61P 25/28* (2018.01); *C12N 7/00* (2013.01); *C12N 15/86* (2013.01); *C12N 2310/141* (2013.01); *C12N 2310/3519* (2013.01); *C12N 2330/51* (2013.01); *C12N 2750/14121* (2013.01); *C12N 2750/14141* (2013.01); *C12N 2750/14143* (2013.01); *C12N 2750/14171* (2013.01)

(58) Field of Classification Search
None
See application file for complete search history.

(56) References Cited

U.S. PATENT DOCUMENTS

| | | | |
|---|---|---|---|
| 5,478,745 A | 12/1995 | Samulski et al. |
| 5,871,982 A | 2/1999 | Wilson et al. |
| 6,251,677 B1 | 6/2001 | Wilson et al. |
| 6,485,966 B2 | 11/2002 | Gao et al. |
| 6,498,244 B1 | 12/2002 | Patel et al. |
| 6,544,786 B1 | 4/2003 | Xiao et al. |
| 6,953,690 B1 | 10/2005 | Gao et al. |
| 6,962,815 B2 | 11/2005 | Bartlett |
| 7,022,519 B2 | 4/2006 | Gao et al. |
| 7,198,951 B2 | 4/2007 | Gao et al. |
| 7,235,393 B2 | 6/2007 | Gao et al. |
| 7,427,396 B2 | 9/2008 | Arbetman et al. |
| 7,456,015 B2 | 11/2008 | Bohn et al. |
| 7,906,111 B2 | 3/2011 | Wilson et al. |
| 8,222,221 B2 | 7/2012 | Corey et al. |
| 8,524,446 B2 | 9/2013 | Gao et al. |
| 8,734,809 B2 | 5/2014 | Gao et al. |
| 9,217,155 B2 | 12/2015 | Gao et al. |
| 9,249,424 B2 | 2/2016 | Wolf et al. |
| 9,701,984 B2 | 7/2017 | Gao et al. |
| 10,457,940 B2 | 10/2019 | Mueller et al. |
| 11,046,957 B2 | 6/2021 | Mueller et al. |
| 2001/0016355 A1 | 8/2001 | Samulski et al. |
| 2002/0164783 A1 | 11/2002 | Feldhaus |
| 2002/0192823 A1 | 12/2002 | Bartlett |
| 2003/0103939 A1 | 6/2003 | Engelhardt et al. |
| 2003/0110526 A1 | 6/2003 | Brown et al. |
| 2003/0138772 A1 | 7/2003 | Gao et al. |
| 2004/0101514 A1 | 5/2004 | Liu et al. |
| 2004/0219528 A1 | 11/2004 | Morris et al. |
| 2005/0014262 A1 | 1/2005 | Gao et al. |
| 2005/0032219 A1 | 2/2005 | Aubourg et al. |
| 2005/0037988 A1 | 2/2005 | Zamore et al. |
| 2005/0137153 A1 | 6/2005 | McSwiggen et al. |
| 2005/0197313 A1 | 9/2005 | Roelvink et al. |
| 2005/0255086 A1 | 11/2005 | Davidson et al. |
| 2005/0255089 A1 | 11/2005 | Chiorini et al. |
| 2005/0287122 A1 | 12/2005 | Bartlett et al. |
| 2006/0063174 A1 | 3/2006 | Turner et al. |
| 2006/0093589 A1 | 5/2006 | Warrington et al. |
| 2006/0153826 A1 | 7/2006 | Arnould et al. |
| 2006/0189564 A1 | 8/2006 | Burright et al. |
| 2006/0228800 A1 | 10/2006 | Lin et al. |
| 2006/0292117 A1 | 12/2006 | Loiler et al. |

(Continued)

FOREIGN PATENT DOCUMENTS

| | | |
|---|---|---|
| EA | 023938 B1 | 7/2016 |
| EP | 2261242 A1 | 12/2010 |

(Continued)

OTHER PUBLICATIONS

Extended European Search Report for Application No. EP 17853966.4, dated Mar. 19, 2020.
Invitation to Pay Additional Fees for Application No. PCT/US2017/052902, dated Dec. 4, 2017.
International Search Report and Written Opinion for Application No. PCT/US2017/052902, dated Feb. 5, 2018.
International Preliminary Report on Patentability for Application No. PCT/US2017/052902, dated Apr. 4, 2019.
Aartsma-Rus et al., New insights in gene-derived therapy: the example of Duchenne muscular dystrophy. Ann N Y Acad Sci. Dec. 2010;1214:199-212. doi: 10.1111/j.1749-6632.2010.05836.x. Epub Dec. 1, 2010.

(Continued)

*Primary Examiner* — Brian Whiteman
(74) *Attorney, Agent, or Firm* — Wolf, Greenfield & Sacks, P.C.

(57) ABSTRACT

Aspects of the disclosure relate to compositions and methods useful for treating Huntington's disease. In some embodiments, the disclosure provides interfering nucleic acids (e.g., artificial miRNAs) targeting the huntingtin gene (HTT) and methods of treating Huntington's disease using the same.

20 Claims, 46 Drawing Sheets

Specification includes a Sequence Listing.

(56) References Cited

U.S. PATENT DOCUMENTS

| | | |
|---|---|---|
| 2007/0036760 A1 | 2/2007 | Wilson et al. |
| 2007/0243526 A1 | 10/2007 | Kay et al. |
| 2007/0253936 A1 | 11/2007 | Kay et al. |
| 2007/0292410 A1 | 12/2007 | Cashman et al. |
| 2008/0199961 A1 | 8/2008 | Rasko et al. |
| 2008/0200420 A1 | 8/2008 | Zamore et al. |
| 2008/0292595 A1 | 11/2008 | Arbetman et al. |
| 2009/0042828 A1 | 2/2009 | Xu et al. |
| 2009/0111766 A1 | 4/2009 | Atkinson et al. |
| 2009/0149409 A1 | 6/2009 | Bohn et al. |
| 2009/0197338 A1 | 8/2009 | Vandenberghe et al. |
| 2009/0215879 A1 | 8/2009 | DiPrimio et al. |
| 2009/0239240 A1 | 9/2009 | Chu |
| 2010/0104561 A1 | 4/2010 | Zhong et al. |
| 2010/0186103 A1 | 7/2010 | Gao et al. |
| 2010/0227909 A1 | 9/2010 | Cleary et al. |
| 2010/0323001 A1 | 12/2010 | Pachuk |
| 2011/0171262 A1 | 7/2011 | Bakker et al. |
| 2011/0172293 A1 | 7/2011 | Fish et al. |
| 2011/0212520 A1 | 9/2011 | Davidson et al. |
| 2011/0258716 A1 | 10/2011 | Baltimore et al. |
| 2012/0077870 A1 | 3/2012 | Blanks et al. |
| 2012/0137379 A1 | 5/2012 | Gao et al. |
| 2012/0270930 A1 | 10/2012 | Van Der Maarel et al. |
| 2012/0309050 A1 | 12/2012 | Kumon et al. |
| 2013/0030042 A1 | 1/2013 | Couto |
| 2013/0101558 A1 | 4/2013 | Gao et al. |
| 2013/0109742 A1 | 5/2013 | Hewitt et al. |
| 2013/0142861 A1 | 6/2013 | Tsou et al. |
| 2013/0195801 A1 | 8/2013 | Gao et al. |
| 2013/0281516 A1 | 10/2013 | Gao et al. |
| 2013/0323226 A1 | 12/2013 | Wilson et al. |
| 2014/0066595 A1 | 3/2014 | Anderson et al. |
| 2014/0142161 A1 | 5/2014 | Flotte et al. |
| 2014/0142288 A1 | 5/2014 | Davidson et al. |
| 2014/0147418 A1 | 5/2014 | Chiorini et al. |
| 2014/0179770 A1 | 6/2014 | Zhang et al. |
| 2014/0201857 A1 | 7/2014 | Fahrenkrug et al. |
| 2014/0335054 A1 | 11/2014 | Gao et al. |
| 2014/0370597 A1 | 12/2014 | Aronin et al. |
| 2015/0065560 A1 | 3/2015 | Bjorklund et al. |
| 2015/0258180 A1 | 9/2015 | Mahuran et al. |
| 2016/0017005 A1 | 1/2016 | Asokan et al. |
| 2016/0060624 A1 | 3/2016 | Davidson et al. |
| 2016/0076054 A1 | 3/2016 | Auricchio et al. |
| 2016/0153005 A1 | 6/2016 | Zhang et al. |
| 2016/0185832 A1 | 6/2016 | Drivas et al. |
| 2016/0194374 A1 | 7/2016 | Wijnholds et al. |
| 2016/0272976 A1 | 9/2016 | Kaspar |
| 2016/0355808 A1 | 12/2016 | Khvorova et al. |
| 2017/0029785 A1 | 2/2017 | Zhao et al. |
| 2017/0114340 A1 | 4/2017 | Mueller et al. |
| 2017/0165377 A1 | 6/2017 | Gao et al. |
| 2018/0094264 A1 | 4/2018 | Mueller et al. |

FOREIGN PATENT DOCUMENTS

| | | |
|---|---|---|
| EP | 2468891 A2 | 6/2012 |
| JP | 2008-538286 A | 10/2008 |
| WO | WO 2003/042397 A2 | 5/2003 |
| WO | WO 2005/033321 | 4/2005 |
| WO | WO 2006/031267 A2 | 3/2006 |
| WO | WO 2006/066066 A2 | 6/2006 |
| WO | WO 2006/119432 A2 | 11/2006 |
| WO | WO 2007/000668 A2 | 1/2007 |
| WO | WO 2007/027775 A2 | 3/2007 |
| WO | WO 2008/091703 A2 | 7/2008 |
| WO | WO 2008/125846 A2 | 10/2008 |
| WO | WO 2008/147839 A1 | 12/2008 |
| WO | WO 2008/150897 A2 | 12/2008 |
| WO | WO 2009/043936 A1 | 4/2009 |
| WO | WO 2009/109665 A1 | 9/2009 |
| WO | WO 2009/146178 A1 | 12/2009 |
| WO | WO 2010/027446 A2 | 3/2010 |
| WO | WO 2010/034314 A1 | 4/2010 |
| WO | WO 2010/071454 A1 | 6/2010 |
| WO | WO 2010/099383 A2 | 9/2010 |
| WO | WO 2010/129021 A1 | 11/2010 |
| WO | WO 2010/138263 A2 | 12/2010 |
| WO | WO 2011/094198 A1 | 8/2011 |
| WO | WO 2012/123430 A1 | 9/2012 |
| WO | WO 2013/055865 A1 | 4/2013 |
| WO | WO 2013/123503 A1 | 8/2013 |
| WO | WO 2013/170078 A1 | 11/2013 |
| WO | WO 2013/190059 A1 | 12/2013 |
| WO | WO 2014/160092 A1 | 10/2014 |
| WO | WO 2014/186746 A1 | 11/2014 |
| WO | WO 2014/197748 A2 | 12/2014 |
| WO | WO 2015/121501 A1 | 8/2015 |
| WO | WO 2015/164786 A1 | 10/2015 |
| WO | WO 2015/168666 A1 | 11/2015 |
| WO | WO 2016/065001 A1 | 4/2016 |
| WO | WO 2017/023724 A1 | 2/2017 |

OTHER PUBLICATIONS

Adachi et al., Drawing a high-resolution functional map of adeno-associated virus capsid by massively parallel sequencing. Nat Commun. 2014;5:3075. doi: 10.1038/ncomms4075.

Ahmed et al., A Single Intravenous rAAV Injection as Late as P20 Achieves Efficacious and Sustained CNS Gene Therapy in Canavan Mice. Mol Ther. Jul. 2, 2013. doi: 10.1038/mt.2013.138. [Epub ahead of print].

Akache et al., The 37/67-kilodalton laminin receptor is a receptor for adeno-associated virus serotypes 8, 2, 3, and 9. J Virol. Oct. 2006;80(19):9831-6.

Alisky et al., Gene therapy for amyotrophic lateral sclerosis and other motor neuron diseases. Hum Gene Ther. Nov. 20, 2000;11(17):2315-29.

Arbetman et al., Novel caprine adeno-associated virus (AAV) capsid (AAV-Go.1) is closely related to the primate AAV-5 and has unique tropism and neutralization properties. J Virol. Dec. 2005;79(24):15238-45.

Arbuthnot et al., Hepatic delivery of RNA interference activators for therapeutic application. Curr Gene Ther. Apr. 2009;9(2):91-103.

Asokan et al., The AAV vector toolkit: poised at the clinical crossroads. Mol Ther. Apr. 2012;20(4):699-708. doi: 10.1038/mt.2011.287. Epub Jan. 24, 2012.

Azzouz et al., VEGF delivery with retrogradely transported lentivector prolongs survival in a mouse ALS model. Nature. May 27, 2004;429(6990):413-7.

Baek et al., AAV-mediated gene delivery in adult GM1-gangliosidosis mice corrects lysosomal storage in CNS and improves survival. PLoS One. Oct. 18, 2010;5(10):e13468. doi: 10.1371/journal.pone.0013468.

Bartlett et al., Efficient expression of protein coding genes from the murine U1 small nuclear RNA promoters. Proc Natl Acad Sci U S A. Aug. 20, 1996;93(17):8852-7.

Berns et al., Biology of adeno-associated virus. Curr Top Microbiol Immunol. 1996;218:1-23.

Beutler et al., AAV for pain: steps towards clinical translation. Gene Ther. Apr. 2009;16(4):461-9. Epub Mar. 5, 2009.

Bish et al., Adeno-associated virus (AAV) serotype 9 provides global cardiac gene transfer superior to AAV1, AAV6, AAV7, and AAV8 in the mouse and rat. Hum Gene Ther. Dec. 2008;19(12):1359-68. doi: 10.1089/hum.2008.123.

Boillée et al., Onset and progression in inherited ALS determined by motor neurons and microglia. Science. Jun. 2, 2006;312(5778):1389-92.

Borel et al., Recombinant AAV as a platform for translating the therapeutic potential of RNA interference. Mol Ther. Apr. 2014;22(4):692-701. doi:10.1038/mt.2013.285. Epub Dec. 19, 2013.

Boudreau et al., Nonallele-specific silencing of mutant and wild-type huntingtin demonstrates therapeutic efficacy in Huntington's disease mice. Mol Ther. Jun. 2009;17(6):1053-63. doi: 10.1038/mt.2009.17. Epub Feb. 24, 2009.

Bourdenx et al., Systemic gene delivery to the central nervous system using Adeno-associated virus. Front Mol Neurosci. Jun. 2, 2014;7:50. doi: 10.3389/fnmol.2014.00050. eCollection 2014.

(56) References Cited

OTHER PUBLICATIONS

Brown et al., A microRNA-regulated lentiviral vector mediates stable correction of hemophilia B mice. Blood. Dec. 15, 2007;110(13):4144-52. Epub Aug. 28, 2007.
Brown et al., Endogenous microRNA can be broadly exploited to regulate transgene expression according to tissue, lineage and differentiation state. Nat Biotechnol. Dec. 2007;25(12):1457-67. Epub Nov. 16, 2007.
Brown et al., Endogenous microRNA regulation suppresses transgene expression in hematopoietic lineages and enables stable gene transfer. Nat Med. May 2006;12(5):585-91. Epub Apr. 23, 2006.
Buning et al., Receptor targeting of adeno-associated virus vectors. Gene Ther. Jul. 2003;10(14):1142-51.
Bussing et al., let-7 microRNAs in development, stem cells and cancer. Trends Mol Med. Sep. 2008;14(9):400-9. doi: 10.1016/j.molmed.2008.07.001. Epub Jul. 31, 2008.
Calcedo et al., Worldwide epidemiology of neutralizing antibodies to adeno-associated viruses. J Infect Dis. Feb. 1, 2009;199(3):381-90.
Calloni et al., Scaffolds for Artificial miRNA Expression in Animal Cells. Hum Gene Ther Methods. Oct. 2015;26(5):162-74. doi: 10.1089/hgtb.2015.043. Epub Sep. 25, 2015.
Carroll, Slightly long CAG repeats are more common than we thought. HDBuzz.net. Jul. 5, 2016. 9 pages. Retreived from http://eurohuntington.org.
Carter et al., Adeno-associated virus gene expression and regulation. CRC Handbook of parvoviruses. 1990:227-54.
Carter, in "Handbook of Parvoviruses", ed., p. Tijsser, CRC Press, pp. 155-168 (1990).
Cearley et al., Expanded repertoire of AAV vector serotypes mediate unique patterns of transduction in mouse brain. Mol Ther. Oct. 2008;16(10):1710-8. doi: 10.1038/mt.2008.166. Epub Aug. 19, 2008.
Cearley et al., Transduction characteristics of adeno-associated virus vectors expressing cap serotypes 7, 8, 9, and Rh10 in the mouse brain. Mol Ther. Mar. 2006;13(3):528-37. Epub Jan. 18, 2006.
Chadderton et al., Improved retinal function in a mouse model of dominant retinitis pigmentosa following AAV-delivered gene therapy. Mol Ther. Apr. 2009;17(4):593-9. Epub Jan. 27, 2009.
Chang et al., miR-122, a mammalian liver-specific microRNA, is processed from her mRNA and may downregulate the high affinity cationic amino acid transporter CAT-1. RNA Biol. Jul. 2004;1(2): 106-13. Epub Jul. 1, 2004.
Chen et al., Comparative study of anti-hepatitis B virus RNA interference by double-stranded adeno-associated virus serotypes 7, 8, and 9. Mol Ther. Feb. 2009;17(2):352-9. Epub Dec. 9, 2008.
Chen et al., Molecular signatures of disease brain endothelia provide new sites for CNS-directed enzyme therapy. Nat Med. Oct. 2009;15(10):1215-8. doi: 10.1038/nm.2025. Epub Sep. 13, 2009.
Chen et al., Regulation of immune responses and tolerance: the microRNA perspective. Immunol Rev. May 2013;253(1):112-28. doi:10.1111/imr.12060.
Cheng et al., Development of optimized AAV3 serotype vectors: mechanism of high-efficiency transduction of human liver cancer cells. Gene Ther. Apr. 2012;19(4):375-84. doi: 10.1038/gt.2011.105. Epub Jul. 21, 2011.
Chiorini et al., Cloning and characterization of adeno-associated virus type 5. J Virol. Feb. 1999;73(2):1309-19.
Choudhury et al., Identification of Novel vectors capable of CNS transduction in adult mice after single round selection using DNA shuffled AAV capsid library. Mol Ther. May 1, 2013;21(1):S1.
Christensen et al., A let-7 microRNA-binding site polymorphism in the KRAS 3' UTR is associated with reduced survival in oral cancers. Carcinogenesis. Jun. 2009;30(6): 1003-7. doi: 10.1093/carcin/bgp099. Epub Apr. 20, 2009.
Cideciyan et al., Human RPE65 gene therapy for Leber congenital amaurosis: persistence of early visual improvements and safety at 1 year. Hum Gene Ther. Sep. 2009;20(9):999-1004.
Conlon et al., Efficient hepatic delivery and expression from a recombinant adeno-associated virus 8 pseudotyped alphal-antitrypsin vector. Mol Ther. Nov. 2005;12(5):867-75. Epub Aug. 8, 2005.
Conlon et al., Ribozyme Approaches towards Down-Regulation of Pi*Z Mutant Human a-1 Anti-Trypsin. Mol. Therapy. 2004;9:S333. Abstract 875.
Coulouarn et al., Loss of miR-122 expression in liver cancer correlates with suppression of the hepatic phenotype and gain of metastatic properties. Oncogene. Oct. 8, 2009;28(40):3526-36. doi: 10.1038/onc.2009.211. Epub Jul. 20, 2009.
Cruz et al., In vivo post-transcriptional gene silencing of alpha-1 antitrypsin by adeno-associated virus vectors expressing siRNA. Lab Invest. Sep. 2007;87(9):893-902. Epub Jun. 25, 2007.
Cruz et al., The promise of gene therapy for the treatment of alpha-1 antitrypsin deficiency. Pharmacogenomics. Sep. 2007;8(9):1191-8.
Csak et al., microRNA-122 regulates hypoxia-inducible factor-1 and vimentin in hepatocytes and correlates with fibrosis in diet-induced steatohepatitis. Liver Int. Feb. 2015;35(2):532-41. doi: 10.1111/liv.12633. Epub Jul. 28, 2014.
Czech, MicroRNAs as therapeutic targets. N Engl J Med. Mar. 16, 2006;354(11):1194-5.
Davidoff et al., Sex significantly influences transduction of murine liver by recombinant adeno-associated viral vectors through an androgen-dependent pathway. Blood. Jul. 15, 2003;102(2):480-8. Epub Mar. 13, 2003.
Davidson et al., Recombinant adeno-associated virus type 2, 4, and 5 vectors: transduction of variant cell types and regions in the mammalian central nervous system. Proc Natl Acad Sci U S A. Mar. 28, 2000;97(7):3428-32.
Daya et al., Gene therapy using adeno-associated virus vectors. Clin Microbiol Rev. Oct. 2008;21(4):583-93. doi: 10.1128/CMR.00008-08.
Di Giorgio et al., Non-cell autonomous effect of glia on motor neurons in an embryonic stem cell-based ALS model. Nat Neurosci. May 2007;10(5):608-14. Epub Apr. 15, 2007.
Dominov et al., A novel dysferlin mutant pseudoexon bypassed with antisense oligonucleotides. Ann Clin Transl Neurol. Sep. 2014;1(9):703-20. doi: 10.1002/acn3.96. Epub Sep. 27, 2014.
Duque et al., Intravenous administration of self-complementary AAV9 enables transgene delivery to adult motor neurons. Mol Ther. Jul. 2009;17(7): 1187-96. doi: 10.1038/mt.2009.71. Epub Apr. 14, 2009.
Eberling et al., Results from a phase I safety trial of hAADC gene therapy for Parkinson disease. Neurology. May 20, 2008;70(21):1980-3. doi: 10.1212/01.wn1.0000312381.29287.ff. Epub Apr. 9, 2008.
Ebert et al., MicroRNA sponges: competitive inhibitors of small RNAs in mammalian cells. Nat Methods. Sep. 2007;4(9):721-6. Epub Aug. 12, 2007.
Ehlert et al., Cellular toxicity following application of adeno-associated viral vector-mediated RNA interference in the nervous system. BMC Neurosci. Feb. 18, 2010;11:20.
Elmen et al., LNA-mediated microRNA silencing in non-human primates. Nature. Apr. 2008;452(17): 896-900.
Elmen et al., Antagonism of microRNA-122 in mice by systemically administered LNA-antimiR leads to up-regulation of a large set of predicted target mRNAs in the liver. Nucleic Acids Res. Mar. 2008;36(4):1153-62. Epub Dec. 23, 2007.
Esau et al., miR-122 regulation of lipid metabolism revealed by in vivo antisense targeting. Cell Metab. Feb. 2006;3(2):87-98.
Fabani et al., miR-122 targeting with LNA/2'-O-methyl oligonucleotide mixmers, peptide nucleic acids (PNA), and PNA-peptide conjugates. RNA. Feb. 2008;14(2):336-46. Epub Dec. 11, 2007.
Fechner et al., Cardiac-targeted RNA interference mediated by an AAV9 vector improves cardiac function in coxsackievirus B3 cardiomyopathy. J Mol Med (Berl). Sep. 2008;86(9):987-97. doi: 10.1007/s00109-008-0363-x. Epub Jun. 12, 2008.
Feigin et al., Modulation of metabolic brain networks after subthalamic gene therapy for Parkinson's disease. Proc Natl Acad Sci U S A. Dec. 4, 2007;104(49):19559-64. Epub Nov. 27, 2007.
Fisher et al., Transduction with recombinant adeno-associated virus for gene therapy is limited by leading-strand synthesis. J Virol. Jan. 1996;70(1):520-32.

(56) References Cited

OTHER PUBLICATIONS

Flotte et al., Gene therapy for alpha-1 antitrypsin deficiency. Hum Mol Genet. Apr. 15, 2011;20(R1):R87-92. doi: 10.1093/hmg/ddr156. Epub Apr. 16, 2011.
Flotte et al., Phase I trial of intramuscular injection of a recombinant adeno-associated virus alpha 1-antitrypsin (rAAV2-CB-hAAT) gene vector to AAT-deficient adults. Hum Gene Ther. Jan. 2004;15(1):93-128.
Forman et al., A search for conserved sequences in coding regions reveals that the let-7 microRNA targets Dicer within its coding sequence. Proc Natl Acad Sci U S A. Sep. 30, 2008;105(39):14879-84. doi: 10.1073/pnas.0803230105. Epub Sep. 23, 2008.
Foust et al., Intravascular AAV9 preferentially targets neonatal-neurons and adult-astrocytes. Nature Biotechnology, 27; 59-65 2009.
Foust et al., Over the barrier and through the blood: to CNS delivery we go. Cell Cycle. Dec. 15, 2009;8(24):4017-8.
Fraldi et al., Functional correction of CNS lesions in an MPS-IIIA mouse model by intracerebral AAV-mediated delivery of sulfamidase and SUMF1 genes. Hum Mol Genet. Nov. 15, 2007;16(22):2693-702. Epub Aug. 27, 2007.
Fu et al., Self-complementary adeno-associated virus serotype 2 vector: global distribution and broad dispersion of AAV-mediated transgene expression in mouse brain. Mol Ther. Dec. 2003;8(6):911-7.
Gadalla et al., Improved survival and reduced phenotypic severity following AAV9/MECP2 gene transfer to neonatal and juvenile male Mecp2 knockout mice. Mol Ther. Jan. 2013;21(1):18-30. doi:10.1038/mt.2012.200. Epub Sep. 25, 2012.
Gao et al., Adeno-associated virus-mediated gene transfer to non-human primate liver can elicit destructive transgene-specific T cell responses. Hum Gene Ther. Sep. 2009;20(9):930-42. doi: 10.1089/hum.2009.060.
Gao et al., Adeno-associated viruses undergo substantial evolution in primates during natural infections. Proc Natl Acad Sci U S A. May 13, 2003;100(10):6081-6. Epub Apr. 25, 2003.
Gao et al., Inadvertent gene transfer of co-packaged rep and cap sequences during the production of AAV vector and its potential impact on vector performance. Molecular Therapy. May 2008;16(Suppl. 1):S105-S106. Abstract 279.
Gao et al., New recombinant serotypes of AAV vectors. Curr Gene Ther. Jun. 2005;5(3):285-97.
Gao et al., Novel adeno-associated viruses from rhesus monkeys as vectors for human gene therapy. Proc Natl Acad Sci U S A. Sep. 3, 2002;99(18):11854-9. Epub Aug. 21, 2002.
Gao et al., RAAV-mediated targeting in adult mice and its potential in generating animal models of tissue-specific somatic transgenics or knock down. Molecular Therapy. May 2008;16(1):S118-S119. Abstract 316.
GENBANK Submission; Accession No. ADZ26851; Wilson et al.; Jun. 30, 2005.
GENBANK Submission; Accession No. AF028705.1; Rutledge et al.; Jan. 12, 1998.
GENBANK Submission; NCBI, Accession No. AAB95450; Rutledge et al.; Jan. 12, 1998.
GENBANK Submission; NCBI, Accession No. AAS99264; Gao et al.; Jun. 24, 2004.
GenBank Submission; NCBI, Accession No. ABA71701; Schmidt et al.; May 10, 2006.
GENBANK Submission; NCBI, Accession No. ACB55301; Vandenberghe et al.; Jul. 31, 2008.
GENBANK Submission; NCBI, Accession No. ACB55310; Vandenberghe et al.; Jul. 31, 2008.
GENBANK Submission; NCBI, Accession No. AY530579.10; 2004.
GENBANK Submission; NCBI, Accession No. NP 049542; Xiao et al.; Mar. 11, 2010.
GENBANK Submission; NCBI, Accession No. YP 680426; Ruffing et al.; Nov. 19, 2010.
Gentner et al., Stable knockdown of microRNA in vivo by lentiviral vectors. Nat Methods. Jan. 2009;6(1):63-6. doi: 10.1038/nmeth.1277. Epub Nov. 30, 2008.
Girard et al., miR-122, a paradigm for the role of microRNAs in the liver. J Hepatol. Apr. 2008;48(4):648-56. doi: 10.1016/j.jhep.2008.01.019. Epub Feb. 12, 2008.
Gramantieri et al., Cyclin G1 is a target of miR-122a, a microRNA frequently down-regulated in human hepatocellular carcinoma. Cancer Res. Jul. 1, 2007;67(13):6092-9.
Grimm et al., Fatality in mice due to oversaturation of cellular microRNA/short hairpin RNA pathways. Nature. May 25, 2006;441(7092):537-41.
Grimm, Small silencing RNAs: state-of-the-art. Adv Drug Deliv Rev. Jul. 25, 2009;61(9):672-703. doi: 10.1016/j.addr.2009.05.002. Epub May 7, 2009.
Haraguchi et al., Vectors expressing efficient RNA decoys achieve the long-term suppression of specific microRNA activity in mammalian cells. Nucleic Acids Res. Apr. 2009;37(6):e43. doi: 10.1093/nar/gkp040. Epub Feb. 17, 2009.
Haussecker et al., miR-122 continues to blaze the trail for microRNA therapeutics. Mol Ther. Feb. 2010;18(2):240-2. doi: 10.1038/mt.2009.313.
Hernandez et al., Latent adeno-associated virus infection elicits humoral but not cell-mediated immune responses in a nonhuman primate model. J Virol. Oct. 1999;73(10):8549-58.
Horwich et al., Design and delivery of antisense oligonucleotides to block microRNA function in cultured *Drosophila* and human cells. Nat Protoc. 2008;3(10):1537-49. doi: 10.1038/nprot.2008.145.
Hsu et al., Essential metabolic, anti-inflammatory, and anti-tumorigenic functions of miR-122 in liver. J Clin Invest. Aug. 2012;122(8):2871-83. doi:10.1172/JCI63539. Epub Jul. 23, 2012.
Hutvagner et al., Sequence-specific inhibition of small RNA function. PLoS Biol. Apr. 2004;2(4):E98. Epub Feb. 24, 2004.
Iida et al., Systemic Delivery of Tyrosine-Mutant AAV Vectors Results in Robust Transduction of Neurons in Adult Mice. BioMed Res Int. 2013;2013.
Jakobsson et al., Lentiviral vectors for use in the central nervous system. Mol Ther. Mar. 2006;13(3):484-93. Epub Jan. 3, 2006.
Janson et al., Clinical protocol. Gene therapy of Canavan disease: AAV-2 vector for neurosurgical delivery of aspartoacylase gene (ASPA) to the human brain. Hum Gene Ther. Jul. 20, 2002;13(11):1391-412.
Johnson et al., RAS is regulated by the let-7 microRNA family. Cell. Mar. 11, 2005;120(5):635-47.
Kaspar et al., Retrograde viral delivery of IGF-1 prolongs survival in a mouse ALS model. Science. Aug. 8, 2003;301(5634):839-42.
Koornneef et al., Apolipoprotein B knockdown by AAV-delivered shRNA lowers plasma cholesterol in mice. Mol Ther. Apr. 2011;19(4):731-40. doi:10.1038/mt.2011.6. Epub Feb. 8, 2011.
Kota et al., AAV8-Mediated Delivery of miR-26a inhibits cancer cell proliferation and induces tumor-specific apoptosis in a liver cancer model. Mol. Therapy. May 2009. 17(1):S300. Abstract 783.
Kota et al., Therapeutic microRNA delivery suppresses tumorigenesis in a murine liver cancer model. Cell. Jun. 12, 2009;137(6):1005-17. doi: 10.1016/j.cell.2009.04.021.
Kotin et al., Organization of adeno-associated virus DNA in latently infected Detroit 6 cells. Virology. Jun. 1989;170(2):460-7.
Kotin et al., Site-specific integration by adeno-associated virus. Proc Natl Acad Sci U S A. Mar. 1990;87(6):2211-5.
Krutzfeldt et al., Silencing of microRNAs in vivo with 'antagomirs'. Nature. Dec. 2005;1;438(7068):685-9. Epub Oct. 30, 2005.
Kutay et al., Downregulation of miR-122 in the rodent and human hepatocellular carcinomas. J Cell Biochem. Oct. 15, 2006;99(3):671-8.
Lanford et al., Therapeutic silencing of microRNA-122 in primates with chronic hepatitis C virus infection. Science. Jan. 8, 2010;327(5962):198-201. Epub Dec. 3, 2009.
Lawlor et al., Efficient gene delivery and selective transduction of glial cells in the mammalian brain by AAV serotypes isolated from nonhuman primates. Mol Ther. Oct. 2009;17(10):1692-702. doi:; 10.1038/mt.2009.170.
Leone et al., Aspartoacylase gene transfer to the mammalian central nervous system with therapeutic implications for Canavan disease.

(56) References Cited

OTHER PUBLICATIONS

Ann Neurol. Jul. 2000;48(1):27-38. Erratum in: Ann Neurol Sep. 2000;48(3):398. Bilianuk L [corrected to Bilaniuk L].
Lewis et al., Conserved seed pairing, often flanked by adenosines, indicates that thousands of human genes are microRNA targets. Cell. Jan. 14, 2005;120(1):15-20.
Lewis et al., Prediction of mammalian microRNA targets. Cell. Dec. 26, 2003;115(7):787-98.
Li et al., Efficient and Targeted Transduction of Nonhuman Primate Liver With Systemically Delivered Optimized AAV3B Vectors. Mol Ther. Dec. 2015;23(12):1867-76. doi: 10.1038/mt.2015.174. Epub Sep. 25, 2015.
Li et al., Intronic microRNA: discovery and biological implications. DNA Cell Biol. Apr. 2007;26(4):195-207.
Li et al., Protein trans-splicing as a means for viral vector-mediated in vivo gene therapy. Hum Gene Ther. Sep. 2008;19(9):958-64. doi: 10.1089/hum.2008.009.
Lin et al., Impact of preexisting vector immunity on the efficacy of adeno-associated virusbased HIV-1 Gag vaccines. Hum Gene Ther. Jul. 2008;19(7):663-9.
Liu et al., Does the Mutant CAG Expansion in Huntingtin mRNA Interfere with Exonucleolytic Cleavage of its First Exon? J Huntingtons Dis. 2016;5(1):33-8. doi: 10.3233/JHD-150183.
Lowenstein, Crossing the rubicon. Nat Biotechnol. Jan. 2009;27(1):42-4.
Loya et al., Transgenic microRNA inhibition with spatiotemporal specificity in intact organisms. Nat Methods. Dec. 2009;6(12):897-903. doi: 10.1038/nmeth.1402. Epub Nov. 15, 2009.
Lux et al., Green fluorescent protein-tagged adeno-associated virus particles allow the study of cytosolic and nuclear trafficking. J Virol. Sep. 2005;79(18):11776-87.
Lynn, Meta-regulation: microRNA regulation of glucose and lipid metabolism. Trends Endocrinol Metab. Nov. 2009;20(9):452-9. doi: 10.1016/j.tem.2009.05.007. Epub Sep. 30, 2009.
Ma et al., Therapeutic silencing of miR-10b inhibits metastasis in a mouse mammary tumor model. Nat Biotechnol. Apr. 2010;28(4):341-7. doi: 10.1038/nbt.1618. Epub Mar. 28, 2010.
Maguire et al., Directed evolution of adeno-associated virus for glioma cell transduction. J Neurooncol. Feb. 2010;96(3):337-47. doi:10.1007/sll060-009-9972-7. Epub Jul. 19, 2009.
Maguire et al., Gene therapy for the nervous system: challenges and new strategies. Neurotherapeutics. Oct. 2014;11(4):817-39. doi: 10.1007/s13311-014-0299-5.
Malinkevich et al., 1002. rAAV Mediated Delivery of Target Specific Micro RNA Sponges for Study of Micro RNA Function in Mouse Models. Gene regulation. May 1, 2009;17(1):S382.
Mandel et al., Recombinant adeno-associated viral vectors as therapeutic agents to treat neurological disorders. Mol Ther. Mar. 2006;13(3):463-83. Epub Jan. 18, 2006.
Manfredsson et al., AAV9: a potential blood-brain barrier buster. Mol Ther. Mar. 2009;17(3):403-5.
Matalon et al., Adeno-associated virus-mediated aspartoacylase gene transfer to the brain of knockout mouse for canavan disease. Mol Ther. May 2003;7(5 Pt 1):580-7.
McBride et al., Artificial miRNAs mitigate shRNA-mediated toxicity in the brain: implications for the therapeutic development of RNAi. Proc Natl Acad Sci U S A. Apr. 15, 2008;105(15):5868-73. Epub Apr. 8, 2008.
McCarty et al., Adeno-associated virus terminal repeat (TR) mutant generates self-complementary vectors to overcome the rate-limiting step to transduction in vivo. Gene Ther. Dec. 2003;10(26):2112-8.
McCarty et al., Integration of adeno-associated virus (AAV) and recombinant AAV vectors. Annu Rev Genet. 2004;38:819-45.
McCarty et al., Self-complementary recombinant adeno-associated virus (scAAV) vectors promote efficient transduction independently of DNA synthesis. Gene Ther. Aug. 2001;8(16):1248-54.
McCarty, Self-complementary AAV vectors; advances and applications. Mol Ther. Oct. 2008;16(10):1648-56. Epub Aug. 5, 2008.
McCurdy et al., Sustained normalization of neurological disease after intracranial gene therapy in a feline model. Sci Transl Med. Apr. 9, 2014;6(231):231ra48. doi: 10.1126/scitranslmed.3007733.
Meijer et al., Controlling brain tumor growth by intraventricular administration of an AAV vector encoding IFN-beta. Cancer Gene Ther. Aug. 2009;16(8):664-71. doi: 10.1038/cgt.2009.8. Epub Feb. 6, 2009.
Meister et al., Sequence-specific inhibition of microRNA- and siRNA-induced RNA silencing. RNA. Mar. 2004;10(3):544-50.
Mietzsch et al., OneBac 2.0: Sf9 Cell Lines for Production of AAV5 Vectors with Enhanced Infectivity and Minimal Encapsidation of Foreign DNA. Hum Gene Ther. Oct. 2015;26(10):688-97. doi:10.1089/hum.2015.050. Epub Aug. 6, 2015.
Miniarikova et al., Design, Characterization, and Lead Selection of Therapeutic miRNAs Targeting Huntingtin for Development of Gene Therapy for Huntington's Disease. Mol Ther Nucleic Acids. Mar. 22, 2016;5(3):e297. doi: 10.1038/mtna.2016.7. 16 pages.
Moffett et al., N-Acetylaspartate in the CNS: from neurodiagnostics to neurobiology. Prog Neurobiol. Feb. 2007;81(2):89-131. Epub Jan. 5, 2007.
Mueller et al., Development of Simultaneous Gene Augmentation and Reduction of Mutant Gene Expression with a Single Recombinant AAV for Alpha-1 Antitrypsin Disease. Molecular Therapy May 2009;17(1):S391-S392. Abstract 1030.
Mueller et al., Sustained miRNA-mediated knockdown of mutant AAT with simultaneous augmentation of wild-type AAT has minimal effect on global liver miRNA profiles. Mol Ther. Mar. 2012;20(3):590-600. Epub Jan. 17, 2012.
Mueller et al., Using rAAV Delivered miRNAs To Knockdown Misfolded Human Alpha 1 Antitrypsin in a Transgenic Mouse Model. Molecular Therapy May 2010;18(1):S21. Abstract 51.
NCBI Blast Protein Sequence. RID-09JSKF33114. Alignment of Seq ID Nos. 87, 179. 2016.
O'Reilly et al., RNA interference-mediated suppression and replacement of human rhodopsin in vivo. Am J Hum Genet. Jul. 2007;81(1):127-35. Epub May 23, 2007.
Passini et al., CNS-targeted gene therapy improves survival and motor function in a mouse model of spinal muscular atrophy. J Clin Invest. Apr. 2010;120(4):1253-64. doi: 10.1172/JCI41615. Epub Mar. 15, 2010.
Pertin et al., Efficacy and specificity of recombinant adeno-associated virus serotype 6 mediated gene transfer to drg neurons through different routes of delivery. Poster sessions. Eur J. Pain. 2009;13:S74. Abstract 229.
Pfeifer et al., Pharmacological potential of RNAi—focus on miRNA. Pharmacol Ther. Jun. 2010;126(3):217-27. doi: 10.1016/j.pharmthera.2010.03.006. Epub Apr. 11, 2010.
Pfister et al., Artificial miRNAs Reduce Human Mutant Huntingtin Throughout the Striatum in a Transgenic Sheep Model of Huntington's Disease. Hum Gene Ther. Jun. 2018;29(6):663-673. doi: 10.1089/hum.2017.199. Epub Feb. 23, 2018.
Pfister et al., Safe and Efficient Silencing with a Pol II, but Not a Pol III, Promoter Expressing an Artificial miRNA Targeting Human Huntingtin. Mol Ther Nucleic Acids. Jun. 16, 2017;7:324-334. doi: 10.1016/j.omtn.2017.04.011. Epub Apr. 14, 2017.
Ralph et al., Silencing mutant SOD1 using RNAi protects against neurodegeneration and extends survival in an ALS model. Nat Med. Apr. 2005;11(4):429-33. Epub Mar. 13, 2005.
Raoul et al., Lentiviral-mediated silencing of SOD1 through RNA interference retards disease onset and progression in a mouse model of ALS. Nat Med. Apr. 2005;11(4):423-8. Epub Mar. 13, 2005.
Schattgen et al., Cutting Edge: DNA in the Lung Microenvironment during Influenza Virus Infection Tempers Inflammation by Engaging the DNA Sensor AIM2. J Immunol. Jan. 1, 2016;196(1):29-33. doi:10.4049/jimmunol.1501048.
Schnepp et al., Characterization of adeno-associated virus genomes isolated from human tissues. J Virol. Dec. 2005;79(23):14793-803.
Sen et al., Micromanaging vascular biology: tiny microRNAs play big band. J Vasc Res. 2009;46(6):527-40. doi: 10.1159/000226221. Epub Jun. 30, 2009.

(56) References Cited

OTHER PUBLICATIONS

Snyder et al., Comparison of adeno-associated viral vector serotypes for spinal cord and motor neuron gene delivery. Hum Gene Ther. Sep. 2011;22(9):1129-35. doi: 10.1089/hum.2011.008. Epub Jul. 25, 2011.
Sondhi et al., Enhanced survival of the LINCL mouse following CLN2 gene transfer using the rh.10 rhesus macaque-derived adeno-associated virus vector. Mol Ther. Mar. 2007;15(3):481-91. Epub Dec. 19, 2006.
Stanek et al., Silencing mutant huntingtin by adeno-associated virus-mediated RNA interference ameliorates disease manifestations in the YAC128 mouse model of Huntington's disease. Hum Gene Ther. May 2014;25(5):461-74. doi: 10.1089/hum.2013.200. Epub Mar. 21, 2014.
Stoica et al., Targeting Human SOD1 Using AAV mediated RNAi in a mouse model of amyotrophic lateral sclerosis. Mol ther. Jun. 2013;21(1):S149.
Storek et al., Intrathecal long-term gene expression by self-complementary adeno-associated virus type 1 suitable for chronic pain studies in rats. Mol Pain. Jan. 30, 2006;2:4.
Storkebaum et al., Treatment of motoneuron degeneration by intracerebroventricular delivery of VEGF in a rat model of ALS. Nat Neurosci. Jan. 2005;8(1):85-92. Epub Nov. 28, 2004.
Suckau et al., 851. The Effect of Genome Size and Design of scAAV Vectors on Efficiency of shRNA Expression and Gene Knockdown. May 1, 2007; 15(1):S325.
Tanimizu et al., Downregulation of miR122 by grainyhead-like 2 restricts the hepatocytic differentiation potential of adult liver progenitor cells. Development. Dec. 2014;141(23):4448-56. doi:10. 1242/dev.1 13654. Epub Nov. 18, 2014.
Tenenbaum et al., Recombinant AAV-mediated gene delivery to the central nervous system. J Gene Med. Feb. 2004;6 Suppl 1:S212-22.
Tomar et al., Use of adeno-associated viral vector for delivery of small interfering RNA. Oncogene. Aug. 2, 20038;22(36):5712-5.
Tokumaru et al., let-7 regulates Dicer expression and constitutes a negative feedback loop. Carcinogenesis. Nov. 2008;29(11):2073-7. doi: 10.1093/carcin/bgn187. Epub Aug. 11, 2008.
Towne et al., Systemic AAV6 delivery mediating RNA interference against SOD1: neuromuscular transduction does not alter disease progression in fALS mice. Mol Ther. Jun. 2008;16(6):1018-25. doi: 10.1038/mt.2008.73. Epub Apr. 15, 2008.
Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015.
Tsai et al., MicroRNA-122, a tumor suppressor microRNA that regulates intrahepatic metastasis of hepatocellular carcinoma. Hepatology. May 2009;49(5):1571-82. doi: 10.1002/hep.22806.
UNIPROT Submission; Accession No. A8IGP7; Nov. 13, 2013.
UNIPROT Submission; Accession No. H3GK32; Feb. 6, 2013.
UNIPROT Submission; Accession No. T2BRA8; Nov. 13, 2013.
Vandenberghe et al., Heparin binding directs activation of T cells against adeno-associated virus serotype 2 capsid. Nat Med. Aug. 2006;12(8):967-71. Epub Jul. 16, 2006.
Vandenberghe et al., Tailoring the AAV vector capsid for gene therapy. Gene Ther. Mar. 2009;16(3):311-9. Epub Dec. 4, 2008.
Vandendriessche et al., Efficacy and safety of adeno-associated viral vectors based on serotype 8 and 9 vs. lentiviral vectors for hemophilia B gene therapy. J Thromb Haemost. Jan. 2007;5(1):16-24. Epub Sep. 26, 2006.
Vaucheret et al., The action of ARGONAUTE1 in the miRNA pathway and its regulation by the miRNA pathway are crucial for plant development. Genes Dev. May 15, 2004;18(10):1187-97. Epub May 6, 2004.
Vermeulen et al., Double-stranded regions are essential design components of potent inhibitors of RISC function. RNA. May 2007;13(5):723-30. Epub Mar. 30, 2007.
Vulchanova et al., Differential adeno-associated virus mediated gene transfer to sensory neurons following intrathecal delivery by direct lumbar puncture. Mol Pain. May 28, 2010;6:31. doi: 10.1186/ 1744-8069-6-31.
Waldman et al., Applications of microRNA in cancer: Exploring the advantages of miRNA. Clin Transl Sci. Jun. 2009;2(3):248-9. doi: 10.1111/j.1752-8062.2009.00110.x.
Wang et al., Neuroprotective effects of glial cell line-derived neurotrophic factor mediated by an adeno-associated virus vector in a transgenic animal model of amyotrophic lateral sclerosis. J Neurosci. Aug. 15, 2002;22(16):6920-8.
Wang et al., Rescue and replication of adeno-associated virus type 2 as well as vector DNA sequences from recombinant plasmids containing deletions in the viral inverted terminal repeats: selective encapsidation of viral genomes in progeny virions. J Virol. Mar. 1996;70(3):1668-77.
Wang et al., Somatically Repairing Compound Heterozygous Recessive Mutations by Chromosomal Cut-and-Paste for in Vivo Gene Therapy. May 2016. 24(1):S289. Abstract 733.
Wang et al., The design of vectors for RNAi delivery system. Curr Pharm Des. 2008;14(13):1327-40.
Wang et al., The potential of adeno-associated viral vectors for gene delivery to muscle tissue. Expert Opin Drug Deliv. Mar. 2014;11(3):345-64. doi: 10.1517/17425247.2014.871258. Epub Jan. 3, 2014.
Wang et al., Therapeutic gene silencing delivered by a chemically modified small interfering RNA against mutant SOD1 slows amyotrophic lateral sclerosis progression. J Biol Chem. Jun. 6, 2008;283(23):15845-52. doi: 10.1074/jbc.M800834200. Epub Mar. 26, 2008.
Wang et al., Widespread spinal cord transduction by intrathecal injection of rAAV delivers efficacious RNAi therapy for amyotrophic lateral sclerosis. Hum Mol Genet. Feb. 1, 2014;23(3):668-81. doi: 10.1093/hmg/ddt454. Epub Sep. 18, 2013.
Watson et al., Intrathecal administration of AAV vectors for the treatment of lysosomal storage in the brains of MPS I mice. Gene Ther. Jun. 2006;13(11):917-25.
Wein et al., Efficient bypass of mutations in dysferlin deficient patient cells by antisense-induced exon skipping. Hum Mutat. Feb. 2010;31(2):136-42. doi: 10.1002/humu.21160.
Weismann et al., Systemic AAV9 gene transfer in adult GM1 gangliosidosis mice reduces lysosomal storage in CNS and extends lifespan. Hum Mol Genet. Aug. 1, 2015;24(15):4353-64. doi: 10.1093/ hmg/ddv168. Epub May 10, 2015.
Weismann, Approaches and Considerations Towards a Safe and Effective Adena-Associated Virus Mediated Therapeutic Intervention for GM 1-Gangliosidosis: A Dissertation. University Massachusetts Medical School. Aug. 5, 2014.
Xia et al., Allele-specific RNAi selectively silences mutant SOD1 and achieves significant therapeutic benefit in vivo. Neurobiol Dis. Sep. 2006;23(3):578-86. Epub Jul. 20, 2006.
Xie et al., 676. DNA Sequences Encoding shRNAs Can Replace Mutant ITR in scAAV Genome for Efficient Replication and Packaging and Transcribe shRNAs by pol III Promoter Activity of wt ITR for Efficient Gene Silencing Mol Therapy. May 2015;23(1):S269.
Xie et al., Characterization of positioning effect of pol III-shRNA transcription unit in scAAV vector genome on the packaging efficiency and functionality of shRNA silencing. Molecular Therapy. May 2010;18(1): S262. Abstract 671.
Xie et al., Isolation of transcriptionally active novel AAV capsid sequences from chimpanzee tissues for vector development. Meeting Abstract: 12th Annual Meeting of the American Society of Gene Therapy. May 1, 2009. Abstract 91.
Xie et al., MicroRNA regulated tissue specific transduction by rAAV vector. Molecular Therapy. May 2009;17(1): S279. Abstract 732.
Xie et al., MicroRNA-regulated, systemically delivered rAAV9: a step closer to CNS-restricted transgene expression. Mol Ther. Mar. 2011;19(3):526-35. doi: 10.1038/mt.2010.279. Epub Dec. 21, 2010.
Xie et al., rAAV-mediated delivery of micro RNA scavengers leads to efficient and stable knockdown of cognate micro RNAs, upregulation of their natural target genes and phenotypic changes in mice. Molecular Therapy. May 2010;18(1): S140. Abstract362.
Xie et al., Short DNA Hairpins Compromise Recombinant Adeno-Associated Virus Genome Homogeneity. Mol Ther. Jun. 7, 2017;25(6):1363-1374. doi: 10.1016/j.ymthe.2017.03.028. Epub Apr. 24, 2017.

AAV TREATMENT OF HUNTINGTON'S DISEASE

RELATED APPLICATIONS

This application is a continuation under 35 U.S.C. § 120 of U.S. application Ser. No. 16/573,412, filed Sep. 17, 2019, now U.S. Pat. No. 11,046,957, which is a continuation under 35 U.S.C. § 120 of U.S. application Ser. No. 15/705,909, filed Sep. 15, 2017, now U.S. Pat. No. 10,457,940, which claims priority under 35 U.S.C. § 119(e) to U.S. provisional application Ser. No. 62/398,487, filed Sep. 22, 2016, entitled "AAV TREATMENT OF HUNTINGTON'S DISEASE", the entire contents of each application are incorporated herein by reference.

FEDERALLY SPONSORED RESEARCH

This invention was made with government support under NS038194 awarded by the National Institutes of Health. The government has certain rights in the invention.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on May 21, 2021, is named U012070084US04-SEQ-LJG and is 57,381 bytes in size.

BACKGROUND

Huntington's disease (HD) is a devastating inherited neurodegenerative disease caused by an expansion of the CAG repeat region in exon 1 of the huntingtin gene. While the Huntingtin protein (HTT) is expressed throughout the body, the polyglutamine expanded protein is especially toxic to medium spiny neurons in the striatum and their cortical connections. Patients struggle with emotional symptoms including depression and anxiety and with characteristic movement disturbances and chorea. There is currently no cure for Huntington's disease; therapeutic options are limited to ameliorating disease symptoms.

SUMMARY

Aspects of the disclosure relate to compositions and methods useful for treating Huntington's disease (HD). In some embodiments, inhibitory nucleic acids (e.g., miRNAs, such as artificial miRNAs) are provided that hybridize specifically to and inhibit expression of human huntingtin (HTT).

Accordingly, in some aspects, the disclosure provides an isolated nucleic acid comprising or encoding the sequence set forth in any one of SEQ ID NO: 2-10 or 21-22. In some embodiments, human huntingtin comprises a sequence as set forth in SEQ ID NO: 1. In some embodiments, the disclosure provides an nucleic acid (e.g., a miRNA) that is complementary to at least two (e.g., 2, 3, 4, 5, 6, 7, 8, 9, 10, 11, 12, 13, 14, 15, 16, 17, 18, 19, 20, 21, 22, 23, 24 or 25) continuous bases of SEQ ID NO: 1.

In some aspects, the disclosure provides an isolated nucleic acid comprising: a first region comprising a first adeno-associated virus (AAV) inverted terminal repeat (ITR), or a variant thereof; and, a second region comprising a transgene encoding one or more miRNAs. In some embodiments, the sequence encoding each miRNA comprises a sequence set forth in any one of SEQ ID NOs: 2-10 flanked by sequence encoding a miRNA backbone sequence.

In some embodiments, each miRNA backbone sequence is a mir-155 backbone sequence, a mir-30 backbone sequence, or a mir-64 backbone sequence.

In some embodiments, the transgene further comprises a nucleic acid sequence encoding a promoter. In some embodiments, the promoter is a chicken beta-actin (CBA) promoter or a U6 promoter.

In some embodiments, the transgene further comprises a nucleic acid sequence encoding a protein. In some embodiments, the protein is a therapeutic protein (e.g., non-mutant huntingtin) or a reporter protein (e.g., a fluorescent protein, such as GFP).

In some embodiments, the one or more miRNAs is located in an untranslated portion of the transgene. In some embodiments, the untranslated portion is an intron. In some embodiments, the untranslated portion is between the last codon of the nucleic acid sequence encoding a protein and a poly-A tail sequence. In some embodiments, the untranslated portion is between the last nucleic acid base of a promoter sequence and the first base of a poly-A tail sequence.

In some embodiments, the isolated nucleic acid further comprises a third region that comprises a second adeno-associated virus (AAV) inverted terminal repeat (ITR), or a variant thereof.

In some embodiments, the first or second ITR variant lacks a functional terminal resolution site (TRS), optionally wherein the ITR variant is a ΔTRS ITR.

In some embodiments, at least one of the miRNAs hybridizes with and inhibits expression of human huntingtin.

In some aspects, the disclosure provides a vector comprising an isolated nucleic acid as described by the disclosure. In some embodiments, the vector is a plasmid.

In some aspects, the disclosure provides a host cell comprising an isolated nucleic acid or a vector as described by the disclosure.

In some aspects, the disclosure provides a recombinant AAV (rAAV) comprising: a capsid protein; and, an isolated nucleic acid as described by the disclosure.

In some embodiments, the capsid protein is an AAV9 capsid protein. In some embodiments, the capsid protein comprises the sequence set forth in SEQ ID NO: 20.

In some embodiments, the rAAV is a self-complementary AAV (scAAV).

In some embodiments, the rAAV is formulated for delivery to the central nervous system (CNS).

Aspects of the disclosure relate to isolated nucleic acids capable of reducing (e.g., inhibiting) expression of pathogenic huntingtin and thus may be useful for the treatment of Huntington's disease. Accordingly, in some aspects, the disclosure provides a method for treating Huntington's disease in a subject in need thereof, the method comprising administering to a subject having or at risk of developing Huntington's disease a therapeutically effective amount of an isolated nucleic acid or rAAV as described by the disclosure.

In some embodiments, the subject comprises a huntingtin gene having more than 36 CAG repeats, more than 40 repeats, or more than 100 repeats. In some embodiments, the subject is less than 20 years of age, or is diagnosed as having juvenile HD.

In some embodiments, the administration results in delivery of the isolated nucleic acid or rAAV to the central nervous system (CNS) of the subject. In some embodiments, the administration is via injection, optionally intravenous injection or intrastriatal injection.

BRIEF DESCRIPTION OF DRAWINGS

FIG. 4A shows positions of target sites on the human huntingtin mRNA. FIG. 4B shows HeLa cells transfected with plasmids expressing artificial miRNAs targeting human huntingtin; the huntingtin mRNA levels were measured after 48 hours by qPCR. Huntingtin expression was normalized to HPRT to account for well to well variation in cell number and are expressed relative to the untreated/naïve control. Error bars represent standard error. FIG. 4C shows candidate miRNAs selected for in vivo testing based on the results in cell culture. Mice were injected unilaterally in the striatum. One month post-injection, the striatum was harvested and GFP positive tissue was dissected out. Data are normalized to HPRT and expressed relative to the GFP-only control.

FIG. 5A shows data relating to AAV9 constructs expressing a miRNA from the CBA (polII) and U6 promoters. The CBA-promoter driven miRNA is located in the 3'-UTR of the GFP gene, whereas the construct containing the U6 promoter driven artificial miRNA co-expresses GFP from a separate promoter. FIG. 5B shows relative quantity of huntingtin mRNA in the injected striatum following injection of the U6 and CBA-promoter driven artificial miRNAs targeting sites 5155 (left) and 6433 (right). Data are expressed relative to the non-injected side. FIG. 5C shows relative quantity of huntingtin mRNA in mice injected unilaterally with the U6 and CBA-promoter driven miRNA targeting site 6433. Data are expressed relative to the group of mice injected with a GFP-expressing control vector.

FIG. 6A shows six months post-injection, mice injected with the U6-promoter driven mir-HTT-6433 failed to make nests. Pictures were taken 24 hours after placing new nestlets in the cage. FIG. 6B shows cage monitoring of Yac128 mice treated with PBS, CBA-mir-HTT-6433 or U6-mir-HTT-6433. The amount of time spent moving around the cage was recorded for 24-27 hours. Average time per hour was calculated by dividing the total amount of time by the number of hours of recording.

FIG. 7A shows representative images of DARPP-32 staining on the injected side in Yac128 mice at 1 (top) and 6 (bottom) months post-injection. FIG. 7B shows quantification of DARPP-32 positive area 6 months post-injection.

FIG. 8A shows representative images of Iba1 staining on the injected side in Yac128 mice at 1 (top) and 6 (bottom) months post-injection. Images were taken at the site of injection. Quantification of total (FIG. 8B), activated (FIG. 8C) and resting (FIG. 8D) microglia at 6 months post injection are shown.

FIG. 9A shows start positions of reads mapping to the huntingtin targeting artificial miRNA hairpin (mir-155 backbone). Positions are reported relative to the mature strand and reads are normalized to the total number of endogenous miRNA mapped in each sample. The horizontal line represents the background levels of the artificial miRNA found in control samples. FIG. 9B shows relative quantification of mature miR-HTT (from mir-155 backbone) by quantitative RT-PCR. FIG. 9C shows start portions of reads mapping to the huntingtin targeting artificial miRNA embedded in a mir-30 backbone and expressed from a U6 promoter.

FIG. 10A shows mRNAs were divided into those containing canonical miRNA binding matching the artificial miRNA sites (legend) and those without. In the group of mice injected with AAV-CbA-mir-HTT-6433, there is no difference between mRNAs with and without such sites. FIG. 10B shows in contrast, in the AAV-U6-mir-HTT-6433 group there is a shift toward repression of mRNAs with perfect 8mer sites.

FIG. 11A shows GFP staining in the striatum of mice were injected with a vector encoding both the huntingtin targeting artificial miRNA and EGFP. ImageJ was used to measure the percent of the striatum that was GFP positive. FIG. 11B shows quantitative RT-PCR measuring human huntingtin mRNA in the striatum of Yac128 mice. FIG. 11C shows representative photographs of mice injected with a vector encoding both the huntingtin targeting miRNA and EGFP at three different doses. Data indicate reducing vector dose results in reduced spread and knockdown.

FIGS. 12-12B show data indicating that Yac128 mice show a decline in ability to cross the beam following injection of the U6-promoter driven huntingtin targeting artificial miRNA. FIG. 12A shows mice injected at 2-3 months show a clear increase in time to cross the beam and some of them fail to cross altogether. FIG. 12B shows Yac128 mice injected with either PBS or CBA-mir-HTT-6433 at 7 months of age show an age-related decline in behavior on the beam. Injection with U6-mir-HTT-6433 (red dots) accelerates this decline.

FIG. 13A shows the amount of time taken to cross the beam for control (naïve) mice and mice injected with AAV-U6-mir-HTT-6433 and AAV-CbA-mir-HTT-6433. FIG. 13B shows quantification of DARPP-32 positive striatal area in control (naïve) mice and mice injected with AAV-U6-mir-HTT-6433 and AAV-CbA-mir-HTT-6433.

FIG. 14A shows distribution in mice injected with AAV-CbA-mir-HTT-6433; levels of the mir-HTT-6433 guide and passenger strands are shown in green, in red are all endogenous miRNA species showing significant changes in the mice injected with AAV-CbA-mir-HTT-6433. FIG. 14B shows distribution in mice injected with AAV-U6-mir-HTT-6433.

FIG. 15A shows mice injected with AAV-CbA-mir-HTT-6433 show few changes in mRNA expression; in green are all genes which show significant p-values, in blue are those that remain significant after adjustment for multiple comparison. FIG. 15B shows mice injected with AAV-U6-mir-HTT-6433 show more changes in mRNA expression compared to the CBA. FIG. 15C shows mRNA profiles in mice treated with mir-HTT-6433; 7 RNAs are significantly differentially expressed between the U6 and CbA treated groups.

FIG. 25A shows the predicted hairpin structure of mir-155-6433 (SEQ ID NO: 23).

FIG. 25B shows the predicted hairpin structure of mir-30-6433 (SEQ ID NO: 24). FIG. 26A shows a schematic overview of a sheep brain dissected in the coronal plane (top), such that the entire striatum was contained within 4, 6 mm blocks. The anterior block contains the anterior portion of the striatum which is not divided by the internal capsule (middle). The medial blocks, to which the injection is targeted have a defined putamen and caudate are shown on the bottom. FIG. 26B shows AAV vector genomes in control (AAV9) and treated (AAV9miRHTT) treated animals. Vector genomes were measured by digital droplet PCR using genomic HPRT as the reference gene. The values are plotted on a log scale.

FIG. 29A shows sheep htt mRNA levels were determined as described in methods and are expressed relative to sheep calnexin (Canx). Shown are results from Study 2. There is no difference in endogenous sheep htt mRNA levels between AAV9 and AAV9miRHTT treated groups. FIG. 29B shows levels of endogenous sheep huntingtin and human mHTT protein detected with anti-htt1-17 antibody (Ab1) in putamen from Study 2, 6 months post-injection. Sample Western blot shows signal for wt htt (arrow) and human mutant htt (arrowhead) for the injected and non-injected sides of the brain in 4 different sheep injected on one side with AAV9miRHTT. Graph shows mean wt sheep htt and human mHTT signals determined from the densitometry as percent injected side to non-injected side. Note that treatment with AAV9miRHTT does not affect levels of endogenous sheep huntingtin protein but significantly reduces levels of human mHTT. Asterisk indicates p=0.005 with unpaired t-test.

FIG. 32A shows a graph indicating mean levels of mHTT normalized to actin in the cortex ipsilateral to the miRHTT injected striatum. Data are from study 1, 1 and 6 months post-injection, NS, based on unpaired t-test. FIG. 32B shows a bar graph indicating levels of mHTT normalized to actin in the caudate and putamen contralateral to the miRHTT-injected striatum. Data are from study 1, 1 and 6 months post-injection, NS, based on unpaired t-test.

DETAILED DESCRIPTION

Figure 1:
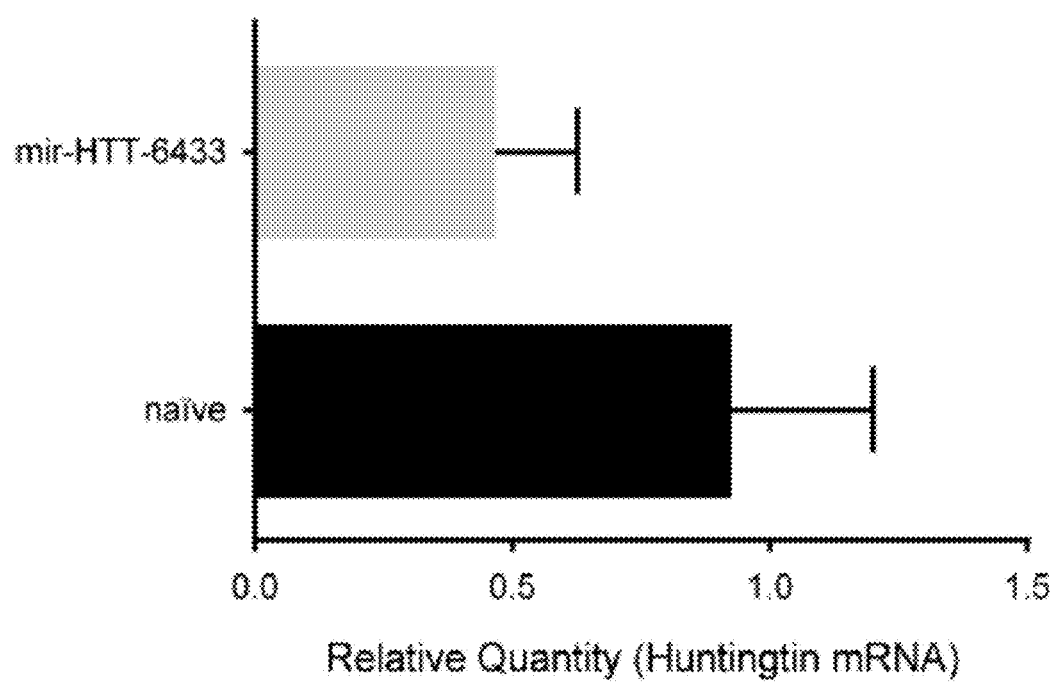
FIG. 1 shows HeLa cells transfected with a plasmid expressing mir-HTT-6433, targeting human huntingtin. 48 hours after transfection, cells were harvested and RNA was extracted for quantitative RT-PCR (qRT-PCR). Results indicate that mir-HTT-6433 reduces the endogenous human huntingtin by up to 50%.
Figure 2:
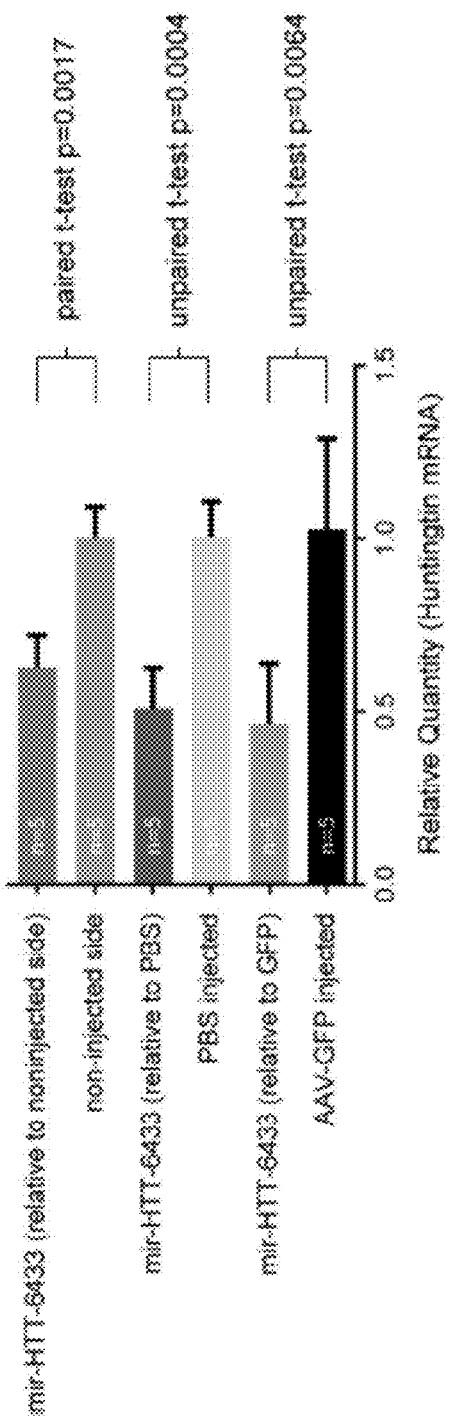
FIG. 2 shows mir-HTT-6433 packaged into an AAV9 vector and injected directly into the striatum of transgenic mice expressing mutant human huntingtin (Yac128 mice). One month post-injection, levels of human huntingtin mRNA were measured by qRT-PCR. In one set of animals (n=5) levels of human huntingtin were compared on the injected side with levels on the non-injected side. A significant (p=0.0017) reduction of huntingtin mRNA was observed on the injected side. In a second set of animals (n=5/group) levels of huntingtin mRNA were compared in animals injected with mir-HTT-6433 to animals who received an injection of vehicle only. A significant reduction (p=0.0004) of huntingtin was observed in these animals as well. In a third set of animals (n=5/group) the levels of huntingtin mRNA were compared in animals injected with mir-HTT-6433 to those injected with an AAV9-GFP. There was a significant (p=0.0064) reduction in huntingtin mRNA in these animals as well. In sum, data indicate that mir-HTT-6433 reduces huntingtin mRNA in vivo in the brain by 50%.

Aspects of the invention relate to certain interfering RNAs (e.g., miRNAs, such as artificial miRNAs) that when delivered to a subject are effective for reducing the expression of pathogenic huntingtin protein (HTT) in the subject. Accordingly, methods and compositions described by the disclosure are useful, in some embodiments, for the treatment of Huntington's disease.

Methods for Treating Huntington's Disease

Methods for delivering a transgene (e.g., an inhibitory RNA, such as a miRNA) to a subject are provided by the disclosure. The methods typically involve administering to a subject an effective amount of an isolated nucleic acid encoding an interfering RNA capable of reducing expression of huntingtin (htt) protein, or a rAAV comprising a nucleic acid for expressing an inhibitory RNA capable of reducing expression of huntingtin protein.

In some aspects, the disclosure provides inhibitory miRNA that specifically binds to (e.g., hybridizes with) at least two (e.g., 2, 3, 4, 5, 6, 7, 8, 9, 10, 11, 12, 13, 14, 15, 16, 17, 18, 19, 20, 21, 22, 23, 24, 25, or more) continuous bases of human huntingtin (e.g., SEQ ID NO: 1). As used herein "continuous bases" refers to two or more nucleotide bases that are covalently bound (e.g., by one or more phosphodiester bond, etc.) to each other (e.g. as part of a nucleic acid molecule). In some embodiments, the at least one miRNA is about 50%, about 60% about 70% about 80% about 90%, about 95%, about 99% or about 100% identical to the two or more (e.g., 2, 3, 4, 5, 6, 7, 8, 9, 10, 11, 12, 13, 14, 15, 16, 17, 18, 19, 20, 21, 22, 23, 24, 25, or more) continuous nucleotide bases of SEQ ID NO: 1. In some embodiments, the inhibitory RNA is a miRNA which is comprises or is encoded by the sequence set forth in any one of SEQ ID NOs: 2-10.

As used herein, "Huntington's disease", or "HD", refers to a neurodegenerative disease characterized by progressively worsening movement, cognitive and behavioral changes caused by a tri-nucleotide repeat expansion (e.g., CAG, which is translated into a poly-Glutamine, or PolyQ, tract) in the HTT gene that results in production of pathogenic mutant huntingtin protein (HTT, or mHTT). In some embodiments, mutant huntingtin protein accelerates the rate of neuronal cell death in certain regions of the brain. Generally, the severity of HD is correlated to the size of the tri-nucleotide repeat expansion in a subject. For example, a subject having a CAG repeat region comprising between 36 and 39 repeats is characterized as having "reduced penetrance" HD, whereas a subject having greater than 40 repeats is characterized as having "full penetrance" HD. Thus, in some embodiments, a subject having or at risk of having HD has a HTT gene comprising between about 36 and about 39 CAG repeats (e.g., 36, 37, 38 or 39 repeats). In some embodiments, a subject having or at risk of having HD has a HTT gene comprising 40 or more (e.g., 40, 45, 50, 60, 70, 80, 90, 100, 200, or more) CAG repeats. In some embodiments, a subject having a HTT gene comprising more than 100 CAG repeats develops HD earlier than a subject having fewer than 100 CAG repeats. In some embodiments, a subject having a HTT gene comprising more than 100 CAG repeats may develop HD symptoms before the age of about 20 years, and is referred to as having juvenile HD (also referred to as akinetic-rigid HD, or Westphal variant HD). The number of CAG repeats in a HTT gene allele of a subject can be determined by any suitable modality known in the art. For example, nucleic acids (e.g., DNA) can be isolated from a biological sample (e.g., blood) of a subject and the number of CAG repeats of a HTT allele can be determined by a hybridization-based method, such as PCR or nucleic acid sequencing (e.g., Illumina sequencing, Sanger sequencing, SMRT sequencing, etc.).

An "effective amount" of a substance is an amount sufficient to produce a desired effect. In some embodiments, an effective amount of an isolated nucleic acid is an amount sufficient to transfect (or infect in the context of rAAV mediated delivery) a sufficient number of target cells of a target tissue of a subject. In some embodiments, a target tissue is central nervous system (CNS) tissue (e.g., brain tissue, spinal cord tissue, cerebrospinal fluid (CSF), etc.). In some embodiments, an effective amount of an isolated nucleic acid (e.g., which may be delivered via an rAAV) may be an amount sufficient to have a therapeutic benefit in a subject, e.g., to reduce the expression of a pathogenic gene or protein (e.g., HTT), to extend the lifespan of a subject, to improve in the subject one or more symptoms of disease (e.g., a symptom of Huntington's disease), etc. The effective amount will depend on a variety of factors such as, for example, the species, age, weight, health of the subject, and the tissue to be targeted, and may thus vary among subject and tissue as described elsewhere in the disclosure.

Isolated Nucleic Acids

In some aspects, the disclosure provides isolated nucleic acids that are useful for reducing (e.g., inhibiting) expression of human huntingtin (HTT). A "nucleic acid" sequence refers to a DNA or RNA sequence. In some embodiments, proteins and nucleic acids of the disclosure are isolated. As used herein, the term "isolated" means artificially produced. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. As used herein with respect to proteins or peptides, the term "isolated" refers to a protein or peptide that has been isolated from its natural environment or artificially produced (e.g., by chemical synthesis, by recombinant DNA technology, etc.).

The skilled artisan will also realize that conservative amino acid substitutions may be made to provide functionally equivalent variants, or homologs of the capsid proteins. In some aspects the disclosure embraces sequence alterations that result in conservative amino acid substitutions. As used herein, a conservative amino acid substitution refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g., Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made among amino acids within the following groups: (a) M, I, L, V; (b) F, Y, W; (c) K, R, H; (d) A, G; (e) S, T; (f) Q, N; and (g) E, D. Therefore, one can make conservative amino acid substitutions to the amino acid sequence of the proteins and polypeptides disclosed herein.

The isolated nucleic acids of the invention may be recombinant adeno-associated virus (AAV) vectors (rAAV vectors). In some embodiments, an isolated nucleic acid as described by the disclosure comprises a region (e.g., a first region) comprising a first adeno-associated virus (AAV) inverted terminal repeat (ITR), or a variant thereof. The isolated nucleic acid (e.g., the recombinant AAV vector) may be packaged into a capsid protein and administered to a subject and/or delivered to a selected target cell. "Recombinant AAV (rAAV) vectors" are typically composed of, at a minimum, a transgene and its regulatory sequences, and 5' and 3' AAV inverted terminal repeats (ITRs). The transgene may comprise, as disclosed elsewhere herein, one or more regions that encode one or more inhibitory RNAs (e.g., miRNAs) comprising a nucleic acid that targets an endogenous mRNA of a subject. The transgene may also comprise a region encoding, for example, a protein and/or an expression control sequence (e.g., a poly-A tail), as described elsewhere in the disclosure.

Generally, ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al., "Molecular Cloning. A Laboratory Manual", 2d ed., Cold Spring Harbor Laboratory, New York (1989); and K. Fisher et al., J Virol., 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types. In some embodiments, the isolated nucleic acid (e.g., the rAAV vector) comprises at least one ITR having a serotype selected from AAV1, AAV2, AAV5, AAV6, AAV6.2, AAV7, AAV8, AAV9, AAV10, AAV11, and variants thereof. In some embodiments, the isolated nucleic acid comprises a region (e.g., a first region) encoding an AAV2 ITR.

In some embodiments, the isolated nucleic acid further comprises a region (e.g., a second region, a third region, a fourth region, etc.) comprising a second AAV ITR. In some embodiments, the second AAV ITR has a serotype selected from AAV1, AAV2, AAV5, AAV6, AAV6.2, AAV7, AAV8, AAV9, AAV10, AAV11, and variants thereof. In some embodiments, the second ITR is a mutant ITR that lacks a functional terminal resolution site (TRS). The term "lacking a terminal resolution site" can refer to an AAV ITR that comprises a mutation (e.g., a sense mutation such as a non-synonymous mutation, or missense mutation) that abrogates the function of the terminal resolution site (TRS) of the ITR, or to a truncated AAV ITR that lacks a nucleic acid sequence encoding a functional TRS (e.g., a ΔTRS ITR). Without wishing to be bound by any particular theory, a rAAV vector comprising an ITR lacking a functional TRS produces a self-complementary rAAV vector, for example as described by McCarthy (2008) *Molecular Therapy* 16(10): 1648-1656.

In addition to the major elements identified above for the recombinant AAV vector, the vector also includes conventional control elements which are operably linked with elements of the transgene in a manner that permits its transcription, translation and/or expression in a cell transfected with the vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A number of expression control sequences, including promoters which are native, constitutive, inducible and/or tissue-specific, are known in the art and may be utilized.

As used herein, a nucleic acid sequence (e.g., coding sequence) and regulatory sequences are said to be operably linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., miRNA).

In some aspects, the disclosure provides an isolated nucleic acid comprising a transgene, wherein the transgene comprises a nucleic acid sequence encoding one or more microRNAs (e.g., miRNAs). A "microRNA" or "miRNA" is a small non-coding RNA molecule capable of mediating transcriptional or post-translational gene silencing. Typically, miRNA is transcribed as a hairpin or stem-loop (e.g., having a self-complementarity, single-stranded backbone) duplex structure, referred to as a primary miRNA (pri-miRNA), which is enzymatically processed (e.g., by Drosha, DGCR8, Pasha, etc.) into a pre-miRNA. The length of a pri-miRNA can vary. In some embodiments, a pri-miRNA ranges from about 100 to about 5000 base pairs (e.g., about 100, about 200, about 500, about 1000, about 1200, about 1500, about 1800, or about 2000 base pairs) in length. In some embodiments, a pri-miRNA is greater than 200 base pairs in length (e.g., 2500, 5000, 7000, 9000, or more base pairs in length.

Pre-miRNA, which is also characterized by a hairpin or stem-loop duplex structure, can also vary in length. In some embodiments, pre-miRNA ranges in size from about 40 base pairs in length to about 500 base pairs in length. In some embodiments, pre-miRNA ranges in size from about 50 to 100 base pairs in length. In some embodiments, pre-miRNA ranges in size from about 50 to about 90 base pairs in length (e.g., about 50, about 52, about 54, about 56, about 58, about 60, about 62, about 64, about 66, about 68, about 70, about 72, about 74, about 76, about 78, about 80, about 82, about 84, about 86, about 88, or about 90 base pairs in length).

Generally, pre-miRNA is exported into the cytoplasm, and enzymatically processed by Dicer to first produce an imperfect miRNA/miRNA* duplex and then a single-stranded mature miRNA molecule, which is subsequently loaded into the RNA-induced silencing complex (RISC). Typically, a mature miRNA molecule ranges in size from about 19 to about 30 base pairs in length. In some embodiments, a mature miRNA molecule is about 19, about 20, about 21, about 22, about 23, about 24, about 25, about 26, about 27, about 28, about 29, or 30 base pairs in length. In some embodiments, an isolated nucleic acid of the disclosure comprises a sequence encoding a pri-miRNA, a pre-miRNA, or a mature miRNA comprising a sequence set forth in any one of SEQ ID NOs: 2-10 or 21-22.

It should be appreciated that an isolated nucleic acid or vector (e.g., rAAV vector), in some embodiments comprises a nucleic acid sequence encoding more than one (e.g., a plurality, such as 2, 3, 4, 5, 10, or more) miRNAs. In some embodiments, each of the more than one miRNAs targets (e.g., hybridizes or binds specifically to) the same target gene (e.g., an isolated nucleic acid encoding three unique miRNAs, where each miRNA targets the HTT gene). In some embodiments, each of the more than one miRNAs targets (e.g., hybridizes or binds specifically to) a different target gene.

In some aspects, the disclosure provides isolated nucleic acids and vectors (e.g., rAAV vectors) that encode one or more artificial miRNAs. As used herein "artificial miRNA" or "amiRNA" refers to an endogenous pri-miRNA or pre-miRNA (e.g., a miRNA backbone, which is a precursor miRNA capable of producing a functional mature miRNA), in which the miRNA and miRNA* (e.g., passenger strand of the miRNA duplex) sequences have been replaced with corresponding amiRNA/amiRNA* sequences that direct highly efficient RNA silencing of the targeted gene, for example as described by Eamens et al. (2014), *Methods Mol. Biol.* 1062:211-224. For example, in some embodiments an artificial miRNA comprises a miR-155 pri-miRNA backbone into which a sequence encoding a mature HTT-specific miRNA (e.g., any one of SEQ ID NOs: 2-10) has been inserted in place of the endogenous miR-155 mature miRNA-encoding sequence. In some embodiments, miRNA (e.g., an artificial miRNA) as described by the disclosure comprises a miR-155 backbone sequence, a miR-30 backbone sequence, a mir-64 backbone sequence, or a miR-122 backbone sequence.

A region comprising a transgene (e.g., a second region, third region, fourth region, etc.) may be positioned at any suitable location of the isolated nucleic acid. The region may be positioned in any untranslated portion of the nucleic acid, including, for example, an intron, a 5' or 3' untranslated region, etc.

In some cases, it may be desirable to position the region (e.g., the second region, third region, fourth region, etc.) upstream of the first codon of a nucleic acid sequence encoding a protein (e.g., a protein coding sequence). For example, the region may be positioned between the first codon of a protein coding sequence) and 2000 nucleotides upstream of the first codon. The region may be positioned between the first codon of a protein coding sequence and 1000 nucleotides upstream of the first codon. The region may be positioned between the first codon of a protein coding sequence and 500 nucleotides upstream of the first codon. The region may be positioned between the first codon of a protein coding sequence and 250 nucleotides upstream of the first codon. The region may be positioned between the first codon of a protein coding sequence and 150 nucleotides upstream of the first codon.

In some cases (e.g., when a transgene lacks a protein coding sequence), it may be desirable to position the region (e.g., the second region, third region, fourth region, etc.) upstream of the poly-A tail of a transgene. For example, the region may be positioned between the first base of the poly-A tail and 2000 nucleotides upstream of the first base. The region may be positioned between the first base of the poly-A tail and 1000 nucleotides upstream of the first base. The region may be positioned between the first base of the poly-A tail and 500 nucleotides upstream of the first base. The region may be positioned between the first base of the poly-A tail and 250 nucleotides upstream of the first base. The region may be positioned between the first base of the poly-A tail and 150 nucleotides upstream of the first base. The region may be positioned between the first base of the poly-A tail and 100 nucleotides upstream of the first base. The region may be positioned between the first base of the poly-A tail and 50 nucleotides upstream of the first base. The region may be positioned between the first base of the poly-A tail and 20 nucleotides upstream of the first base. In some embodiments, the region is positioned between the last nucleotide base of a promoter sequence and the first nucleotide base of a poly-A tail sequence.

In some cases, the region may be positioned downstream of the last base of the poly-A tail of a transgene. The region may be between the last base of the poly-A tail and a position 2000 nucleotides downstream of the last base. The region may be between the last base of the poly-A tail and a position 1000 nucleotides downstream of the last base. The region may be between the last base of the poly-A tail and a position 500 nucleotides downstream of the last base. The region may be between the last base of the poly-A tail and a position 250 nucleotides downstream of the last base. The region may be between the last base of the poly-A tail and a position 150 nucleotides downstream of the last base.

It should be appreciated that in cases where a transgene encodes more than one miRNA, each miRNA may be positioned in any suitable location within the transgene. For example, a nucleic acid encoding a first miRNA may be positioned in an intron of the transgene and a nucleic acid sequence encoding a second miRNA may be positioned in another untranslated region (e.g., between the last codon of a protein coding sequence and the first base of the poly-A tail of the transgene).

In some embodiments, the transgene further comprises a nucleic acid sequence encoding one or more expression control sequences (e.g., a promoter, etc.). Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene.

For nucleic acids encoding proteins, a polyadenylation sequence generally is inserted following the transgene sequences and before the 3' AAV ITR sequence. A rAAV construct useful in the present disclosure may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional and many such sequences are available [see, e.g., Sambrook et al., and references cited therein at, for example, pages 3.18 3.26 and 16.17 16.27 and Ausubel et al., Current Protocols in Molecular Biology, John Wiley & Sons, New York, 1989]. In some embodiments, a Foot and Mouth Disease Virus 2A sequence is included in polyprotein; this is a small peptide (approximately 18 amino acids in length) that has been shown to mediate the cleavage of polyproteins (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459). The cleavage activity of the 2A sequence has previously been demonstrated in artificial systems including plasmids and gene therapy vectors (AAV and retroviruses) (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459; de Felipe, P et al., Gene Therapy, 1999; 6: 198-208; de Felipe, Petal., Human Gene Therapy, 2000; 11: 1921-1931; and Klump, H et al., Gene Therapy, 2001; 8: 811-817).

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al., Cell, 41:521-530 (1985)], the SV40 promoter, the dihydrofolate reductase promoter, the β-actin promoter, the phosphoglycerol kinase (PGK) promoter, and the EF1α promoter [Invitrogen]. In some embodiments, a promoter is an enhanced chicken β-actin promoter. In some embodiments, a promoter is a U6 promoter.

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., Proc. Natl. Acad. Sci. USA, 93:3346-3351 (1996)), the tetracycline-repressible system (Gossen et al., Proc. Natl. Acad. Sci. USA, 89:5547-5551 (1992)), the tetracycline-inducible system (Gossen et al., Science, 268:1766-1769 (1995), see also Harvey et al., Curr. Opin. Chem. Biol., 2:512-518 (1998)), the RU486-inducible system (Wang et al., Nat. Biotech., 15:239-243 (1997) and Wang et al., Gene Ther., 4:432-441 (1997)) and the rapamycin-inducible system (Magari et al., J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (a-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter, Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et al., J. Bone Miner. Res., 11:654-64 (1996)), CD2 promoter (Hansal et al., J. Immunol., 161:1063-8 (1998); immunoglobulin heavy chain promoter; T cell receptor α-chain promoter, neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)), among others which will be apparent to the skilled artisan.

Aspects of the disclosure relate to an isolated nucleic acid comprising more than one promoter (e.g., 2, 3, 4, 5, or more promoters). For example, in the context of a construct having a first region comprising a first region encoding a protein and an second region encoding an inhibitory RNA (e.g., miRNA), it may be desirable to drive expression of the protein coding region using a first promoter sequence (e.g., a first promoter sequence operably linked to the protein coding region), and to drive expression of the inhibitory RNA encoding region with a second promoter sequence (e.g., a second promoter sequence operably linked to the inhibitory RNA encoding region). Generally, the first promoter sequence and the second promoter sequence can be the same promoter sequence or different promoter sequences. In some embodiments, the first promoter sequence (e.g., the promoter driving expression of the protein coding region) is a RNA polymerase III (polIII) promoter sequence. Non-limiting examples of polIII promoter sequences include U6 and H1 promoter sequences. In some embodiments, the second promoter sequence (e.g., the promoter sequence driving expression of the inhibitory RNA) is a RNA polymerase II (polII) promoter sequence. Non-limiting examples of polII promoter sequences include T7, T3, SP6, RSV, and cytomegalovirus promoter sequences. In some embodiments, a polIII promoter sequence drives expression of an inhibitory RNA (e.g., miRNA) encoding region. In some embodiments, a polII promoter sequence drives expression of a protein coding region.

In some embodiments, the nucleic acid comprises a transgene that encodes a protein. The protein can be a therapeutic protein (e.g., a peptide, protein, or polypeptide useful for the treatment or prevention of disease states in a mammalian subject) or a reporter protein. In some embodiments, the therapeutic protein is useful for treatment or prevention of Huntington's disease, for example Polyglutamine binding peptide 1 (QBP1), PTD-QBP1, ED11, C4 intrabody, VL12.3 intrabody, MW7 intrabody, Happ1 antibodies, Happ3 antibodies, mEM48 intrabody, certain monoclonal antibodies (e.g., 1C2), and peptide P42 and variants thereof, as described in Marelli et al. (2016) *Orphanet Journal of Rare Disease* 11:24; doi:10.1186/s13023-016-0405-3. In some embodiments, the therapeutic protein is wild-type huntingtin protein (e.g., huntingtin protein having a PolyQ repeat region comprising less than 36 repeats).

Without wishing to be bound by any particular theory, allele-specific silencing of mutant huntingtin (HTT) may provide an improved safety profile in a subject compared to non-allele specific silencing (e.g., silencing of both wild-type and mutant HTT alleles) because wild-type HTT expression and function is preserved in the cells. Aspects of the invention relate to the inventors' recognition and appreciation that isolated nucleic acids and vectors that incorporate one or more inhibitory RNA (e.g., miRNA) sequences targeting the HTT gene in a non-allele-specific manner while driving the expression of hardened wild-type HTT gene (a wild-type HTT gene that is not targeted by the miRNA) are capable of achieving concomitant mutant HTT knockdown e.g., in the CNS tissue, with increased expression of wild-type HTT. Generally, the sequence of the nucleic acid encoding endogenous wild-type and mutant HTT mRNAs, and the nucleic acid of the transgene encoding the "hardened" wild-type HTT mRNA are sufficiently different such that the "hardened" wild-type HTT transgene mRNA is not targeted by the one or more inhibitory RNAs (e.g., miRNAs). This may be accomplished, for example, by introducing one or more silent mutations into the HTT transgene sequence such that it encodes the same protein as the endogenous wild-type HTT gene but has a different nucleic acid sequence. In this case, the exogenous mRNA may be referred to as "hardened." Alternatively, the inhibitory RNA (e.g., miRNA) can target the 5' and/or 3' untranslated regions of the endogenous wild-type HTT mRNA. These 5' and/or 3' regions can then be removed or replaced in the transgene mRNA such that the transgene mRNA is not targeted by the one or more inhibitory RNAs.

Reporter sequences (e.g., nucleic acid sequences encoding a reporter protein) that may be provided in a transgene include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, and others well known in the art. When associated with regulatory elements which drive their expression, the reporter sequences, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for β-galactosidase activity. Where the transgene is green fluorescent protein or luciferase, the vector carrying the signal may be measured visually by color or light production in a luminometer. Such reporters can, for example, be useful in verifying the tissue-specific targeting capabilities and tissue specific promoter regulatory activity of a nucleic acid.

Recombinant Adeno-Associated Viruses (rAAVs)

In some aspects, the disclosure provides isolated AAVs. As used herein with respect to AAVs, the term "isolated" refers to an AAV that has been artificially produced or obtained. Isolated AAVs may be produced using recombinant methods. Such AAVs are referred to herein as "recombinant AAVs". Recombinant AAVs (rAAVs) preferably have tissue-specific targeting capabilities, such that a nuclease and/or transgene of the rAAV will be delivered specifically to one or more predetermined tissue(s). The AAV capsid is an important element in determining these tissue-specific targeting capabilities. Thus, an rAAV having a capsid appropriate for the tissue being targeted can be selected.

Methods for obtaining recombinant AAVs having a desired capsid protein are well known in the art. (See, for example, US 2003/0138772), the contents of which are incorporated herein by reference in their entirety). Typically the methods involve culturing a host cell which contains a nucleic acid sequence encoding an AAV capsid protein; a functional rep gene; a recombinant AAV vector composed of, AAV inverted terminal repeats (ITRs) and a transgene; and sufficient helper functions to permit packaging of the recombinant AAV vector into the AAV capsid proteins. In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, the functions of the capsid proteins are to protect the viral genome, deliver the genome and interact with the host. In some aspects, capsid proteins deliver the viral genome to a host in a tissue specific manner.

In some embodiments, an AAV capsid protein is of an AAV serotype selected from the group consisting of AAV2, AAV3, AAV4, AAV5, AAV6, AAV8, AAVrh8, AAV9, and AAV10. In some embodiments, an AAV capsid protein is of a serotype derived from a non-human primate, for example AAVrh8 serotype. In some embodiments, an AAV capsid protein is of an AAV9 serotype. In some embodiments, the AAV capsid protein comprises the sequence set forth in SEQ ID NO: 20.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

In some embodiments, the instant disclosure relates to a host cell containing a nucleic acid that comprises a coding sequence encoding a protein (e.g., wild-type huntingtin protein, optionally "hardened" wild-type huntingtin protein). In some embodiments, the instant disclosure relates to a composition comprising the host cell described above. In some embodiments, the composition comprising the host cell above further comprises a cryopreservative.

The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al., Molecular Cloning: A Laboratory Manual, Cold Spring Harbor Press, Cold Spring Harbor, N.Y. Similarly, methods of generating rAAV virions are well known and the selection of a suitable method is not a limitation on the present disclosure. See, e.g., K. Fisher et al., J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an recombinant AAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter.

A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or functional RNA (e.g., guide RNA) from a transcribed gene.

The foregoing methods for packaging recombinant vectors in desired AAV capsids to produce the rAAVs of the disclosure are not meant to be limiting and other suitable methods will be apparent to the skilled artisan.

In some embodiments, any one or more thymidine (T) nucleotides or uridine (U) nucleotides in a sequence provided herein, including a sequence provided in the sequence listing, may be replaced with any other nucleotide suitable for base pairing (e.g., via a Watson-Crick base pair) with an adenosine nucleotide. For example, in some embodiments, any one or more thymidine (T) nucleotides in a sequence provided herein, including a sequence provided in the sequence listing, may be suitably replaced with a uridine (U) nucleotide or vice versa.

Modes of Administration

The rAAVs of the disclosure may be delivered to a subject in compositions according to any appropriate methods known in the art. For example, an rAAV, preferably suspended in a physiologically compatible carrier (i.e., in a composition), may be administered to a subject, i.e. host animal, such as a human, mouse, rat, cat, dog, sheep, rabbit, horse, cow, goat, pig, guinea pig, hamster, chicken, turkey, or a non-human primate (e.g., Macaque). In some embodiments a host animal does not include a human.

Delivery of the rAAVs to a mammalian subject may be by, for example, intramuscular injection or by administration into the bloodstream of the mammalian subject. Administration into the bloodstream may be by injection into a vein, an artery, or any other vascular conduit. In some embodiments, the rAAVs are administered into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177,403, can also be employed by the skilled artisan to administer the virions into the vasculature of an isolated limb to potentially enhance transduction into muscle cells or tissue. Moreover, in certain instances, it may be desirable to deliver the virions to the CNS of a subject. By "CNS" is meant all cells and tissue of the brain and spinal cord of a vertebrate. Thus, the term includes, but is not limited to, neuronal cells, glial cells, astrocytes, cerebrospinal fluid (CSF), interstitial spaces, bone, cartilage and the like. Recombinant AAVs may be delivered directly to the CNS or brain by injection into, e.g., the ventricular region, as well as to the striatum (e.g., the caudate nucleus or putamen of the striatum), spinal cord and neuromuscular junction, or cerebellar lobule, with a needle, catheter or related device, using neurosurgical techniques known in the art, such as by stereotactic injection (see, e.g., Stein et al., J Virol 73:3424-3429, 1999; Davidson et al., PNAS 97:3428-3432, 2000; Davidson et al., Nat.

Genet. 3:219-223, 1993; and Alisky and Davidson, Hum. Gene Ther. 11:2315-2329, 2000). In some embodiments, rAAV as described in the disclosure are administered by intravenous injection. In some embodiments, the rAAV are administered by intracerebral injection. In some embodiments, the rAAV are administered by intrathecal injection. In some embodiments, the rAAV are administered by intrastriatal injection. In some embodiments, the rAAV are delivered by intracranial injection. In some embodiments, the rAAV are delivered by cisterna *magna* injection. In some embodiments, the rAAV are delivered by cerebral lateral ventricle injection.

Aspects of the instant disclosure relate to compositions comprising a recombinant AAV comprising a capsid protein and a nucleic acid encoding a transgene, wherein the transgene comprises a nucleic acid sequence encoding one or more miRNAs. In some embodiments, each miRNA comprises a sequence set forth in any one of SEQ ID NOs: 2-10. In some embodiments, the nucleic acid further comprises AAV ITRs. In some embodiments, the rAAV comprises an rAAV vector represented by the sequence set forth in any one of SEQ ID NO: 16-19, or a portion thereof. In some embodiments, a composition further comprises a pharmaceutically acceptable carrier.

The compositions of the disclosure may comprise an rAAV alone, or in combination with one or more other viruses (e.g., a second rAAV encoding having one or more different transgenes). In some embodiments, a composition comprises 1, 2, 3, 4, 5, 6, 7, 8, 9, 10, or more different rAAVs each having one or more different transgenes.

Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The rAAVs are administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected organ (e.g., intraportal delivery to the liver), oral, inhalation (including intranasal and intratracheal delivery), intraocular, intravenous, intramuscular, subcutaneous, intradermal, intratumoral, and other parental routes of administration. Routes of administration may be combined, if desired.

The dose of rAAV virions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors that are well known in the art.

An effective amount of an rAAV is an amount sufficient to target infect an animal, target a desired tissue. In some embodiments, an effective amount of an rAAV is an amount sufficient to produce a stable somatic transgenic animal model. The effective amount will depend primarily on factors such as the species, age, weight, health of the subject, and the tissue to be targeted, and may thus vary among animal and tissue. For example, an effective amount of the rAAV is generally in the range of from about 1 ml to about 100 ml of solution containing from about $10^9$ to $10^{16}$ genome copies. In some cases, a dosage between about $10^{11}$ to $10^{13}$ rAAV genome copies is appropriate. In certain embodiments, $10^{12}$ or $10^{13}$ rAAV genome copies is effective to target CNS tissue. In some cases, stable transgenic animals are produced by multiple doses of an rAAV.

In some embodiments, a dose of rAAV is administered to a subject no more than once per calendar day (e.g., a 24-hour period). In some embodiments, a dose of rAAV is administered to a subject no more than once per 2, 3, 4, 5, 6, or 7 calendar days. In some embodiments, a dose of rAAV is administered to a subject no more than once per calendar week (e.g., 7 calendar days). In some embodiments, a dose of rAAV is administered to a subject no more than bi-weekly (e.g., once in a two calendar week period). In some embodiments, a dose of rAAV is administered to a subject no more than once per calendar month (e.g., once in 30 calendar days). In some embodiments, a dose of rAAV is administered to a subject no more than once per six calendar months. In some embodiments, a dose of rAAV is administered to a subject no more than once per calendar year (e.g., 365 days or 366 days in a leap year).

In some embodiments, rAAV compositions are formulated to reduce aggregation of AAV particles in the composition, particularly where high rAAV concentrations are present (e.g., ~$10^{13}$ GC/ml or more). Methods for reducing aggregation of rAAVs are well known in the art and, include, for example, addition of surfactants, pH adjustment, salt concentration adjustment, etc. (See, e.g., Wright F R, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens.

Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the rAAV-based therapeutic constructs in suitably formulated pharmaceutical compositions disclosed herein either subcutaneously, intraopancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver rAAVs. In some embodiments, a preferred mode of administration is by portal vein injection.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the rAAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use.

In addition to the methods of delivery described above, the following techniques are also contemplated as alternative methods of delivering the rAAV compositions to a host. Sonophoresis (i.e., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

Kits and Related Compositions

The agents described herein may, in some embodiments, be assembled into pharmaceutical or diagnostic or research kits to facilitate their use in therapeutic, diagnostic or research applications. A kit may include one or more containers housing the components of the disclosure and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

In some embodiments, the instant disclosure relates to a kit for producing a rAAV, the kit comprising a container housing an isolated nucleic acid comprising an miRNA comprising or encoded by the sequence set forth in any one of SEQ ID NOs: 2-10. In some embodiments, the kit further comprises a container housing an isolated nucleic acid encoding an AAV capsid protein, for example an AAV9 capsid protein.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container.

Exemplary embodiments of the invention will be described in more detail by the following examples. These embodiments are exemplary of the invention, which one skilled in the art will recognize is not limited to the exemplary embodiments.

EXAMPLES

Example 1: Materials and Methods

Cell Culture and Screening Assays

HeLa cells were maintained in DMEM, high glucose with 10% heat inactivated FBS and 1% Penicillin Streptomycin (ThermoFisher). Twenty-four hours before transfection, cells were seeded onto 6-well plates at $0.8$-$1.0 \times 10^6$ cells/well. On the day of transfection, growth medium was replaced with 1.6 ml of Opti-MEM (ThermoFisher). Plasmids were transfected using 2 µl/well of DharmaFECT Duo (Dharmacon). Each well received 0.6 µg of plasmid DNA. Forty-eight hours after transfection, the cells were harvested and total RNA was extracted using the MirVana RNA isolation kit. cDNA was produced using 1 µg of RNA/reaction using oligo-dT and Superscript III (Invitrogen). Huntingtin mRNA was measured using a TaqMan assay (ThermoFisher). Relative levels of huntingtin mRNA were calculated using the $\Delta\Delta C(T)$ method with human Hypoxanthine-guanine phosphoribosyltransferase (HPRT) as the housekeeping gene.

Mouse Housing, Injections and Maintenance

YAC128 and wild type FVB mice were obtained. Mice were bred on the FVB background by mating wildtype male mice with YAC128 females. The resulting heterozygous YAC128 and wild type mice were maintained on a 12:12 light schedule and were given access to food and water ad libitum. Genotypes were verified by PCR of DNA extracted from tail snips or ear punches. Mice were injected with selected AAV directly into the striatum by means of a small animal stereotax SAS-4100 (ASI Instruments, Warren, Mich.) aided by UMPC3 or UMPC4 microinjectors (World Precision Instruments, Sarasota, Fla.). Mice were anesthetized with 284 mg/kg of tribromoethanol and placed in the stereotax. Surgery was performed using the bregma as the zero point, measuring anterior 1.0 mm, lateral 2.0 mm, and lowering a 33 gauge needle 3.0 mm into the striatum. The pumps were set to deliver 3.0 ul at a rate of 125 nl/minute. After the injections the mice were allowed to recover on a warming pad and then placed back in their cages in the housing area.

Tissue Extraction

At the appropriate time-point, mice were sacrificed and tissue extracted for RNA analysis or immunohistochemistry. For RNA extraction, mice were anesthetized and killed by cervical dislocation. Brains were removed and the striatum was dissected out. When available, GFP expression was used to guide the dissection so that only GFP positive tissue was analyzed. Tissue was placed immediately in RNALater (Ambion). Subsequently they were stored frozen at −80° C. At the end of the experiment the mice meant for immunocytochemistry were deeply anesthetized and perfused intracardially with saline followed by 4% paraformaldehyde. Samples were post fixed overnight in cold 2% paraformaldehyde and then stored in phosphate buffered saline at 4° C. Coronal sections were made by slicing 40 micron sections on the Leica VT1000s vibratome.

Mouse Behaviors

Beam walking: Mice were trained to cross a (size of beam) beam. After training, the mice were recorded as they crossed from one end of the beam to the other. Three trials per mouse were recorded. Based on the recording, the amount of time it took for the mice to cross from mark on one end of the beam to the other was measured.

Home cage activity: Mice were placed singly in an automated home cage phenotyping scanning system (Clever Sys, Inc., Reston Va.) for 26 hours. To calculate the average active time per hour, the first hour of data during which the mouse acclimates to the new environment was removed; then the total time spent walking by the total recorded time, minus one hour, was calculated.

Immunohistochemistry and Quantification

Fixed tissue slices were blocked with 3% hydrogen peroxide for three minutes and then incubated with 0.5% triton x for 20 minutes. Immunocytochemistry was performed using Vector Laboratories Elite ABC kit reagents for rabbit or mouse derived antibodies against DARPP32 (Abcam ab40801; 1:10,000 dilution), Iba1 (Wako 019-19741; 1:1,000 dilution), GFP (Life Technologies G10362; 1:1000 dilution) and NeuN (EMD Millipore MAB377; 1:1000 dilution). Sections were stained for 2 minutes with diaminobenzidine using the Metal Enhanced DAB Substrate Kit (Pierce).

Small RNA Library Cloning and Analysis

Total RNA was extracted using the MirVana RNA isolation kit. Size selection of the 18-30 nucleotide RNAs was performed using 5 μg of total RNA on a 15% denaturing polyacrylamide gel. Following size selection, the small RNAs were ethanol precipitated and ligated to a pre-adenylated 3'-adapter (5'-rAppTGGAATTCTCGGGTGC-CAAGG/ddC/-3'; SEQ ID NO: 11). The ligated products were annealed to the RT primer (5'-CCTTGGCACCCGAGAATTCCA-3'; SEQ ID NO: 12) and ligated to a 5'-adapter (RNA: 5'-GUUCAGAGUUCUACA-GUCCGACGAUC-3'; SEQ ID NO: 13). Reverse transcription was performed using AMV Reverse transcriptase mix (NEB) and PCR amplified using AccuPrime Pfx DNA Polymerase (Invitrogen) with one universal primer (5'-AAT-GATACGGCGACCACCGAGATCTA-CACGTTCAGAGTTCTACAGTCCGA-3'; SEQ ID NO: 14) and one barcoded primer (5'-CAAGCAGAAGACGG-CATACGAGATNNNNNNGTGACTG-GAGTTCCTTGGCACCCGAGAA TTCCA-3'; SEQ ID NO: 15). Libraries were sequenced and mapped to the mm9 genome and to the AAV genome. miRNA species were classified based on the position of the 5'-end mapping on the miRNA hairpin, therefore each species consists of all the small RNAs with shared seed sequences. The 3'-end was not considered in species assignment. Differential expression of endogenous miRNAs was analyzed using the edgeR package.

mRNA Library Cloning and Analysis

RNA was extracted as above. Libraries were constructed by standard methods. Reads were mapped using topHat2 and differential expression was calculated using the deseq2 package.

Sheep Experiments

A transgenic sheep model of Huntington's disease (e.g., transgenic sheep expressing pathogenic human huntingtin protein) were injected with either scAAV9-CBA-mir-HTT (comprising miRNA 6433 in a mir-155 backbone), scAAV-U6-mir-HTT (comprising miRNA 6433 in a mir-155 backbone), or empty scAAV9 control vector. Sheep were sacrificed at either one month or six months post-injection. Tissue and nucleic acid samples were prepared and analyzed by quantitative PCR and immunohistochemistry.

Example 2: Mouse In Vivo Experiments

Design and Selection of Huntingtin Targeting Artificial miRNAs

Figure 4A:
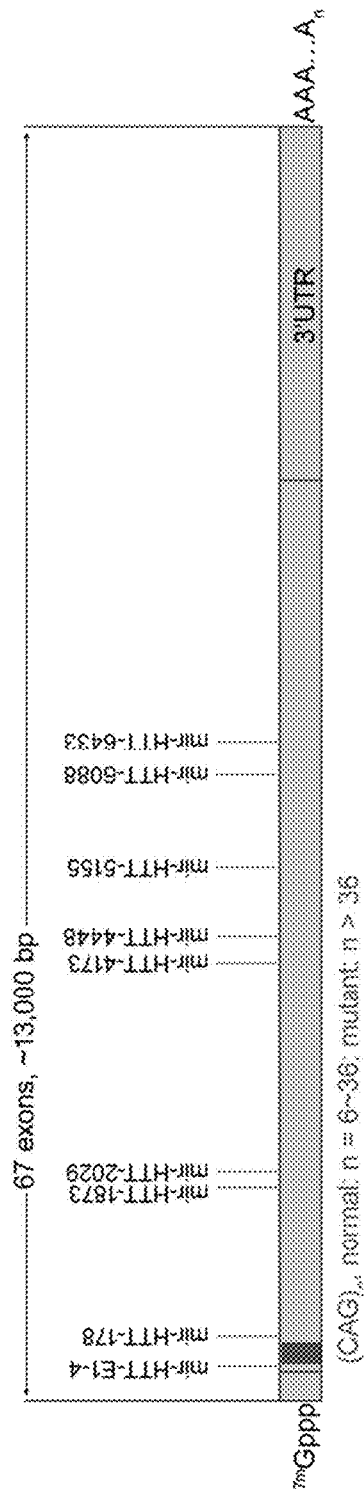
FIGS. 4A-4C show artificial miRNAs targeting human huntingtin reduce the huntingtin mRNA in cell culture and in vivo.
Figure 4B:
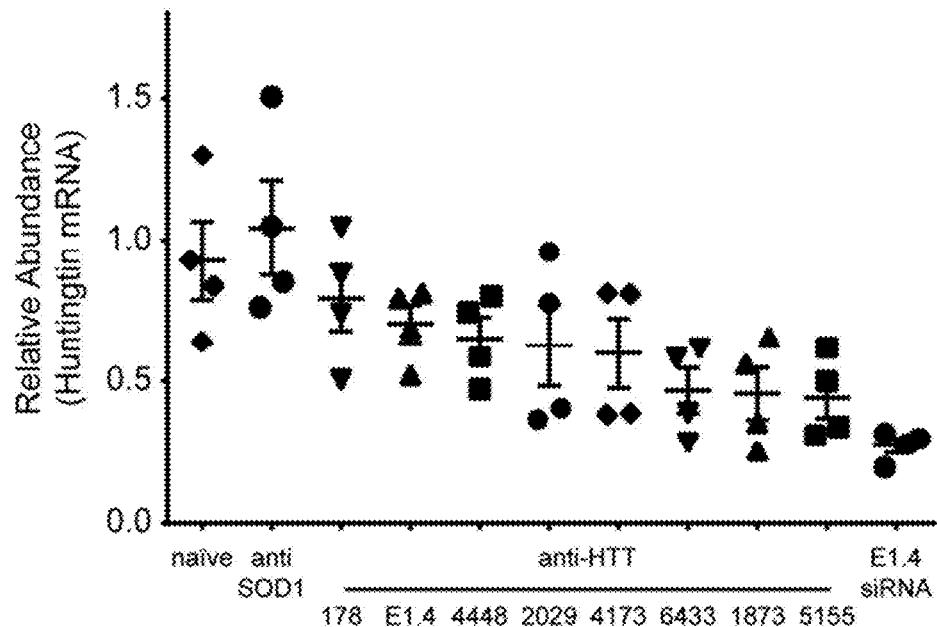
Figure 4C:
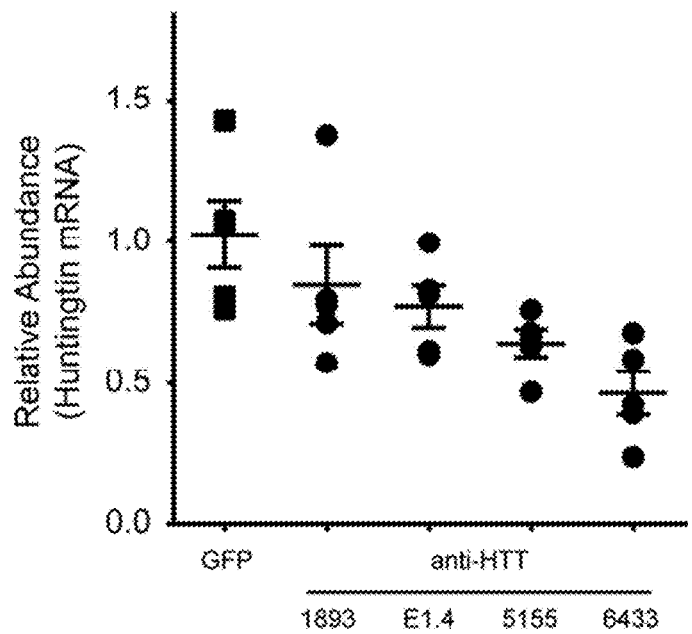
Figure 5A:
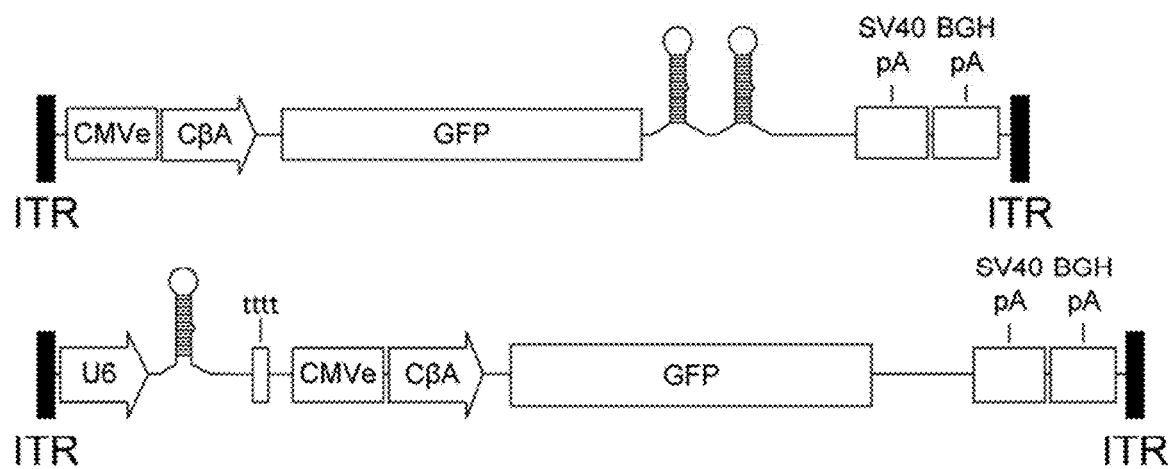
FIGS. 5A-5C show expressing an artificial miRNA from the U6 promoter does not improve silencing of huntingtin in the mouse striatum.
Figure 25A:
FIGS. 25A-25B show predicted hairpin structures of artificial miRNA targeting human huntingtin.
Figure 25B:

Nine sequences targeting the human huntingtin mRNA (Table 1, FIG. 1) were tested. A schematic depicting the locations of the nine targeting sequences is provided in FIG. 4A. Two copies of the artificial miRNA were cloned in tandem into a backbone based on the endogenous miRNA-155 or miR-30 and the entire artificial miRNA was inserted into the 3'-UTR of EGFP (FIG. 5A, top). The predicted hairpins structures of mir-155-based and mir-30-based anti-HTT amiRNAs are shown in FIGS. 25A-25B, respectively. The resulting plasmids were transfected into Hela cells. Forty-eight hours later, the cells were harvested and levels of endogenous huntingtin mRNA were measured by quantitative RT-PCR (qRT-PCR). Three out of the nine artificial miRNAs reduced huntingtin by greater than 50% (FIGS. 1-2 and 4B-4C).

TABLE 1

Huntingtin mir targets

| Name | Mature miRNA Sequences | SEQ ID NO: |
|---|---|---|
| miR-1873-anti-HTT | 5'-TAAATGTGCCTGTTGAAGGGC-3' | 2 |
| miR-2029-anti-HTT | 5'-AAGAGGTGCAGAGTCATCATC-3' | 3 |
| miR-4173-anti-HTT | 5'-TTCTGGAGGACATCAAACCAT-3' | 4 |
| miR-4448-anti-HTT | 5'-TGAACTGGCCCACTTCAATGT-3' | 5 |
| m1R-6088-anti-HTT | 5'-TTCCATTGGCAACTGGGCCAT-3' | 6 |
| miR-6433-anti-HTT | 5'-TAAGCATGGAGCTAGCAGGCT-3' | 7 |
| miR-TS1-anti-HTT | 5'-TAGCGTTGAAGTACTGTCCCC-3' | 8 |
| miR-TS2-anti-HTT | 5'-TTGAGGCAGCAGCGGCTGTGC-3' | 9 |
| miR-E14-anti-HTT | 5'-TTCATCAGCTTTTCCAGGGTC-3' | 10 |

Figure 11A:
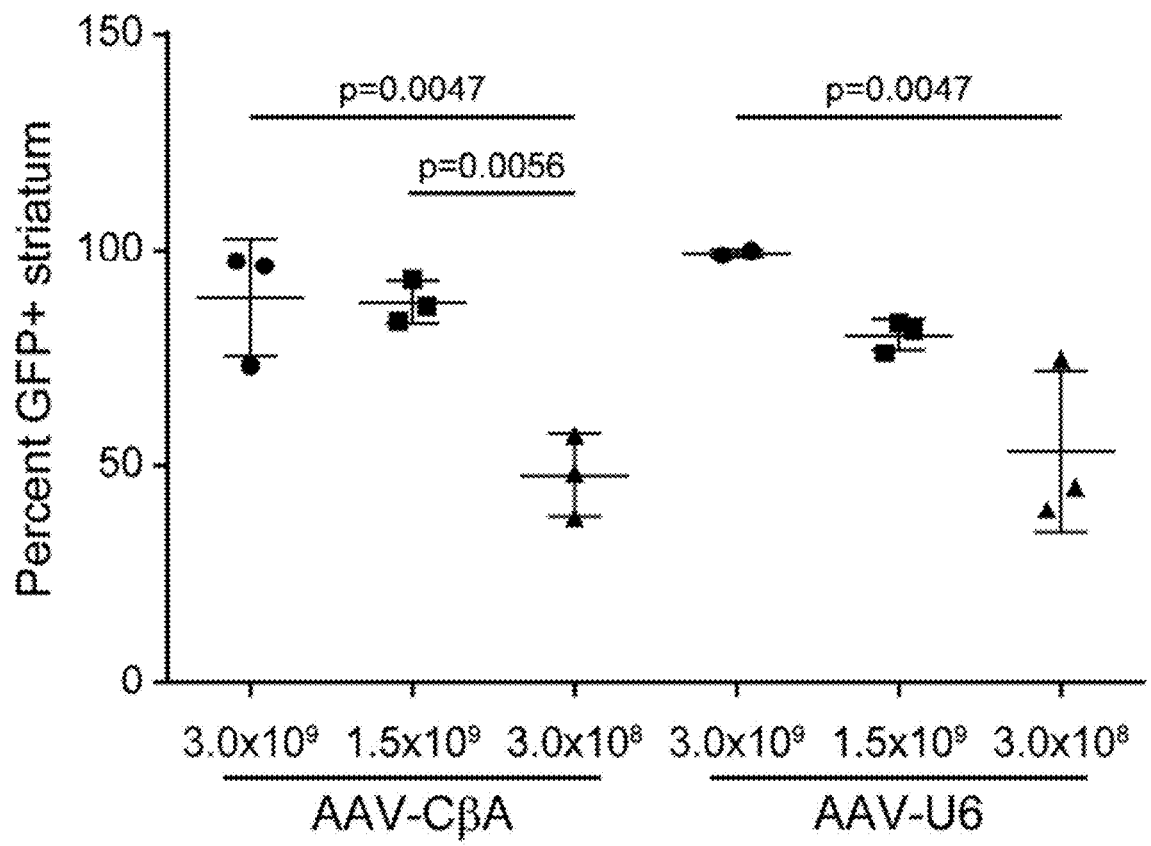
FIGS. 11A-11C show reducing the vector dose results in reduced spread and knockdown in the mouse striatum.
Figure 11B:
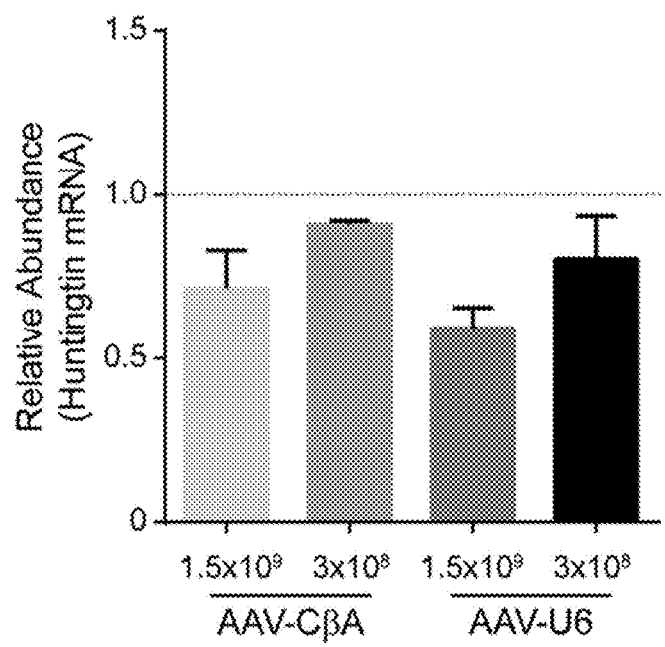
Figure 11C:
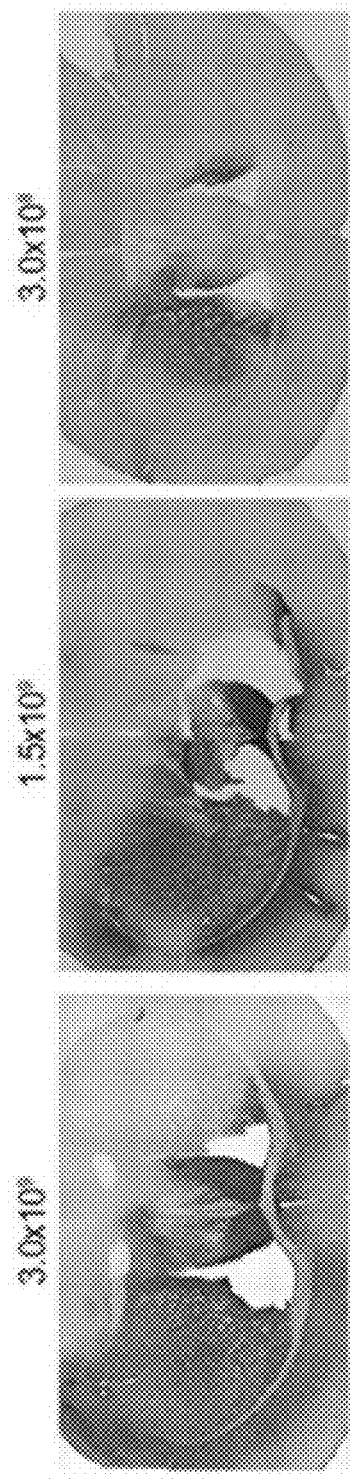

Three sequences from the initial screen were selected for in vivo experiments. An artificial miRNA based on a known siRNA (E1.4) was also tested. Candidate sequences were packaged into a self-complementary AAV9 vector and injected it directly into the striatum of transgenic mice expressing human huntingtin with a stretch of approximately 128 polyglutamine encoding repeats (Yac128 mice). One month later, distribution of AAV9 and expression of the GFP reporter were evaluated at three different doses. At the highest dose, GFP staining was present throughout the striatum (FIG. 11A) and human huntingtin mRNA was significantly reduced in mice treated with either AAV9-CβA-anti-HTT-6433 ($p=0.006$) or AAV9-CβA-anti-HTT-5155 ($p=0.013$, FIG. 4C; mir-155 backbone was used). Reducing the dose of the vector resulted in reduced GFP expression (FIG. 11A) and at a 1:10 dilution, no significant reduction in human huntingtin mRNA was achieved (FIG. 11B). FIG. 11C provides representative photos of mice injected with a vector encoding both the huntingtin targeting miRNA and EGFP at three different doses.

Figure 5B:
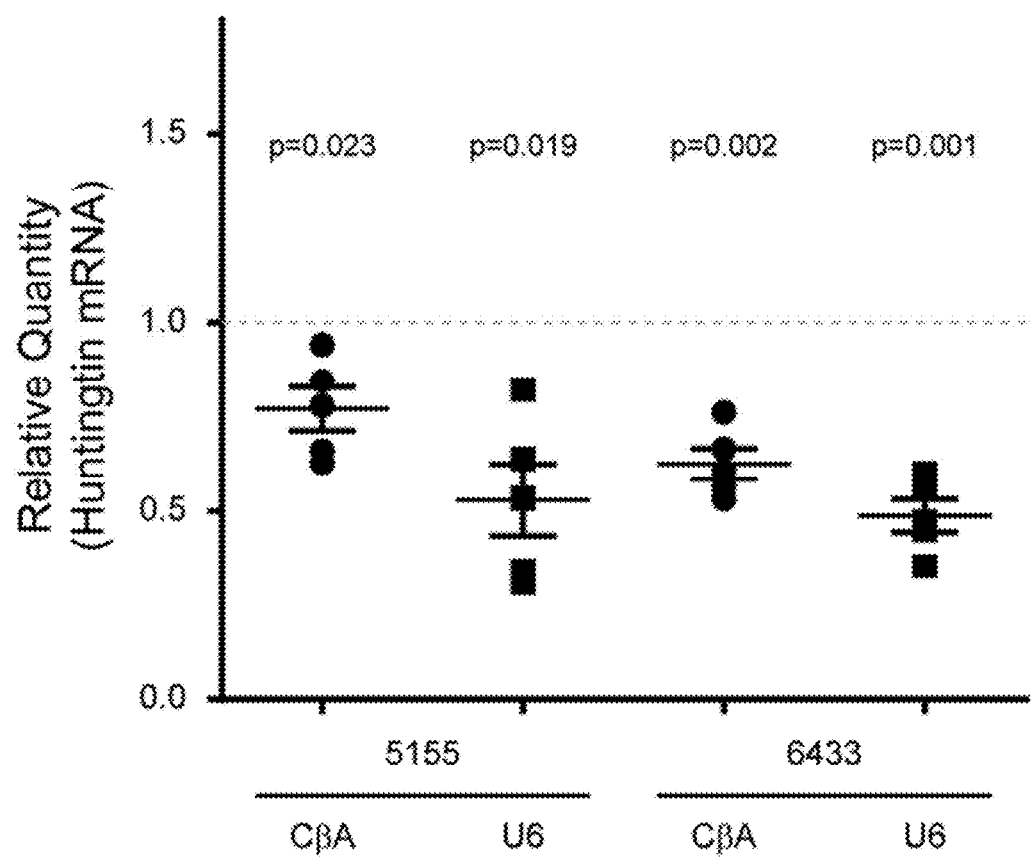
Figure 5C:
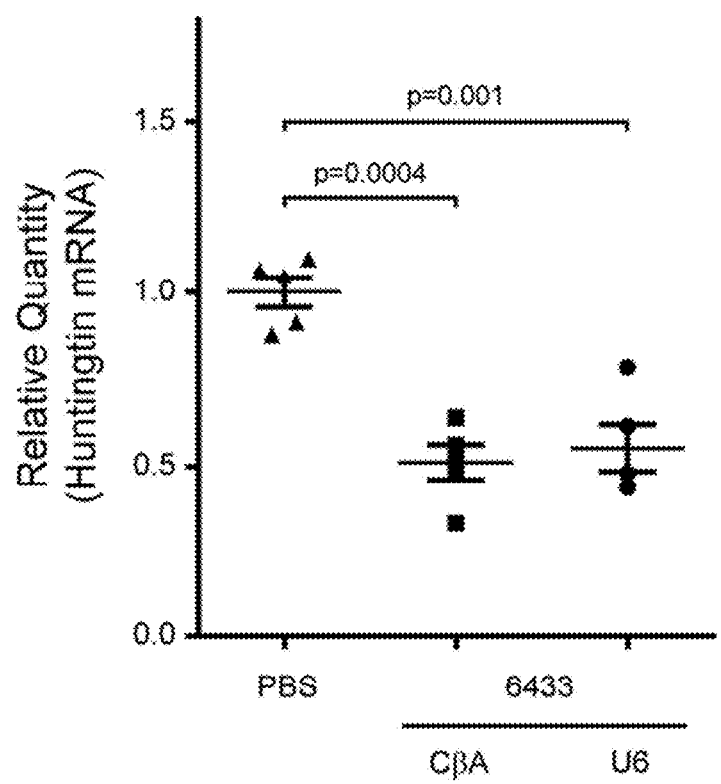

Expressing an Artificial miRNA from the U6 Promoter does not Improve Silencing of Huntingtin A single copy of the most potent miRNA (HTT-6433) was cloned into an AAV9 vector under the control of the U6 promoter (FIG. 5A, bottom). Mice were injected unilaterally with either the original two copy AAV9-CBA-anti-HTT-6433 (comprising SEQ ID NO: XX), AAV9-CBA-anti-HTT-5155, AAV9-U6-anti-HTT-6433 (comprising SEQ ID NO: XX or AAV9-U6-anti-HTT-5155. One month later, the striatum was harvested and GFP expression was confirmed and the level of huntingtin mRNA was measured by qRT-PCR. Regardless of the sequence of the artificial miRNA, no significant difference in knockdown between mice treated with AAV9-U6-anti-HTT and AAV9-CBA-anti-HTT was observed. In both the mice treated with the AAV9-U6-anti-HTT-6433 and AAV9-CBA-anti-HTT-6433, the quantity of huntingtin mRNA on the injected side was approximately 50% of that on the non-injected side (FIG. 5B). Note that using the contralateral (non-injected) side as a control for each animal reduces the animal to animal variability. In mice injected with AAV9-GFP unilaterally, a small number of GFP positive neurons on the contralateral side are occasionally observed, indicating that some virus spreads to the un-injected side. Therefore, using the contralateral side as the control may underestimate knockdown. To eliminate the potential confounding effects of using the contralateral side as a control, the experiment was repeated using a group of animals injected with PBS only as the control. Data indicate that both AAV9-U6-anti-HTT-6433 and AAV9-CBA-mir-HTT-6433 reduced huntingtin mRNA by approximately 50% (FIG. 5C).

Figure 3:
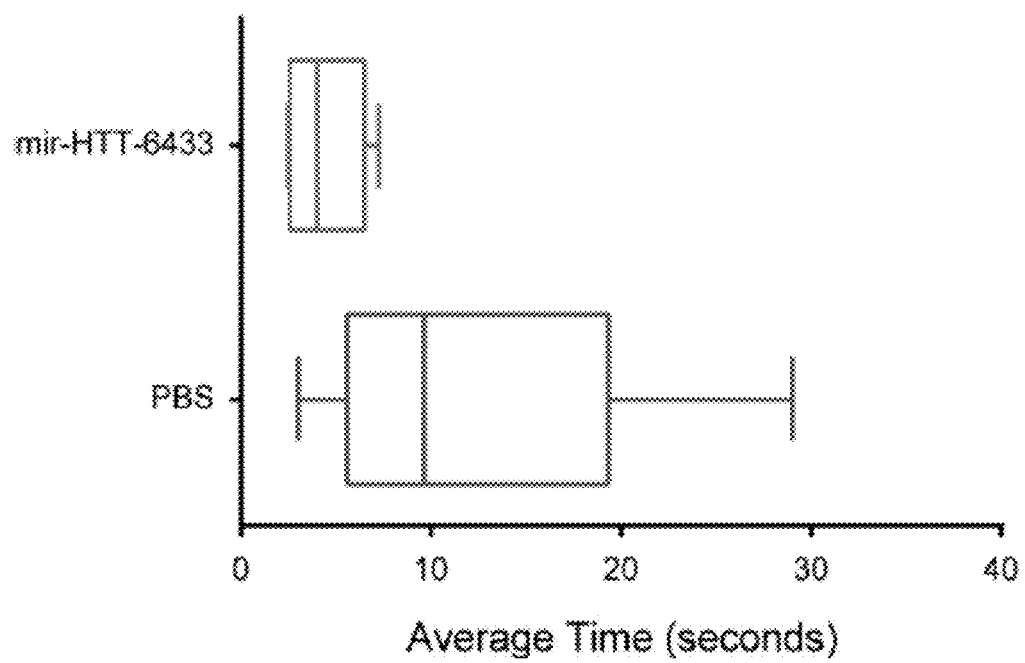
FIG. 3 shows injection of transgenic mice expressing mutant huntingtin (human) unilaterally with AAV9-mir-HTT-6433 or PBS. Six months post-injection, mice were tested on a balance beam. Data indicate that mice treated with mir-HTT-6433 show a decrease in the amount of time it took to cross the beam when compared to HD mice treated with PBS.
Figure 6A:
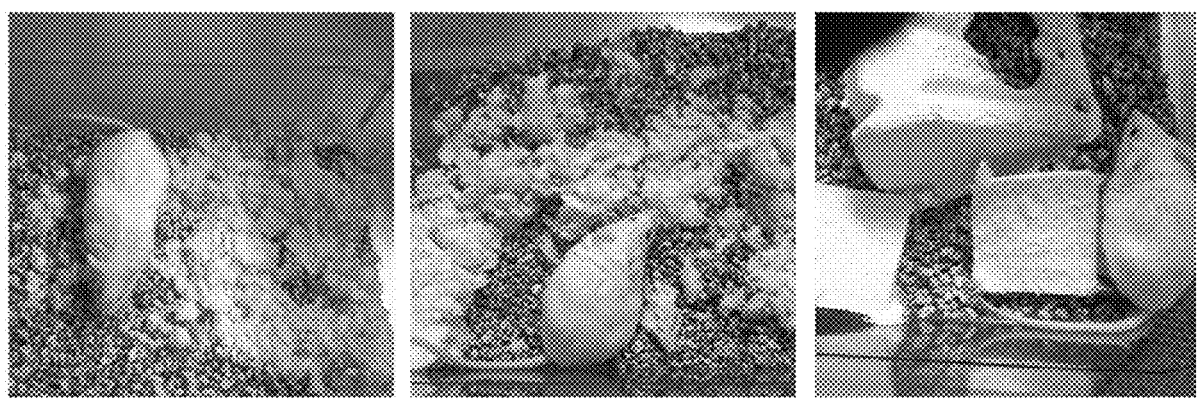
FIGS. 6A-6B show long-term striatal expression of mir-HTT-6433 from a U6 promoter causes behavioral abnormalities.
Figure 6B:
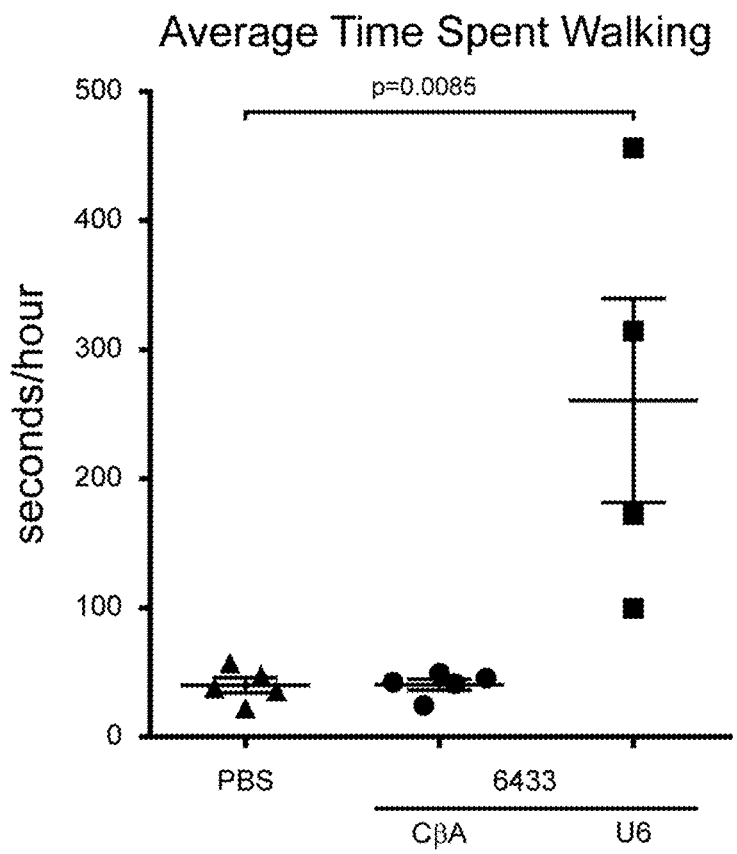
Figure 12A:
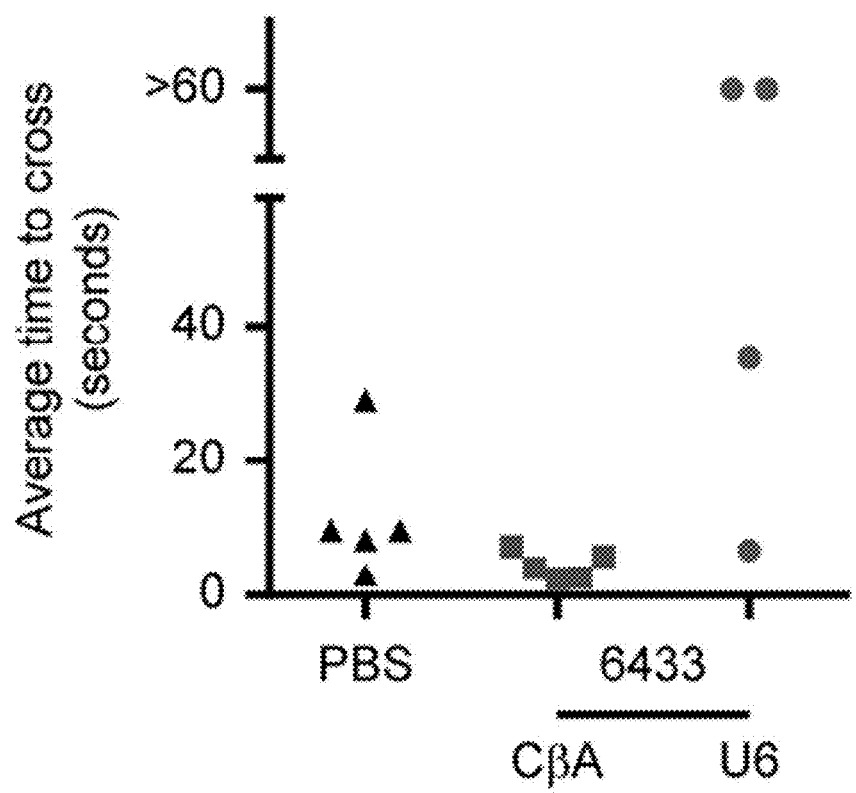
Figure 12B:
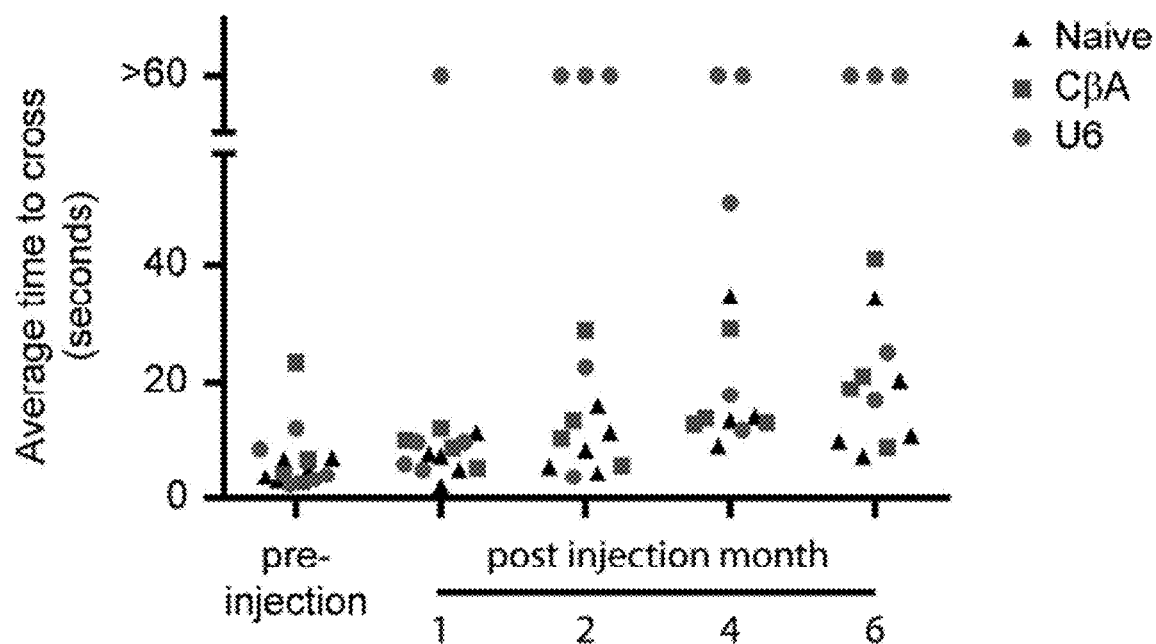

Long-Term Striatal Expression of Mir-HTT-6433 from a U6 Promoter is Toxic in Mice AAV9-U6-anti-HTT-6433 or AAV9-CBA-anti-HTT-6433 were unilaterally injected directly into the striatum of Yac128 mice. Six months after injection, it was observed that the mice injected with AAV9-U6-anti-HTT-6433 were not nesting and some exhibited a hyperactive phenotype. To document these abnormalities, the nestlets in each cage were replaced. Twenty-four hours later, the new nestlets of the AAV9-U6-anti-HTT-6433 were unused whereas PBS and AAV9-CBA-anti-HTT-6433 injected mice made nests as expected (FIG. 6A). Using a home-cage monitoring system, the mice were recorded for twenty-four hours. Mice treated with AAV9-U6-anti-HTT-6433 spent significantly more time moving around their home cage than mice treated with PBS or with AAV9-CBA-anti-HTT-6433 (FIG. 6B). The average time it took for the mice to cross the beam was also measured. For this test, the mice are required to complete the beam crossing three times. On average, AAV9-CBA-anti-HTT-6433 treated mice trended to cross faster than mice that received only a PBS injection (FIGS. 3 and 12A). Of the four remaining mice in the AAV9-U6-anti-HTT-6433 group, two were unable to successfully cross, either jumping or falling off the beam (FIG. 12A). In a second experiment carried out on older Yac128 mice (7 months of age), an age related increase in time to cross the beam was observed. This increase was present in both naïve mice and in mice treated with AAV9-CBA-anti-HTT-6433 and was accelerated in mice treated with AAV9-U6-anti-HTT-6433 (FIG. 12B).

Figure 7A:
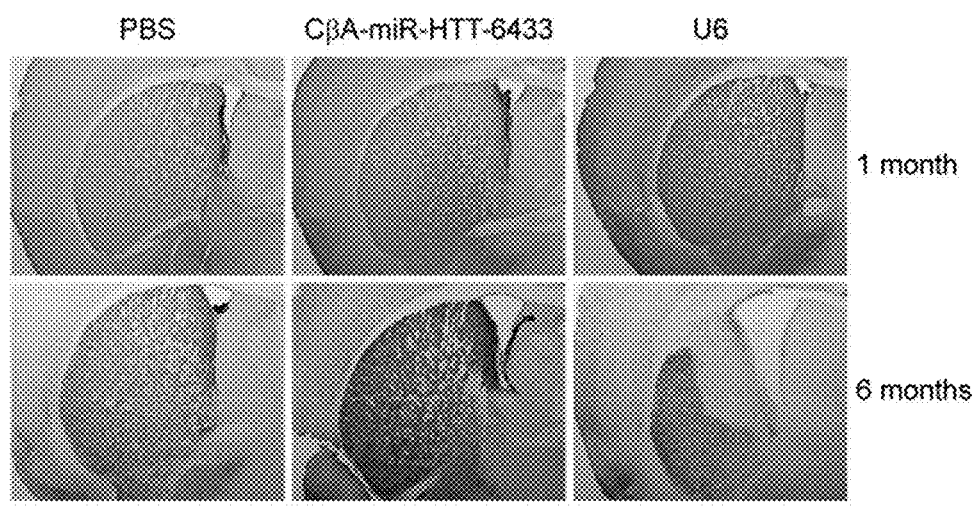
FIGS. 7A-7B show long-term expression of mir-HTT-6433 from a U6 promoter causes striatal shrinkage.
Figure 7B:
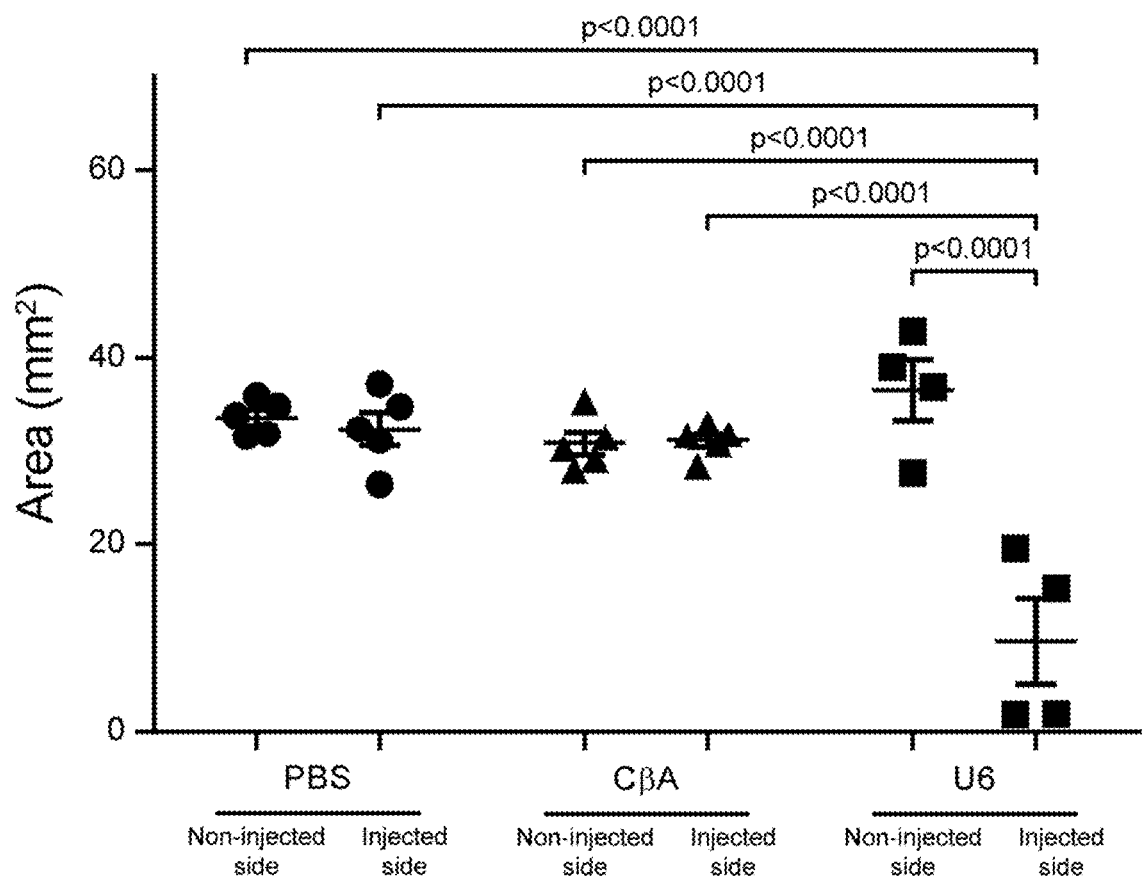
Figure 8A:
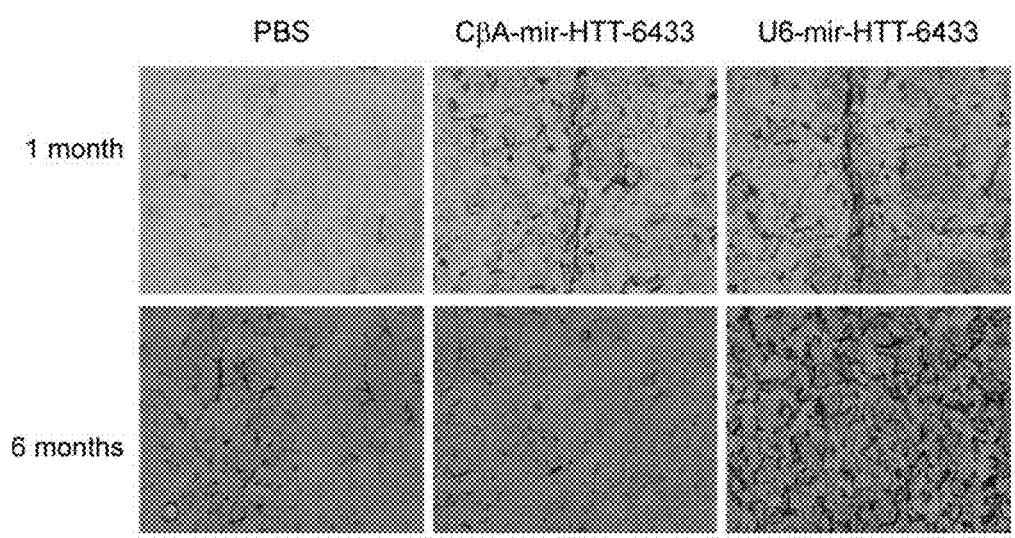
FIGS. 8A-8D show long-term expression of mir-HTT-6433 from a U6 promoter causes persistent activation of microglia.
Figure 8B:
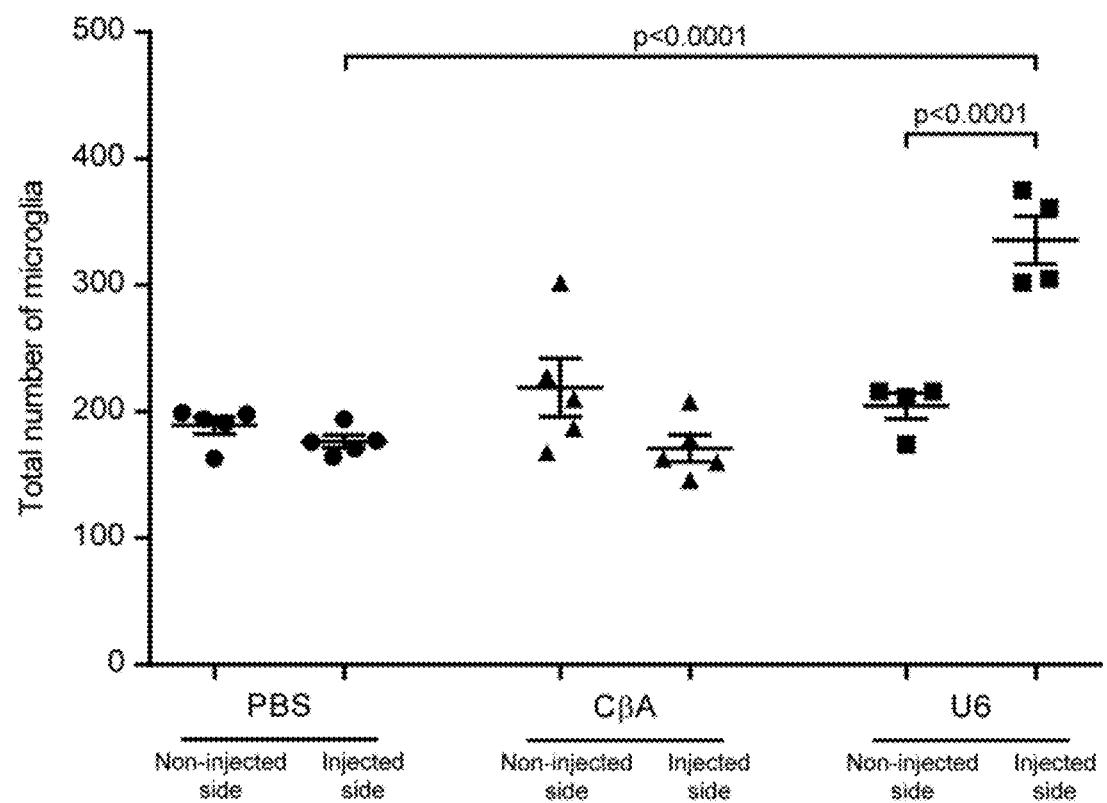
Figure 8C:
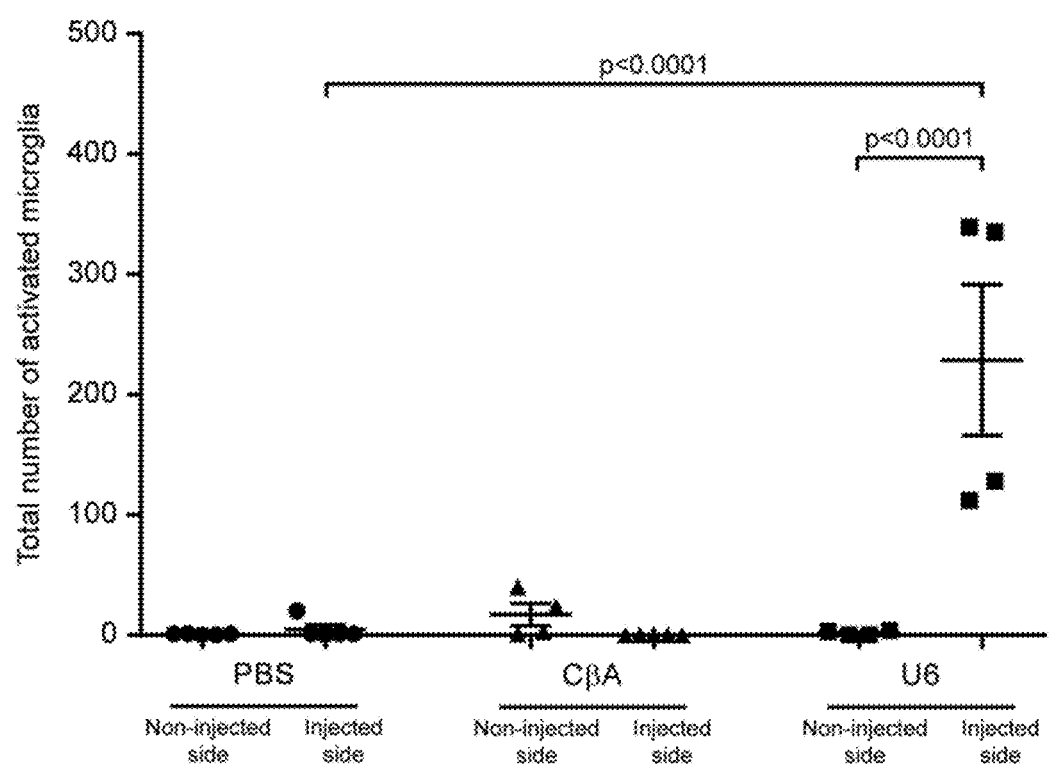
Figure 8D:
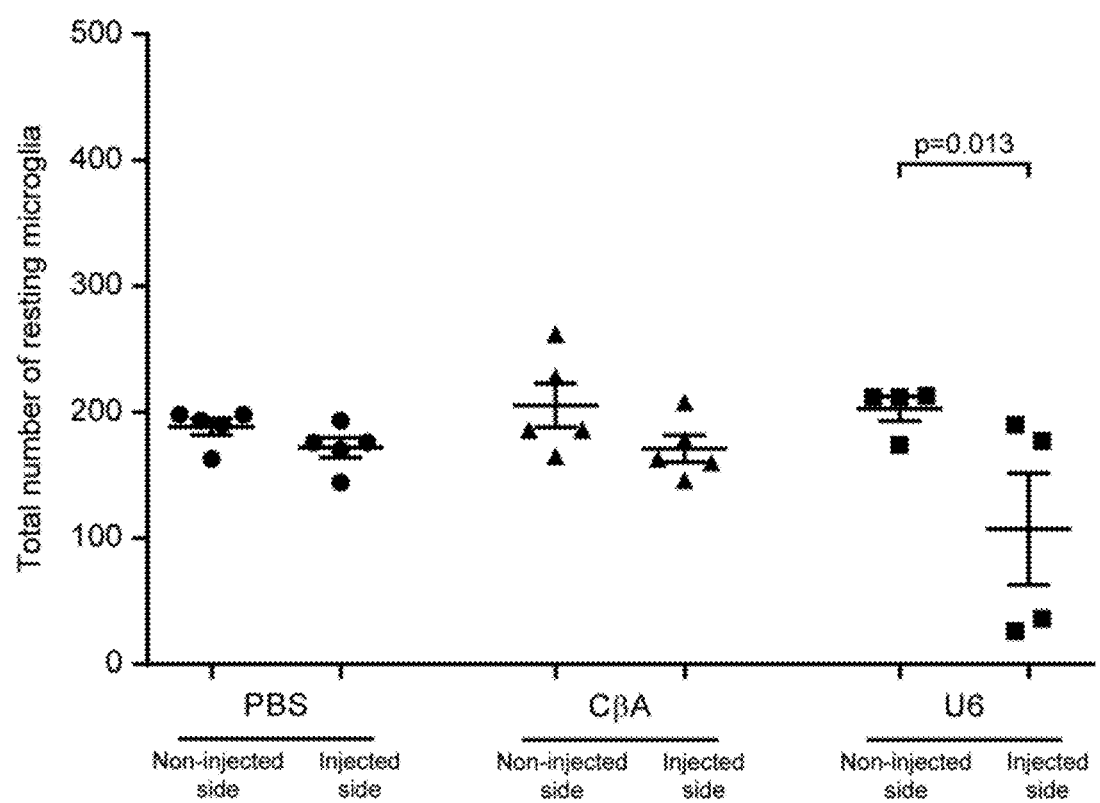
Figure 13A:
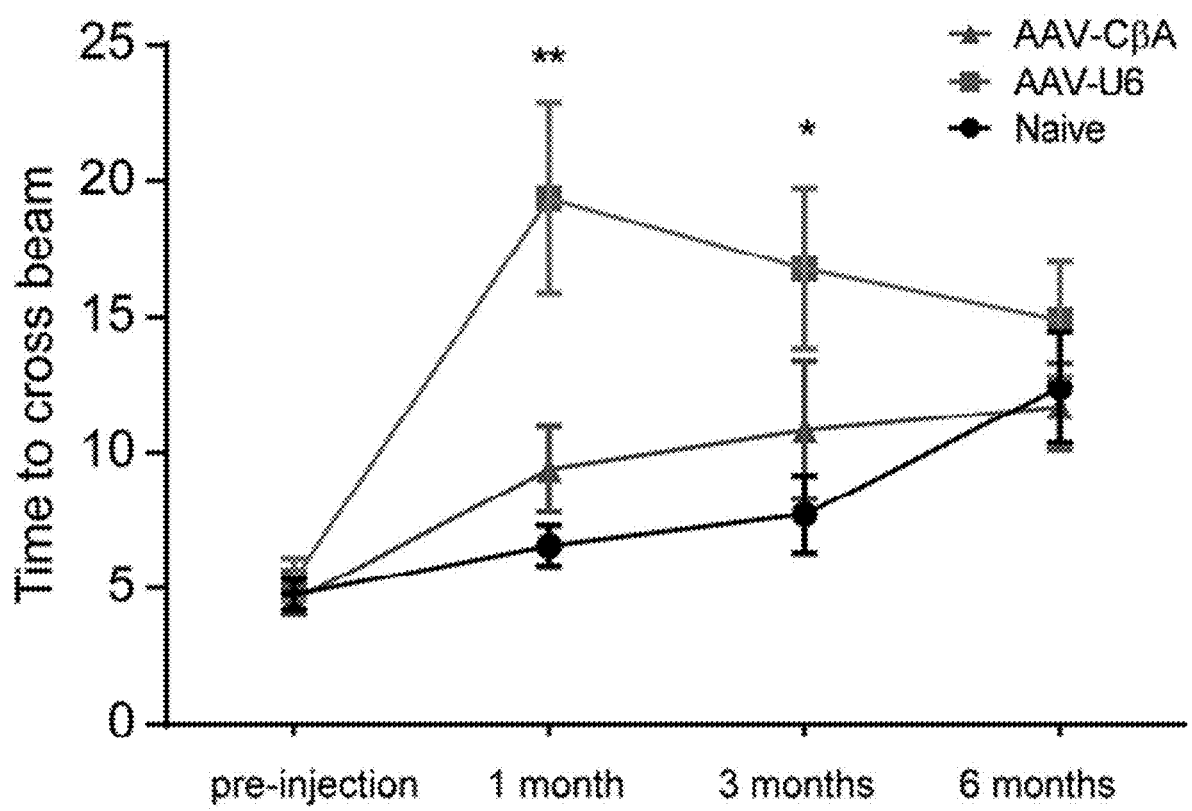
FIGS. 13A-13B show C57BL/6 mice show an initial deterioration in behavior on the beam following injection of the U6-promoter driven huntingtin targeting artificial miRNA.
Figure 13B:
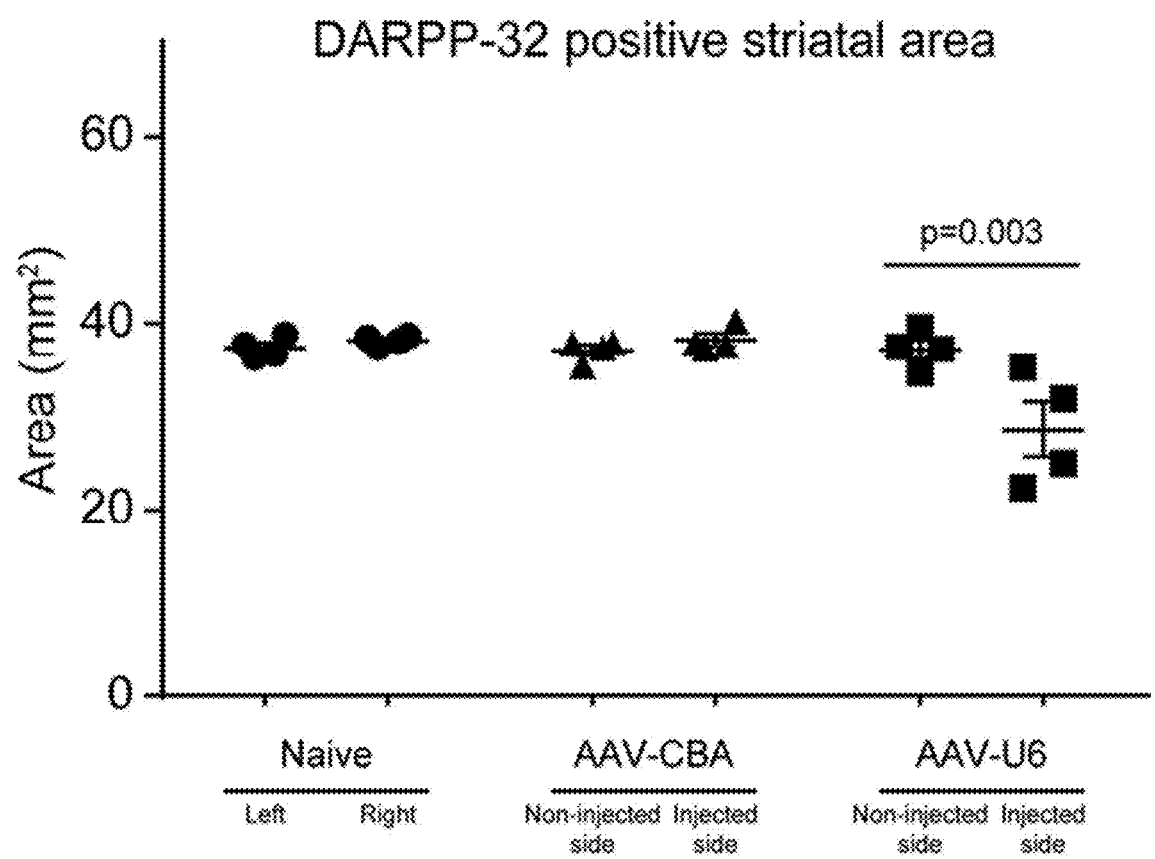

Neuropathological findings correlated with the behavioral outcomes described above. On the injected side, the AAV9-U6-anti-HTT-6433 mice showed enlargement of the ventricle, loss of DARPP-32 positive neurons and striatal shrinkage (FIGS. 7A-7B). In the remaining striatum, they exhibited increased Iba1 staining (FIG. 8A, bottom), an increase in total and activated microglia and a decrease in the number of resting microglia (FIGS. 8B-8D). Wild-type C57Bl/6 mice and FVB mice were injected with the same vectors and the consequences of the U6 driven miR were assessed to determine if the toxicity was dependent on the presence of mutant Huntington in that context. In FVB mice, the effect was similar to that in Yac128 mice with rapid degeneration on the beam and severely enlarged ventricles. However, in C57BL6 mice, the effect was present but less pronounced. While there was an initial increase in time to cross the beam in the U6 cohort, at the study endpoint there was no significant difference between groups (FIG. 13A). Striatal shrinkage was also less severe in the C57BL6 mice (Figure FIG. 13B).

Figure 9A:
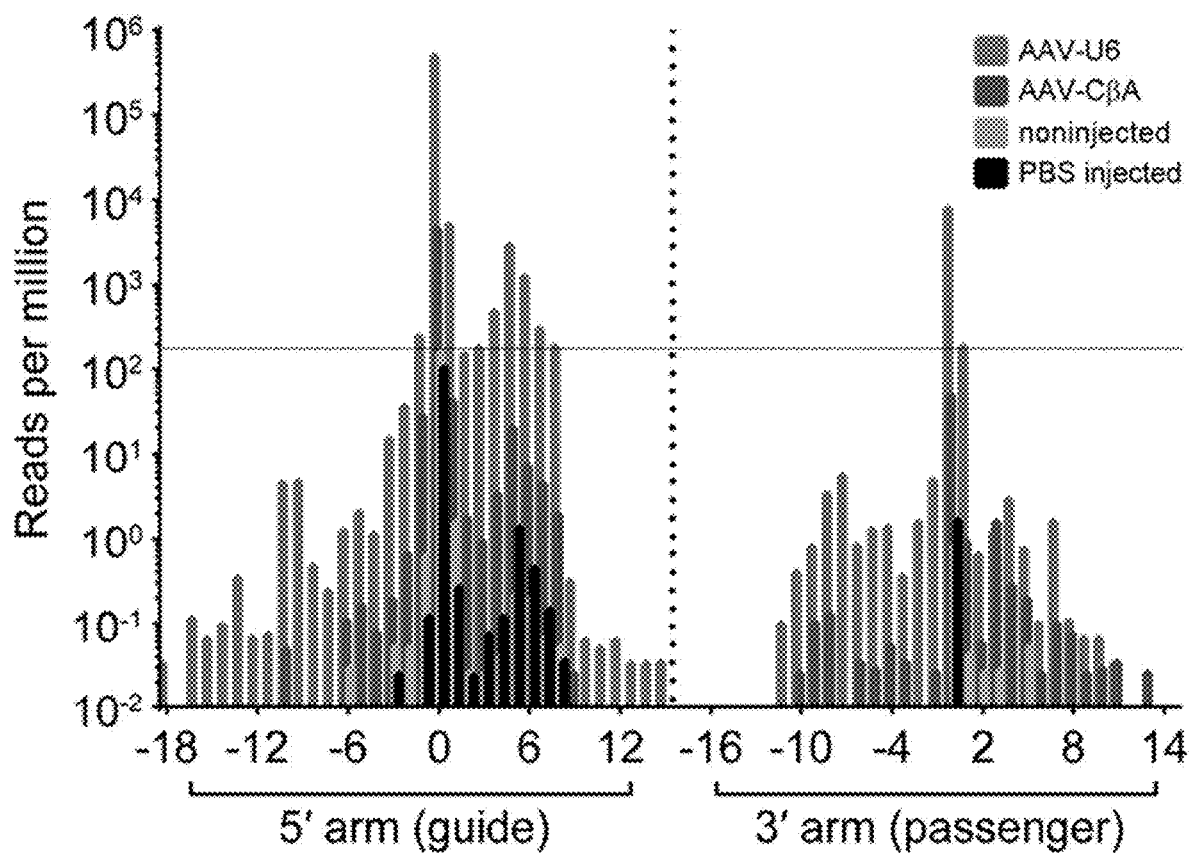
FIGS. 9A-9C show expression of the mir155 based artificial miRNA from a U6 promoter results in overexpression of the huntingtin targeting guide strand and other sequences.
Figure 9B:
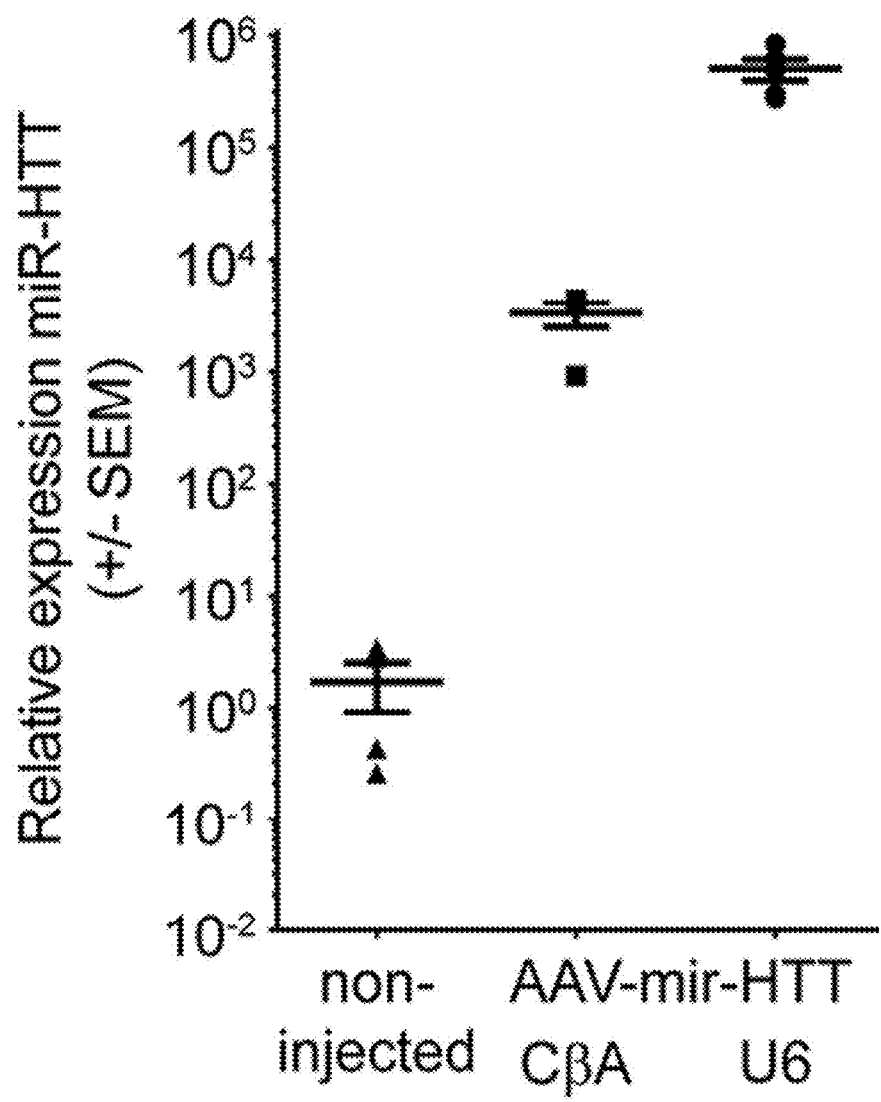

Expression of the Artificial miRNA Targeting Huntingtin from a U6 Promoter Results in Overexpression of the Huntingtin Targeting Small RNA Groups of mice were injected unilaterally with scAAV9 vectors expressing the artificial miRNA 6433 from the U6 and CβA promoters. The small RNAs produced at two weeks post-injection were cloned and sequenced. In both groups, ninety-six percent of the sequences mapping to the AAV genome mapped to the expected small RNA product, with only a small percentage representing imprecise Dicer or Drosha cleavage. In the group injected with the U6 promoter driven artificial miRNA, the huntingtin targeting sequence dominated the sequencing results, accounting for half (50%) of all mappable sequences whereas in the mice injected with the CBA vector, only 5% of the sequences matched the vector encoded small RNA (FIG. 9A). Thus, potentially, small RNAs with alternative seed sequences, including the sense strand and slippage products, may be present at levels comparable to those of functional endogenous miRNAs (FIG. 9A). The relative quantity of the huntingtin targeting small RNA was measured by qPCR to confirm the overexpression of the huntingtin targeting sequence. It was observed that expression of the small RNA was 150 to 250 times higher in the mice injected with the U6 promoter driven construct (FIG. 9B).

Figure 9C:
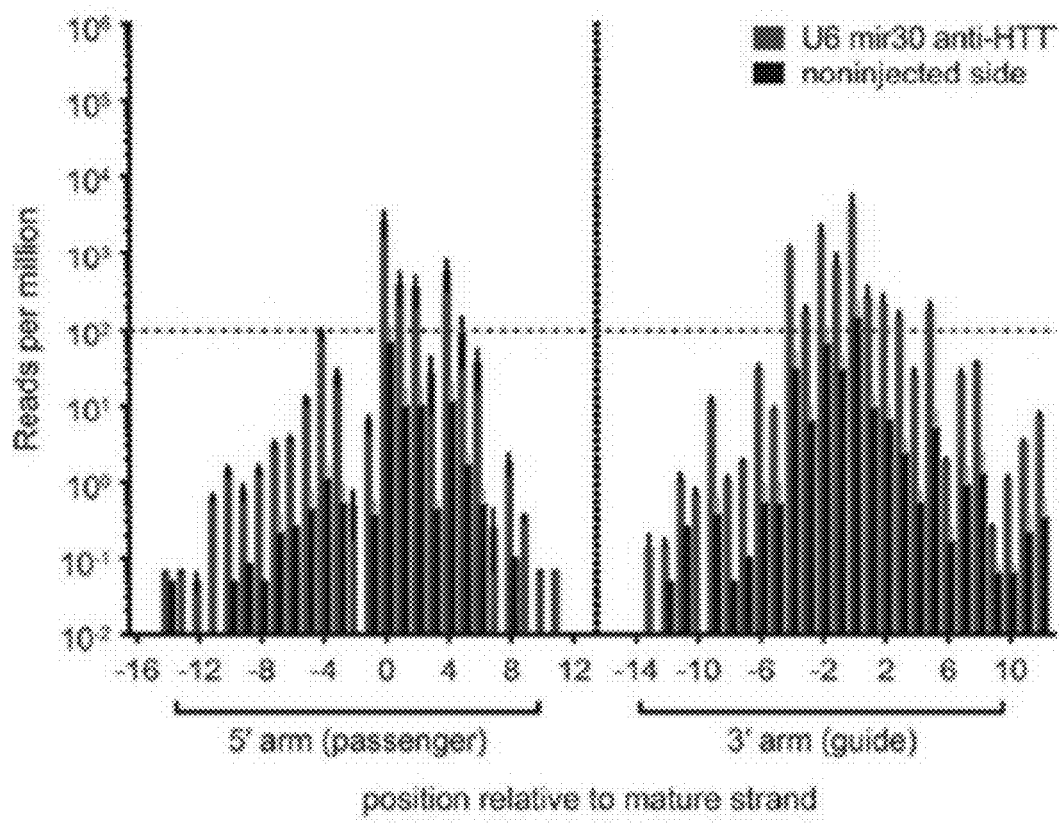

Endogenous miRNA 30 sequences are commonly used as a scaffold for artificial miRNA. To determine if the isomir profiles derived from this scaffold were more favorable, we embedded the anti-HTT-6433 sequence in a miR-30 backbone and injected into 10 week old Yac128 mice (FIG. 9C). The mir-30 scaffold produces levels of the mature artificial miRNA which are comparable to those produced by the CβA promoter (FIG. 9A) and reduces human huntingtin by close to 50%. Unlike the mir-155 scaffold, the mir-30 scaffold produces the mature sense (passenger) strand at levels comparable to the antisense (guide) strand. The combination of CβA promoter with mir-155 backbone produces only the intended antisense strand above background (FIG. 9A).

Figure 14A:
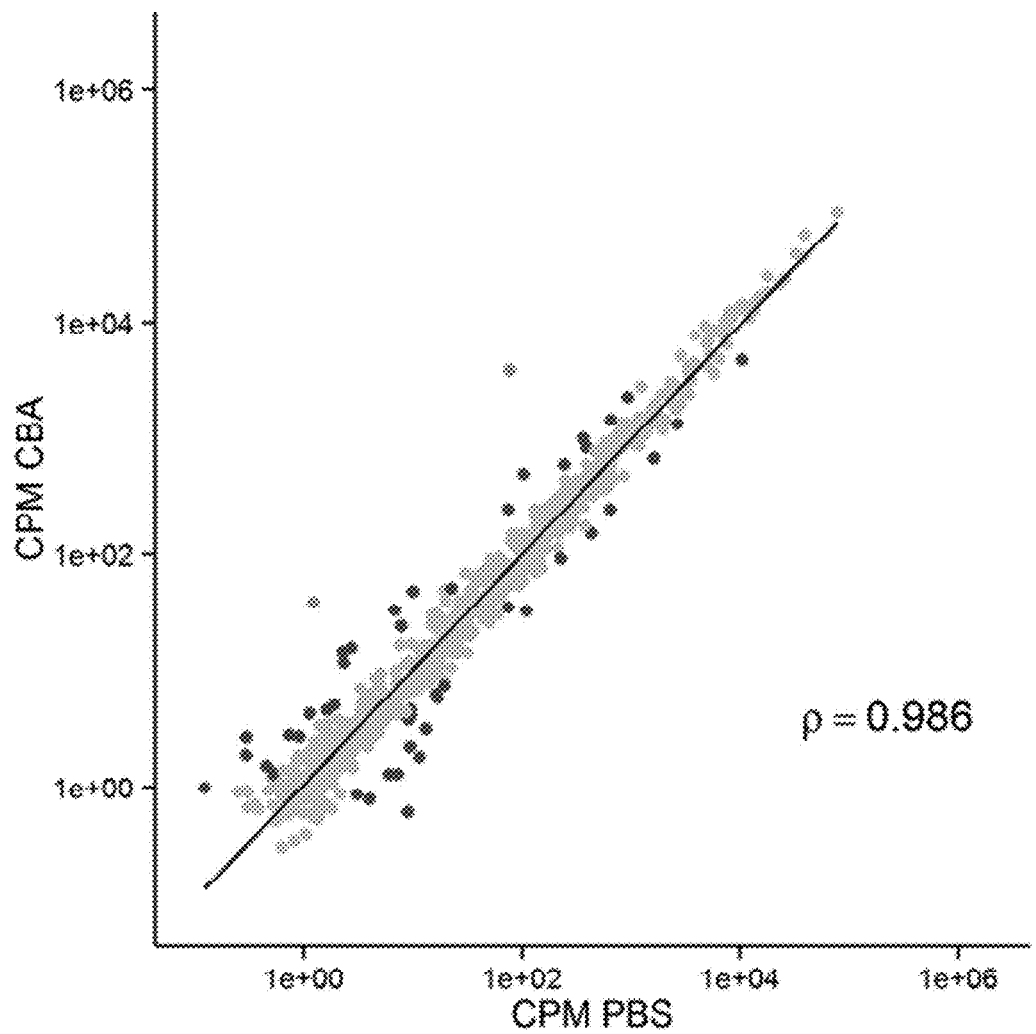
FIGS. 14A-14B show the distribution of endogenous miRNAs is largely unaffected following injection with mir-HTT-6433.
Figure 14B:
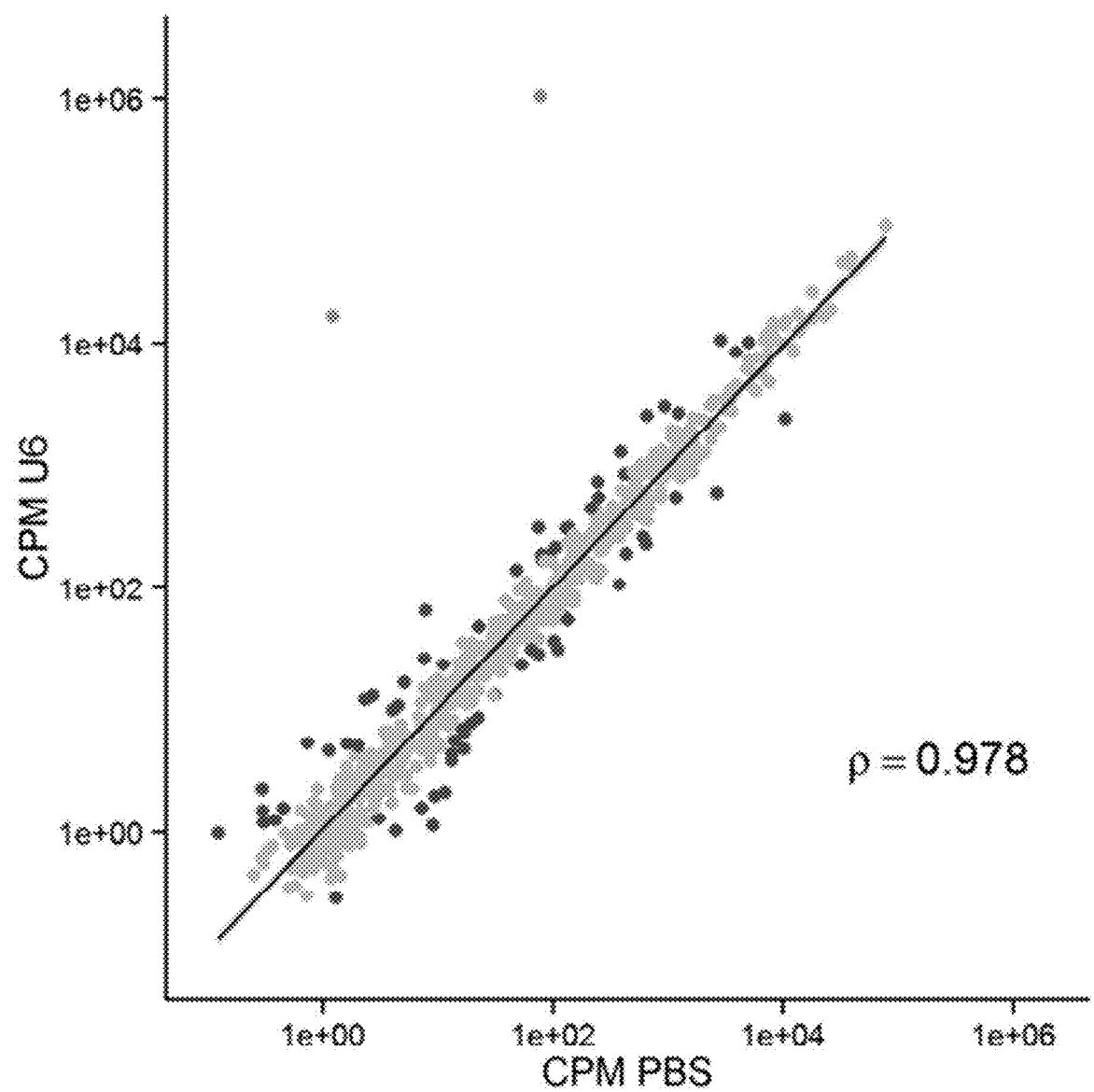

Although over half of the reads in the sample could be mapped to the AAV-encoded artificial miRNA, overexpression of the artificial miRNA targeting huntingtin had minimal effects on the distribution of endogenous miRNAs (FIGS. 14A-14B). In fact, the largest differences were observed when the injected groups were compared to the non-injected (contralateral) side, suggesting that the injection itself produces a local change in miRNA profiles. This may reflect a local inflammatory response to injury which could resolve over time.

Figure 10A:
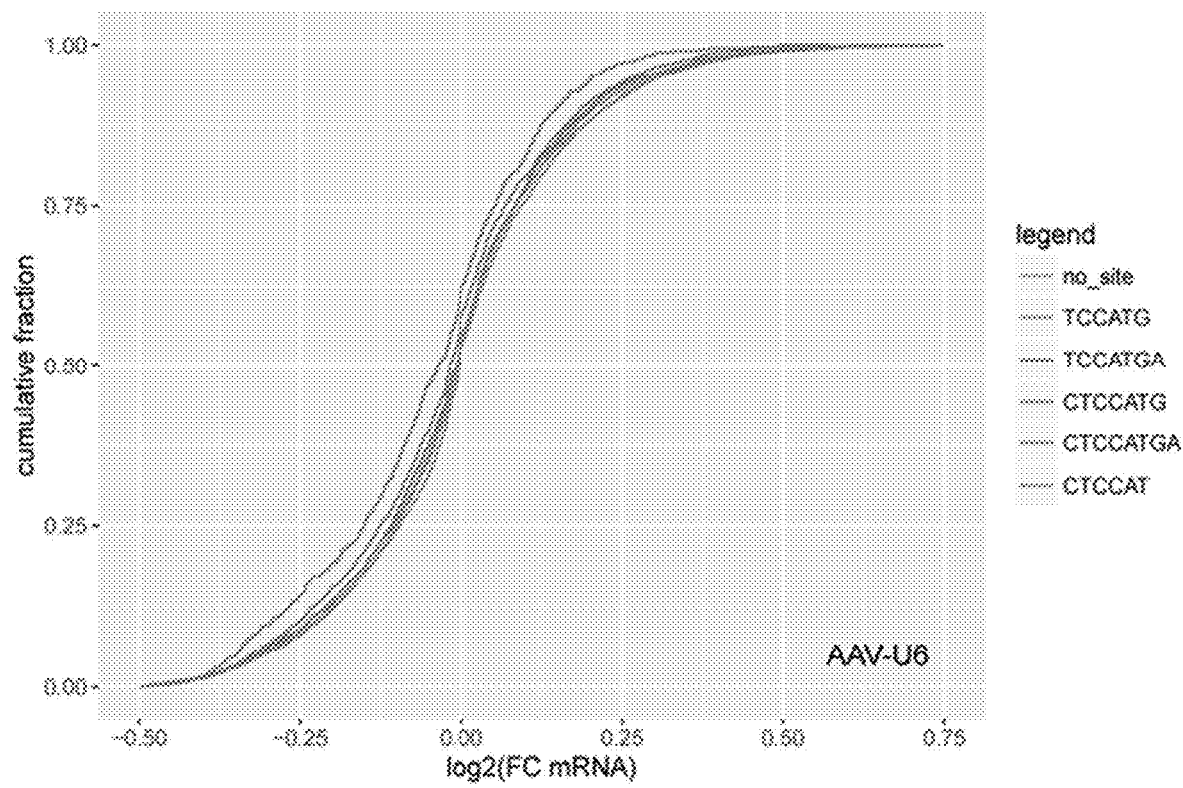
FIGS. 10A-10B show expression of mir-HTT-6433 preferentially decreases mRNAs with target sites.
Figure 10B:
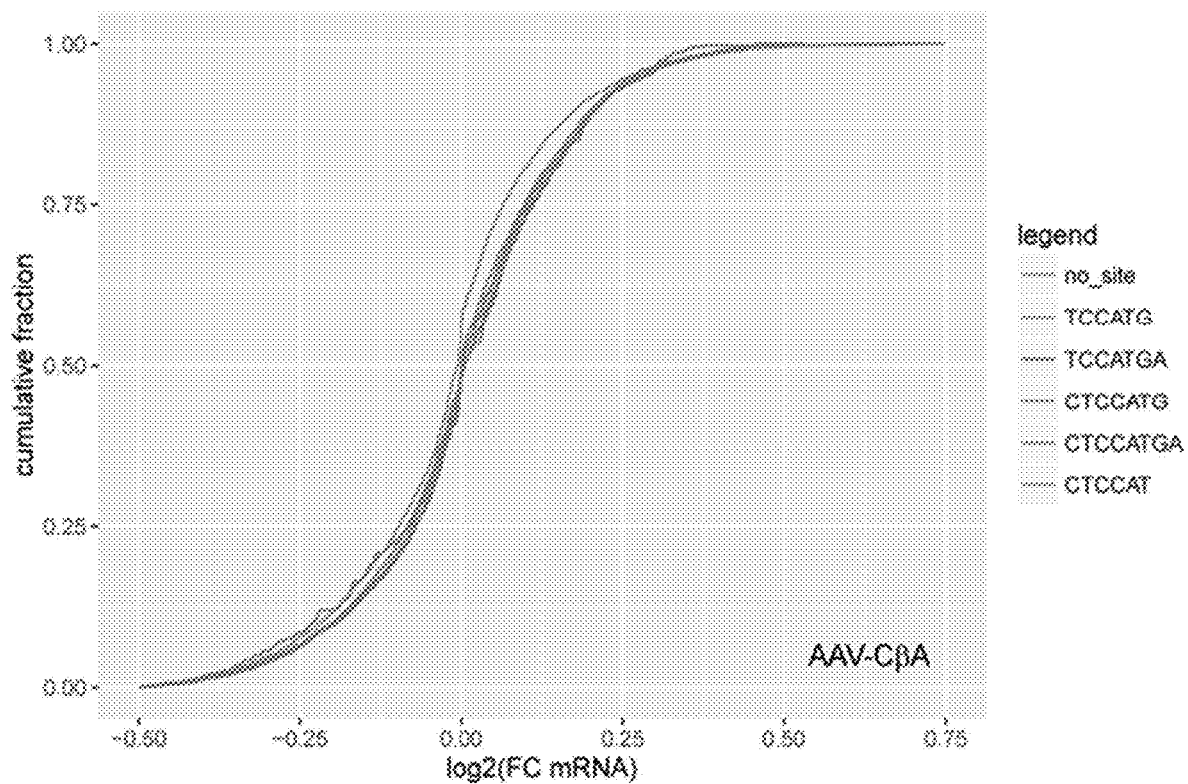
Figure 15A:
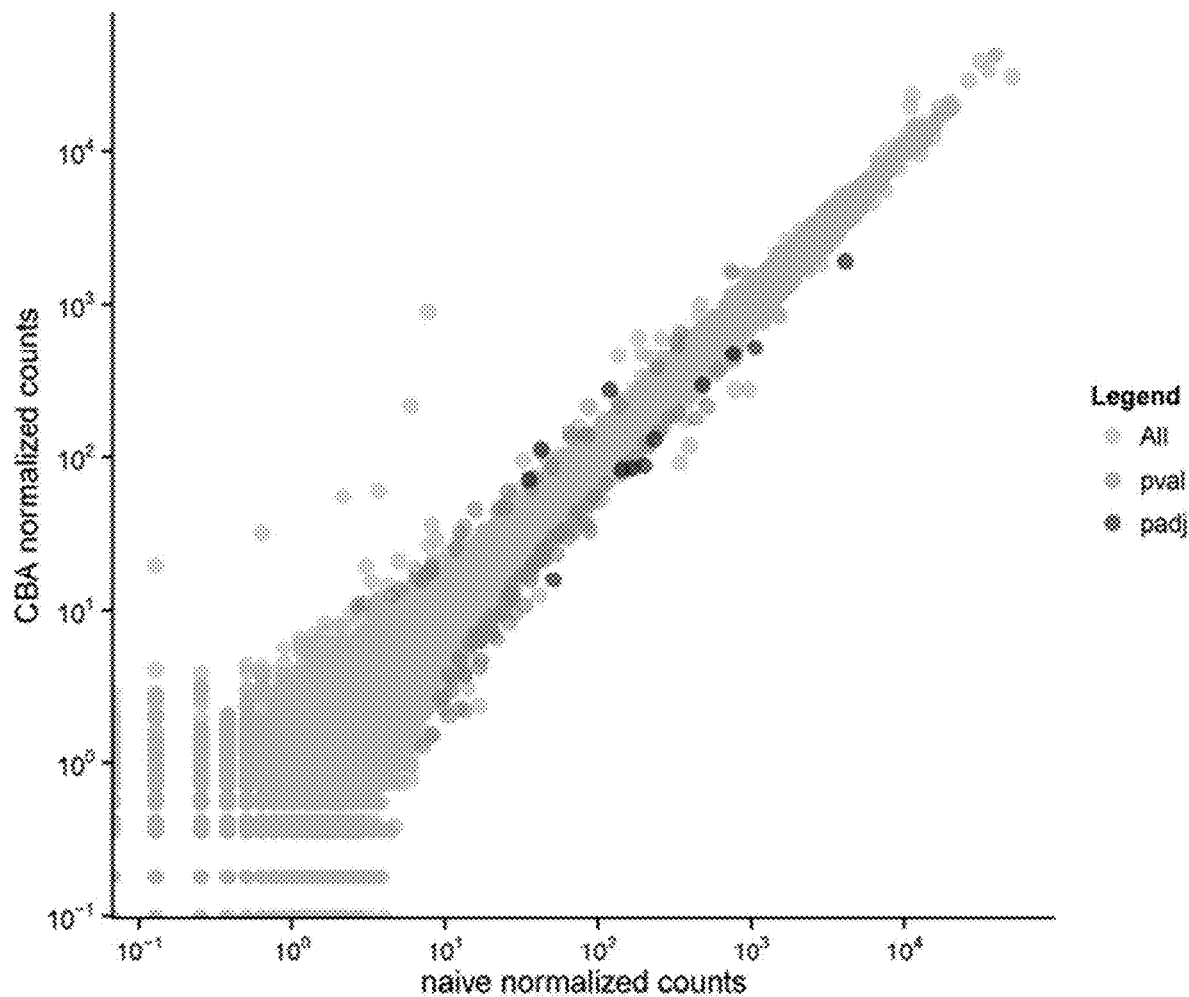
FIGS. 15A-15C show mRNA profiles in mice treated with mir-HTT-6433.
Figure 15B:
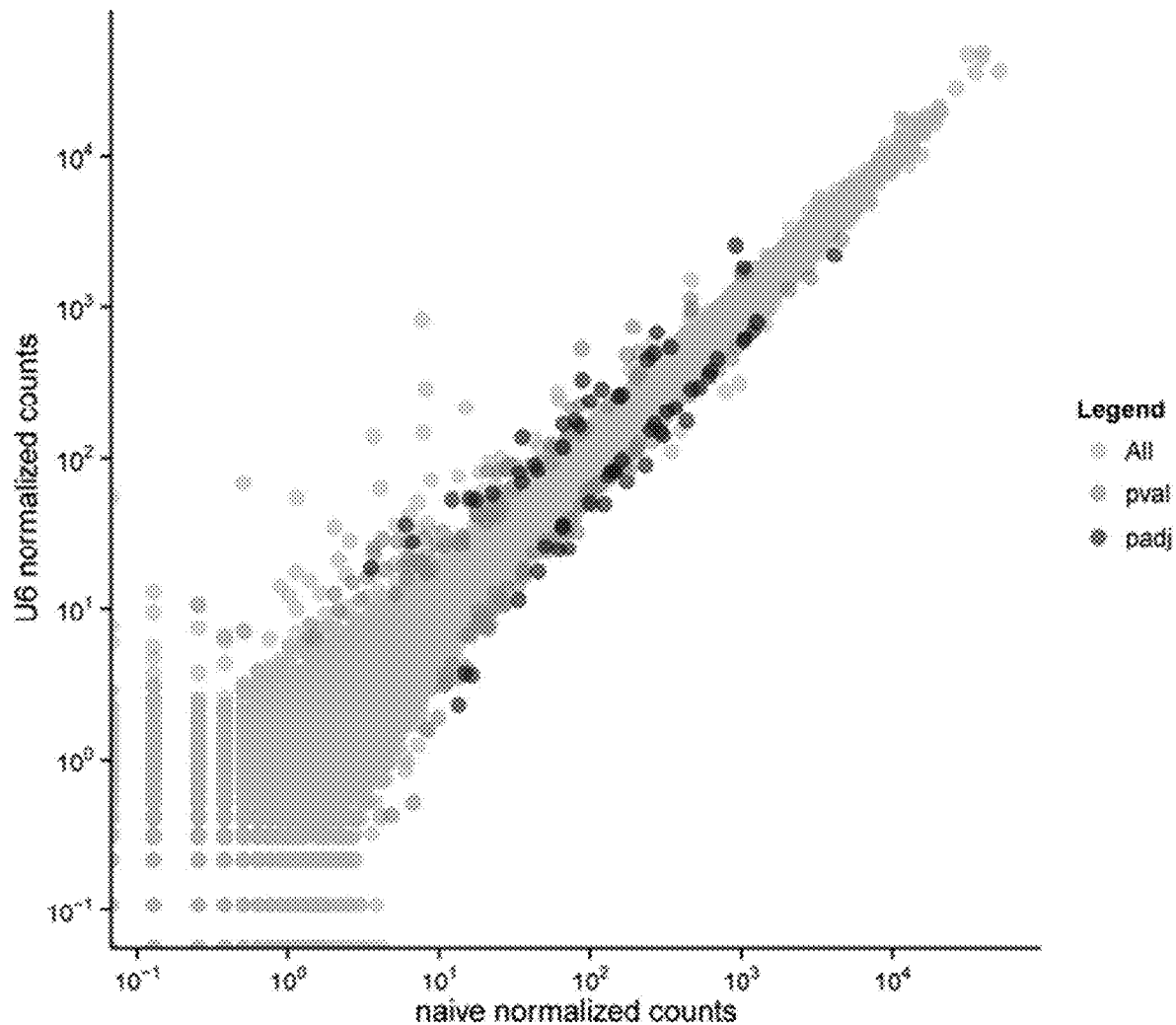
Figure 15C:
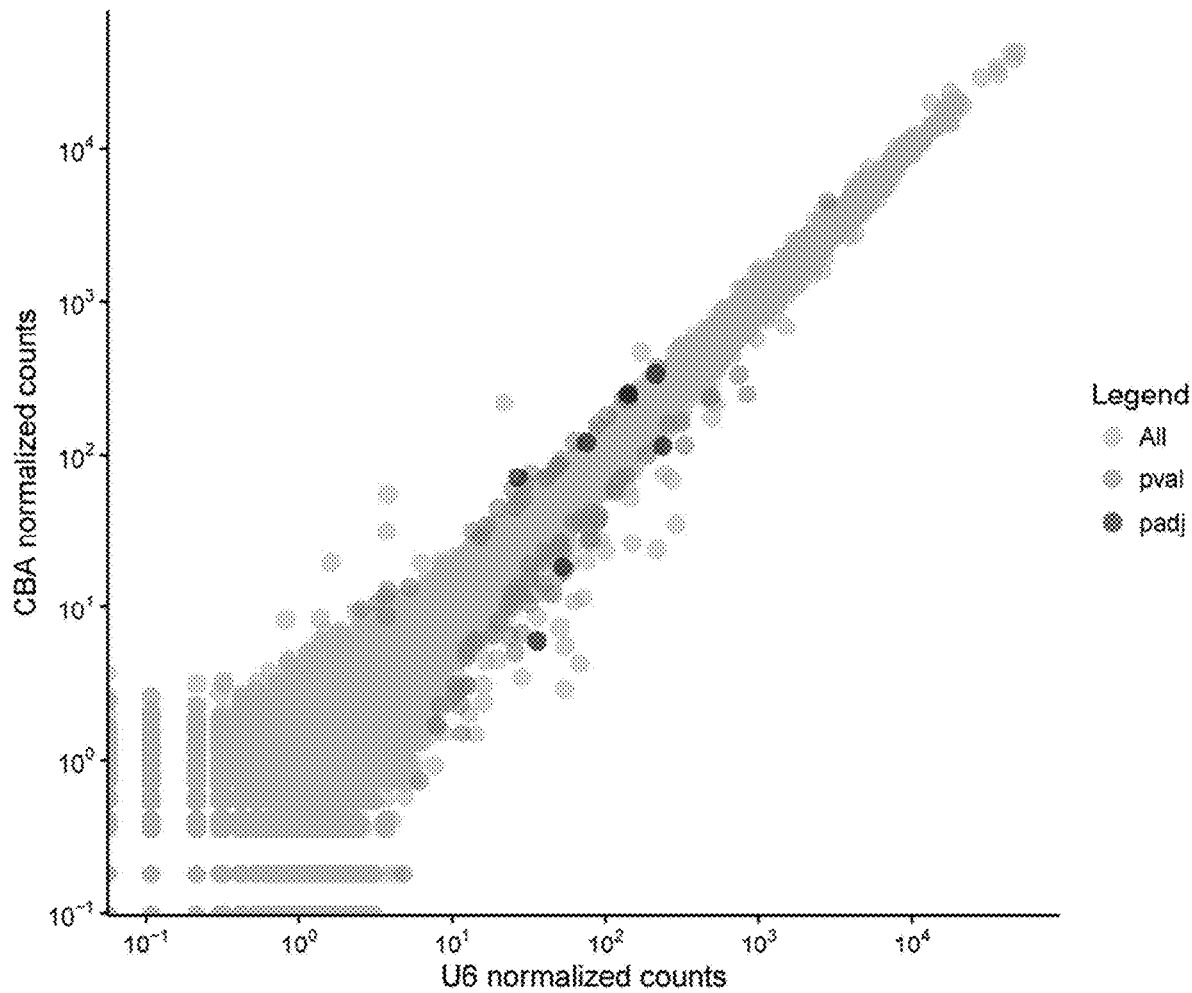

Expression of the Artificial miRNA Targeting Huntingtin from a U6 Promoter Disrupts the Expression of Multiple mRNAs RNAseq analysis of the striatum of mice treated with either the AAV9-U6-anti-HTT-6433 or AAV9-CBA-anti- HTT-6433 was performed to investigate the consequences of overexpression of the huntingtin targeting miRNA. Two weeks post-injection, striatal mRNA profiles on the injected and non-injected sides were compared. Data indicate that there were few significant differences in mice treated with the CBA-mirHTT-6433 (FIG. 14A). In mice treated with the AAV9-U6-anti-HTT-6433, both mRNAs that were increased and those that were decreased in response to treatment were observed (FIG. 14B). When the profiles of AAV9-U6-anti-HTT-6433 and AAV9-CBA-anti-HTT-6433 were compared at two weeks, it was observed that only 8 mRNAs were significantly differentially expressed between these two groups. RNAs were sorted according to presence or absence of predicted target sites for the artificial miRNA and plotted the cumulative distribution of changes in mRNAs where the target sites were present or absent. In the mice injected with the AAV-U6-6433, a small shift toward downregulation of genes containing in their 3'-UTRs, perfect 8mer target sites matching the most abundant AAV-derived small RNA species were observed (FIG. 10B). This shift was not apparent in the mice injected with AAV-CBA-6433 (FIG. 10A) nor with any of the other AAV-derived small RNA species (FIGS. 15A-15C).

Example 3: Sheep In Vivo Experiments

A sheep model of human Huntington's disease was used in this example. Briefly, transgenic sheep that express human huntingtin (human htt) protein were produced. Sheep were injected intrastriatally with either scAAV9 CBA-mir-HTT ("CBA Promoter"), scAAV9 U6-mir-HTT ("U6 Promoter"), or empty scAAV9 control vector. Each construct comprises a single copy of the anti-huntingtin mir-6433 sequence (SEQ ID NO: 7) inserted into a mir-155 backbone located within an intron that is between the CBA promoter or the U6 promoter, respectively, and a β-globulin polyadenylation sequence. Constructs used to produce rAAVs administered in this experiment are set forth in SEQ ID NOs: 18 (scAAV9 CBA-mir-HTT) and 19 (scAAV9 U6-mir-HTT).

Sheep were sacrificed at either one month or six months post-injection. Tissue and nucleic acid samples were prepared and analyzed by quantitative PCR and immunohistochemistry.

Figure 16:
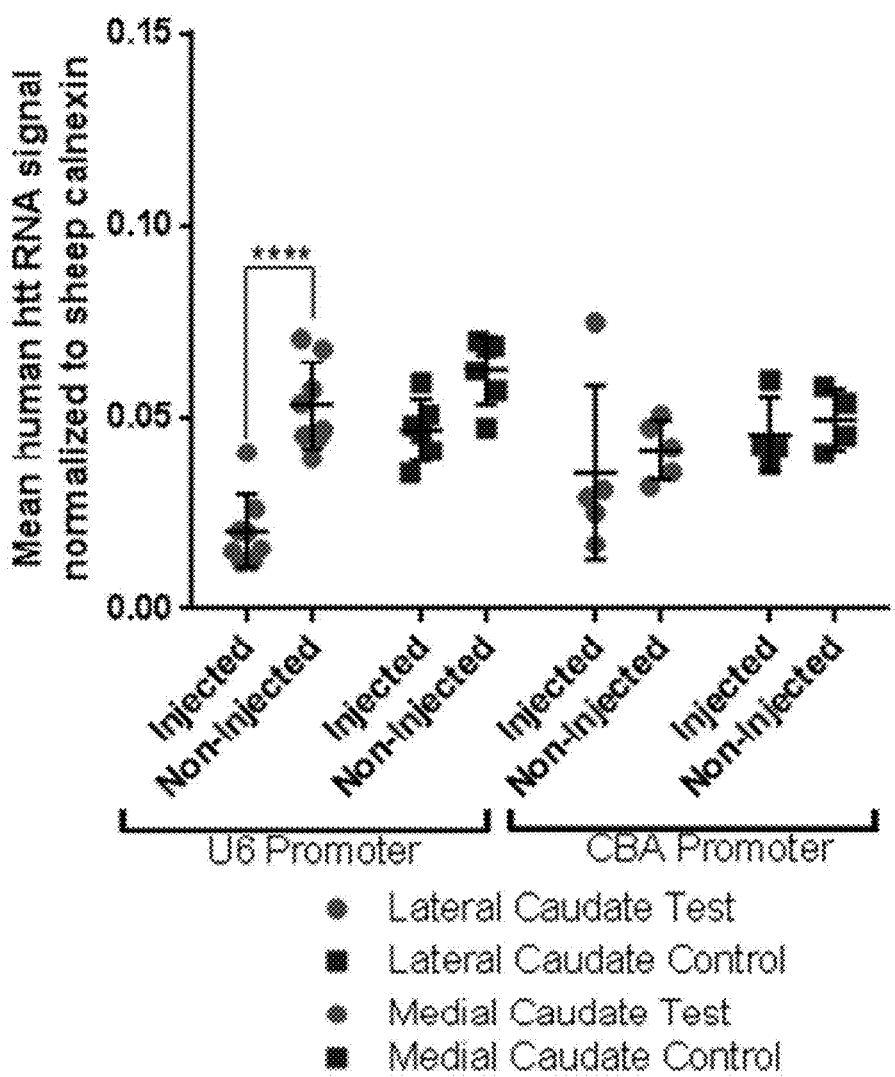
FIG. 16 shows data relating to relative expression of human huntingtin (human htt) RNA in the middle caudate of a sheep model of Huntington's disease one month after intrastriatal injection of either scAAV9 CBA-mir-HTT ("CBA Promoter"), scAAV9 U6-mir-HTT ("U6 Promoter"), or empty scAAV9 control vector. Data for htt expression level in un-injected control sheep is also shown. Relative htt expression levels were normalized to sheep calnexin. Note: a mir155 backbone was used in each of the CBA and U6 constructs.
Figure 17:
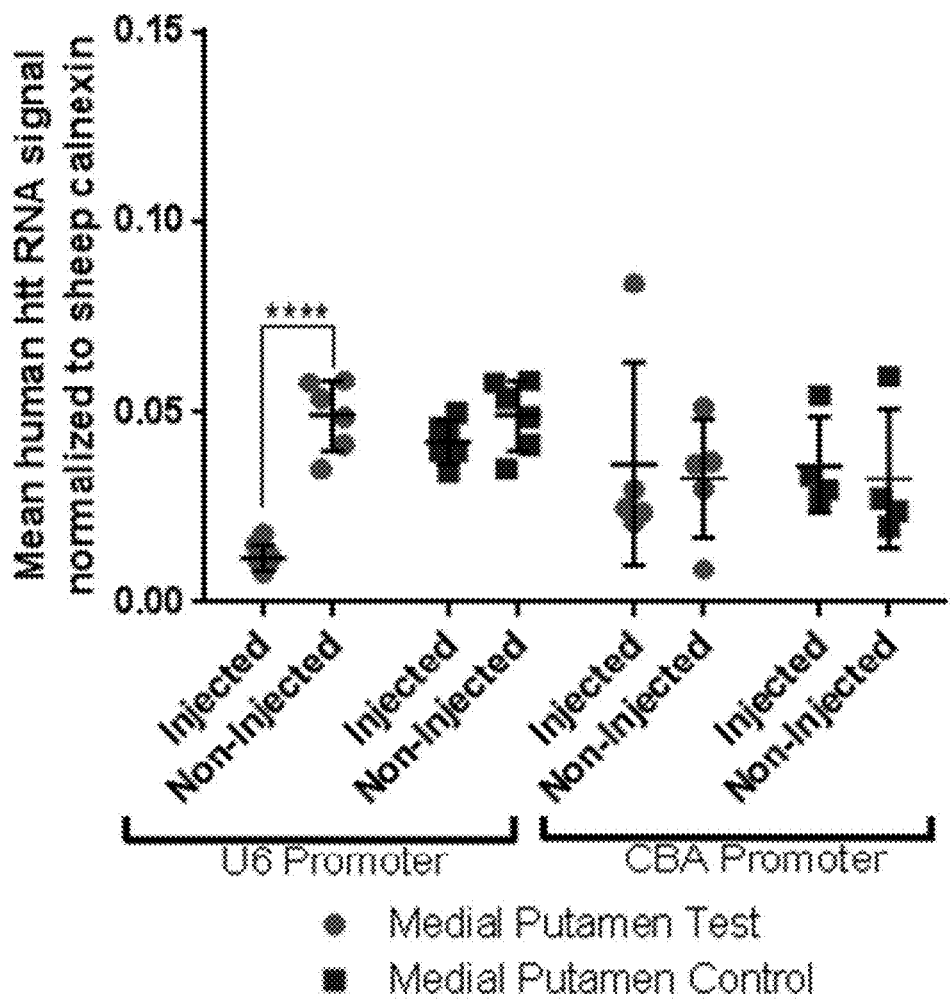
FIG. 17 shows data relating to relative expression of human huntingtin (human htt) RNA in the middle putamen of a sheep model of Huntington's disease one month after intrastriatal injection of either scAAV9 CBA-mir-HTT ("CBA Promoter"), scAAV9 U6-mir-HTT ("U6 Promoter"), or empty scAAV9 control vector. Data for expression level in un-injected control sheep is also shown. Relative htt expression levels were normalized to sheep calnexin.

Data indicate that at the one month time point, injection of mir-HTT expressed under the U6 promoter resulted in a reduction of htt expression in both the middle caudate and middle putamen of sheep when compared to un-injected and empty-scAAV9-injected control mice. FIG. 16 shows data relating to reduction of human htt expression in the middle caudate of sheep one month-post injection of scAAV9 U6-mir-HTT. FIG. 17 shows data relating to reduction of human huntingtin expression in the middle putamen of a sheep model one month post-injection of scAAV9 U6-mir-HTT. Note that unlike the mouse model described in the previous example, the mir-HTT expressed from the U6 promoter was not toxic in the sheep model of Huntington's disease.

Data indicate that at the six month time point, injection of mir-HTT expressed under the CBA promoter resulted in a reduction of htt expression in both the middle caudate and middle putamen of sheep when compared to un-injected and empty scAAV9-injected control mice.

Figure 18:
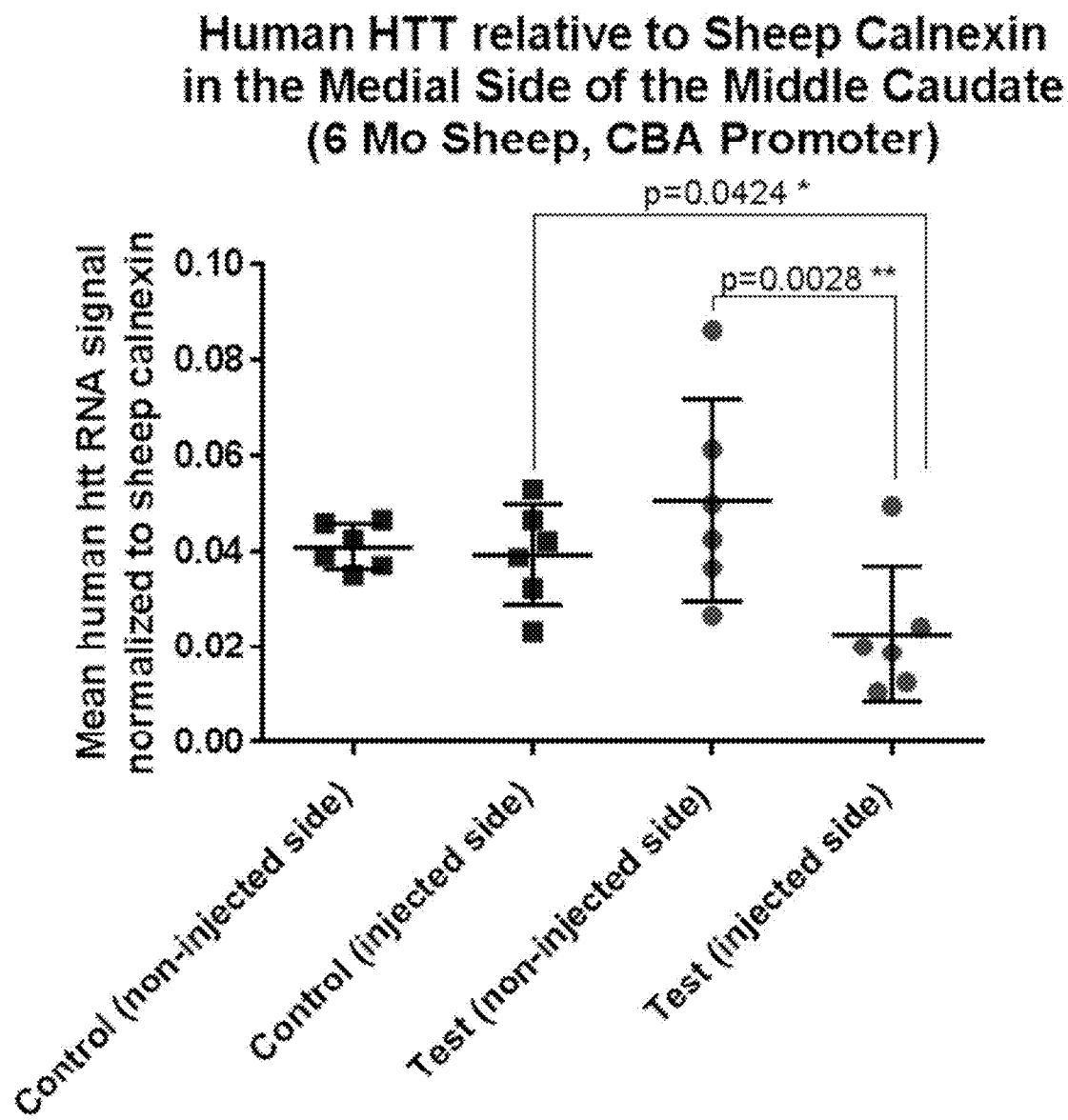
FIG. 18 shows data relating to relative expression of human huntingtin (human htt) RNA in the medial side of the middle caudate of a sheep model of Huntington's disease six months after intrastriatal injection of either scAAV9 CBA-mir-HTT ("CBA Promoter") or empty scAAV9 control vector. Data for expression level in the non-injected side and the injected side are shown. Relative htt expression levels were normalized to sheep calnexin.
Figure 19:
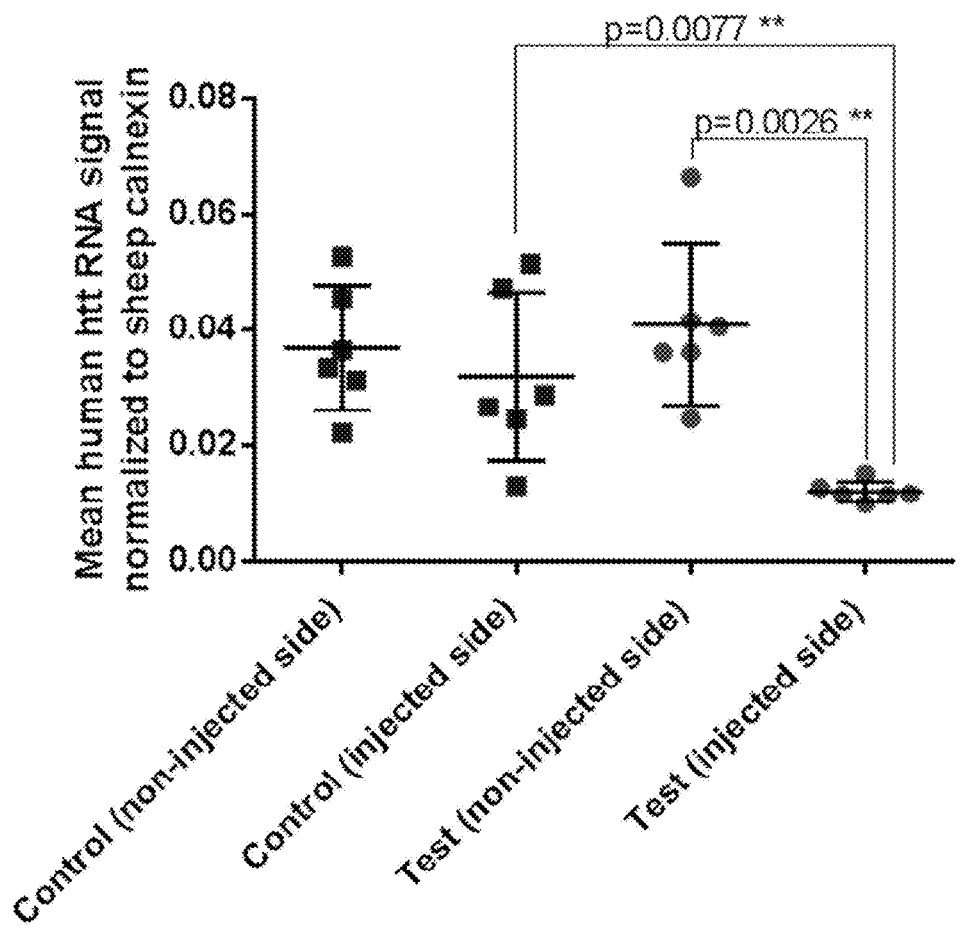
FIG. 19 shows data relating to relative expression of human huntingtin (human htt) RNA in the lateral side of the middle caudate of a sheep model of Huntington's disease six months after intrastriatal injection of either scAAV9 CBA-mir-HTT ("CBA Promoter") or empty scAAV9 control vector. Data for expression level in the non-injected side and the injected side are shown. Relative htt expression levels were normalized to sheep calnexin.
Figure 20:
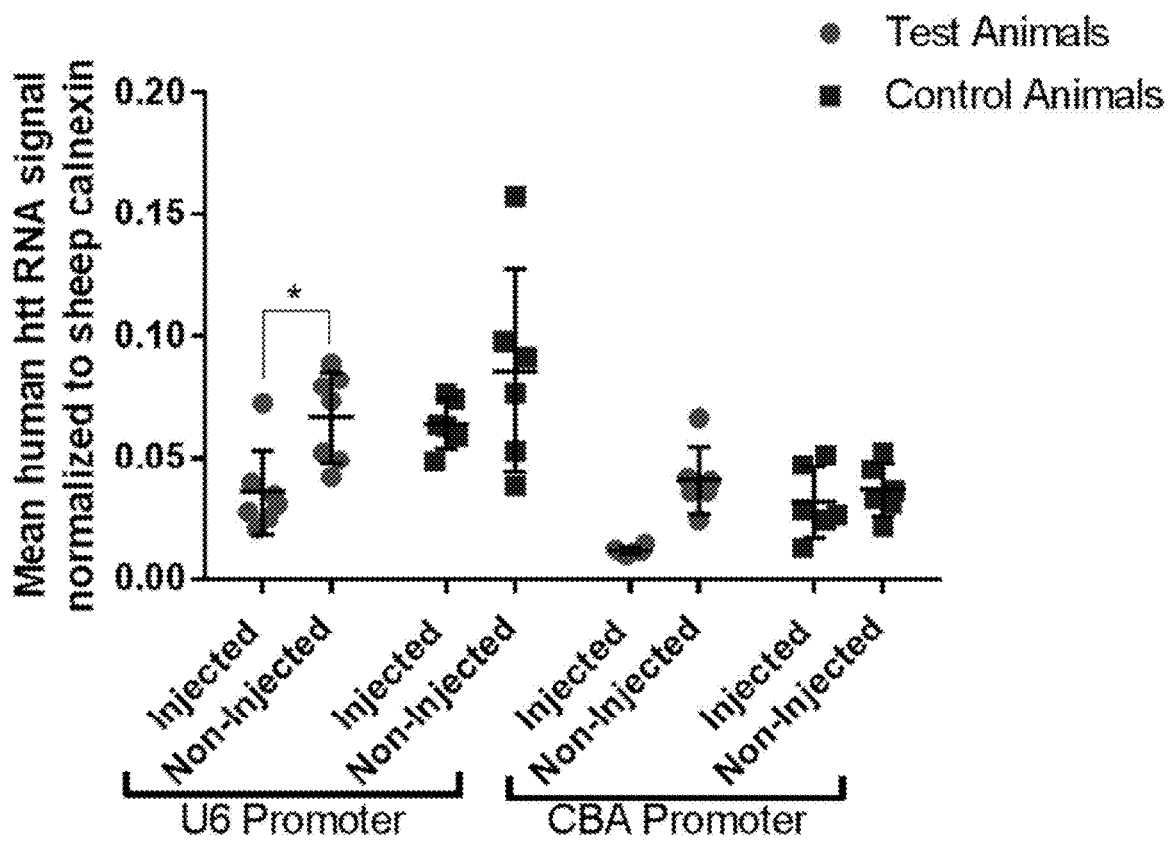
FIG. 20 shows data relating to relative expression of human huntingtin (human htt) RNA in the middle caudate of a sheep model of Huntington's disease six months after intrastriatal injection of either scAAV9 CBA-mir-HTT ("CBA Promoter"), scAAV9 U6-mir-HTT ("U6 Promoter"), or empty scAAV9 control vector. Data for htt expression level in un-injected control sheep is also shown. Relative htt expression levels were normalized to sheep calnexin.

FIGS. 18 and 19 show data relating to reduction of human htt expression in the medial (FIG. 18) and lateral (FIG. 19) sides of the middle caudate of the sheep. Data indicate mir-HTT expressed from a CBA promoter causes a reduction of human htt expression in the injected side of the brain when compared to the non-injected side of the brain and empty scAAV9-injected control mice. The effects of expression of mir-HTT from the CBA and U6 promoters on silencing of htt in the middle caudate was also compared six months post-injection. Data indicates that mir-HTT expressed from either U6 promoter or CBA promoter results in a reduction of human htt expression in the middle caudate when compared to non-injected and empty scAAV9-injected control animals (FIG. 20).

Figure 21:
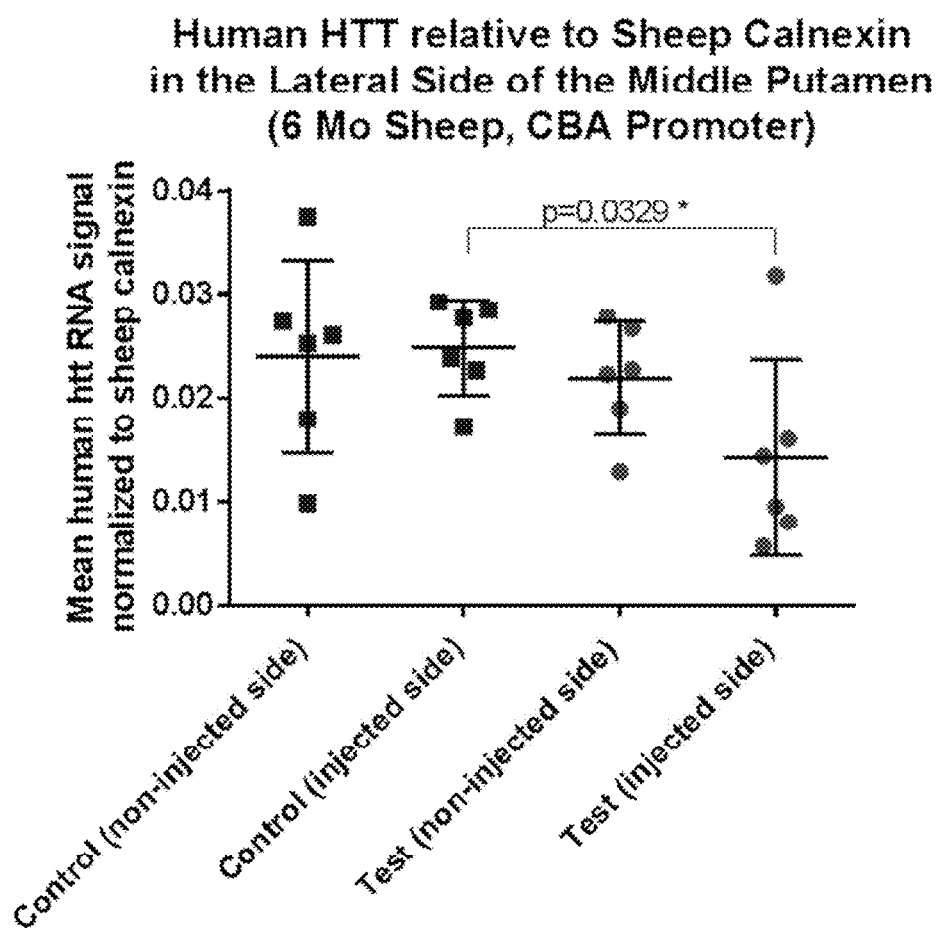
FIG. 21 shows data relating to relative expression of human huntingtin (human htt) RNA in the lateral side of the middle putamen of a sheep model of Huntington's disease six months after intrastriatal injection of either scAAV9 CBA-mir-HTT ("CBA Promoter") or empty scAAV9 control vector. Data for expression level in the non-injected side and the injected side are shown. Relative htt expression levels were normalized to sheep calnexin.
Figure 22:
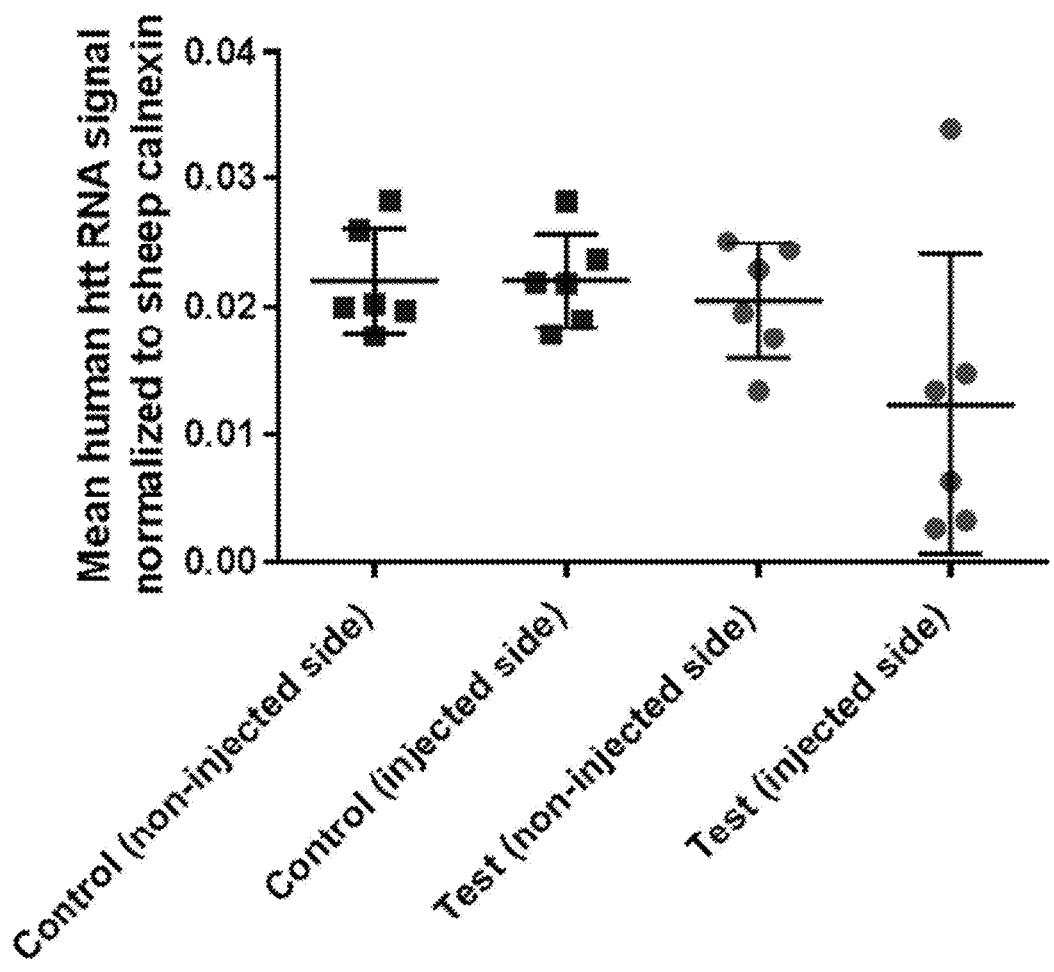
FIG. 22 shows data relating to relative expression of human huntingtin (human htt) RNA in the medial side of the middle putamen of a sheep model of Huntington's disease six months after intrastriatal injection of either scAAV9 CBA-mir-HTT ("CBA Promoter") or empty scAAV9 control vector. Data for expression level in the non-injected side and the injected side are shown. Relative htt expression levels were normalized to sheep calnexin.
Figure 23:
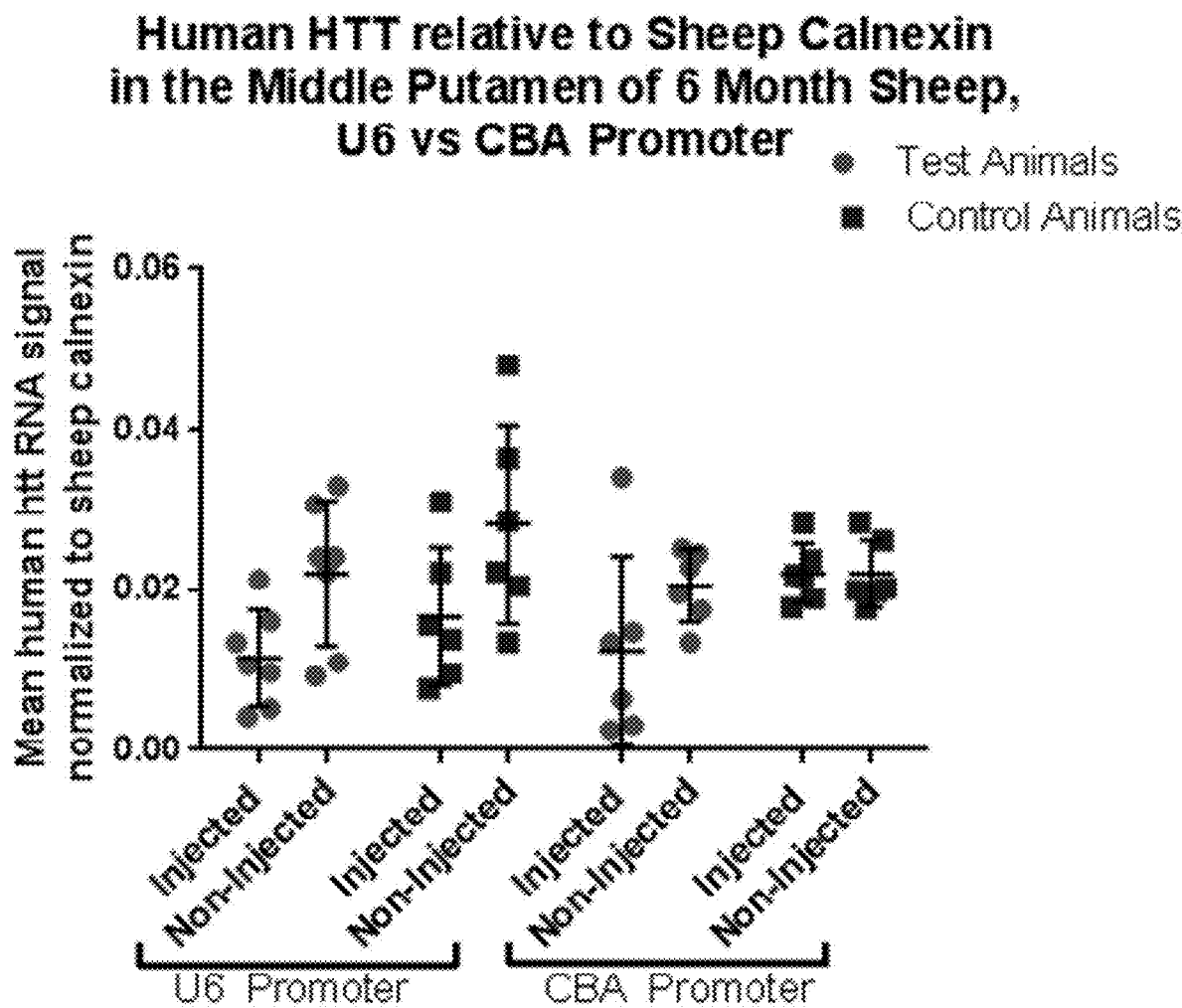
FIG. 23 shows data relating to relative expression of human huntingtin (human htt) RNA in the middle putamen of a sheep model of Huntington's disease six months after intrastriatal injection of either scAAV9 CBA-mir-HTT ("CBA Promoter"), scAAV9 U6-mir-HTT ("U6 Promoter"), or empty scAAV9 control vector. Data for htt expression level in un-injected control sheep is also shown. Relative htt expression levels were normalized to sheep calnexin.

FIGS. 21 and 22 show data relating to reduction of human htt expression in the lateral (FIG. 21) and medial (FIG. 22) sides of the middle putamen of the sheep six months post-injection. Data indicate mir-HTT expressed from a CBA promoter causes a reduction of human htt expression in the injected side of the brain when compared to the non-injected side of the brain and empty scAAV9-injected control mice. The effects of expression of mir-HTT from the CBA and U6 promoters on silencing of htt in the middle caudate was also compared six months post-injection. Data indicates that mir-HTT expressed from either U6 promoter or CBA promoter results in a reduction of human htt expression in the middle putamen when compared to non-injected and empty scAAV9-injected control animals (FIG. 23).

Figure 24:
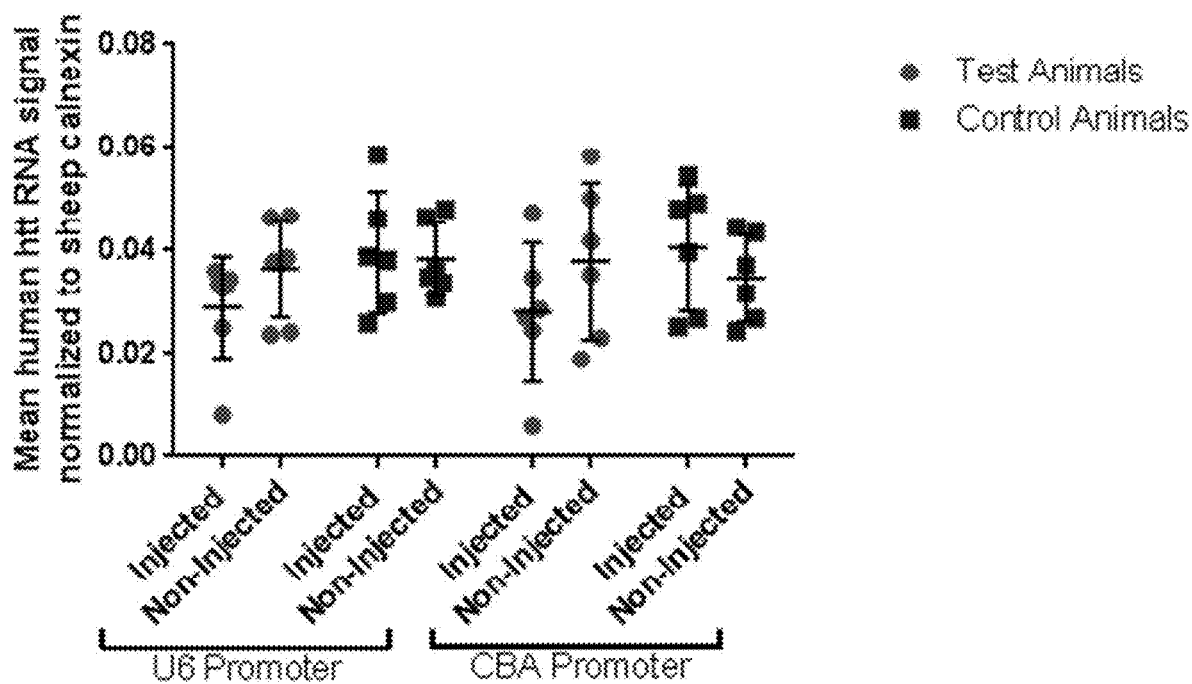
FIG. 24 shows data relating to relative expression of human huntingtin (human htt) RNA in the anterior striatum of a sheep model of Huntington's disease six months after intrastriatal injection of either scAAV9 CBA-mir-HTT ("CBA Promoter"), scAAV9 U6-mir-HTT ("U6 Promoter"), or empty scAAV9 control vector. Data for htt expression level in un-injected control sheep is also shown. Relative htt expression levels were normalized to sheep calnexin.

FIG. 24 shows data relating to relative expression of human huntingtin (human htt) RNA in the anterior striatum of a sheep model of Huntington's disease six months after intrastriatal injection of either scAAV9 CBA-mir-HTT ("CBA Promoter"), scAAV9 U6-mir-HTT ("U6 Promoter"), or empty scAAV9 control vector.

Example 4: Artificial miRNAs Reduce Human Mutant Huntingtin Throughout the Striatum in a Transgenic Sheep Model of Huntington's Disease Animals and Animal Procedures Merino sheep were used in this example. Prior to the administration of anesthetic, the animals were fasted overnight for approximately 8 hours. Animals were given a pre-operative physical including heart rate, respiratory rate, temperature and weight. Baseline samples of serum (5 ml) and CSF were collected.

The study was conducted in two parts with two different cohorts of sheep. For the first study, forty-one transgenic animals (21 Wethers, 20 Ewes), aged approximately 8 months were injected unilaterally with 300 µl of self-complementary AAV9 (scAAV9) vector at a titer of $1 \times 10^{13}$ gc/ml for a total of $3 \times 10^{12}$ genome copies. For the second study, fourteen animals aged 14 months were injected with this vector and fourteen with the control vector. Gadolinium was added to the vector formulation to allow post-surgical imaging of the injection spread. The animals were moved to the operating room and prepped for surgery. They were rested in the sphinx position on a foam cushion on folded extremities or with extremities dangling. A stereotactic frame (Kopf, large animal) was used to hold the animal's head in place. Cerebrospinal fluid was collected via lumbar puncture using a 19 gauge spinal tap cannula. The rAAV was delivered directly to the striatum, targeting the internal capsule. The animal's head was shaved, prepped with betadine, and draped with clear plastic. A curvilinear incision was made using a #15 scalpel to expose the bregma. Once the bregma was identified, a 3-4 mm burr hole was placed 10 mm rostral to the bregma and 11 mm lateral of the midline using an electric drill. The convection enhanced delivery (CED) cannula (MRI Interventions, Irvine, Calif.)

was secured in the manipulator and primed with agent to be injected to remove air from the line. The dura was opened with a 1.5 mm incision using a #11 scalpel and the CED cannula was advanced 25 mm from dural surface to the target depth. The outer cannula (1.65 mm) sealed the dural incision to prevent CSF leakage during the infusion. The infusion began 5 minutes after cannula insertion to allow for tissue around the tip to stabilize. The infusion rate was set at 3.33 µl/minute until a total volume of 300 µl was injected. Ten minutes after infusion was completed the cannula was slowly withdrawn and a bone wax plug was used to repair skull and prevent CSF leakage. The wound was cleansed with saline and closed using a 3.0 vicryl suture. Standard anesthesia wake-up and recovery procedure was followed. Post-surgery MRI was performed to determine the spread of gadolinium. One animal from the first study was excluded following surgery because no gadolinium was visible upon imaging and a second animal from the second study was excluded because the gadolinium appeared to be primarily in the ventricle. After the surgery, the animals were kept under observation for three days and housed indoors for 5. They were then transferred outdoors and house outdoors in paddocks for the remainder of the study. Animals were monitored visually for signs of distress and changes in behavior throughout the study. Two animals suffered surgical complications, resulting in partial limb paralysis. This was thought to be due to the positioning of the animals under anesthesia. One was anesthetized early and one was moved from the six month to the one-month cohort. Animals were weighed periodically throughout the post-injection period and samples of cerebrospinal fluid, blood and serum were taken and saved for further analysis.

For cell counts and differentials, blood was collected via jugular venipuncture into a potassium EDTA blood collection tube (Lavender top; LT) and a complete blood examination with differential (CBE differential) was performed. For clinical chemistry, blood was collected via jugular venipuncture into a serum collection tube (red top; RT). The samples were submitted for multiple biochemical analysis (MBA).

At one and six-months post-injection animals were harvested, with animals being used for either histology or biochemical analysis. Animals were transported to operating table and placed in ventral recumbency while approximately 6 mL of CSF was collected. The animal was repositioned in dorsal recumbency. The carotid arteries were exposed and cannulated at a depth of 4 cm from the tip of the cannula. The jugular veins were exposed and 200-500 U Heparin/kg were injected into the jugular vein. Five minutes after administering the Heparin, sheep were euthanized by intravenous injection of Lethabarb (325 mg pentabarbitone sodium/ml) at 1 ml/2 kg of body weight. The infusion pump was primed with cold 9% NaCl and connected to the carotid cannulas. The animal was perfused with approximately 8 L of cold 9% NaCl at a pressure of 500 mmHg. For histology, the infusion was switched to 8 L 4% paraformaldehyde at a pressure of 500 mmHg. The brain and liver were extracted. The tissues were post-fixed in 4% paraformaldehyde for 24 hours at 4° C. and transferred to 30% sucrose in 1X phosphate buffered saline for a minimum of 14 days at 4° C.

For RNA, protein, and DNA assays, sheep were perfused with cold 9% NaCl as described above. Collection of the peripheral tissue was performed in the following order: liver, adrenal gland, ovaries (if applicable), muscle, and heart. Cross contamination was prevented by the use of different instruments and washing necropsy surfaces with 10% bleach and 70% ethanol. The organ was removed from the body and a 3 mm biopsy punch was used to collect samples. A total of ten samples were collected from each organ; two samples were snap frozen in liquid nitrogen and eight samples were stored in RNA later at 4° C. for 24 hours (300 µl of RNA later for liver, muscle and heart samples, 500 µl of RNA later for adrenal gland and ovary samples).

The brain was removed from the skull using a circular saw and bone forceps. After extraction, the brain was weighed and placed ventrally in a custom made plexiglass brain matrix. Nine cuts were made to the brain to fully contain the striatum in 4 6 mm blocks. The first cut was made posterior to the olfactory bulb attachment (approximately 18 mm from the beginning of the matrix) and the subsequent four cuts were made at 6 mm intervals. The striatum was divided into four 6 mm blocks from posterior to anterior: 2p (posterior), 2 m1 (medial 1), 2m2 (medial 2) and 2a (anterior). The striatal dissection was performed in the following order: 2p, 2 m1, 2a. The striatum in the right (non-injected) hemisphere was dissected first in all blocks and scalpel blade was changed between hemispheres. The dissection was performed in a petri dish on dry ice and care was taken to remove as much white matter from the striatal tissue as possible. Once dissected out, the striatal pieces (caudate and putamen) were split in half; with the medial piece (closest to midline of block) was stored in 1 ml of RNA later at 4° C. and the lateral piece was snap frozen in liquid nitrogen. The striatal dissection for the 6 month cohort in the CBA study was done in a manner to produce four striatal samples from both the caudate and putamen. The dorsal sections (both medial and lateral) were snap frozen in liquid nitrogen and the ventral sections (both medial and lateral) were stored in 1 ml of RNA later at 4° C. RNA later was removed after twenty four hours and samples were stored at −80° C.

The 2m2 block was generously covered with OCT and frozen in a 2-methylbutane and dry ice bath. The remainder of the 2a, 2 m1, and 2p block was frozen in the same manner. Ten cortex samples were taken from each block in a dorsal to ventral manner; two were snap frozen in liquid nitrogen and eight were stored in 1 ml RNA later at 4° C.

Sectioning of Tissue for Histological Analysis

Prior to tissue sectioning for histological analysis the striatum was isolated from the brain, generously covered with OCT, and stored at −20° C. for twenty four hours. Coronal sections measuring 40 µm thick were cut with a sliding microtome (Reichert-Jung Tetrander sliding microtome) through the entire striatum. The sections were stored in 0.01% sodium azide in 1X phosphate buffered saline at 4° C.

Vector Cloning and rAAV9 Production

For the first study, the test vector contained a U6 promoter driving an artificial miRNA based on the endogenous mir155 backbone (AAV9-U6-miR$^{HTT}$). The artificial miRNA targets human, but not the sheep huntingtin. A chimeric cytomegalovirus enhancer/chicken β-actin (CBA) promoter driving a chimeric intron was included to improve AAV packaging. The control vector (AAV9) contained only the empty CBA promoter and the intron. For the second study, the test vector contained the CMV enhancer and CBA promoter, the intron and the miRNA-155 based artificial miRNA (AAV9-CBA-miR$^{HTT}$).

For packaging, the rAAV vector plasmid, a packaging plasmid and an adenovirus helper plasmid are co-transfected into HEK 293 cells. The packaging plasmid expresses the regulatory and AAV9 capsid proteins leading to excision, replication and packaging of the recombinant genome from the rAAV vector plasmid into AAV virions. The recombinant viruses are purified by standard CsCl gradient sedimentation and desalted by dialysis.

Analysis of Huntingtin mRNA Levels

The RNA levels in the RNA later preserved samples were analyzed using a branched DNA assay (bDNA). Samples were processed according to the manufacturer's guidelines for preparation of tissue homogenates from tissues stored in RNA later (Affymetrix eBioscience, Quantigene® Sample Processing Kit). The homogenized samples were analyzed according to the manufacturer's guidelines for the bDNA assay (QuantiGene® 2.0 Reagent System). The samples were analyzed with a probe to detect human huntingtin (Human HD, SA-50339 from Quantigene), ovine huntingtin (Sheep Huntingtin, SF-10586 from Quantigene), and ovine calnexin as a housekeeping gene (Sheep Calnexin, SF-10622 from Quantigene). The assay results were measured with a Tecan Infinite M1000 PRO luminometer (integration time set at 200 ms).

Analysis of miR-Htt levels

Biopsy punches (2 mm) were sampled from the lateral caudate and the medial putamen, from frozen blocks. The RNA extractions were performed using the TRIzol manufacturer's guidelines (Ambion) with some modifications made. After the phase separation in the TRIzol extraction, the aqueous phase was transferred to RNA Clean & Concentrator (Zymo) column and that protocol was followed. RNA was stored at −80° C. until analysis. RNA quality and concentration were determined on a Fragment Analyzer (Advanced Analytical Technologies Inc.). Immediately prior to analysis, the RNA was diluted to 20 ng/μl. Artificial miRNA guide strands were retro-transcribed using the TaqMan MicroRNA Reverse Transcription Kit (Cat #4366596, Thermo Scientific), 2 μl of RNA and guide strand specific stem-loop primers (ThermoFisher custom assay targeting UAAGCAUGGAGCUAGCAGGCU (SEQ ID NO: 25) or assay id 002407, let-7e*), according to the manufacturer's instructions. ddPCR reactions were setup using 50 of RT products, a 1× concentration of the miR-Htt assay and a 0.3× concentration of the let-7e* assay to allow for multiplexing. Droplets were generated with a QX200 Droplet Generator (Cat #1864002, Biorad), and monitored for positive signal following endpoint PCR amplification (40 cycles). Relative expression of miR$^{HTT}$ was determined by calculating the ratio between absolute concentrations of miR$^{HTT}$ and let-7e*.

Vector Genome Distribution

Genomic DNA was extracted from samples that had been snap frozen in liquid nitrogen using the Gentra Puregene Tissue kit (Qiagen). The genomic DNA concentrations were measured using the NanoDrop ONE$^c$ spectrophotometer. Droplet Digital PCR (ddPCR, Biorad) was performed according to the manufacturer's recommendations, using 50 ng of DNA as input and TaqMan assays detecting the vector-specific CB and U6 promoter and the HPRT reference gene. Results are expressed as vector genome per diploid genome (vg/dg).

Analysis of Huntingtin Protein Levels—Mesoscale Detection Assay (MSD) for mHTT

Striatal samples were homogenized in buffer composed of 10 mM HEPES, 250 mM sucrose, 1 mM EDTA and protease inhibitors (Roche) and sonicated 10 s at 10% amplitude. Protein concentration was measured using Bradford assay. A 96-well QuicPlex standard plate (MSD) was coated with rabbit monoclonal anti-HTT proline 1220 region antibody (D7F7, Cell Signaling, 1:250) in PBS, overnight at 4° C. The plate was washed 3×10 min with PBST (PBS+0.05% Tween20) and blocked with 3% bovine serum albumin (BSA) in PBS for 2 hours at RT. After washing 3×10 min with PBST, technical duplicates of samples with 20 μg of protein in 25 μL of homogenization buffer or blanks (homogenization buffer) were distributed into the plate and incubated overnight at 4° C. on an orbital shaker. The plate was washed 3×10 min in PBST and incubated in secondary/detection antibody mix as follows: For detection of mHTT, mouse monoclonal anti-polyQ antibody MW1 (DSHB) was mixed with anti-mouse SulfoTag detection antibody (MSD) at 1 μg/mL of each antibody in 1% BSA in PBS. 30 μL of detection antibody mix was applied per well and incubated for 3 hours at RT on an orbital shaker. The plate was washed 3×10 min in PBST and 150 μL of 2× Read Buffer (MSD) was applied per well right before readout on QuickPlex SQ120 (MSD).

Western Blotting

Small pieces of tissue were removed from frozen blocks and homogenized on ice in 200 μl mM HEPES pH7.2, 250 mM sucrose, 1 mM EDTA+protease inhibitor tablet (mini, complete, EDTA-free Roche #11836170001). Samples were sonicated for 10 seconds and protein concentration was determined using the Bradford method (BioRad #500-0006). Equal concentrations of protein (25 μg) were separated by SDS-PAGE on 3-8% Tris-Acetate gels (Life Technologies #EA03785BOX) and transferred to nitrocellulose using TransBlot Turbo (BioRad). Blots were blocked in 5% non-fat dry milk in Tris-buffered saline+0.1% Tween-20 (TBST) for 1 hour and incubated overnight in primary antibody at 4° C. diluted in blocking solution. Primary antibodies used were: anti-poly-Q (MW1, Coriell, 1:500 or 3B5H10, Sigma, 1:1000), anti-huntingtin (MAB2166, EMD Millipore, 1:1000 or Abl, DiFiglia et al., 1995, 1:1000), anti-DARPP32 (#ab40801, Abcam, 1:10,000), anti-actin (A4700, Sigma, 1:1000), and anti-spectrin (MAB1622, EMD Milliopore, 1:4000). Blots were washed in TBST, incubated in peroxidase labeled secondary antibodies diluted 1:5000 in blocking solution for 1 hour at room temperature, washed in TBST and incubated in SuperSignal West Pico Chemiluminescent Substrate (Pierce #34080). Images were obtained with a CCD imaging system (Alpha Innotech) and Hyperfilm ECL (GE Healthcare). Densitometry was performed on the digital images using ImageJ software (NIH). Statistical analysis was performed using upaired t-tests and results were expressed as mean value for the injected side.

Immunohistochemistry for DARPP32, NeuN, and Iba1

To quantify the DARPP32 positive cells, every twentieth section was incubated for three minutes in 3% hydrogen peroxide in 1×PBS, twenty minutes in 0.5% Triton-X-100, and then four hours in 1.5% normal goat serum (Vector Labs, S-1000) in 1×PBS. Sections were incubated in anti-DARPP32 (AbCam, ab40801, 1:1,000 dilution) in 1.5% normal goat serum overnight at 4° C. Sections were then incubated in biotinylated goat, anti-rabbit IgG antibody (Vector Labs, AP-1000, 1:200 dilution) in 1×PBS for 10 minutes. The sections were incubated with 2% Elite A and 2% Elite B reagent from the Vectastain Elite ABC Kit (Vector Labs, PK-6100) in 1×PBS for five minutes. The Metal Enhanced DAB kit (ThermoFisher Scientific, 34065) was used to visualize the DARPP32 positive cells. The sections were incubated in 1×3, 3'-diaminobenzidine in stable peroxide buffer.

To quantify the NeuN positive cells, every twentieth section was incubated for three minutes in 3% hydrogen peroxide in 1×PBS, twenty minutes in 0.5% Triton-X-100, and then overnight in 1.5% normal goat serum (Vector Labs, S-1000) in 1×PBS at 4° C. overnight. The sections were incubated in anti-NeuN (Chemicon, MAB377, 1:1,000 dilution) in 1.5% normal goat serum for one 30 hour at 4° C. The sections were then incubated for 40 minutes in a fluorescent AF594 goat, anti-mouse IgG (ThermoFisher Scientific, A-11005, 1:2,000 dilution) to visualize the NeuN positive cells.

To quantify the Iba1 positive cells, every twentieth section was incubated for one hour in a solution of 5% normal goat serum (Vector Labs, S-1000), 1% bovine serum albumin (Sigma, A-3059), 0.2% Triton-X-100, and 0.03% hydrogen peroxide in 1×PBS. The sections were incubated in anti-Iba1 (Wako Chemicals, 019-19741, 1:1,000 dilution) in 5% normal goat serum (Vector Labs, S-1000) and 1% bovine serum albumin (Sigma, A-3059) at 4° C. overnight. Sections were incubated biotinylated goat, anti-rabbit IgG antibody (Vector Labs, AP-1000, 1:200 dilution) in 1×PBS for ten minutes. The sections were incubated with 2% Elite A and 2% Elite B reagent from the Vectastain Elite ABC Kit (Vector Labs, PK-6100) in 1×PBS for five minutes. The Metal Enhanced DAB kit (ThermoFisher Scientific, 34605) was used to visualize the reaction by incubating section in 1×3',3-diaminobenzidine in stable peroxide buffer.

The quantification of DARPP32 and Iba1 positive cells in the left and right hemisphere of the brain was done by taking images (20× for DARPP32 and 40× for Iba1) with a Nikon Eclipse E600 microscope of each section. In order to consistently capture images between different sections, the first image was captured in the medial, dorsal edge of the striatum and the stage was moved 0.5 cm toward the ventral edge. Once the ventral edge was reached, the stage was moved 0.5 cm laterally and 0.5 cm dorsally until ten images were captured. Random numbers were assigned to each image to eliminate bias when quantifying cells. The cells were counted using ImageJ software (NIH).

The quantification of NeuN positive cells was performed using the Nikon Eclipse E600 with a Chiu Technical Corporation Mercury 100-W lamp at 60×. The stereological method used for capturing DARPP32 and Iba1 images was also used to quantify the NeuN positive cells. The area of the striatum, caudate, and putamen for each section was measured by manually circling the DARPP32 stained regions using ImageJ software (NIH) on the injected and non-injected sides of every 20th section through the striatum (29-35 sections per side per animal). The observer was blinded to the conditions. Total volume for each region was determined by multiplying the area by the section thickness (40 microns) by the number of sections between slides (20) and adding together for each animal. Statistical analysis was performed using Microsoft excel, paired and unpaired t-tests, N=3 or 4 animals per group.

Vector Genome and miRNA Distribution Following Injection

Silencing of an expanded mouse huntingtin in a knock-in model of HD and of the human mHTT transgene mRNA in a transgenic mouse model of HD have been observed. In this example, two cohorts of HD sheep (study 1 and study 2) were unilaterally injected the striatum. In study 1, the sheep were injected at 8-9 months of age with scAAV9-U6-miR$^{HTT}$ (AAV9miR$^{HTT}$) or scAAV9-CBA-empty (AAV9) where a non-coding stuffer sequence is inserted between the promoter and the poly-A signal. In study 2 the sheep were injected at 14 months of age with scAAV9-CBA-miR$^{HTT}$ or scAAV9-CBA-empty (AAV9). The brains were harvested one and six months after AAV9-miR$^{HTT}$ administration.

Figure 26A:
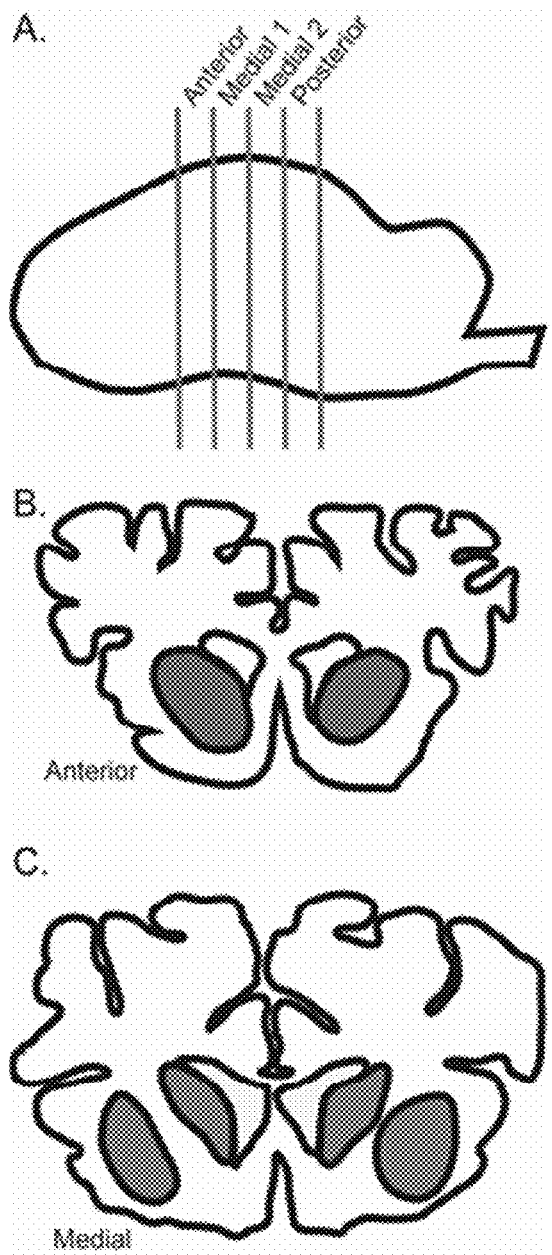
FIGS. 26A-26B show delivery of AAV vectors to sheep brain.
Figure 26B:
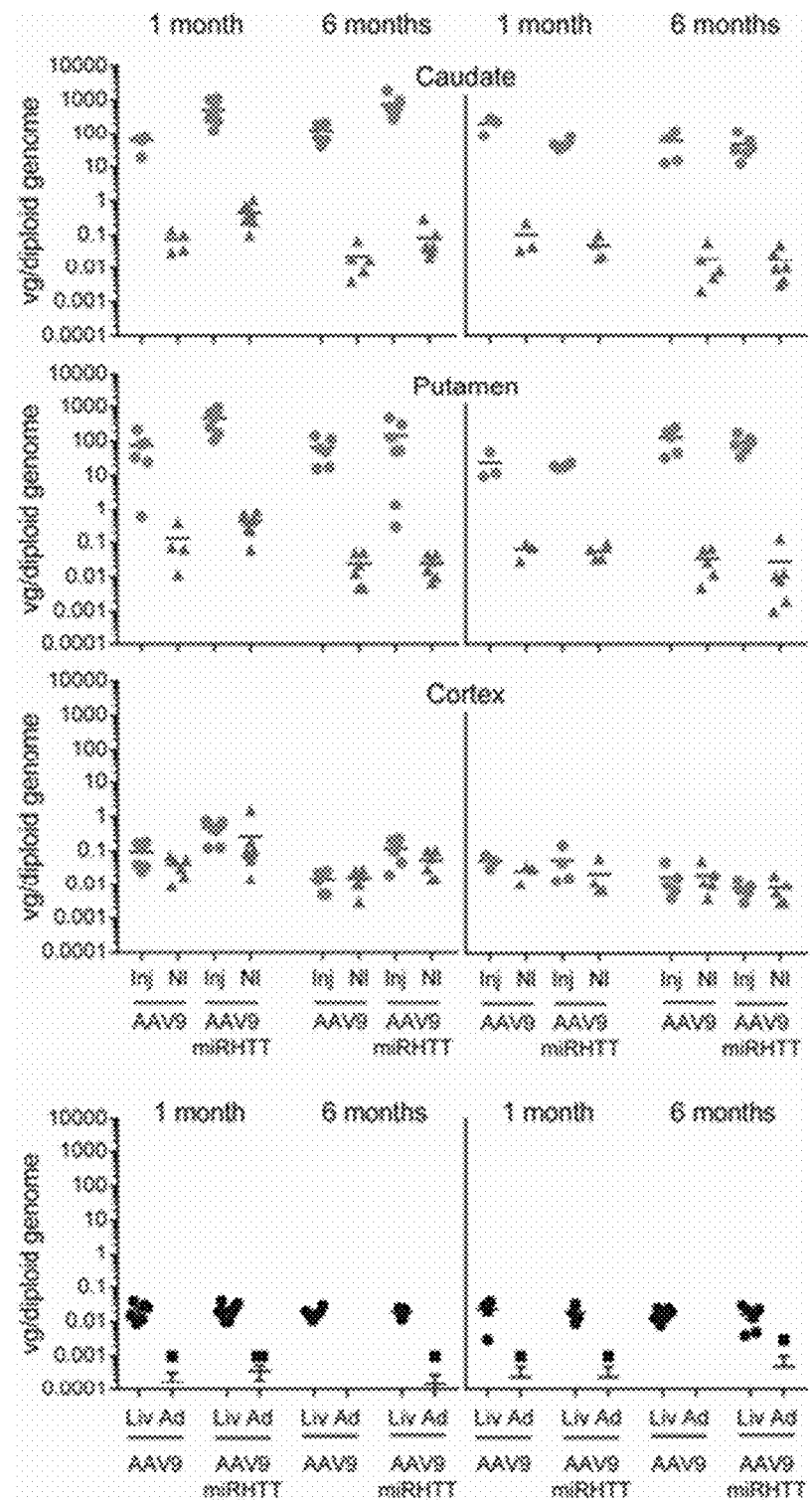

Genome copies were determined in a subset of regions (FIG. 26A) by droplet digital PCR (ddPCR, FIG. 26B). The genome copies were highest in the caudate and putamen on the injected compared to the non-injected side and were at the highest levels in the scAAV9-U6-miR$^{HTT}$ treatment groups at 1 and 6 months post-injection. Small amounts of vector genome were present in the cortex and liver, but were undetectable in the adrenals (FIG. 26B).

Figure 27:
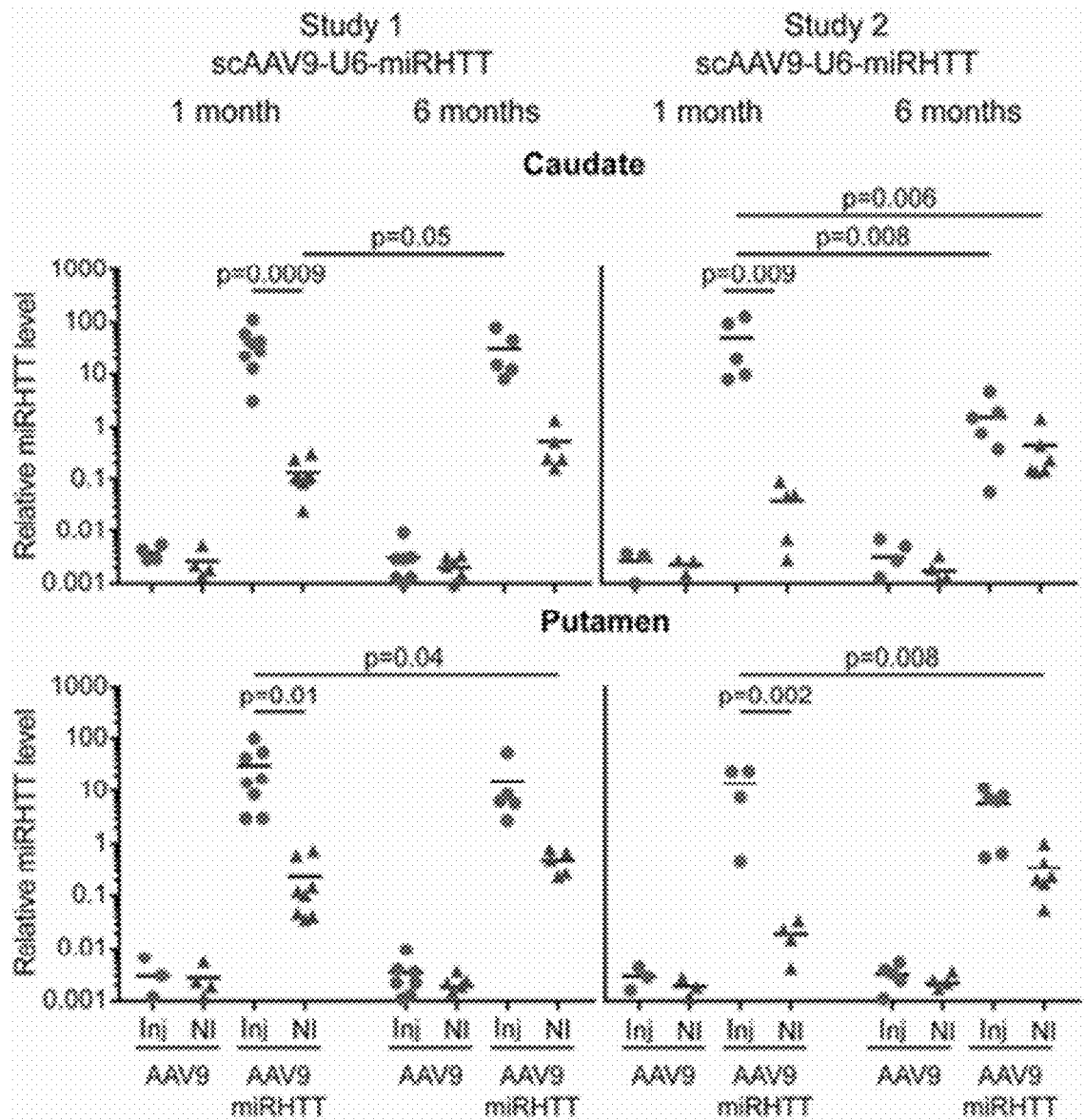
FIG. 27 shows the artificial miRNA guide strand was quantified by digital droplet PCR. Relative miRNA levels were calculated by normalizing to let-7e*, and this value was plotted on a log scale. Samples with RQN<5 were excluded. The number reported is the total number of samples that survived this quality threshold and were used in the miRNA analysis. P values were calculated using 2-way ANOVA with Tukey's correction for multiple testing.

RNA quality was measured using the fragment analyzer, which generates a score, called the RNA Quality Number (RQN). The RQN is generated by analyzing the electropherogram and integrates a number of different measures of RNA integrity, such as ratio between the 28S and 18S ribosomal peak sharpness and baseline. Scores generally range from 0 (completely degraded) to 10. Samples with scores greater than 5 were used to analyze the levels of artificial miR guide strand. Two animals from study 1 and two from study 2 were excluded from the analysis due to low RQN scores. The levels of the artificial miRNA guide strands were measured using ddPCR and normalized to the endogenous let7e* (FIG. 27). The relative quantity of artificial miR antisense strand was 3.5-1000 fold higher on the injected side than the non-injected side and higher at one month compared to six months post-injection. miRNA guide strands were detected at low levels on the side contralateral to injection with AAV9-miR$^{HTT}$.

Figure 28:
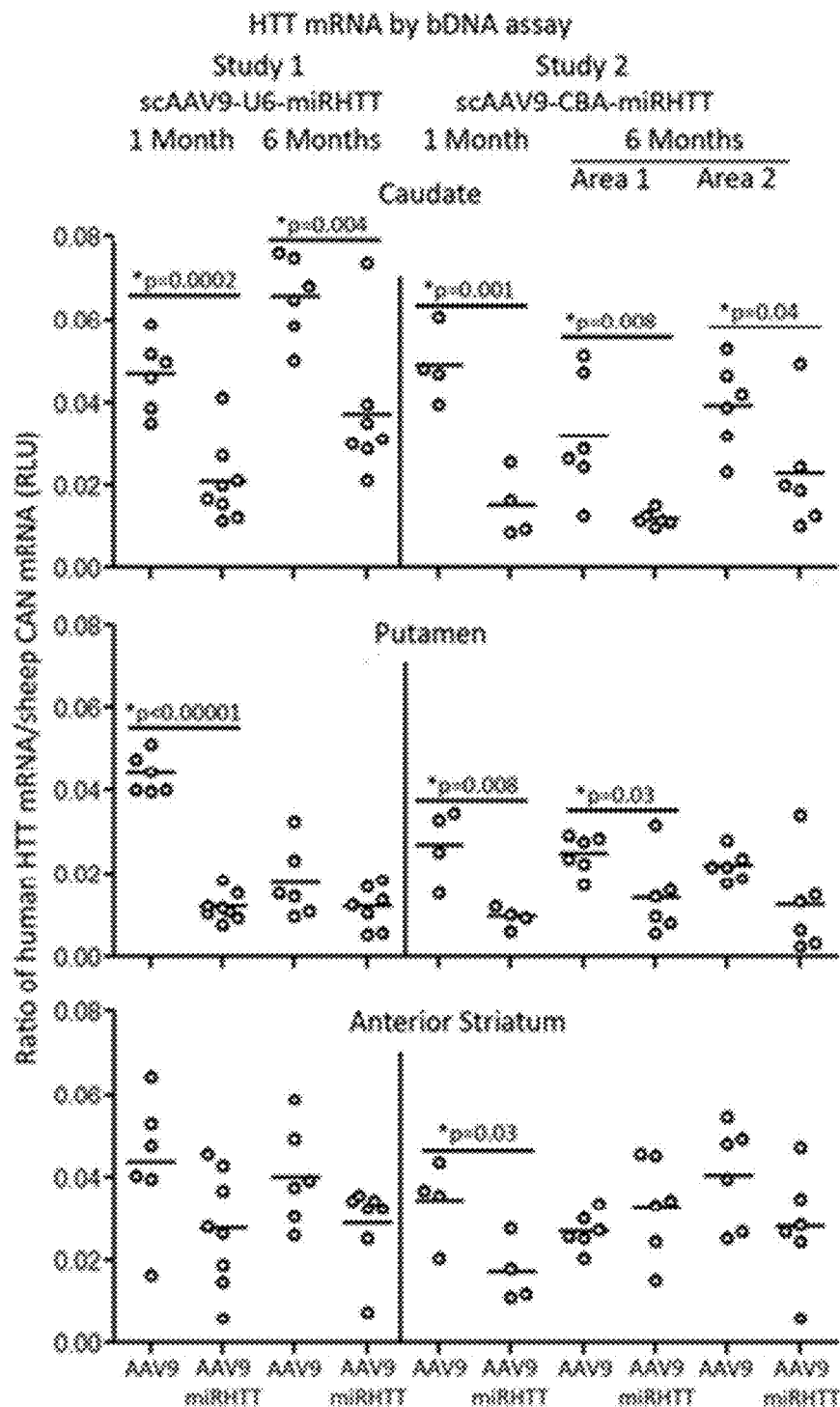
FIG. 28 shows scAAV9-anti-HTT-6433 reduces human mutant huntingtin mRNA in the striatum. Data shown are the signal for HTT mRNA normalized to sheep calnexin. Asterisks indicate significant differences in means between treatment groups (AAV9 or AAV9miRHTT) at p, 0.03 or less with unpaired t-tests. The U6-promoter driven artificial miRNA significantly lowers human mutant HTT mRNA caudate and putamen at 1 month post-injection and in putamen at 6 months post-injection. The CBA-promoter driven artificial miRNA lowers the HTT mRNA in the caudate, putamen and anterior striatum at 1 month post-injection and in the caudate and putamen at 6 month post-injection. The medial region of the caudate, lateral putamen and anterior striatum were examined in the analysis.
Figure 29A:
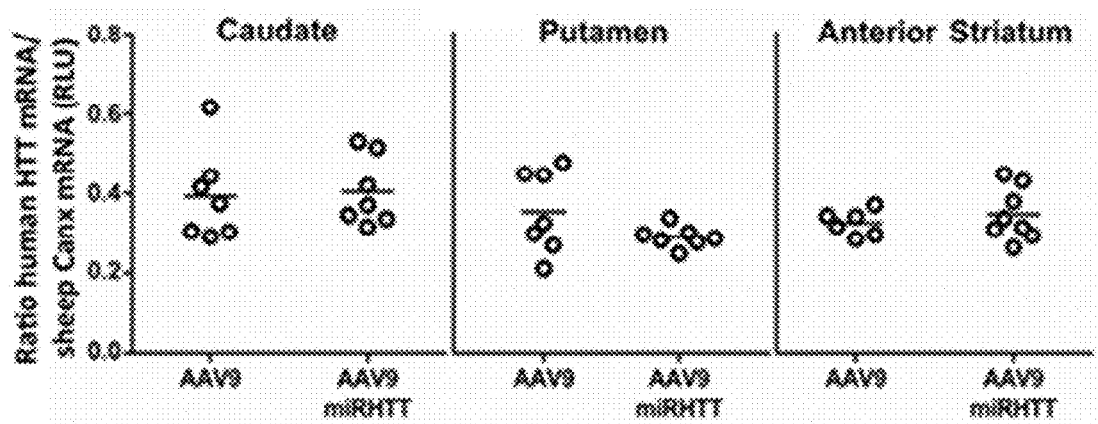
FIGS. 29A-29B show levels of endogenous sheep htt mRNA and protein in AAV9 and AAV9miRHTT treated sheep.

A Single Administration of scAAV9-miR$^{HTT}$ Long-Term Reduces the Human Mutant Huntingtin mRNA in Caudate and Putamen HTT mRNA in the anterior and medial striatum was measured using a branched DNA (bDNA) assay that specifically recognizes human and not sheep HTT mRNA. This assay does not require RNA isolation and all samples were included in the analysis. At one-month post-injection, closest to the injection in the medial block, scAAV9-U6-miR$^{HTT}$ (study 1) reduced human HTT mRNA by more than 50% in both the caudate and putamen (FIG. 28). No significant silencing was detected in the anterior striatum, which was farther from the injection site (FIG. 28). At six-months post-injection, mRNA silencing was pronounced in the caudate (FIG. 28). In the scAAV9-CβA-miR$^{HTT}$ cohort (study 2), marked silencing of HTT mRNA occurred in the medial putamen, medial caudate and anterior striatum (FIG. 28) at one month and in the medial caudate and part of the medial putamen (FIG. 28) at six-months post-injection. The anterior striatum did not show significant lowering at six months. There was no significant silencing of the endogenous sheep HTT mRNA (FIG. 29A).

Figure 30:
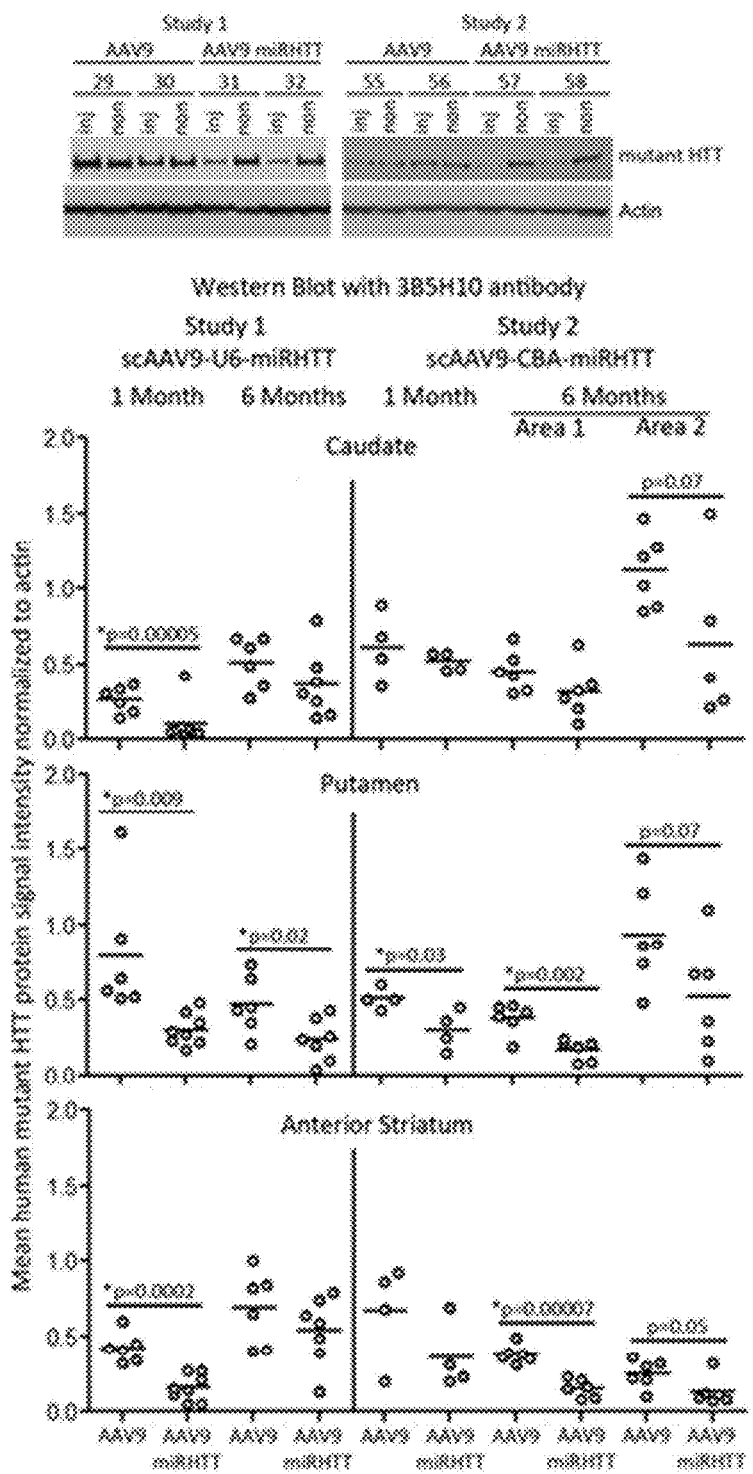
FIG. 30 shows that AAV9-miRHTT reduces the human mutant huntingtin protein in the striatum. Sample Western blots of putamen from Studies 1 and 2 show mutant HTT detected with antibody 3B5H10 and actin as loading control (top). A graph shows distribution of individual values and mean (horizontal bar) for sheep treated with either AAV9 (control) or AAV9-miRHTT (bottom). Shown are results for different striatal regions (caudate, putamen and anterior striatum) in studies 1 and 2 and 1 and 6 months post-injection. In study 2, 6 months post-injection two areas (Area 1 and 2) were examined in each region. Asterisks indicate significant difference on the injected side between AAV9 and AAV9-miRHTT at p<0.05 or less based on unpaired t-tests.

Western Blot Assay and Electrochemiluminescence (MSD Assay) Show that scAAV9-miR$^{HTT}$ Reduces Human Mutant Huntingtin Protein in the Caudate and Putamen HTT protein was detected by Western blot (FIG. 30) and electrochemiluminesence (Meso Scale Discovery (MSD, FIG. 30) in the same sample preparations. In study 1, the 3BH510 antibody which preferentially detects mHTT (mutant HTT) compared to wild-type HTT, was used to detect mHTT protein by Western blot (FIG. 30). One month after treatment with scAAV9-U6-miR$^{HTT}$, there was a significant reduction in mHTT protein in the caudate, putamen and anterior striatum, and in putamen at six-months post-treatment, compared to treatment with AAV9 lacking miR$^{HTT}$. In study 2 (FIG. 30, bottom), scAAV9-CβA-miR$^{HTT}$ treatment significantly silenced mHTT at one month post-injection in the putamen and at six months post-injection in caudate, putamen and anterior striatum.

Figure 31:
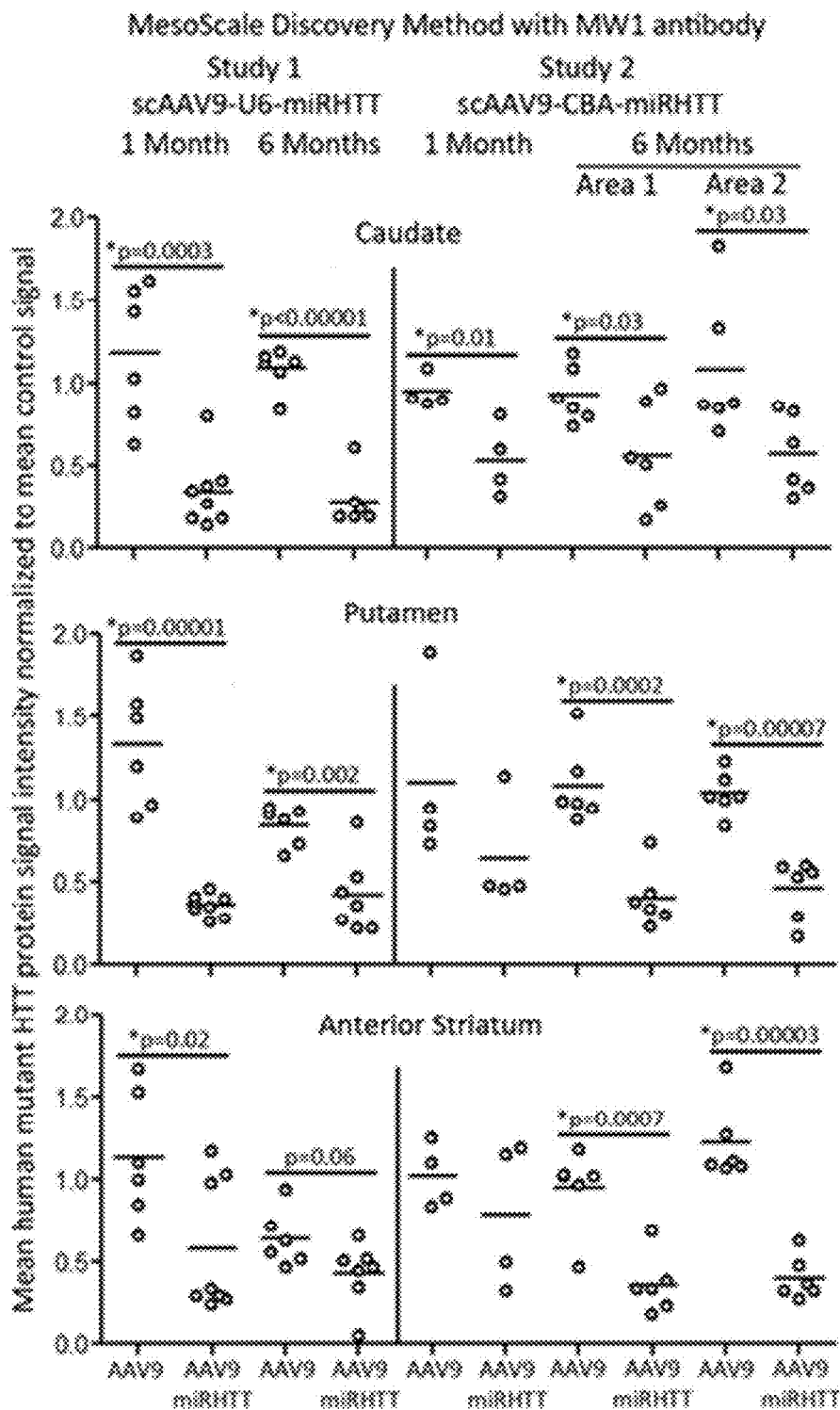
FIG. 31 shows human mutant HTT levels detected by MSD assay at 1 and 6 months post-injection in study 1 (U6 promoter) and study 2 (CBA promoter). Graph shows distribution of individual values and means (horizontal bars) for sheep treated with either AAV9 (control) or AAV9-miRHTT. Results are shown for different striatal regions (caudate, putamen and anterior striatum). Asterisks * indicate significant difference on the injected side between AAV9 and AAV9-miRHTT at p<0.05 or less based on unpaired t-tests.

Results with the MSD assay using MW1 for detection showed that scAAV9-U6-miR$^{HTT}$ treatment (study 1) significantly lowered mHTT protein levels in the caudate, putamen, and anterior striatum at one and six-months post-treatment. scAAV9-CBA-miR$^{HTT}$ markedly silenced mHTT protein in caudate at one month post-injection and in caudate, putamen and anterior striatum 6 months after treatment (FIG. 31). These results indicated that there was good agreement between results with the MSD assay (FIG. 31) and those obtained by Western blot assay (FIG. 30). Table 2: Mean percent of mutant huntingtin protein lowering by Western blot and MSD assays in Studies 1 and 2. The human mutant huntingtin protein was measured by Western blot with anti-htt polyQ antibody 3B5H10 in study 1 and antibodies 3B5H10, MAB2166 (anti-HTT443-456), which does not recognize sheep HTT (Reid et al., 2013), and anti-polyQ monoclonal antibody MW1 in study 2. In the MSD assays MW1 was used as the detection antibody. This table reports the mean percent mHTT lowering for the caudate, putamen, and anterior striatum. Percent lowering was calculated by dividing the average signal for the injected side in the AAV9miRHTT treated sheep by the average signal for the injected side in the AAV9 alone treated animals.

these two different methods of mHTT detection in the magnitude of mHTT lowering.

Figure 32A:
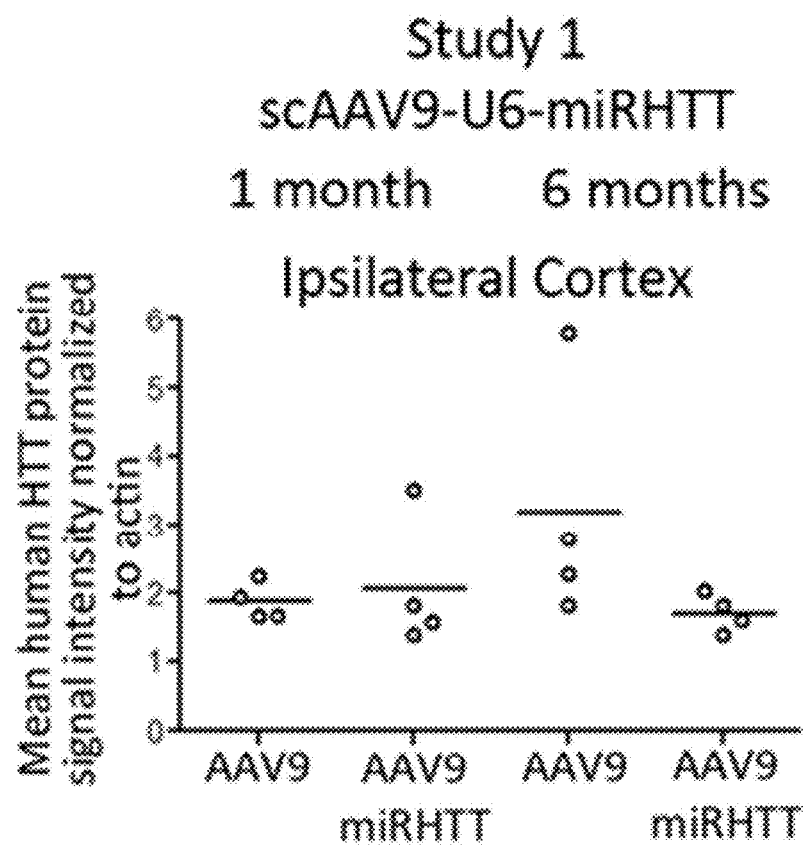
FIGS. 32A-32B show mHTT levels are unchanged in the ipsilateral cortex and contralateral caudate putamen of miRHTT injected sheep striatum.
Figure 32B:
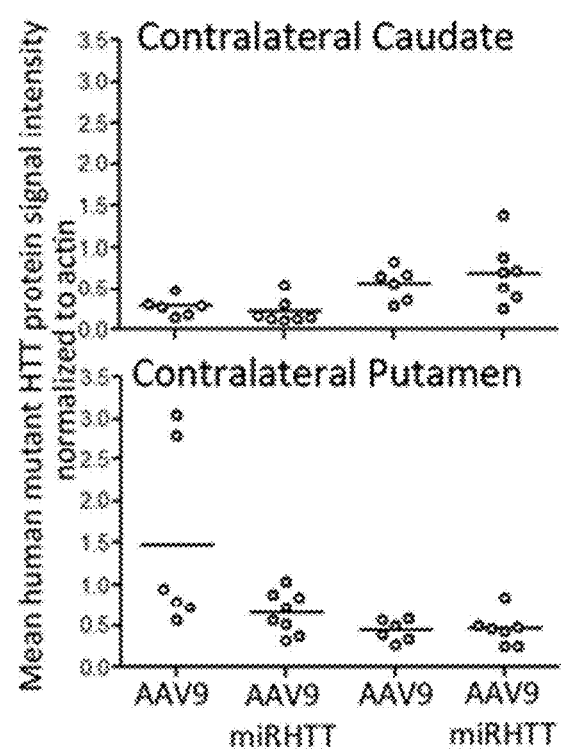

By Western blot analysis, the cortex overlying the AAV9-miR$^{HTT}$ injected striatum did not show a decline in mHTT protein levels compared to the AAV9 injected cortex (FIG. 32A). A low level of mRNA guide strand was detected in the caudate and putamen on the side contralateral to the AAV9-miR$^{HTT}$ injected striatum. These regions did not show reduced levels of mHTT protein by Western blot analysis (FIG. 32B).

Figure 29B:
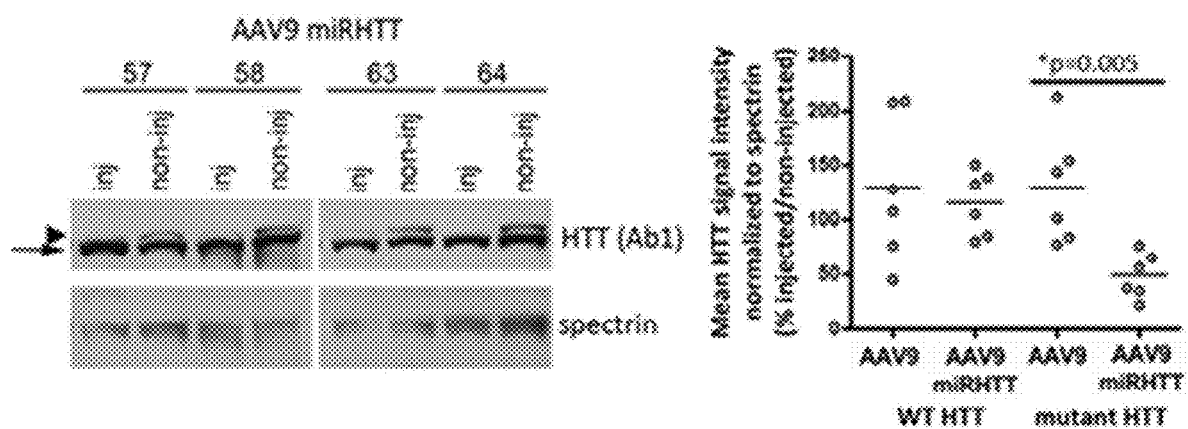

To investigate whether treatment with AAV9-miR$^{HTT}$ against the human HD gene affected the levels of endogenous sheep HTT, the levels of the human transgene mHTT with levels of endogenous sheep HTT were directly compared using Western blot analysis by taking advantage of differences in migration of the two proteins on SDS PAGE (FIG. 29B). Western blot analysis with Abl antibody, which recognizes htt1-17, showed that unlike human mHTT, the endogenous sheep HTT was not lowered by treatment with miR$^{HTT}$ (FIG. 29B).

DARPP32 Labeled Neurons and Striatal Volume are Unaffected by miRNA Treatment

To examine the safety of injection of the AAV vectors, immunohistochemistry for DARPP32, a marker of medium spiny neurons, was performed and the number of DARPP32 positive cells was counted. There was no significant difference between the number of cells in the AAV9-miR$^{HTT}$ treated and AAV9 treated groups (Table 3) and no significant difference between treatment groups in the number of cells stained for NeuN, a marker of neuronal cells. Striatal volumes were determined using cross-sectional area measurements of striatum in DARPP32 labeled sections and were found to be unchanged compared to controls after miRNA treatment (Table 4).

TABLE 1

Mean percent of mutant huntingtin protein lowering by Western blot and MSD assays in Studies 1 and 2.

| | Study# (promoter) | | | | | | | | | | |
|---|---|---|---|---|---|---|---|---|---|---|---|
| | Study 1 (U6) | | | | Study 2 (CBA) | | | | | | |
| | Assay mutant htt antibody | | | | | | | | | | |
| | Western blot (3B5H10) | | MSD MW1 | | Western blot (3B5H10) | | Western blot (MAB2166) | | Western blot (MW1) | | MSD MW1 |
| | Post-injection Interval (months) | | | | | | | | | | |
| | 1 | 6 | 1 | 6 | 1 | 6 | 1 | 6 | 1 | 6 | 1 | 6 |
| Caudate | 78** | 30 | 71** | 74** | 16 | 30, 43 | 61 | 46, 58* | 50* | 65*, 70 | 43* | 40*, 47* |
| Putamen | 61* | 47* | 73** | 50* | 40* | 55*, 44 | 68* | 65*, 67* | 54 | 51*, 56* | 42 | 63**, 56** |
| Anterior Striatum | 63** | 22 | 49* | 33 | 46 | 60**, 48 | 46 | 81*, 62* | −8 | 74*, 53* | 22 | 62**, 67** |

Since antibodies that detect mHTT may have different sensitivities, two other antibodies to detect human mHTT protein by Western blot, MAB2166 and MW1, were included in study 2 (Table 2). In the HD transgenic sheep MAB2166 recognizes only human huntingtin and not sheep HTT. MW1 preferentially recognizes the expanded polyglutamine region in HTT and was also used for detection of mHTT in the MSD assay. Table 2 compares the mean percent lowering of mHTT detected by Western blot with three anti-mHTT antibodies (3B5H10, 2166, and MW1) and by MSD assay with MW1 in studies 1 and 2. All three antibodies in Western blot analysis detected significant mHTT lowering in multiple neostriatal regions in study 2 (49% to 81%). Results of mHTT lowering by MSD assay were consistent when two samples from the same striatal region were analyzed in study 2. A comparison of the results by Western blots and by MSD assays with MW1 in study 2 are also noteworthy. There was good agreement between

TABLE 3

Number of DARPP32 and Neu N positive cells. Data were analyzed by paired t-test (injected to non-injected side). A significant difference was found between injected and non-injected sides only in WT sheep injected with AAV9-CBA-miRHTT at six months post injection, [1]p = 0.002 by paired t-test.

| Study# (promoter) | | Group | Post-injection interval (months) | Side | # of DARPP32 positive cells | # of NeuN positive cells |
|---|---|---|---|---|---|---|
| Study 1 (U6) | HD | AAV9 | 1 | inj | 4201 ± 389 | |
| | | | | non-inj | 4056 ± 488 | |
| | | | 6 | inj | 2819 ± 614 | 1185 ± 70 |
| | | | | non-inj | 3314 ± 364 | 1368 ± 180 |

TABLE 3-continued

Number of DARPP32 and Neu N positive cells. Data were analyzed by paired t-test (injected to non-injected side). A significant difference was found between injected and non-injected sides only in WT sheep injected with AAV9-CBA-miRHTT at six months post injection, [1]p = 0.002 by paired t-test.

| Study# (promoter) | Group | | Post-injection interval (months) | Side | # of DARPP32 positive cells | # of NeuN positive cells |
|---|---|---|---|---|---|---|
| | AAV9 miRHTT | | 1 | inj | 4327 ± 1444 | |
| | | | | non-inj | 4587 ± 838 | |
| | | | 6 | inj | 3884 ± 1222 | 1547 ± 315 |
| | | | | non-inj | 4149 ± 924 | 1633 ± 262 |
| Study 2 (CBA) | HD | AAV9 | 6 | inj | 2459 ± 85 | 1111 ± 314 |
| | | | | non-inj | 2324 ± 347 | 1184 ± 330 |
| | | AAV9 miRHTT | 6 | inj | 2061 ± 321 | 1404 ± 61 |
| | | | | non-inj | 2084 ± 460 | 1499 ± 46 |
| | | No Injection | 6 | left | 1852 ± 232 | 1440 ± 76 |
| | | | | right | 2047 ± 306 | 1183 ± 220 |
| Study 2 (CBA) | WT | AAV9 | 6 | inj | 2121 ± 96 | 1157 ± 180 |
| | | | | non-inj | 2148 ± 146 | 1106 ± 86 |
| | | AAV9 miRHTT | 6 | inj | 1799 ± 223 | 1285 ± 151[1] |
| | | | | non-inj | 1895 ± 327 | 1434 ± 142 |
| | | No Injection | 6 | left | 1963 ± 181 | 1188 ± 328 |
| | | | | right | 2101 ± 219 | 1056 ± 258 |

TABLE 4

Striatal volume. Volume was determined from cross-sectional areas of 29-35 40 μm sections per side per animal, N = 3 sheep per group. [1]p = 0.01, [2]p = 0.03, [3]p = 0.02, using a paired t test.

| | | | | Volume (mm3), Mean ± SD | | |
|---|---|---|---|---|---|---|
| | | | | Study 1 (U6) | | Study 2 (CBA) |
| | | | | 1 month post-injection | 6 months post-injection | 6 months post-injection |
| Caudate | HD | AAV9 | inj | 293 ± 54 | 241 ± 13 | |
| | | | non-inj | 300 ± 48 | 248 ± 17 | |
| | | | % inj/non-inj | 97.3 ± 4.2 | 97.2 ± 3.2 | |
| | | AAV9 miRHTT | inj | 257 ± 48 | 302 ± 15 | 280 ± 79 |
| | | | non-inj | 290 ± 48 | 325 ± 33 | 304 ± 49 |
| | | | % inj/non-inj | 88.6 ± 9.3 | 93.8 ± 15 | 91.1 ± 12 |
| | WT | AAV9 miRHTT | inj | | | 283 ± 67[1] |
| | | | non-inj | | | 309 ± 65 |
| | | | % inj/non-inj | | | 91.4 ± 2.7 |
| Putamen | HD | AAV9 | inj | 298 ± 46 | 247 ± 33 | |
| | | | non-inj | 307 ± 52 | 274 ± 11 | |
| | | | % inj/non-inj | 97.0 ± 1.4 | 90.3 ± 13 | |
| | | AAV9 miRHTT | inj | 278 ± 57 | 318 ± 39[2] | 281 ± 10 |
| | | | non-inj | 285 ± 50 | 340 ± 45 | 314 ± 21 |
| | | | % inj/non-inj | 97.5 ± 8.9 | 93.6 ± 1.2 | 89.9 ± 6.9 |
| | WT | AAV9 miRHTT | inj | | | 292 ± 45 |
| | | | non-inj | | | 329 ± 63 |
| | | | % inj/non-inj | | | 89.2 ± 3.7 |
| Striatum (Rostral pole + Caudate + Putamen) | HD | AAV9 | inj | 1041 ± 172 | 947 ± 28 | |
| | | | non-inj | 1034 ± 150 | 1006 ± 49 | |
| | | | % inj/non-inj | 101 ± 2.3 | 94.3 ± 5.6 | |
| | | AAV9 miRHTT | inj | 1023 ± 85 | 1030 ± 31[3] | 1165 ± 145 |
| | | | non-inj | 1037 ± 96 | 1110 ± 31 | 1222 ± 116 |
| | | | % inj/non-inj | 98.8 ± 4.7 | 92.8 ± 1.7 | 95.1 ± 4.0 |
| | WT | AAV9 miRHTT | inj | | | 1159 ± 76 |
| | | | non-inj | | | 1210 ± 32 |
| | | | % inj/non-inj | | | 95.7 ± 3.8 |

A Transient Increase in Activated Microglia Occurs after Direct Injection with scAAV9

Immuno-histochemical localization of Iba1, a protein which is localized to microglia and upregulated upon their activation, was investigated. Labeled cells were identified based on morphology as resting or activated microglia (Table 5). Injection of scAAV9-U6-miR$^{HTT}$ or the corresponding control vector increased the number of activated microglia on the injected side at one-month post-injection, but six months after injection the injected and non-injected sides were indistinguishable. In the second study, the microglial response was examined only at the study end point (6 months) at which time, there was no significant difference between groups. The findings suggest that the transient increase in activated microglia is independent of AAV cargo and can occur with any vector or with surgery alone.

TABLE 5

Number and classification based on morphology of IBA1 positive cells. Statistical analysis was done by paired t-test (injected side vs. non-injected side). A significant increase in activated microglia on the injected side compared to non-injected side was found in HD sheep injected with AAV9-U6-miR$^{HTT}$ ([1]p = 0.01) and in WT sheep injected with AAV9 ([2]p = 0.006) at six months. A significant decrease in resting microglia was found at one month in HD sheep injected with both AAV9 ([3]p = 0.05) and AAV9-U6-miR$^{HTT}$ ([4]p = 0.04) and a significant increase in total microglia was found in HD sheep injected with AAV9 at six months in study 2 ([4]p = 0.04). All analyses were done by paired t-test comparing injected to non-injected side.

| Study[#] (promoter) | Group | | Post-injection interval (months) | Side | # of Iba1 activated microglia | # of Iba1 resting microglia | Total # Iba1 positive cells |
|---|---|---|---|---|---|---|---|
| Study 1 (U6) | HD | AAV9 | 1 | inj | 253 ± 178 | 180 ± 102[3] | 433 ± 168 |
| | | | | non-inj | 2.0 ± 2 | 305 ± 70 | 307 ± 68 |
| | | | 6 | inj | 29 ± 19 | 351 ± 104 | 380 ± 123 |
| | | | | non-inj | 12 ± 6 | 377 ± 214 | 388 ± 219 |
| | | AAV9 miRHTT | 1 | inj | 195 ± 2 | 201 ± 77[4] | 396 ± 135 |
| | | | | non-inj | 2.8 ± 3 | 347 ± 116 | 350 ± 113 |
| | | | 6 | inj | 29 ± 8[1] | 279 ± 202 | 308 ± 194 |
| | | | | non-inj | 6.7 ± 4 | 311 ± 148 | 318 ± 144 |
| Study 2 (CBA) | HD | AAV9 | 6 | inj | 38 ± 10 | 263 ± 31 | 301 ± 23[4] |
| | | | | non-inj | 23 ± 3 | 248 ± 29 | 271 ± 32 |
| | | AAV9 miRHTT | 6 | inj | 10 ± 4 | 240 ± 38 | 251 ± 37 |
| | | | | non-inj | 6.0 ± 4 | 260 ± 32 | 266 ± 36 |
| | | No Injection | 6 | left | 8.3 ± 5 | 256 ± 90 | 265 ± 85 |
| | | | | right | 13 ± 17 | 192 ± 112 | 204 ± 100 |
| Study 2 (CBA) | WT | AAV9 | 6 | inj | 16 ± 4[2] | 288 ± 39 | 303 ± 35 |
| | | | | non-inj | 7.0 ± 4 | 256 ± 50 | 263 ± 46 |
| | | AAV9 miRHTT | 6 | inj | 22 ± 18 | 261 ± 29 | 283 ± 26 |
| | | | | non-inj | 8.7 ± 7 | 303 ± 59 | 312 ± 55 |
| | | No Injection | 6 | left | 10 ± 12 | 246 ± 108 | 256 ± 96 |
| | | | | right | 9.3 ± 8 | 298 ± 63 | 307 ± 69 | scAAV9-miRH$^{TT}$ Treatment does not Affect Blood Counts, Electrolytes, or Liver and Kidney Function Blood samples were taken at four times: baseline (pre-treatment), 28 (or 30) days, 90 days, and 180 days post treatment. A complete blood count, electrolytes were measured, and liver and kidney function tests were performed (Table 6). No changes in any of these measurements were found between AAV9-miR$^{HTT}$ injected sheep and controls. In addition, there were no changes in weight at these times.

TABLE 6

Clinical pathology and complete blood counts for all sheep.

| | Baseline | | | | Day 28 | | | | Day 90 | | | | Day 180 | | | |
|---|---|---|---|---|---|---|---|---|---|---|---|---|---|---|---|---|
| | Control | | Test | | Control | | Test | | Control | | Test | | Control | | Test | |
| | Mean | n | Mean | n | Mean | n | Mean | n | Mean | n | Mean | n | Mean | n | Mean | n |
| sodium mmol/L | 146 | 19 | 147 | 22 | 148 | 18 | 148 | 20 | 146 | 10 | 145 | 10 | 146 | 10 | 145 | 10 |
| potassium mmol/L | 4.14 | 18 | 4.15 | 22 | 5.26 | 18 | 5.17 | 20 | 5.21 | 10 | 5.38 | 9 | 5.21 | 10 | 5.38 | 9 |
| chloride mmol/L | 105 | 19 | 106 | 22 | 109 | 18 | 109 | 20 | 109 | 10 | 109 | 10 | 109 | 10 | 109 | 10 |
| bicarbonate mmol/L | 27 | 19 | 26 | 22 | 26 | 18 | 26 | 20 | 26 | 10 | 26 | 10 | 26 | 10 | 26 | 10 |
| Anion mmol/L | 18 | 18 | 19 | 22 | 18 | 18 | 18 | 20 | 17 | 10 | 16 | 10 | 17 | 10 | 16 | 10 |
| glucose mmol/L | 4.57 | 18 | 4.15 | 21 | 2.73 | 18 | 3.48 | 20 | 2.89 | 10 | 2.70 | 10 | 2.89 | 10 | 2.70 | 10 |
| urea mmol/L | 7.56 | 19 | 7.44 | 22 | 5.46 | 18 | 5.24 | 20 | 6.08 | 10 | 5.75 | 10 | 6.08 | 10 | 5.75 | 10 |
| creatinine μmol/L | 53 | 19 | 51 | 22 | 62 | 18 | 60 | 20 | 57 | 10 | 55 | 10 | 57 | 10 | 55 | 10 |
| cholesterol mmol/L | 1 | 19 | 1 | 22 | 2 | 18 | 1 | 20 | 1 | 10 | 2 | 10 | 1 | 10 | 2 | 10 |
| osmo mmol/L | 291 | 18 | 292 | 22 | 293 | 18 | 294 | 20 | 291 | 10 | 288 | 9 | 291 | 10 | 288 | 9 |
| urate mmol/L | 0.00 | 19 | 0.09 | 22 | 0.00 | 18 | 0.00 | 20 | 0.00 | 10 | 0.00 | 10 | 0.00 | 10 | 0.00 | 10 |
| phosphate mmol/L | 2.31 | 19 | 2.31 | 22 | 2.09 | 18 | 1.97 | 20 | 1.95 | 10 | 2.14 | 10 | 1.95 | 10 | 2.14 | 10 |
| T Cal mmol/L | 2.48 | 19 | 2.40 | 22 | 2.44 | 18 | 2.42 | 20 | 2.54 | 10 | 2.46 | 10 | 2.54 | 10 | 2.46 | 10 |
| Ion Cal mmol/L | 1.28 | 18 | 1.25 | 22 | 1.28 | 13 | 1.26 | 12 | 1.33 | 10 | 1.29 | 10 | 1.33 | 10 | 1.29 | 10 |
| albumin g/L | 36 | 19 | 35 | 22 | 35 | 18 | 35 | 20 | 35 | 10 | 35 | 10 | 35 | 10 | 35 | 10 |
| globulin g/L | 29 | 19 | 29 | 22 | 28 | 18 | 28 | 20 | 28 | 10 | 28 | 10 | 28 | 10 | 28 | 10 |
| Total Protein g/L | 65 | 19 | 64 | 22 | 63 | 18 | 63 | 20 | 63 | 10 | 64 | 10 | 63 | 10 | 64 | 10 |
| Total Bilirubin μmol/L | 2 | 19 | 1 | 22 | 1 | 18 | 1 | 20 | 0 | 10 | 1 | 10 | 0 | 10 | 1 | 10 |
| GGT U/L | 55 | 19 | 58 | 22 | 58 | 18 | 63 | 20 | 47 | 10 | 51 | 10 | 47 | 10 | 51 | 10 |
| ALP U/L | 153 | 19 | 140 | 22 | 157 | 18 | 151 | 20 | 202 | 10 | 211 | 10 | 202 | 10 | 211 | 10 |
| ALT U/L | 16 | 19 | 16 | 22 | 15 | 18 | 17 | 20 | 21 | 10 | 21 | 10 | 21 | 10 | 21 | 10 |
| AST U/L | 84 | 19 | 78 | 22 | 82 | 18 | 91 | 20 | 111 | 10 | 107 | 9 | 111 | 10 | 107 | 9 |
| LDH U/L | 498 | 18 | 496 | 22 | 532 | 18 | 536 | 20 | 624 | 10 | 577 | 9 | 624 | 10 | 577 | 9 |
| Haemoglobin g/L | 102 | 19 | 100 | 22 | 115 | 18 | 113 | 21 | 115 | 10 | 120 | 10 | 115 | 10 | 120 | 10 |
| Red Blood Cells ×10$^{12}$/L | 9.02 | 19 | 9.07 | 22 | 10.17 | 18 | 10.47 | 21 | 10.07 | 10 | 10.41 | 10 | 10.07 | 10 | 10.41 | 10 |
| Packed Cell Volume L/L | 0.34 | 19 | 0.34 | 22 | 0.38 | 18 | 0.40 | 21 | 0.39 | 10 | 0.40 | 10 | 0.39 | 10 | 0.40 | 10 |

TABLE 6-continued

Clinical pathology and complete blood counts for all sheep.

| | Baseline | | | | Day 28 | | | | Day 90 | | | | Day 180 | | | |
|---|---|---|---|---|---|---|---|---|---|---|---|---|---|---|---|---|
| | Control | | Test | | Control | | Test | | Control | | Test | | Control | | Test | |
| | Mean | n | Mean | n | Mean | n | Mean | n | Mean | n | Mean | n | Mean | n | Mean | n |
| Mean Cell Volume fl | 37.71 | 19 | 37.97 | 22 | 37.79 | 18 | 37.94 | 21 | 38.39 | 10 | 37.92 | 10 | 38.39 | 10 | 37.92 | 10 |
| Mean Cell Haem pg | 11.28 | 19 | 11.08 | 22 | 11.36 | 18 | 11.30 | 21 | 11.44 | 10 | 11.52 | 10 | 11.44 | 10 | 11.52 | 10 |
| Mean Cell Haem Conc g/L | 299 | 19 | 292 | 22 | 301 | 18 | 298 | 21 | 299 | 10 | 305 | 10 | 299 | 10 | 305 | 10 |
| Red cell Dist Width % | 20 | 19 | 20 | 22 | 20 | 18 | 20 | 21 | 19 | 10 | 19 | 10 | 19 | 10 | 19 | 10 |
| Platelets ×10$^9$/L | 343 | 16 | 334 | 22 | 397 | 17 | 347 | 20 | 305 | 9 | 241 | 9 | 305 | 9 | 241 | 9 |
| White Cell Count 10$^9$/L | 4.87 | 19 | 5.35 | 22 | 5.82 | 18 | 5.89 | 21 | 5.89 | 10 | 6.16 | 10 | 5.89 | 10 | 6.16 | 10 |
| Neutrophils % | 40 | 19 | 41 | 22 | 46 | 18 | 64 | 21 | 40 | 10 | 41 | 10 | 40 | 10 | 41 | 10 |
| Lymphocytes % | 58 | 19 | 56 | 22 | 51 | 18 | 51 | 21 | 53 | 10 | 58 | 10 | 53 | 10 | 58 | 10 |
| Monocytes % | 1 | 19 | 1 | 22 | 2 | 18 | 2 | 21 | 4 | 10 | 5 | 10 | 4 | 10 | 5 | 10 |
| Eosinophils % | 1 | 19 | 1 | 22 | 1 | 18 | 0 | 21 | 4 | 10 | 2 | 10 | 4 | 10 | 2 | 10 |
| Basophils % | 0 | 19 | 0 | 22 | 0 | 18 | 0 | 21 | 0 | 10 | 0 | 10 | 0 | 10 | 0 | 10 |

SEQUENCES

```
>SEQ ID NO: 1 Huntingtin mRNA; NCBI Ref. Seq NM_002111.8)
GCTGCCGGGACGGGTCCAAGATGGACGGCCGCTCAGGTTCTGCTTTTACCTGCGGCCC
AGAGCCCCATTCATTGCCCCGGTGCTGAGCGGCGCCGCGAGTCGGCCCGAGGCCTCCG
GGGACTGCCGTGCCGGGCGGGAGACCGCCATGGCGACCCTGGAAAAGCTGATGAAGG
CCTTCGAGTCCCTCAAGTCCTTCCAGCAGCAGCAGCAGCAGCAGCAGCAGCAGCAGCA
GCAGCAGCAGCAGCAGCAGCAGCAGCAACAGCCGCCACCGCCGCCGCCGCC
GCCGCCTCCTCAGCTTCCTCAGCCGCCGCCGCAGGCACAGCCGCTGCTGCCTCAGCCGC
AGCCGCCCCGCCGCCGCCCCGCCGCCACCCGGCCCGGCTGTGGCTGAGGAGCCGCT
GCACCGACCAAAGAAAGAACTTTCAGCTACCAAGAAAGACCGTGTGAATCATTGTCTG
ACAATATGTGAAAACATAGTGGCACAGTCTGTCAGAAATTCTCCAGAATTTCAGAAAC
TTCTGGGCATCGCTATGGAACTTTTTCTGCTGTGCAGTGATGACGCAGAGTCAGATGTC
AGGATGGTGGCTGACGAATGCCTCAACAAAGTTATCAAAGCTTTGATGGATTCTAATCT
TCCAAGGTTACAGCTCGAGCTCTATAAGGAAATTAAAAAGAATGGTGCCCCTCGGAGT
TTGCGTGCTGCCCTGTGGAGGTTTGCTGAGCTGGCTCACCGGTTCGGCCTCAGAAATG
CAGGCCTTACCTGGTGAACCTTCTGCCGTGCCTGACTCGAACAAGCAAGAGACCCGAA
GAATCAGTCCAGGAGACCTTGGCTGCAGCTGTTCCCAAAATTATGGCTTCTTTTGGCAA
TTTTGCAAATGACAATGAAATTAAGGTTTTGTTAAAGGCCTTCATAGCGAACCTGAAGT
CAAGCTCCCCCACCATTCGGCGGACAGCGGCTGGATCAGCAGTGAGCATCTGCCAGCA
CTCAAGAAGGACACAATATTTCTATAGTTGGCTACTAAATGTGCTCTTAGGCTTACTCG
TTCCTGTCGAGGATGAACACTCCACTCTGCTGATTCTTGGCGTGCTGCTCACCCTGAGG
TATTTGGTGCCCTTGCTGCAGCAGGTCAAGGACACAAGCCTGAAAGGCAGCTTCG
GAGTGACAAGGAAAGAAATGGAAGTCTCTCCTTCTGCAGAGCAGCTTGTCCAGGTTTA
TGAACTGACGTTACATCATACACAGCACCAAGACCACAATGTTGTGACCGGAGCCCTG
GAGCTGTTGCAGCAGCTCTTCAGAACGCCTCCACCCGAGCTTCTGCAAACCCTGACCGC
AGTCGGGGCATTGGGCAGCTCACCGCTGCTAAGGAGGAGTCTGGTGGCCGAAGCCGT
AGTGGGAGTATTGTGGAACTTATAGCTGGAGGGGGTTCCTCATGCAGCCCTGTCCTTTC
AAGAAAACAAAAAGGCAAAGTGCTCTTAGGAGAAGAAGAAGCCTTGGAGGATGACTC
TGAATCGAGATCGGATGTCAGCAGCTCTGCCTTAACAGCCTCAGTGAAGGATGAGATC
AGTGGAGAGCTGGCTGCTTCTTCAGGGGTTTCCACTCCAGGGTCAGCAGGTCATGACAT
CATCACAGAACAGCCACGGTCACAGCACACACTGCAGGCGGACTCAGTGGATCTGGCC
AGCTGTGACTTGACAAGCTCTGCCACTGATGGGGATGAGGAGGATATCTTGAGCCACA
GCTCCAGCCAGGTCAGCGCCGTCCCATCTGACCCTGCCATGGACCTGAATGATGGGAC
CCAGGCCTCGTCGCCCATCAGCGACAGCTCCCAGACCACCACCGAAGGGCCTGATTCA
GCTGTTACCCCTTCAGACAGTTCTGAAATTGTGTTAGACGGTACCGACAACCAGTATTT
GGGCCTGCAGATTGGACAGCCCCAGGATGAAGATGAGGAAGCCACAGGTATTCTTCCT
GATGAAGCCTCGGAGGCCTTCAGGAACTCTTCCATGGCCCTTCAACAGGCACATTTATT
GAAAAACATGAGTCACTGCAGGCAGCCTTCTGACAGCAGTGTTGATAAATTTGTGTTG
AGAGATGAAGCTACTGAACCGGGTGATCAAGAAAACAAGCCTTGCCGCATCAAAGGT
GACATTGGACAGTCCACTGATGATGACTCTGCACCTCTTGTCCATTGTGTCCGCCTTTTA
TCTGCTTCGTTTTTGCTAACAGGGGGAAAAATGTGCTGGTTCCGGACAGGGATGTGA
GGGTCAGCGTGAAGGCCCTGGCCCTCAGCTGTGTGGGAGCAGCTGTGGCCCTCCACCC
GGAATCTTTCTTCAGCAAACTCTATAAAGTTCCTCTTGACACCACGGAATACCCTGAGG
AACAGTATGTCTCAGACATCTTGAACTACATCGATCATGGAGACCCACAGGTTCGAGG
AGCCACTGCCATTCTCTGTGGGACCCTCATCTGCTCCATCCTCAGCAGGTCCCGCTTCC
ACGTGGGAGATTGGATGGGCACCATTAGAACCCTCACAGGAAATACATTTTCTTTGGC
GGATTGCATTCCTTTGCTGCGAAAACACTGAAGGATGAGTCTTCTGTTACTTGCAAGT
TAGCTTGTACAGCTGTGAGGAACTGTGTCATGAGTCTCTGCAGCAGCAGCTACAGTGA
GTTAGGACTGCAGCTGATCATCGATGCTGACTCTGAGGAACAGTTCCTATTGGCTGG
TGAGGACAGAGCTTCTGGAAACCTTGCAGAGATTGACTTCAGGTGGTGAGCTTTTTG
GAGGCAAAAGCAGAAAACTTACACAGAGGGGCTCATCATTATACAGGGCTTTTAAAAC
TGCAAGAACGAGTGCTCAATAATGTTGTCATCCATTTGCTTGGAGATGAAGACCCCAG
GGTGCGACATGTTGCCGCAGCATCACTAATTAGGCTTGTCCCAAAGCTGTTTTATAAAT
GTGACCAAGGACAAGCTGATCCAGTAGTGGCCGTGGCAAGAGATCAAAGCAGTGTTTA
CCTGAAACTTCTCATGCATGAGACGCAGCCTCCATCTCATTTCTCCGTCAGCACAATAA
```

| SEQUENCES |
|---|
| CCAGAATATATAGAGGCTATAACCTACTACCAAGCATAACAGACGTCACTATGGAAAA |
| TAACCTTTCAAGAGTTATTGCAGCAGTTTCTCATGAACTAATCACATCAACCACCAGAG |
| CACTCACATTTGGATGCTGTGAAGCTTTGTGTCTTCTTTCCACTGCCTTCCCAGTTTGCA |
| TTTGGAGTTTAGGTTGGCACTGTGGAGTGCCTCCACTGAGTGCCTCAGATGAGTCTAGG |
| AAGAGCTGTACCGTTGGGATGGCCACAATGATTCTGACCCTGCTCTCGTCAGCTTGGTT |
| CCCATTGGATCTCTCAGCCCATCAAGATGCTTTGATTTTGGCCGGAAACTTGCTTGCAG |
| CCAGTGCTCCCAAATCTCTGAGAAGTTCATGGGCCTCTGAAGAAGAAGCCAACCCAGC |
| AGCCACCAAGCAAGAGGAGGTCTGGCCAGCCCTGGGGGACCGGGCCCTGGTGCCCATG |
| GTGGAGCAGCTCTTCTCTCACCTGCTGAAGGTGATTAACATTTGTGCCCACGTCCTGGA |
| TGACGTGGCTCCTGGACCCGCAATAAAGGCAGCCTTGCCTTCTCTAACAAACCCCCCTT |
| CTCTAAGTCCCATCCGACGAAAGGGGAAGGAGAAAGAACCAGGAGAACAAGCATCTG |
| TACCGTTGAGTCCCAAGAAAGGCAGTGAGGCCAGTGCAGCTTCTAGACAATCTGATAC |
| CTCAGGTCCTGTTACAACAAGTAAATCCTCATCACTGGGGAGTTTCTATCATCTTCCTTC |
| ATACCTCAAACTGCATGATGTCCTGAAAGCTACACACGCTAACTACAAGGTCACGCTG |
| GATCTTCAGAACAGCACGGAAAAGTTTGGAGGGTTTCTCCGCTCAGCCTTGGATGTTCT |
| TTCTCAGATACTAGAGCTGGCCACACTGCAGGACATTGGGAAGTGTGTTGAAGAGATC |
| CTAGGATACCTGAAATCCTGCTTTAGTCGAGAACCAATGATGGCAACTGTTTGTGTTCA |
| ACAATTGTTGAAGACTCTCTTTGGCACAAACTTGGCCTCCCAGTTTGATGGCTTATCTTC |
| CAACCCCAGCAAGTCACAAGGCCGAGCACAGCGCCTTGGCTCCTCCAGTGTGAGGCCA |
| GGCTTGTACCACTACTGCTTCATGGCCCGTACACCCACTTCACCCAGGCCCTCGCTGA |
| CGCCAGCCTGAGGAACATGGTGCAGGCGGAGCAGGAGAACGACACCTCGGGATGGTT |
| TGATGTCCTCCAGAAAGTGTCTACCCAGTTGAAGACAAACCTCACGAGTGTCACAAAG |
| AACCGTGCAGATAAGAATGCTATTCATAATCACATTCGTTTGTTTGAACCTCTTGTTAT |
| AAAAGCTTTAAAACAGTACACGACTACAACATGTGTGCAGTTACAGAAGCAGGTTTTA |
| GATTTGCTGGCGCAGCTGGTTCAGTTACGGGTTAATTACTGTCTTCTGGATTCAGATCA |
| GGTGTTTATTGGCTTTGTATTGAAACAGTTTGAATACATTGAAGTGGGCCAGTTCAGGG |
| AATCAGAGGCAATCATTCCAAACATCTTTTTCTTCTTGGTATTACTATCTTATGAACGCT |
| ATCATTCAAAACAGATCATTGGAATTCCTAAAATCATTCAGCTCTGTGATGGCATCATG |
| GCCAGTGGAAGGAAGGCTGTGACACATGCCATACCGGCTCTGCAGCCCATAGTCCACG |
| ACCTCTTTGTATTAAGAGGAACAAATAAAGCTGATGCAGGAAAGAGCTTGAAACCCA |
| AAAAGAGGTGGTGGTGTCAATGTTACTGAGACTCATCCAGTACCATCAGGTGTTGGAG |
| ATGTTCATTCTTGTCCTGCAGCAGTGCCACAAGGAGAATGAAGACAAGTGGAAGCGAC |
| TGTCTCGACAGATAGCTGACATCATCCTCCCAATGTTAGCCAAACAGCAGATGCACATT |
| GACTCTCATGAAGCCCTTGGAGTGTTAAATACATTATTTGAGATTTTGGCCCCTTCCTCC |
| CTCCGTCCGGTAGACATGCTTTTACGGAGTATGTTCGTCACTCCAAACACAATGGCGTC |
| CGTGAGCACTGTTCAACTGTGGATATCGGGAATTCTGGCCATTTTGAGGGTTCTGATTT |
| CCCAGTCAACTGAAGATATTGTTCTTTCTCGTATTCAGGAGCTCTCCTTCTCTCCGTATT |
| TAATCTCCTGTACAGTAATTAATAGGTTAAGAGATGGGGACAGTACTTCAACGCTAGA |
| AGAACACAGTGAAGGGAAACAAATAAAGAATTTGCCAGAAGAAACATTTTCAAGGTTT |
| CTATTACAACTGGTTGGTATTCTTTTAGAAGACATTGTTACAAAACAGCTGAAGGTGGA |
| AATGAGTGAGCAGCAACATACTTTCTATTGCCAGGAACTAGGCACACTGCTAATGTGT |
| CTGATCCACATCTTCAAGTCTGGAATGTTCCGGAGAATCACAGCAGCTGCCACTAGGCT |
| GTTCCGCAGTGATGGCTGTGGCGGCAGTTTCTACACCCTGGACAGCTTGAACTTGCGGG |
| CTCGTTCCATGATCACCACCCACCCGGCCCTGGTGCTGCTCTGGTGTCAGATACTGCTG |
| CTTGTCAACCACCGACTACCGCTGGTGGGCAGAAGTGCAGCAGACCCCGAAAAGAC |
| ACAGTCTGTCCAGCACAAAGTTACTTAGTCCCCAGATGTCTGGAGAAGAGGAGGATTC |
| TGACTTGGCAGCCAAACTTGGAATGTGCAATAGAGAAATAGTACGAAGAGGGCTCTC |
| ATTCTCTTCTGTGATTATGTCTGTCAGAACCTCCATGACTCCGAGCACTTAACGTGGCTC |
| ATTGTAAATCACATTCAAGATCTGATCAGCCTTTCCCACGAGCCTCCAGTACAGGACTT |
| CATCAGTGCCGTTCATCGGAACTCTGCTGCCAGCGGCCTGTTCATCCAGGCAATTCAGT |
| CTCGTTGTGAAAACCTTTCAACTCCAACCATGCTGAAGAAAACTCTTCAGTGCTTGGAG |
| GGGATCCATCTCAGCCAGTCGGGAGCTGTGCTCACGCTGTATGTGGACAGGCTTCTGTG |
| CACCCCTTTCCGTGTGCTGGCTCGCATGGTCGACATCCTTGCTTGTCGCCGGGTAGAAA |
| TGCTTCTGGCTGCAAATTTACAGAGCAGCATGGCCCAGTTGCCAATGGAAGAACTCAA |
| CAGAATCCAGGAATACCTTCAGAGCAGCGGGCTCGCTCAGAGACACCAAAGGCTCTAT |
| TCCCTGCTGGACAGGTTTCGTCTCTCCACCATGCAAGACTCACTTAGTCCCTCTCCTCCA |
| GTCTCTTCCCACCCGCTGGACGGGATGGGCACGTGTCACTGGAAACAGTGAGTCCGG |
| ACAAAGACTGGTACGTTCATCTTGTCAAATCCCAGTGTTGGACCAGGTCAGATTCTGCA |
| CTGCTGGAAGGTGCAGAGCTGGTGAATCGGATTCCTGCTGAAGATATGAATGCCTTCA |
| TGATGAACTCGGAGTTCAACCTAAGCCTGCTAGCTCCATGCTTAAGCCTAGGGATGAGT |
| GAAATTTCTGGTGGCCAGAAGAGTGCCCTTTTTGAAGCAGCCCGTGAGGTGACTCTGG |
| CCCGTGTGAGCGGCACCGTGCAGCAGCTCCCTGCTGTCCATCATGTCTTCCAGCCCGAG |
| CTGCCTGCAGAGCCGGCGGCCTACTGGAGCAAGTTGAATGATCTGTTTGGGGATGCTG |
| CACTGTATCAGTCCCTGCCCACTCTGGCCCGGGCCCTGGCACAGTACCTGGTGGTGGTC |
| TCCAAACTGCCCAGTCATTTGCACCTTCCTCCTGAGAAAGAGAAGGACATTGTGAAATT |
| CGTGGTGGCAACCCTTGAGGCCCTGTCCTGGCATTTGATCCATGAGCAGATCCCGCTGA |
| GTCTGGATCTCCAGGCAGGGCTGGACTGCTGCTGCCTGGCCCTGCAGCTGCCTGGCCTC |
| TGGAGCGTGGTCTCCTCCACAGAGTTTGTGACCCACGCCTGCTCCTCATCTACTGTGT |
| GCACTTCATCCTGGAGGCCGTTGCAGTGCAGCCTGGAGAGCAGCTTCTTAGTCCAGAA |
| AGAAGGACAAATACCCCAAAAGCCATCAGCGAGGAGGAGGAGGAAGTAGATCCAAAC |
| ACACAGAATCCTAAGTATATCACTGCAGCCTGTGAGATGGTGGCAGAAATGGTGGAGT |
| CTCTGCAGTCGGTGTTGGCCTTGGGTCATAAAAGGAATAGCGGCGTGCCGGCGTTTCTC |
| ACGCCATTGCTAAGGAACATCATCATCAGCCTGGCCCGCCTGCCCCTTGTCAACAGCTA |
| CACACGTGTGCCCCCACTGGTGTGGAAGCTTGGATGGTCACCCAAACCGGGAGGGGAT |
| TTTGGCACAGCATTCCCTGAGATCCCCGTGGAGTTCCTCCAGGAAAAGGAAGTCTTTAA |
| GGAGTTCATCTACCGCATCAACACACTAGGCTGGACCAGTCGTACTCAGTTTGAAGAA |
| ACTTGGGCCACCCTCCTTGGTGTCCTGGTGACGCAGCCCCTCGTGATGGAGCAGGAGG |

```
AGAGCCCACCAGAAGAAGACACAGAGAGGACCCAGATCAACGTCCTGGCCGTGCAGG
CCATCACCTCACTGGTGCTCAGTGCAATGACTGTGCCTGTGGCCGGCAACCCAGCTGTA
AGCTGCTTGGAGCAGCAGCCCCGGAACAAGCCTCTGAAAGCTCTCGACACCAGGTTTG
GGAGGAAGCTGAGCATTATCAGAGGGATTGTGGAGCAAGAGATTCAAGCAATGGTTTC
AAAGAGAGAGAATATTGCCACCCATCATTTATATCAGGCATGGGATCCTGTCCCTTCTC
TGTCTCCGGCTACTACAGGTGCCCTCATCAGCCACGAGAAGCTGCTGCTACAGATCAAC
CCCGAGCGGGAGCTGGGGAGCATGAGCTACAAACTCGGCCAGGTGTCCATACACTCCG
TGTGGCTGGGGAACAGCATCACACCCCTGAGGGAGGAGGAATGGGACGAGGAAGAGG
AGGAGGAGGCCGACGCCCTGCACCTTCGTCACCACCCACGTCTCCAGTCAACTCCAG
GAAACACCGGGCTGGAGTTGACATCCACTCCTGTTCGCAGTTTTTGCTTGAGTTGTACA
GCCGCTGGATCCTGCCGTCCAGCTCAGCCAGGAGGACCCCGGCCATCCTGATCAGTGA
GGTGGTCAGATCCCTTCTAGTGGTCTCAGACTTGTTCACCGAGCGCAACCAGTTTGAGC
TGATGTATGTGACGCTGACAGAACTGCGAAGGGTGCACCCTTCAGAAGACGAGATCCT
CGCTCAGTACCTGGTGCCTGCCACCTGCAAGGCAGCTGCCGTCCTTGGGATGGACAAG
GCCGTGGCGGAGCCTGTCAGCCGCCTGCTGGAGAGCACGCTCAGGAGCAGCCACCTGC
CCAGCAGGGTTGGAGCCCTGCACGGCGTCCTCTATGTGCTGGAGTGCGACCTGCTGGA
CGACACTGCCAAGCAGCTCATCCCGGTCATCAGCGACTATCTCCTCTCCAACCTGAAAG
GGATCGCCCACTGCGTGAACATTCACAGCCAGCAGCACGTACTGGTCATGTGTGCCAC
TGCGTTTTACCTCATTGAGAACTATCCTCTGGACGTAGGGCCGGAATTTTCAGCATCAA
TAATACAGATGTGTGGGTGATGCTGTCTGGAAGTGAGGAGTCCACCCCCTCCATCATT
TACCACTGTGCCCTCAGAGGCCTGGAGCGCCTCCTGCTCTCGAGCAGCTCTCCCGCCT
GGATGCAGAATCGCTGGTCAAGCTGAGTGTGGACAGAGTGAACGTGCACAGCCCGCAC
CGGGCCATGGCGGCTCTGGGCCTGATGCTCACCTGCATGTACACAGGGAAAGGAGAAAG
TCAGTCCGGGTAGAACTTCAGACCCTAATCCTGCAGCCCCCGACAGCGAGTCAGTGAT
TGTTGCTATGGAGCGGGTATCTGTTCTTTTTGATAGGATCAGGAAAGGCTTTCCTTGTG
AAGCCAGAGTGGTGGCCAGGATCCTGCCCCAGTTTCTAGACGACTTCTTCCCACCCCAG
GACATCATGAACAAAGTCATCGGAGAGTTTCTGTCCAACCAGCAGCCATACCCCCAGT
TCATGGCCACCGTGGTGTATAAGGTGTTTCAGACTCTGCACAGCACCACCGGGCAGTCGTCC
ATGGTCCGGGACTGGGTCATGCTGTCCCTCTCCAACTTCACGCAGAGGGCCCCGGTCGC
CATGGCCACGTGGAGCCTCCTGCTTCTTTGTCAGCGCGTCCACCAGCCCGTGGGTCG
CGGCGATCCTCCCACATGTCATCAGCAGGATGGGCAAGCTGGAGCAGGTGGACGTGAA
CCTTTTCTGCCTGGTCGCCACAGACTTCTACAGACACCAGATAGAGGAGGAGGCTCGAC
CGCAGGGCCTTCCAGTCTGTGCTTGAGGTGGTTGCAGCCCCAGGAAGCCCATATCACC
GGCTGCTGACTTGTTTACGAAATGTCCACAAGGTCACCACCTGCTGAGCGCCATGGTGG
GAGAGACTGTGAGGCGGCAGCTGGGGCCGGAGCCTTTGGAAGTCTGCGCCCTTGTGCC
CTGCCTCCACCGAGCCAGCTTGGTCCCTATGGGCTTCCGCACATGCCGCGGGCGGCCAG
GCAACGTGCGTGTCTCTGCCATGTGGCAGAAGTGCTCTTTGTGGCAGTGGCCAGGCAG
GGAGTGTCTGCAGTCCTGGTGGGGCTGAGCCTGAGGCCTTCCAGAAAGCAGGAGCAGC
TGTGCTGCACCCCATGGGGTGACCAGGTCCTTTCTCCTGATAGTCACCTGCTGGTTGTT
GCCAGGTTGCAGCTGCTCTTGCATCTGGGCCAGAAGTCCTCCCTCCTGCAGGCTGGCTG
TTGGCCCCTCCTGCTGTCCTGCAGTAGAAGGTGCCGTGAGCAGGCTTTGGGAACACTGGC
CTGGGTCTCCCTGGTGGGGTGTGCATGCCACGCCCCGTGTCTGGATGCACAGATGCCAT
GGCCTGTGCTGGGCCAGTGGCTGGGGGTGCTAGACACCCGGCACCATTCTCCCTTCTCT
CTTTTCTTCTCAGGATTTAAAATTTAATTATATCAGTAAAGAGATTAATTTTAACGTAAC
TCTTTCTATGCCCGTGTAAAGTATGTGAATCGCAAGGCCTGCTTGCATGCGACAGCGT
CCGGGGTGGTGGACAGGGCCCCCGGCCACGCTCCCTCTCCTGTAGCCACTGGCATAGC
CCTCCTGAGCACCCGCTGACATTTCCGTTGTACATGTTCCTGTTTATGCATTCACAAGGT
GACTGGGATGTAGAGAGGCGTTAGTGGGCAGGTGGCCACAGCAGGACTGAGGACAGG
CCCCCATTATCCTAGGGGTGCGCTCACCTGCAGCCCCTCCTCCTCGGGCACAGACGACT
GTCGTTCTCCACCCACCAGTCAGGGACAGCAGCCTCCCTGTCACTCAGCTGAGAAGGC
CAGCCCTCCCTGGCTGTGAGCAGCCTCCACTGTGTCCAGAGACATGGGCCTCCCACTCC
TGTTCCTTGCTAGCCCTGGGGTGGCGTCTGCCTAGGAGCTGGCTGGCAGGTGTTGGGAC
CTGCTGCTCCATGGATGCATGCCCTAAGAGTGTCACTGAGCTGTGTTTTTGTCTGAGCCT
CTCTCGGTCAACAGCAAAGCTTGGTGTCTTGGCACTGTTAGTGACAGAGCCCAGCATCC
CTTCTGCCCCCGTTCCAGCTGACATCTTGCACGGTGACCCCTTTTAGTCAGGAGAGTGC
AGATCTGTGCTCATCGGAGACTGCCCCACGGCCCTGTCAGAGCCGCCACTCCTATCCCC
AGGCCAGGTCCCTGGACCAGCCTCCTGTTTGCAGGCCCAGAGGGAGCCAAGTCATTAAA
ATGGAAGTGGATTCTGGATGGCCGGGCTGCTGCTGATGTAGGAGCTGGATTTGGGAGC
TCTGCTTGCCGACTGGCTGTGAGACGAGGCAGGGGCTCTGCTTCCTCAGCCCTAGAGGC
GAGCCAGGCAAGGTTGGCGACTGTCATGTGGCTTGGTTTGGTCATGCCCGTCGATGTTT
TGGGTATTGAATGTGGTAAGTGGAGGAAATGTTGGAACTCTGTGCAGGTGCTGCCTTG
AGACCCCCAAGCTTCCACCTGTCCCTCTCCTATGTGGCAGCTGGGGAGCAGCTGAGATG
TGGACTTGTATGCTGCCCACATACGTGAGGGGAGCTGAAAGGGAGCCCCTCCTCTGA
GCAGCCTCTGCCAGGCCTGTATGAGGCTTTTCCCACCAGCTCCCAACAGAGGCCTCCCC
CAGCCAGGACCACCTCGTCCTCGTGGCGGGCAGCAGGAGCGGTAGAAAGGGGTCCG
ATGTTTGAGGAGGCCCTTAAGGGAAGCTACTGAATTATAACACGTAAGAAAATCACCA
TTCCGTATTGGTTGGGGGCTCCTGTTTCTCATCCTAGCTTTTTCCTGGAAAGCCCGCTAG
AAGGTTTGGGAACGAGGGGAAAGTTCTCAGAACTGTTGGCTGCTCCCCACCCGCCTCC
CGCCTCCCCCGCAGGTTATGTCAGCAGCTCTGAGACAGCAGTATCACAGGCCAGATGT
TGTTCCTGGCTAGATGTTTACATTTGTAAGAAATAACACTGTGAATGTAAAACAGAGCC
ATTCCCTTGGAATGCATATCGCTGGGCTCAACATAGAGTTTGTCTTCCTCTTGTTTACGA
CGTGATCTAAACCAGTCCTTAGCAAGGGGCTCAGAACACCCCGCTCTGGCAGTAGGTG
TCCCCCACCCCCAAAGACCTGCCTGTGTGCTCCGGAGATGAATATGAGCTCATTAGTAA
AAATGACTTCACCCCACGCATATACATAAAGTATCCATGCATGTGCATATAGACACATCT
ATAATTTTACACACACACCTCTCAAGACGGAGATGCATGGCCTCAAGAGTGCCCGTGT
CGGTTCTTCCTGGAAGTTGACTTTCCTTAGACCCGCCAGGTCAAGTTAGCCGCGTGACG
GACATCCAGGCGTGGGACGTGGTCAGGGCAGGGCTCATTCATTGCCCACTAGGATCCC
```

| SEQUENCES |
|---|
| ACTGGCGAAGATGGTCTCCATATCAGCTCTCTGCAGAAGGGAGGAAGACTTTATCATG
TTCCTAAAAATCTGTGGCAAGCACCCATCGTATTATCCAAATTTTGTTGCAAATGTGAT
TAATTTGGTTGTCAAGTTTTGGGGGTGGGCTGTGGGGAGATTGCTTTTGTTTTCCTGCTG
GTAATATCGGGAAAGATTTTAATGAAACCAGGGTAGAATTGTTTGGCAATGCACTGAA
GCGTGTTTCTTTCCCAAAATGTGCCTCCCTTCCGCTGCGGGCCCAGCTGAGTCTATGTA
GGTGATGTTTCCAGCTGCCAAGTGCTCTTTGTTACTGTCCACCCTCATTTCTGCCAGCGC
ATGTGTCCTTTCAAGGGGAAAATGTGAAGCTGAACCCCCTCCAGACACCCAGAATGTA
GCATCTGAGAAGGCCCTGTGCCCTAAAGGACACCCCTCGCCCCCATCTTCATGGAGGG
GGTCATTTCAGAGCCCTCGGAGCCAATGAACAGCTCCTCCTCTTGGAGCTGAGATGAG
CCCCACGTGGAGCTCGGGACGGATAGTAGACAGCAATAACTCGGTGTGTGGCCGCCTG
GCAGGTGGAACTTCCTCCCGTTGCGGGGTGGAGTGAGGTTAGTTCTGTGTGTCTGGTGG
GTGGAGTCAGGCTTCTCTTGCTACCTGTGAGCATCCTTCCCAGCAGACATCCTCATCGG
GCTTTGTCCCTCCCCCGCTTCCTCCCTCTGCGGGGAGGACCCGGGACCACAGCTGCTGG
CCAGGGTAGACTTGGAGCTGTCCTCCAGAGGGGTCACGTGTAGGAGTGAGAAGAAGG
AAGATCTTGAGAGCTGCTGAGGGACCTTGGAGAGCTCAGGATGGCTCAGACGAGGACA
CTCGCTTGCCGGGCCTGGGCCTCCTGGGAAGGAGGGAGCTGCTCAGAATGCCGCATGA
CAACTGAAGGCAACCTGGAAGGTTCAGGGGCCGCTCTTCCCCCATGTGCCTGTCACGCT
CTGGTGCAGTCAAAGGAACGCCTTCCCCTCAGTTGTTTCTAAGAGCAGAGTCTCCCGCT
GCAATCTGGGTGGTAACTGCCAGCCTTGGAGGATCGTGGCCAACGTGGACCTGCCTAC
GGAGGGTGGGCTCTGACCCAAGTGGGGCCTCCTTGTCCAGGTCTCACTGCTTTGCACCG
TGGTCAGAGGGACTGTCAGCTGAGCTTGAGCTCCCCTGGAGCCAGCAGGGCTGTGATG
GGCGAGTCCCGGAGCCCCACCCAGACCTGAATGCTTCTGAGAGCAAAGGGAAGGACTG
ACGAGAGATGTATATTTAATTTTTTAACTGCTGCAAACATTGTACATCCAAATTAAAGG
AAAAAAATGGAAACCATCAAAAAAAAAAAAAAAAAAA |

>SEQ ID NO: 2
TAAATGCCTGTTGAAGGGC

>SEQ ID NO: 3
AAGAGGTGCAGAGTCATCATC

>SEQ ID NO: 4
TTCTGGAGGACATCAAACCAT

>SEQ ID NO: 5
TGAACTGGCCCACTTCAATGT

>SEQ ID NO: 6
TTCCATTGGCAACTGGGCCAT

>SEQ ID NO: 7
TAAGCATGGAGCTAGCAGGCT

>SEQ ID NO: 8
TAGCGTTGAAGTACTGTCCCC

SEQ ID NO: 9
TTGAGGCAGCAGCGGCTGTGC

>SEQ ID NO: 10
TTCATCAGCTTTTCCAGGGTC

>SEQ ID NO: 11
TGGAATTCTCGGGTGCCAAGG

>SEQ ID NO: 12
CCTTGGCACCCGAGAATTCCA

>SEQ ID NO: 13
GUUCAGAGUUCUACAGUCCGACGAUC

>SEQ ID NO: 14
AATGATACGGCGACCACCGAGATCTACACGTTCAGAGTTCTACAGTCCGA

>SEQ ID NO: 15
CAAGCAGAAGACGGCATACGAGATNNNNNNGTGACTGGAGTTCCTTGGCACCCGAGA
ATTCCA

>SEQ ID NO: 16
LOCUS           dsCB-GFP-mir155- 5483 bp DNA circular SYN 11-OCT-2012

DEFINITION      Ligation of 6433 into dsCB-GFP-mirFlank-ployA*

ACCESSION       dsCB-GFP-mir155-

KEYWORDS        .

-continued

| SEQUENCES | |
|---|---|
| SOURCE | Unknown. |
| ORGANISM | Unknown<br>Unclassified. |
| REFERENCE | 1 (bases 1 to 5483) |
| AUTHORS | Self |
| JOURNAL | Unpublished. |
| COMMENT | SECID/File created by SciEd Central, Scientific & Educational Software |
| COMMENT | SECNOTESIVector molecule: dsCB-GFP-mirFlank-ployA*<br>Fragment ends: BsmBI<br>Fragment size: 5419<br>Insert molecule: 6433<br>Fragment ends:<br>Fragment size: 64 |
| FEATURES | Location/Qualifiers |
| misc_feature | 662..767<br>/gene = "mutated ITR"<br>/SECDrawAs = "Region" |
| misc_feature | 814..1093<br>/gene = "CMV enhancer"<br>/SECDrawAs = "Region" |
| misc_feature | 870..899<br>/gene = "tentative for<br>/SECDrawAs = "Region" |
| misc_feature | 1100..1126<br>/gene = "Probe"<br>/SECDrawAs = "Region" |
| misc_feature | 1100..1369<br>/gene = "B-Actin promoter"<br>/product = "Chicken"<br>/SECDrawAs = "Region" |
| misc_feature | complement (1168..1190)<br>/gene = "rev"<br>/SECDrawAs = "Region" |
| misc_feature | 1435..1465<br>/gene = "SV40 late 19s int"<br>/SECDrawAs = "Region" |
| misc_feature | 1435..1531<br>/gene = "modSV40 late 16s int"<br>/SECDrawAs = "Region" |
| CDS | 1605..2314<br>/gene = "GFP"<br>/SECDrawAs = "Gene" |
| misc_feature | 2341..2357<br>/gene = "MCS"<br>/SECDrawAs = "Region" |
| misc_feature | 2372..2395<br>/gene = "5'miR Flank'<br>/SECDrawAs = "Region" |
| misc_feature | 2460..2504<br>/gene = "3'miR Flank"<br>/SECDrawAs = "Region" |
| misc_feature | 2573..2699<br>/gene = "Poly A signal"<br>/product = "Rabbit globin poly A"<br>/SECDrawAs = "Region" |

-continued

| SEQUENCES | |
|---|---|
| misc_feature | complement (2788..2917)<br>/gene = "3' ITR"<br>/SECDrawAs = "Region" |
| CDS | 3680..4537<br>/gene = "Amp(R)"<br>/SECDrawAs = "Gene" |

```
ORIGIN
   1 gcccaatacg caaaccgcct ctccccgcgc gttggccgat tcattaatgc agctgattct
  61 aacgaggaaa gcacgttata cgtgctcgtc aaagcaacca tagtacgcgc cctgtagcgg
 121 cgcattaagc gcggcgggtg tggtggttac gcgcagcgtg accgctacac ttgccagcgc
 181 cctagcgccc gctcctttcg ctttcttccc ttcctttctc gccacgttcg ccggctttcc
 241 ccgtcaagct ctaaatcggg ggctcccttt agggttccga tttagtgctt tacggcacct
 301 cgaccccaaa aaacttgatt agggtgatgg ttcacgtagt gggccatcgc cctgatagac
 361 ggtttttcgc cctttgacgt tggagtccac gttctttaat agtggactct tgttccaaac
 421 tggaacaaca ctcaacccta tctcggtcta ttcttttgat ttataaggga ttttgccgat
 481 ttcggcctat tggttaaaaa atgagctgat ttaacaaaaa tttaacgcga attttaacaa
 541 aatattaacg cttacaattt aaatatttgc ttatacaatc ttcctgtttt tggggctttt
 601 ctgattatca accggggtac atatgattga catgctagtt ttacgattac cgttcatcgc
 661 cctgcgcgct cgctcgctca ctgaggccgc ccgggcaaag cccggcgtc gggcgacctt
 721 tggtcgcccg gcctcagtga gcgagcgagc gcgcagagag ggagtggaat tcacgcgtgg
 781 atctgaattc aattcacgcg tggtacctct ggtcgttaca taacttacgg taaatggccc
 841 gcctggctga ccgcccaacg accccgccc attgacgtca ataatgacgt atgttcccat
 901 agtaacgcca atagggactt tccattgacg tcaatgggtg gagtatttac ggtaaactgc
 961 ccacttggca gtacatcaag tgtatcatat gccaagtacg cccctattg acgtcaatga
1021 cggtaaatgg cccgcctggc attatgccca gtacatgacc ttatgggact ttcctacttg
1081 gcagtacatc tactcgaggc cacgttctgc ttcactctcc ccatctcccc ccctcccca
1141 cccccaattt tgtatttatt tattttttaa ttattttgtg cagcgatggg ggcggggggg
1201 gggggggggc gcgcgccagg cggggcgggg cgggcgaggc ggcggggcgg ggcgaggcgg
1261 agaggtgcgg cggcagccaa tcagagcggc gcgctccgaa agtttccttt tatggcgagg
1321 cggcggcggc ggcggcccta taaaaagcga agcgcgcggc gggcgggagc gggatcagcc
1381 accgcggtgg cggcctagag tcgacgagga actgaaaaac cagaaagtta actggtaagt
1441 ttagtctttt tgtctttat ttcaggtccc ggatccggtg gtggtgcaaa tcaaagaact
1501 gctcctcagt ggatgttgcc tttacttcta ggcctgtacg gaagtgttac ttctgctcta
1561 aaagctgcgg aattgtaccc gcggccgatc caccggtcgc caccatggtg agcaagggcg
1621 aggagctgtt caccggggtg gtgcccatcc tggtcgagct ggacggcgac gtaaacggcc
1681 acaagttcag cgtgtccggc gagggcgagg gcgatgccac ctacggcaag ctgaccctga
1741 agttcatctg caccaccggc aagctgcccg tgccctggcc caccctcgtg accaccctga
1801 cctacggcgt gcagtgcttc agccgctacc ccgaccacat gaagcagcac gacttcttca
1861 agtccgccat gcccgaaggc tacgtccagg agcgcaccat cttcttcaag gacgacggca
1921 actacaagac ccgcgccgag gtgaagttcg agggcgacac cctggtgaac cgcatcgagc
1981 tgaagggcat cgacttcaag gaggacggca acatcctggg gcacaagctg gagtacaact
```

| | SEQUENCES |
|---|---|
| 2041 | acaacagcca caacgtctat atcatggccg acaagcagaa gaacggcatc aaggtgaact |
| 2101 | tcaagatccg ccacaacatc gaggacggca gcgtgcagct cgccgaccac taccagcaga |
| 2161 | acacccccat cggcgacggc cccgtgctgc tgcccgacaa ccactacctg agcacccagt |
| 2221 | ccgccctgag caaagacccc aacgagaagc gcgatcacat ggtcctgctg gagttcgtga |
| 2281 | ccgccgccgg gatcactctc ggcatggacg agctgtacaa gtaaagcggc cctagcgttt |
| 2341 | ccggcgacgg tgctagcgtc gaccagtgga tcctggaggc ttgctgaagg ctgtatgctg |
| 2401 | taagcatgga gctagcaggc tgttttggcc actgactgac agcctgctct ccatgcttac |
| 2461 | aggacacaag gcctgttact agcactcaca tggaacaaat ggcccagatc tggccgcact |
| 2521 | cgaaaacggg ccctctagac tcgaggacgg ggtgaactac gcctgaggat ccgatctttt |
| 2581 | tccctctgcc aaaaattatg gggacatcat gaagcccctt gagcatctga cttctggcta |
| 2641 | ataaggaaa tttatttttca ttgcaatagt gtgttggaat ttttgtgtc tctcactcgg |
| 2701 | aagcaattcg ttgatctgaa tttcgaccac ccataatacc cattaccctg gtagataagt |
| 2761 | agcatggcgg gttaatcatt aactacaagg aaccctagt gatggagttg gccactccct |
| 2821 | ctctgcgcgc tcgctcgctc actgaggccg ggcgaccaaa ggtcgcccga cgcccgggct |
| 2881 | ttgcccgggc ggcctcagtg agcgagcgag cgcgcagcct taattaacct aattcactgg |
| 2941 | ccgtcgtttt acaacgtcgt gactgggaaa accctggcgt tacccaactt aatcgccttg |
| 3001 | cagcacatcc cctttcgcc agctggcgta atagcgaaga ggcccgcacc gatcgccctt |
| 3061 | cccaacagtt gcgcagcctg aatggcgaat gggacgcgcc ctgtagcggc gcattaagcg |
| 3121 | cggcgggtgt ggtggttacg cgcagcgtga ccgctacact tgccagcgcc ctagcgcccg |
| 3181 | ctcctttcgc tttcttccct cctttctcg ccacgttcgc cggctttccc cgtcaagctc |
| 3241 | taaatcgggg gctccctttta gggttccgat ttagtgcttt acggcacctc gaccccaaaa |
| 3301 | aacttgatta gggtgatggt tcacgtagtg gccatcgcc ctgatagacg ttttcgcc |
| 3361 | ctttgacgtt ggagtccacg ttctttaata gtggactctt gttccaaact ggaacaacac |
| 3421 | tcaaccctat ctcggtctat tcttttgatt tataagggat tttgccgatt tcggcctatt |
| 3481 | ggttaaaaaa tgagctgatt taacaaaaat ttaacgcgaa ttttaacaaa atattaacgc |
| 3541 | ttacaattta ggtggcactt ttcggggaaa tgtgcgcgga acccctattt gtttattttt |
| 3601 | ctaaatacat tcaaatatgt atccgctcat gagacaataa ccctgataaa tgcttcaata |
| 3661 | atattgaaaa aggaagagta tgagtattca acatttccgt gtcgccctta ttcccttttt |
| 3721 | tgcggcattt tgccttcctg ttttttgctca cccagaaacg ctggtgaaag taaaagatgc |
| 3781 | tgaagatcag ttgggtgcac gagtgggtta catcgaactg gatctcaaca gcggtaagat |
| 3841 | ccttgagagt tttcgccccg aagaacgttt tccaatgatg agcactttta aagttctgct |
| 3901 | atgtggcgcg gtattatccc gtattgacgc cgggcaagag caactcggtc gccgcataca |
| 3961 | ctattctcag aatgacttgg ttgagtactc accagtcaca gaaaagcatc ttacggatgg |
| 4021 | catgacagta agagaattat gcagtgctgc cataaccatg agtgataaca ctgcggccaa |
| 4081 | cttacttctg acaacgatcg gaggaccgaa ggagctaacc gcttttttgc acaacatggg |
| 4141 | ggatcatgta actcgccttg atcgttggga accggagctg aatgaagcca taccaaacga |
| 4201 | cgagcgtgac accacgatgc ctgtagcaat ggcaacaacg ttgcgcaaac tattaactgg |
| 4261 | cgaactactt actctagctt cccggcaaca attaatagac tggatggagg cggataaagt |
| 4321 | tgcaggacca cttctgcgct cggcccttcc ggctggctgg tttattgctg ataaatctgg |

| | |
|---|---|
| 4381 | agccggtgag cgtgggtctc gcggtatcat tgcagcactg gggccagatg gtaagccctc |
| 4441 | ccgtatcgta gttatctaca cgacggggag tcaggcaact atggatgaac gaaatagaca |
| 4501 | gatcgctgag ataggtgcct cactgattaa gcattggtaa ctgtcagacc aagtttactc |
| 4561 | atatatactt tagattgatt taaaacttca tttttaattt aaaaggatct aggtgaagat |
| 4621 | cctttttgat aatctcatga ccaaaatccc ttaacgtgag ttttcgttcc actgagcgtc |
| 4681 | agaccccgta gaaaagatca aggatcttc ttgagatcct ttttttctgc gcgtaatctg |
| 4741 | ctgcttgcaa acaaaaaaac caccgctacc agcggtggtt tgtttgccgg atcaagagct |
| 4801 | accaactctt tttccgaagg taactggctt cagcagagcg cagataccaa atactgttct |
| 4861 | tctagtgtag ccgtagttag gccaccactt caagaactct gtagcaccgc ctacatacct |
| 4921 | cgctctgcta atcctgttac cagtggctgc tgccagtggc gataagtcgt gtcttaccgg |
| 4981 | gttggactca agacgatagt taccggataa ggcgcagcgg tcgggctgaa cggggggttc |
| 5041 | gtgcacacag cccagcttgg agcgaacgac ctacaccgaa ctgagatacc tacagcgtga |
| 5101 | gctatgagaa agcgccacgc ttcccgaagg gagaaaggcg gacaggtatc cggtaagcgg |
| 5161 | cagggtcgga acaggagagc gcacgaggga gcttccaggg ggaaacgcct ggtatcttta |
| 5221 | tagtcctgtc gggtttcgcc acctctgact tgagcgtcga ttttgtgat gctcgtcagg |
| 5281 | ggggcggagc ctatggaaaa acgccagcaa cgcggccttt ttacggttcc tggccttttg |
| 5341 | ctggcctttt gctcacatgt tctttcctgc gttatcccct gattctgtgg ataaccgtat |
| 5401 | taccgccttt gagtgagctg ataccgctcg ccgcagccga acgaccgagc gcagcgagtc |
| 5461 | agtgagcgag gaagcggaag agc | |

```
>SEQ ID NO: 17
//LOCUS          pdsU6-Mir-htt-64 5686 bp DNA circular SYN 17-SEP-2013
  DEFINITION     Ligation of 6433 into pU6-miRNAFlank-GFP*
  ACCESSION      pdsU6-Mir-htt-64
  KEYWORDS       .
  SOURCE         Unknown.
  ORGANISM       Unknown
                 Unclassified.
  REFERENCE      1 (bases 1 to 5686)
  AUTHORS        Self
  JOURNAL        Unpublished.
  COMMENT        SECID/File created by SciEd Central, Scientific & Educational Software
  COMMENT        SECNOTESIVector molecule: pU6-miRNAFlank-GFP*
                 Fragment ends: BsmBI
                 Fragment size: 5622
                 Insert molecule: 6433
                 Fragment ends:
                 Fragment size: 64
  FEATURES       Location/Qualifiers
  misc_feature   662..767
                 /gene = "mutated ITR"
                 /SECDrawAs = "Region"

misc_feature   777..1041
                 /gene = "U6 promoter"
                 /SECDrawAs = "Region"
```

| | SEQUENCES |
|---|---|
| misc_signal | 1041..1041<br>/gene = "Pol III Start"<br>/product = "Transcriptional Start"<br>/SECDrawAs = "Label" |
| CDS | 1042..1065<br>/gene = "5' miR Flank"<br>/SECDrawAs = "Gene" |
| CDS | 1130..1175<br>/gene = "miR 3' Flank"<br>/SECDrawAs = "Gene" |
| misc_signal | 1176..1181<br>/gene = "Pol III term"<br>/product = "pol III terminator"<br>/SECDrawAs = "Label" |
| misc_feature | 1199..1478<br>/gene = "CMV enhancer"<br>/SECDrawAs = "Region" |
| misc_feature | 1255..1284<br>/gene = "tentative for"<br>/SECDrawAs = "Region" |
| misc_feature | 1485..1754<br>/gene = "B-Actin promoter"<br>/product = "Chicken"<br>/SECDrawAs = "Region" |
| misc_feature | 1485..1511<br>/gene = "Probe"<br>/SECDrawAs = "Region" |
| misc_feature | complement (1553..1575)<br>/gene = "rev"<br>/SECDrawAs = "Region" |
| misc_feature | 1820..1916<br>/gene = "modSV40 late 16s int"<br>/SECDrawAs = "Region" |
| misc_feature | 1820..1850<br>/gene = "SV40 late 19s int"<br>/SECDrawAs = "Region" |
| CDS | 1990..2699<br>/gene = "GFP"<br>/SECDrawAs = "Gene" |
| misc_feature | 2726..2737<br>/gene = "MCS"<br>/SECDrawAs = "Region" |
| misc_feature | 2776..2902<br>/gene = "Poly A signal"<br>/product = "Rabbit globin poly A"<br>/SECDrawAs = "Region" |
| misc_feature | complement (2991..3120)<br>/gene = "3' ITR"<br>/SECDrawAs = "Region" |
| CDS | 3883..4740<br>/gene = "Amp(R)"<br>/SECDrawAs = "Gene" |

ORIGIN
```
  1   gcccaatacg caaaccgcct ctccccgcgc gttggccgat tcattaatgc agctgattct
 61   aacgaggaaa gcacgttata cgtgctcgtc aaagcaacca tagtacgcgc cctgtagcgg
121   cgcattaagc gcggcgggtg tggtggttac gcgcagcgtg accgctacac ttgccagcgc
181   cctagcgccc gctcctttcg ctttcttccc ttcctttctc gccacgttcg ccggctttcc
```

| | SEQUENCES |
|---|---|
| 241 | ccgtcaagct ctaaatcggg ggctcccttt agggttccga tttagtgctt tacggcacct |
| 301 | cgaccccaaa aaacttgatt agggtgatgg ttcacgtagt gggccatcgc cctgatagac |
| 361 | ggttttcgc cctttgacgt tggagtccac gttctttaat agtggactct tgttccaaac |
| 421 | tggaacaaca ctcaaccta tctcggtcta ttcttttgat ttataaggga ttttgccgat |
| 481 | ttcggcctat tggttaaaaa atgagctgat ttaacaaaaa tttaacgcga attttaacaa |
| 541 | aatattaacg cttacaattt aaatatttgc ttatacaatc ttcctgtttt tgggcttt |
| 601 | ctgattatca accggggtac atatgattga catgctagtt ttacgattac cgttcatcgc |
| 661 | cctgcgcgct cgctcgctca ctgaggccgc ccgggcaaag cccgggcgtc gggcgacctt |
| 721 | tggtcgcccg gcctcagtga gcgagcgagc gcgcagagag ggagtggaat tctataaagg |
| 781 | tcgggcagga agagggccta tttcccatga ttccttcata tttgcatata cgatacaagg |
| 841 | ctgttagaga gataattaga attaatttga ctgtaaacac aaagatatta gtacaaaata |
| 901 | cgtgacgtag aaagtaataa tttcttgggt agtttgcagt tttaaaatta tgttttaaaa |
| 961 | tggactatca tatgcttacc gtaacttgaa agtatttcga tttcttggct ttatatatct |
| 1021 | tgtggaaagg acgaaacacc gcctggaggc ttgctgaagg ctgtatgctg taagcatgga |
| 1081 | gctagcaggc tgttttggcc actgactgac agcctgctct ccatgcttac aggacacaag |
| 1141 | gcctgttact agcactcaca tggaacaaat ggcccttttt tctagtggta cctctggtcg |
| 1201 | ttacataact tacggtaaat ggcccgcctg gctgaccgcc caacgacccc cgcccattga |
| 1261 | cgtcaataat gacgtatgtt cccatagtaa cgccaatagg gactttccat tgacgtcaat |
| 1321 | gggtggagta tttacggtaa actgcccact tggcagtaca tcaagtgtat catatgccaa |
| 1381 | gtacgccccc tattgacgtc aatgacggta atggcccgc ctggcattat gcccagtaca |
| 1441 | tgaccttatg ggactttcct acttggcagt acatctactc gaggccacgt tctgcttcac |
| 1501 | tctccccatc tcccccccct ccccaccccc aattttgtat ttatttattt tttaattatt |
| 1561 | ttgtgcagcg atgggggcgg ggggggggg gggcgcgcg ccaggcgggg cgggcgggg |
| 1621 | cgaggggcgg ggcggggcga ggcgagagg tgcggcggca gccaatcaga gcggcgcgct |
| 1681 | ccgaaagttt ccttttatgg cgaggcggcg gcggcggcgg ccctataaaa agcgaagcgc |
| 1741 | gcggcgggcg ggagcgggat cagccaccgc ggtggcggcc tagagtcgac gaggaactga |
| 1801 | aaaaccagaa agttaactgg taagtttagt cttttgtct tttatttcag gtcccggatc |
| 1861 | cggtggtggt gcaaatcaaa gaactgctcc tcagtggatg ttgcctttac ttctaggcct |
| 1921 | gtacggaagt gttacttctg ctctaaaagc tgcggaattg tacccgcggc cgatccaccg |
| 1981 | gtcgccacca tggtgagcaa gggcgaggag ctgttcaccg gggtggtgcc catcctggtc |
| 2041 | gagctggacg gcgacgtaaa cggccacaag ttcagcgtgt ccggcgaggg cgagggcgat |
| 2101 | gccacctacg gcaagctgac cctgaagttc atctgcacca ccggcaagct gcccgtgccc |
| 2161 | tggcccaccc tcgtgaccac cctgacctac ggcgtgcagt gcttcagccg ctacccgac |
| 2221 | cacatgaagc agcacgactt cttcaagtcc gccatgcccg aaggctacgt ccaggagcgc |
| 2281 | accatcttct tcaaggacga cggcaactac aagacccgcg ccgaggtgaa gttcgagggc |
| 2341 | gacaccctgg tgaaccgcat cgagctgaag ggcatcgact tcaaggagga cggcaacatc |
| 2401 | ctggggcaca gctggagta caactacaac agccacaacg tctatatcat ggccgacaag |
| 2461 | cagaagaacg gcatcaaggt gaacttcaag atccgccaca acatcgagga cggcagcgtg |
| 2521 | cagctcgccg accactacca gcagaacacc cccatcggcg acggccccgt gctgctgccc |

| | |
|---|---|
| 2581 | gacaaccact acctgagcac ccagtccgcc ctgagcaaag accccaacga gaagcgcgat |
| 2641 | cacatggtcc tgctggagtt cgtgaccgcc gccgggatca ctctcggcat ggacgagctg |
| 2701 | tacaagtaaa gcggccctag cgtttccggc gacggtgcta gactcgagga cggggtgaac |
| 2761 | tacgcctgag gatccgatct tttccctct gccaaaaatt atggggacat catgaagccc |
| 2821 | cttgagcatc tgacttctgg ctaataaagg aaatttattt tcattgcaat agtgtgttgg |
| 2881 | aattttttgt gtctctcact cggaagcaat tcgttgatct gaatttcgac cacccataat |
| 2941 | acccattacc ctggtagata agtagcatgg cggttaatc attaactaca aggaacccct |
| 3001 | agtgatggag ttggccactc cctctctgcg cgctcgctcg ctcactgagg ccgggcgacc |
| 3061 | aaaggtcgcc cgacgcccgg gctttgcccg ggcggcctca gtgagcgagc gagcgcgcag |
| 3121 | ccttaattaa cctaattcac tggccgtcgt tttacaacgt cgtgactggg aaaaccctgg |
| 3181 | cgttacccaa cttaatcgcc ttgcagcaca tccccctttc gccagctggc gtaatagcga |
| 3241 | agaggcccgc accgatcgcc cttcccaaca gttgcgcagc ctgaatggcg aatgggacgc |
| 3301 | gccctgtagc ggcgcattaa gcgcggcggg tgtggtggtt acgcgcagcg tgaccgctac |
| 3361 | acttgccagc gccctagcgc ccgctccttt cgctttcttc ccttcctttc tcgccacgtt |
| 3421 | cgccggcttt ccccgtcaag ctctaaatcg gggctccct ttagggttcc gatttagtgc |
| 3481 | tttacggcac ctcgacccca aaaaacttga ttagggtgat ggttcacgta gtgggccatc |
| 3541 | gccctgatag acggtttttc gccctttgac gttggagtcc acgttcttta atagtggact |
| 3601 | cttgttccaa actggaacaa cactcaaccc tatctcggtc tattcttttg atttataagg |
| 3661 | gattttgccg atttcggcct attggttaaa aaatgagctg atttaacaaa aatttaacgc |
| 3721 | gaattttaac aaaatattaa cgcttacaat ttaggtggca cttttcgggg aaatgtgcgc |
| 3781 | ggaaccccta tttgtttatt tttctaaata cattcaaata tgtatccgct catgagacaa |
| 3841 | taaccctgat aaatgcttca ataatattga aaaaggaaga gtatgagtat tcaacatttc |
| 3901 | cgtgtcgccc ttattccctt ttttgcggca ttttgccttc ctgttttgc tcacccagaa |
| 3961 | acgctggtga agtaaaaga tgctgaagat cagttgggtg cacgagtggg ttacatcgaa |
| 4021 | ctggatctca acagcggtaa gatccttgag agttttcgcc ccgaagaacg ttttccaatg |
| 4081 | atgagcactt ttaaagttct gctatgtggc gcggtattat cccgtattga cgccgggcaa |
| 4141 | gagcaactcg gtcgccgcat acactattct cagaatgact tggttgagta ctcaccagtc |
| 4201 | acagaaaagc atcttacgga tggcatgaca gtaagagaat tatgcagtgc tgccataacc |
| 4261 | atgagtgata acactgcggc caacttactt ctgacaacga tcggaggacc gaaggagcta |
| 4321 | accgcttttt tgcacaacat gggggatcat gtaactcgcc ttgatcgttg gaaccggag |
| 4381 | ctgaatgaag ccataccaaa cgacgagcgt gacaccacga tgcctgtagc aatggcaaca |
| 4441 | acgttgcgca aactattaac tggcgaacta cttactctag cttcccggca caattaata |
| 4501 | gactggatgg aggcggataa agttgcagga ccacttctgc gctcggccct tccggctggc |
| 4561 | tggtttattg ctgataaatc tggagccgt gagcgtgggt ctcgcggtat cattgcagca |
| 4621 | ctggggccag atggtaagcc ctcccgtatc gtagttatct acacgacggg gagtcaggca |
| 4681 | actatggatg aacgaaatag acagatcgct gagataggtg cctcactgat taagcattgg |
| 4741 | taactgtcag accaagttta ctcatatata ctttagattg atttaaaact tcattttaa |
| 4801 | tttaaaagga tctaggtgaa gatcctttt gataatctca tgaccaaaat cccttaacgt |

| SEQUENCES |
| --- |

```
4861    gagttttcgt tccactgagc gtcagacccc gtagaaaaga tcaaaggatc ttcttgagat
4921    ccttttttc  tgcgcgtaat ctgctgcttg caaacaaaaa aaccaccgct accagcggtg
4981    gtttgtttgc cggatcaaga gctaccaact cttttccga  aggtaactgg cttcagcaga
5041    gcgcagatac caaatactgt tcttctagtg tagccgtagt taggccacca cttcaagaac
5101    tctgtagcac cgcctacata cctcgctctg ctaatcctgt taccagtggc tgctgccagt
5161    ggcgataagt cgtgtcttac cgggttggac tcaagacgat agttaccgga taaggcgcag
5221    cggtcgggct gaacggggggg ttcgtgcaca cagcccagct tggagcgaac gacctacacc
5281    gaactgagat acctacagcg tgagctatga gaaagcgcca cgcttcccga agggagaaag
5341    gcggacaggt atccggtaag cggcagggtc ggaacaggag agcgcacgag ggagcttcca
5401    gggggaaacg cctggtatct ttatagtcct gtcgggtttc gccacctctg acttgagcgt
5461    cgatttttgt gatgctcgtc agggggggcgg agcctatgga aaaacgccaa caacgcggcc
5521    tttttacggt tcctggcctt ttgctggcct tttgctcaca tgttctttcc tgcgttatcc
5581    cctgattctg tggataaccg tattaccgcc tttgagtgag ctgataccgc tcgccgcagc
5641    cgaacgaccg agcgcagcga gtcagtgagc gaggaagcgg aagagc
```

>SEQ ID NO: 18
LOCUS          pCVscAsaq+-mir64 5155 bp DNA circular SYN 17-SEP-2013
DEFINITION     Ligation of 6433 into pCVscAsaq+-mirFlank*
ACCESSION      pCVscAsaq+-mir64
KEYWORDS       .
SOURCE         Unknown.
ORGANISM       Unknown
               Unclassified.
REFERENCE      1 (bases 1 to 5155)
AUTHORS        Self
JOURNAL        Unpublished.
COMMENT        SECID/File created by SciEd Central, Scientific & Educational Software
COMMENT        SECNOTESIVector molecule: pCVscAsaq+-mirFlank*
               Fragment ends: BsmBI
               Fragment size: 5090
               Insert molecule: 6433
               Fragment ends:
               Fragment size: 64
FEATURES       Location/Qualifiers
misc_feature   1..105
               /gene = "ITR"
               /SECDrawAs = "Region"

misc_feature   182..449
               /gene = "CMV"
               /product = "CMV Enhancer"
               /SECDrawAs = "Region"

CDS            448..753
               /gene = "CB promoter"
               /product = "Promoter Eukaryotic"
               /SECDrawAs = "Gene"

CDS            754..1819
               /gene = "Intron"
               /product = "Intron"
               /SECDrawAs = "Gene"

| SEQUENCES | |
|---|---|
| CDS | 1820..1839<br>/gene = "MCS"<br>/SECDrawAs = "Gene" |
| misc_feature | 1843..1847<br>/gene = "MCS"<br>/SECDrawAs = "Region" |
| misc_feature | 1862..1885<br>/gene = "5'miR Flank"<br>/SECDrawAs = "Region" |
| misc_feature | 1950..1994<br>/gene = "3'miR Flank"<br>/SECDrawAs = "Region" |
| CDS | 2002..2128<br>/gene = "RBG pA"<br>/product = "PolyA Signal"<br>/SECDrawAs = "Gene" |
| misc_feature | complement (2002..2128)<br>/gene = "RBG\pA"<br>/SECDrawAs = "Info only" |
| misc_feature | 2139..2281<br>/gene = "3'ITR"<br>/SECDrawAs = "Region" |
| CDS | 2317..2509<br>/gene = "lacZ"<br>/SECDrawAs = "Gene" |
| CDS | 2510..2965<br>/gene = "f1 ori"<br>/SECDrawAs = "Gene" |
| misc_feature | 3097..3957<br>/gene = "bla-AmpR"<br>/SECDrawAs = "Region" |
| misc_feature | 4117..4731<br>/gene = "rep-pMB1"<br>/SECDrawAs = "Region" |

```
ORIGIN
    1 ctgcgcgctc gctcgctcac tgaggccgcc cgggcaaagc ccgggcgtcg ggcgaccttt
   61 ggtcgcccgg cctcagtgag cgagcgagcg cgcagagagg gagtgtagcc atgctctagg
  121 aagatcaatt caattcacgc gtcgacattg attattgact agctctggtc gttacataac
  181 ttacggtaaa tggcccgcct ggctgaccgc ccaacgaccc ccgcccattg acgtcaataa
  241 tgacgtatgt tcccatagta acgccaatag ggactttcca ttgacgtcaa tgggtggagt
  301 atttacggta aactgcccac ttggcagtac atcaagtgta tcatatgcca agtccgcccc
  361 ctattgacgt caatgacggt aaatggcccg cctggcatta tgcccagtac atgaccttac
  421 gggactttcc tacttggcag tacatctacg tattagtcat cgctattacc atggtcgagg
  481 tgagcccac gttctgcttc actctcccca tctcccccc ctccccaccc ccaatttgt
  541 atttatttat tttttaatta ttttgtgcag cgatggggc ggggggggg ggggggcgcg
  601 cgccaggcgg ggcggggcgg ggcgaggggc ggggcgggc gaggcggaga ggtgcggcgg
  661 cagccaatca gagcggcgcg ctccgaaagt ttccttttat ggcgaggcgg cggcggcggc
  721 ggccctataa aaagcgaagc gcgcggcggg cgggagtcgc tgcgcgctgc cttcgccccg
  781 tgccccgctc cgccgccgcc tcgcgccgcc cgccccggct ctgactgacc gcgttactcc
  841 cacaggtgag cgggcgggac ggcccttctc ctccgggctg taattagcgc ttggtttaat
  901 gacggcttgt ttcttttctg tggctgcgtg aaagccttga ggggctccgg gagggccctt
```

-continued

| | SEQUENCES |
|---|---|
| 961 | tgtgcggggg ggagcggctc ggggggtgcg tgcgtgtgtg tgtgcgtggg gagcgccgcg |
| 1021 | tgcggctccg cgctgcccgg cggctgtgag cgctgcgggc gcggcgcggg gctttgtgcg |
| 1081 | ctccgcagtg tgcgcgaggg gagcgcggcc gggggcggtg ccccgcggtg cggggggggc |
| 1141 | tgcgagggga acaaaggctg cgtgcggggt gtgtgcgtgg ggggtgagc aggggtgtg |
| 1201 | ggcgcgtcgg tcgggctgca acccccctg cacccccctc cccgagttgc tgagcacggc |
| 1261 | ccggcttcgg gtgcggggct ccgtacgggg cgtggcgcgg ggctcgccgt gccggcggg |
| 1321 | gggtggcggc aggtggggt gccgggcggg gcggggccgc ctcgggccgg ggagggctcg |
| 1381 | ggggaggggc gcggcggccc ccggagcgcc ggcggctgtc gaggcgcggc gagccgcagc |
| 1441 | cattgccttt tatggtaatc gtgcgagagg gcgcagggac ttcctttgtc ccaaatctgt |
| 1501 | gcggagccga aatctgggag gcgccgccgc accccctcta gcgggcgcgg ggcgaagcgg |
| 1561 | tgcggcgccg gcaggaagga aatgggcggg gagggccttc gtgcgtcgcc gcgccgccgt |
| 1621 | ccccttctcc ctctccagcc tcggggctgt ccgcgggggg acggctgcct tcgggggga |
| 1681 | cggggcaggg cggggttcgg cttctggcgt gtgaccggcg gctctagagc ctctgctaac |
| 1741 | catgttcatg ccttcttctt tttcctacag ctcctgggca acgtgctggt tattgtgctg |
| 1801 | tctcatcatt ttggcaaaga attcatcgat accgtcgacg atctagcgtc gaccagtgga |
| 1861 | tcctggaggc ttgctgaagg ctgtatgctg taagcatgga gctagcaggc tgttttggcc |
| 1921 | actgactgac agcctgctct ccatgcttac aggacacaag gcctgttact agcactcaca |
| 1981 | tggaacaaat ggcccagatc cgatcttttt ccctctgcca aaaattatgg ggacatcatg |
| 2041 | aagcccttg agcatctgac ttctggctaa taaggaaat ttattttcat tgcaatagtg |
| 2101 | tgttggaatt ttttgtgtct ctcactcgat cagatctgag gaaccctag tgatggagtt |
| 2161 | ggccactccc tctctgcgcg ctcgctcgct cactgaggcc gcccgggcaa agcccgggcg |
| 2221 | tcgggcgacc tttggtcgcc cggcctcagt gagcgagcga gcgcgcagag agggagtggc |
| 2281 | cccccccccc cccccccct gcattctaga gagctccaat tcgccctata gtgagtcgta |
| 2341 | ttacgcgcgc tcactggccg tcgttttaca acgtcgtgac tgggaaaacc ctggcgttac |
| 2401 | ccaacttaat cgccttgcag cacatccccc tttcgccagc tggcgtaata gcgaagaggc |
| 2461 | ccgcaccgat cgcccttccc aacagttgcg cagcctgaat ggcgaatgga aattgtaagc |
| 2521 | gttaatattt tgttaaaatt cgcgttaaat ttttgttaaa tcagctcatt ttttaaccaa |
| 2581 | taggccgaaa tcggcaaaat cccttataaa tcaaaagaat agaccgagat agggttgagt |
| 2641 | gttgttccag tttggaacaa gagtccacta ttaaagaacg tggactccaa cgtcaaaggg |
| 2701 | cgaaaaaccg tctatcaggg cgatggccca ctacgtgaac catcaccta atcaagtttt |
| 2761 | ttggggtcga ggtgccgtaa agcactaaat cggaaccta aagggagccc ccgatttaga |
| 2821 | gcttgacggg gaaagccggc gaacgtggcg agaaaggaag ggaagaaagc gaaaggagcg |
| 2881 | ggcgctaggg cgctggcaag tgtagcggtc acgctgcgcg taaccaccac acccgccgcg |
| 2941 | cttaatgcgc cgctacaggg cgcgtcaggt ggcactttc ggggaaatgt gcgcggaacc |
| 3001 | cctatttgtt tatttttcta aatacattca aatatgtatc cgctcatgag acaataaccc |
| 3061 | tgataaatgc ttcaataata ttgaaaaagg aagagtatga gtattcaaca tttccgtgtc |
| 3121 | gcccttattc ccttttttgc ggcattttgc cttcctgttt ttgctcaccc agaaacgctg |
| 3181 | gtgaaagtaa aagatgctga agatcagttg ggtgcacgag tgggttacat cgaactggat |

| SEQUENCES |
|---|
| 3241 ctcaacagcg gtaagatcct tgagagtttt cgccccgaag aacgttttcc aatgatgagc |
| 3301 acttttaaag ttctgctatg tggcgcggta ttatcccgta ttgacgccgg gcaagagcaa |
| 3361 ctcggtcgcc gcatacacta ttctcagaat gacttggttg agtactcacc agtcacagaa |
| 3421 aagcatctta cggatggcat gacagtaaga gaattatgca gtgctgccat aaccatgagt |
| 3481 gataacactg cggccaactt acttctgaca acgatcggag gaccgaagga gctaaccgct |
| 3541 tttttgcaca acatggggga tcatgtaact cgccttgatc gttgggaacc ggagctgaat |
| 3601 gaagccatac caaacgacga gcgtgacacc acgatgcctg tagcaatggc aacaacgttg |
| 3661 cgcaaactat taactggcga actacttact ctagcttccc ggcaacaatt aatagactgg |
| 3721 atggaggcgg ataaagttgc aggaccactt ctgcgctcgg cccttccggc tggctggttt |
| 3781 attgctgata aatctggagc cggtgagcgt gggtctcgcg gtatcattgc agcactgggg |
| 3841 ccagatggta agccctcccg tatcgtagtt atctacacga cggggagtca ggcaactatg |
| 3901 gatgaacgaa atagacagat cgctgagata ggtgcctcac tgattaagca ttggtaactg |
| 3961 tcagaccaag tttactcata tatactttag attgatttaa aacttcattt ttaatttaaa |
| 4021 aggatctagg tgaagatcct ttttgataat ctcatgacca aaatccctta acgtgagttt |
| 4081 tcgttccact gagcgtcaga ccccgtagaa aagatcaaag gatcttcttg agatcctttt |
| 4141 tttctgcgcg taatctgctg cttgcaaaca aaaaaaccac cgctaccagc ggtggtttgt |
| 4201 ttgccggatc aagagctacc aactcttttt ccgaaggtaa ctggcttcag cagagcgcag |
| 4261 ataccaaata ctgtccttct agtgtagccg tagttaggcc accacttcaa gaactctgta |
| 4321 gcaccgccta catacctcgc tctgctaatc ctgttaccag tggctgctgc cagtggcgat |
| 4381 aagtcgtgtc ttaccgggtt ggactcaaga cgatagttac cggataaggc gcagcggtcg |
| 4441 ggctgaacgg ggggttcgtg cacacagccc agcttggagc gaacgaccta caccgaactg |
| 4501 agatacctac agcgtgagct atgagaaagc gccacgcttc ccgaagggag aaaggcggac |
| 4561 aggtatccgg taagcggcag ggtcggaaca ggagagcgca cgagggagct tccaggggga |
| 4621 aacgcctggt atctttatag tcctgtcggg tttcgccacc tctgacttga gcgtcgattt |
| 4681 ttgtgatgct cgtcaggggg cggagcctat ggaaaaacg ccagcaacgc ggcctttta |
| 4741 cggttcctgg ccttttgctg gccttttgct cacatgttct ttcctgcgtt atcccctgat |
| 4801 tctgtggata accgtattac cgcctttgag tgagctgata ccgctcgccg cagccgaacg |
| 4861 accgagcgca gcgagtcagt gagcgaggaa gcggaagagc gcccaatacg caaaccgcct |
| 4921 ctccccgcgc gttggccgat tcattaatgc agctggcacg acaggtttcc cgactggaaa |
| 4981 gcgggcagtg agcgcaacgc aattaatgtg agttagctca ctcattaggc accccaggct |
| 5041 ttacacttta tgcttccggc tcgtatgttg tgtggaattg tgagcggata acaatttcac |
| 5101 acaggaaaca gctatgacca tgattacgcc agatttaatt aaggccttaa ttagg |

>SEQ ID NO: 19
LOCUS          U6-mir6433-BGHpA 5223 bp DNA circular SYN 12-SEP-2013

DEFINITION      Ligation of dsAAV CB MCS into U6-MiRBA-6433-GFP

ACCESSION       U6-mir6433-BGHpA

KEYWORDS        .

SOURCE          Unknown.

ORGANISM        Unknown
                 Unclassified.

-continued

| SEQUENCES |
|---|

| | |
|---|---|
| REFERENCE | 1 (bases 1 to 5223) |
| AUTHORS | Self |
| JOURNAL | Unpublished. |
| COMMENT | SECID/File created by SciEd Central, Scientific & Educational Software |
| COMMENT | SECNOTESIVector molecule: U6-MiRBA-6433-GFP<br>Fragment ends: blunt and EagI<br>Fragment size: 4954<br>Insert molecule: dsAAV CB MCS<br>Fragment ends: EagI and blunt<br>Fragment size: 269 |
| FEATURES | Location/Qualifiers |
| misc_feature | 662..767<br>/gene = "mutated ITR"<br>/SECDrawAs = "Region" |
| misc_feature | 777..1041<br>/gene = "U6 promoter"<br>/SECDrawAs = "Region" |
| misc_signal | 1041..1041<br>/gene = "Pol III Start"<br>/product = "Transcriptional Start"<br>/SECDrawAs = "Label" |
| CDS | 1042..1065<br>/gene = "5' miR Flank"<br>/SECDrawAs = "Gene" |
| CDS | 1130..1175<br>/gene = "miR 3' Flank"<br>/SECDrawAs = "Gene" |
| misc_signal | 1176..1181<br>/gene = "Pol III term"<br>/product = "pol III terminator"<br>/SECDrawAs = "Label" |
| misc_feature | 1199..1478<br>/gene = "CMV enhancer"<br>/SECDrawAs = "Region" |
| misc_feature | 1255..1284<br>/gene = "tentative for"<br>/SECDrawAs = "Region" |
| misc_feature | 1485..1511<br>/gene = "Probe"<br>/SECDrawAs = "Region" |
| misc_feature | 1485..1754<br>/gene = "B-Actin promoter"<br>/product = "Chicken"<br>/SECDrawAs = "Region" |
| misc_feature | complement (1553..1575)<br>/gene = "rev"<br>/SECDrawAs = "Region" |
| misc_feature | 1820..1850<br>/gene = "SV40 late 19s int"<br>/SECDrawAs = "Region" |
| misc_feature | 1820..1916<br>/gene = "modSV40 late 16s int"<br>/SECDrawAs = "Region" |
| misc_feature | 2034..2230<br>/gene = "BGHpA"<br>/SECDrawAs = "Region" |

-continued

| SEQUENCES |
|---|

```
misc_feature      2263..2274
                  /gene = "MCS"
                  /SECDrawAs = "Region"

misc_feature      2313..2439
                  /gene = "Poly A signal"
                  /product = "Rabbit globin poly A"
                  /SECDrawAs = "Region"

misc_feature      complement (2528..2657)
                  /gene = "3' ITR"
                  /SECDrawAs = "Region"

CDS               3420..4277
                  /gene = "Amp(R)"
                  /SECDrawAs = "Gene"

ORIGIN
    1      gcccaatacg caaaccgcct ctcccgcgc gttggccgat tcattaatgc agctgattct
   61      aacgaggaaa gcacgttata cgtgctcgtc aaagcaacca tagtacgcgc cctgtagcgg
  121      cgcattaagc gcggcgggtg tggtggttac gcgcagcgtg accgctacac ttgccagcgc
  181      cctagcgccc gctcctttcg ctttcttccc ttcctttctc gccacgttcg ccggctttcc
  241      ccgtcaagct ctaaatcggg ggctcccttt agggttccga tttagtgctt tacggcacct
  301      cgaccccaaa aaacttgatt agggtgatgg ttcacgtagt gggccatcgc cctgatagac
  361      ggttttttcgc cctttgacgt tggagtccac gttctttaat agtggactct tgttccaaac
  421      tggaacaaca ctcaacccta tctcggtcta ttctttgat ttataaggga ttttgccgat
  481      ttcggcctat tggttaaaaa atgagctgat ttaacaaaaa tttaacgcga attttaacaa
  541      aatattaacg cttacaattt aaatatttgc ttatacaatc ttcctgtttt tggggctttt
  601      ctgattatca accggggtac atatgattga catgctagtt tacgattac cgttcatcgc
  661      cctgcgcgct cgctcgctca ctgaggccgc ccgggcaaag cccgggcgtc gggcgacctt
  721      tggtcgcccg gcctcagtga gcgagcgagc gcgcagagag ggagtggaat tctataaagg
  781      tcgggcagga agagggccta tttcccatga ttccttcata tttgcatata cgatacaagg
  841      ctgttagaga gataattaga attaatttga ctgtaaacac aaagatatta gtacaaaata
  901      cgtgacgtag aaagtaataa tttcttgggt agtttgcagt tttaaaatta tgttttaaaa
  961      tggactatca tatgcttacc gtaacttgaa agtatttcga tttcttggct ttatatatct
 1021      tgtggaaagg acgaaacacc gcctggaggc ttgctgaagg ctgtatgctg taagcatgga
 1081      gctagcaggc tgttttggcc actgactgac agcctgctct ccatgcttac aggacacaag
 1141      gcctgttact agcactcaca tggaacaaat ggcccttttt tctagtggta cctctggtcg
 1201      ttacataact tacggtaaat ggcccgcctg gctgaccgcc caacgacccc cgcccattga
 1261      cgtcaataat gacgtatgtt cccatagtaa cgccaatagg gactttccat tgacgtcaat
 1321      gggtggagta tttacggtaa actgcccact ggcagtaca tcaagtgtat catatgccaa
 1381      gtacgccccc tattgacgtc aatgacggta aatggcccgc ctggcattat gcccagtaca
 1441      tgaccttatg gactttcct acttggcagt acatctactc gaggccacgt tctgcttcac
 1501      tctccccatc tcccccccct cccacccc aattttgtat ttatttattt tttaattatt
 1561      ttgtgcagcg atggggggcgg ggggggggg gggcgcgcg ccaggcgggg cggggcgggg
 1621      cgaggggcgg ggcggggcga ggcggagagg tgcggcggca gccaatcaga gcggcgcgct
 1681      ccgaaagttt ccttttatgg cgaggcggcg gcggcggcgg ccctataaaa agcgaagcgc
 1741      gcggcgggcg ggagcgggat cagccaccgc ggtggcggcc tagagtcgac gaggaactga
```

| | |
|---|---|
| 1801 | aaaaccagaa agttaactgg taagtttagt cttttttgtct tttatttcag gtcccggatc |
| 1861 | cggtggtggt gcaaatcaaa gaactgctcc tcagtggatg ttgcctttac ttctaggcct |
| 1921 | gtacggaagt gttacttctg ctctaaaagc tgcggaattg tacccgcggc cgcgtttaaa |
| 1981 | ccctgcaggt ctagaaagct tatcgatacc gtcgactaga gctcgctgat cagcctcgac |
| 2041 | tgtgccttct agttgccagc catctgttgt ttgcccctcc cccgtgcctt ccttgaccct |
| 2101 | ggaaggtgcc actcccactg tcctttccta ataaaatgag gaaattgcat cgcattgtct |
| 2161 | gagtaggtgt cattctattc tggggggtgg ggtggggcag gacagcaagg gggaggattg |
| 2221 | ggaagacaat agcagggtac aagtaaagcg ccctagcgt ttccggcgac ggtgctagac |
| 2281 | tcgaggacgg ggtgaactac gcctgaggat ccgatctttt tccctctgcc aaaaattatg |
| 2341 | gggacatcat gaagcccctt gagcatctga cttctggcta ataaggaaa tttattttca |
| 2401 | ttgcaatagt gtgttggaat ttttttgtgtc tctcactcgg aagcaattcg ttgatctgaa |
| 2461 | tttcgaccac ccataatacc cattaccctg gtagataagt agcatggcgg gttaatcatt |
| 2521 | aactacaagg aaccccctagt gatggagttg gccactccct ctctgcgcgc tcgctcgctc |
| 2581 | actgaggccg ggcgaccaaa ggtcgcccga cgcccgggct ttgcccgggc ggcctcagtg |
| 2641 | agcgagcgag cgcgcagcct taattaacct aattcactgg ccgtcgtttt acaacgtcgt |
| 2701 | gactgggaaa accctggcgt tacccaactt aatcgccttg cagcacatcc cctttcgcc |
| 2761 | agctggcgta atagcgaaga ggcccgcacc gatcgccctt cccaacagtt gcgcagcctg |
| 2821 | aatggcgaat gggacgcgcc ctgtagcggc gcattaagcg cggcgggtgt ggtggttacg |
| 2881 | cgcagcgtga ccgctacact tgccagcgcc ctagcgcccg ctcctttcgc tttcttccct |
| 2941 | tcctttctcg ccacgttcgc cggctttccc cgtcaagctc taaatcgggg gctcccttta |
| 3001 | gggttccgat ttagtgcttt acggcacctc gaccccaaaa aacttgatta gggtgatggt |
| 3061 | tcacgtagtg ggccatcgcc ctgatagacg ttttttcgcc ctttgacgtt ggagtccacg |
| 3121 | ttctttaata gtggactctt gttccaaact ggaacaacac tcaaccctat ctcggtctat |
| 3181 | tcttttgatt tataagggat tttgccgatt tcggcctatt ggttaaaaaa tgagctgatt |
| 3241 | taacaaaaat ttaacgcgaa ttttaacaaa atattaacgc ttacaattta ggtggcactt |
| 3301 | ttcggggaaa tgtgcgcgga acccctattt gtttattttt ctaaatacat tcaaatatgt |
| 3361 | atccgctcat gagacaataa ccctgataaa tgcttcaata atattgaaaa aggaagagta |
| 3421 | tgagtattca acatttccgt gtcgccctta ttccctttt tgcggcattt tgccttcctg |
| 3481 | tttttgctca cccagaaacg ctggtgaaag taaaagatgc tgaagatcag ttgggtgcac |
| 3541 | gagtgggtta catcgaactg gatctcaaca gcggtaagat ccttgagagt tttcgccccg |
| 3601 | aagaacgttt tccaatgatg agcacttta aagttctgct atgtggcgcg gtattatccc |
| 3661 | gtattgacgc cgggcaagag caactcggtc gccgcataca ctattctcag aatgacttgg |
| 3721 | ttgagtactc accagtcaca gaaaagcatc ttacggatgg catgacagta agagaattat |
| 3781 | gcagtgctgc cataaccatg agtgataaca ctgcggccaa cttacttctg acaacgatcg |
| 3841 | gaggaccgaa ggagctaacc gcttttttgc acaacatggg ggatcatgta actcgccttg |
| 3901 | atcgttggga accggagctg aatgaagcca taccaaacga cgagcgtgac accacgatgc |
| 3961 | ctgtagcaat ggcaacaacg ttgcgcaaac tattaactgg cgaactactt actctagctt |
| 4021 | cccggcaaca attaatagac tggatggagg cggataaagt tgcaggacca cttctgcgct |

| | | | | |
|---|---|---|---|---|
| 4081 | cggcccttcc | ggctggctgg | tttattgctg | ataaatctgg | agccggtgag | cgtgggtctc |
| 4141 | gcggtatcat | tgcagcactg | gggccagatg | gtaagccctc | ccgtatcgta | gttatctaca |
| 4201 | cgacggggag | tcaggcaact | atggatgaac | gaaatagaca | gatcgctgag | ataggtgcct |
| 4261 | cactgattaa | gcattggtaa | ctgtcagacc | aagtttactc | atatatactt | tagattgatt |
| 4321 | taaaacttca | ttttttaattt | aaaaggatct | aggtgaagat | ccttttttgat | aatctcatga |
| 4381 | ccaaaatccc | ttaacgtgag | ttttcgttcc | actgagcgtc | agacccccgta | gaaaagatca |
| 4441 | aaggatcttc | ttgagatcct | tttttttctgc | gcgtaatctg | ctgcttgcaa | acaaaaaaac |
| 4501 | caccgctacc | agcggtggtt | tgtttgccgg | atcaagagct | accaactctt | tttccgaagg |
| 4561 | taactggctt | cagcagagcg | cagataccaa | atactgttct | tctagtgtag | ccgtagttag |
| 4621 | gccaccactt | caagaactct | gtagcaccgc | ctacatacct | cgctctgcta | atcctgttac |
| 4681 | cagtggctgc | tgccagtggc | gataagtcgt | gtcttaccgg | gttggactca | agacgatagt |
| 4741 | taccggataa | ggcgcagcgg | tcgggctgaa | cggggggttc | gtgcacacag | cccagcttgg |
| 4801 | agcgaacgac | ctacaccgaa | ctgagatacc | tacagcgtga | gctatgagaa | agcgccacgc |
| 4861 | ttcccgaagg | gagaaaggcg | gacaggtatc | cggtaagcgg | cagggtcgga | acaggagagc |
| 4921 | gcacgaggga | gcttccaggg | ggaaacgcct | ggtatcttta | tagtcctgtc | gggtttcgcc |
| 4981 | acctctgact | tgagcgtcga | tttttgtgat | gctcgtcagg | ggggcggagc | ctatgaaaaa |
| 5041 | acgccagcaa | cgcggccttt | ttacggttcc | tggccttttg | ctggccttttt | gctcacatgt |
| 5101 | tctttcctgc | gttatcccct | gattctgtgg | ataaccgtat | taccgccttt | gagtgagctg |
| 5161 | ataccgctcg | ccgcagccga | acgaccgagc | gcagcgagtc | agtgagcgag | gaagcggaag |
| 5221 | agc | | | | | |

>SEQ ID NO: 20 AAV9 Capsid Protein
MAADGYLPDWLEDNLSEGIREWWALKPGAPQPKANQQHQDNARGLVLPGYKYLGPGNG
LDKGEPVNAADAAALEHDKAYDQQLKAGDNPYLKYNHADAEFQERLKEDTSFGGNLGR
AVFQAKKRLLEPLGLVEEAAKTAPGKKRPVEQSPQEPDSSAGIGKSGAQPAKKRLNFGQTG
DTESVPDPQPIGEPPAAPSGVGSLTMASGGGAPVADNNEGADGVGSSSGNWHCDSQWLG
DRVITTSTRTWALPTYNNHLYKQISNSTSGGSSNDNAYFGYSTPWGYFDFNRFHCHFSPRD
WQRLINNNWGFRPKRLNFKLFNIQVKEVTDNNGVKTIANNLTSTVQVFTDSDYQLPYVLG
SAHEGCLPPFPADVFMIPQYGYLTLNDGSQAVGRSSFYCLEYFPSQMLRTGNNFQFSYEFE
NVPFHSSYAHSQSLDRLMNPLIDQYLYYLSKTINGSGQNQQTLKFSVAGPSNMAVQGRNYI
PGPSYRQQRVSTTVTQNNNSEFAWPGASSWALNGRNSLMNPGPAMASHKEGEDRFFPLSG
SLIFGKQGTGRDNVDADKVMITNEEEIKTTNPVATESYGQVATNHQSAQAQAQTGWVQN
QGILPGMVWQDRDVYLQGPIWAKIPHTDGNFHPSPLMGGFGMKHPPPQILIKNTPVADPP
TAFNKDKLNSFITQYSTGQVSVEIEWELQKENSKRWNPEIQYTSNYYKSNNVEFAVNTEGV
YSEPRPIGTRYLTRNL >SEQ ID NO: 21
GCCTGGAGGCTTGCTGAAGGCTGTATGCTGTAAGCATGGAGCTAGCAGGCTGTTTTGG
CCACTGACTGACAGCCTGCTCTCCTAGCTTACAGGACACAAGGCCTGTTACTAGCACTC
ACATAACAAATGGCCCTTTT >SEQ ID NO: 22
GCTCGAGTGAGCGCAGCCTGCTAGCTCCATGCTTACTGTAAAGCCACCAGATGGGTAA
GCATGGAGCTAGCAGGCTTCGCCTACTAGTTTT

What is claimed is:

1. An isolated nucleic acid comprising a transgene encoding one or more mature, single-stranded miRNAs, wherein the nucleic acid sequence of the transgene encoding each mature, single-stranded miRNA comprises the sequence set forth in SEQ ID NO: 8, and is flanked by a heterologous miRNA backbone sequence.

2. The isolated nucleic acid of claim 1, wherein each heterologous miRNA backbone sequence is a mir-155 backbone sequence, a mir-30 backbone sequence, or a mir-64 backbone sequence.

3. The isolated nucleic acid of claim 1, wherein the transgene comprises a promoter.

4. The isolated nucleic acid of claim 3, wherein the promoter is a chicken beta-actin (CBA) promoter or a U6 promoter.

5. The isolated nucleic acid of claim 1, wherein the transgene comprises the sequence set forth in SEQ ID NO: 21 or 22.

6. The isolated nucleic acid of claim 1, wherein the transgene is flanked by adeno-associated virus (AAV) inverted terminal repeats (ITRs), or variants thereof.

7. The isolated nucleic acid of claim 6, wherein the ITR variant lacks a functional terminal resolution site (TRS).

8. The isolated nucleic acid of claim 7, wherein the ITR variant lacking a TRS is a ΔTRS ITR.

9. A vector comprising the isolated nucleic acid of claim 1.

10. The vector of claim 9, wherein the vector is a plasmid.

11. A recombinant AAV (rAAV) comprising:
(i) a capsid protein; and,
(ii) an isolated nucleic acid comprising a transgene encoding one or more mature, single-stranded miRNAs, wherein the nucleic acid sequence of the transgene encoding each mature, single-stranded miRNA comprises the sequence set forth in SEQ ID NO: 8, and is flanked by a heterologous miRNA backbone sequence.

12. The rAAV of claim 11, wherein the transgene is flanked by full-length AAV ITR sequences.

13. The rAAV of claim 11, wherein the transgene is flanked by a full-length AAV ITR and a ΔTRS ITR.

14. The rAAV of claim 11, wherein the capsid protein is an AAV9 capsid protein.

15. The rAAV of claim 14, wherein the capsid protein comprises the sequence set forth in SEQ ID NO: 20.

16. A method for treating Huntington's disease in a subject in need thereof, the method comprising administering to a subject having Huntington's disease a therapeutically effective amount of the recombinant adeno-associated virus (rAAV), wherein the rAAV comprises:
(i) a capsid protein; and
(ii) an isolated nucleic acid comprising a transgene encoding one or more mature, single-stranded miRNAs, wherein the nucleic acid sequence of the transgene encoding each mature, single-stranded miRNA comprises the sequence set forth in SEQ ID NO: 8, and is flanked by a heterologous miRNA backbone sequence.

17. The method of claim 16, wherein the subject comprises a huntingtin gene having more than 36 CAG repeats, more than 40 repeats, or more than 100 repeats.

18. The method of claim 16, wherein the subject is less than 20 years of age.

19. The method of claim 16, wherein the administration is via injection, optionally wherein the injection is intravenous injection or intrastriatal injection.

20. The method of claim 16, wherein the rAAV comprises an AAV9 capsid protein.

* * * * *

SEQUENCE LISTING

<160> NUMBER OF SEQ ID NOS: 25

<210> SEQ ID NO 1
<211> LENGTH: 13498
<212> TYPE: DNA
<213> ORGANISM: Homo sapiens

<400> SEQUENCE: 1

```
gctgccggga cgggtccaag atggacggcc gctcaggttc tgcttttacc tgcggcccag      60
agccccattc attgccccgg tgctgagcgg cgccgcgagt cggcccgagg cctccgggga     120
ctgccgtgcc gggcgggaga ccgccatggc gaccctggaa aagctgatga aggccttcga     180
gtccctcaag tccttccagc agcagcagca gcagcagcag cagcagcagc agcagcagca     240
gcagcagcag cagcagcagc aacagccgcc accgccgccg ccgccgccgc cgcctcctca     300
gcttcctcag ccgccgccgc aggcacagcc gctgctgcct cagccgcagc cgccccgcc     360
gccgccccg ccgccacccg cccggctgt ggctgaggag ccgctgcacc gaccaaagaa      420
agaactttca gctaccaaga agaccgtgt gaatcattgt ctgacaatat gtgaaaacat      480
agtggcacag tctgtcagaa attctccaga atttcagaaa cttctgggca tcgctatgga     540
acttttctg ctgtgcagtg atgacgcaga gtcagatgtc aggatggtgg ctgacgaatg      600
cctcaacaaa gttatcaaag ctttgatgga ttctaatctt ccaaggttac agctcgagct     660
ctataaggaa attaaaaaga atggtgcccc tcggagtttg cgtgctgccc tgtggaggtt     720
tgctgagctg gctcacctgg ttcggcctca gaaatgcagg ccttacctgg tgaaccttct     780
gccgtgcctg actcgaacaa gcaagagacc cgaagaatca gtccaggaga ccttggctgc     840
agctgttccc aaaattatgg cttcttttgg cattttgca aatgacaatg aaattaaggt     900
tttgttaaag gccttcatag cgaacctgaa gtcaagctcc cccaccattc ggcggacagc     960
ggctggatca gcagtgagca ctgccagca ctcaagaagg acacaatatt tctatagttg    1020
gctactaaat gtgctcttag gcttactcgt tcctgtcgag gatgaacact ccactctgct    1080
gattcttggc gtgctgctca ccctgaggta tttggtgccc ttgctgcagc agcaggtcaa    1140
ggacacaagc ctgaaaggca gcttcggagt gacaaggaaa gaaatggaag tctctccttc    1200
tgcagagcag cttgtccagg tttatgaact gacgttacat catacacagc accaagacca    1260
caatgttgtg accggagccc tggagctgtt gcagcagctc ttcagaacgc ctccacccga    1320
gcttctgcaa accctgaccg cagtcggggg cattgggcag ctcaccgctg ctaaggagga    1380
gtctggtggc cgaagccgta gtgggagtat tgtggaactt atagctggag ggggttcctc    1440
atgcagccct gtcctttcaa gaaaacaaaa aggcaaagtg ctcttaggag aagaagaagc    1500
cttggaggat gactctgaat cgagatcgga tgtcagcagc tctgccttaa cagcctcagt    1560
gaaggatgag atcagtggag agctggctgc ttcttcaggg gtttccactc cagggtcagc    1620
aggtcatgac atcatcacag aacagccacg gtcacagcac acactgcagg cggactcagt    1680
ggatctggcc agctgtgact tgacaagctc tgccactgat ggggatgagg aggatatctt    1740
gagccacagc tccagccagg tcagcgccgt cccatctgac cctgccatgg acctgaatga    1800
tgggacccag gcctcgtcgc ccatcagcga cagctcccag accaccaccg aagggcctga    1860
ttcagctgtt accccttcag acagttctga aattgtgtta gacggtaccg acaaccagta    1920
tttgggcctg cagattggac agccccagga tgaagatgag gaagccacag gtattcttcc    1980
tgatgaagcc tcggaggcct tcaggaactc ttccatggcc cttcaacagg cacatttatt    2040
gaaaaacatg agtcactgca ggcagccttc tgacagcagt gttgataaat ttgtgttgag    2100
agatgaagct actgaaccgg gtgatcaaga aaacaagcct tgccgcatca aggtgacat     2160
ggacagtcc actgatgatg actctgcacc tcttgtccat tgtgtccgcc ttttatctgc    2220
ttcgtttttg ctaacagggg gaaaaaatgt gctggttccg acagggatg tgagggtcag    2280
cgtgaaggcc ctggccctca gctgtgtggg agcagctgtg gccctccacc cggaatcttt    2340
```

```
cttcagcaaa ctctataaag ttcctcttga caccacggaa taccctgagg aacagtatgt    2400
ctcagacatc ttgaactaca tcgatcatgg agacccacag gttcgaggag ccactgccat    2460
tctctgtggg accctcatct gctccatcct cagcaggtcc cgcttccacg tgggagattg    2520
gatgggcacc attagaaccc tcacaggaaa tacattttct ttggcggatt gcattccttt    2580
gctgcggaaa acactgaagg atgagtcttc tgttacttgc aagttagctt gtacagctgt    2640
gaggaactgt gtcatgagtc tctgcagcag cagctacagt gagttaggac tgcagctgat    2700
catcgatgtg ctgactctga ggaacagttc ctattggctg gtgaggacag agcttctgga    2760
aacccttgca gagattgact tcaggctggt gagcttttg gaggcaaaag cagaaaactt    2820
acacagaggg gctcatcatt atacagggct tttaaaactg caagaacgag tgctcaataa    2880
tgttgtcatc catttgcttg gagatgaaga ccccagggtg cgacatgttg ccgcagcatc    2940
actaattagg cttgtcccaa agctgtttta taaatgtgac caaggacaag ctgatccagt    3000
agtggccgtg gcaagagatc aaagcagtgt ttacctgaaa cttctcatgc atgagacgca    3060
gcctccatct catttctccg tcagcacaat aaccagaata tatagaggct ataacctact    3120
accaagcata acagacgtca ctatggaaaa taacctttca agagttattg cagcagtttc    3180
tcatgaacta atcacatcaa ccaccagagc actcacattt ggatgctgtg aagctttgtg    3240 tcttcttttcc actgccttcc cagtttgcat ttggagttta ggttggcact gtggagtgcc    3300
tccactgagt gcctcagatg agtctaggaa gagctgtacc gttgggatgg ccacaatgat    3360
tctgaccctg ctctcgtcag cttggttccc attggatctc tcagcccatc aagatgcttt    3420
gattttggcc ggaaacttgc ttgcagccag tgctcccaaa tctctgagaa gttcatgggc    3480
ctctgaagaa gaagccaacc cagcagccac caagcaagag gaggtctggc cagccctggg    3540
ggaccgggcc ctggtgccca tggtggagca gctcttctct cacctgctga aggtgattaa    3600
catttgtgcc cacgtcctgg atgacgtggc tcctggaccc gcaataaagg cagccttgcc    3660
ttctctaaca aaccccccctt ctctaagtcc catccgacga aggggaagg agaaagaacc    3720 aggagaacaa gcatctgtac cgttgagtcc caagaaaggc agtgaggcca gtgcagcttc    3780
tagacaatct gatacctcag gtcctgttac aacaagtaaa tcctcatcac tggggagttt    3840
ctatcatctt ccttcatacc tcaaactgca tgatgtcctg aaagctacac acgctaacta    3900
caaggtcacg ctggatcttc agaacagcac ggaaaagttt ggagggtttc tccgctcagc    3960
cttggatgtt ctttctcaga tactagagct ggccacactg caggacattg ggaagtgtgt    4020
tgaagagatc ctaggatacc tgaaatcctg ctttagtcga gaaccaatga tggcaactgt    4080
ttgtgttcaa caattgttga agactctctt tggcacaaac ttggcctccc agtttgatgg    4140
cttatcttcc aaccccagca agtcacaagg ccgagcacag cgccttggct cctccagtgt    4200
gaggccaggc ttgtaccact actgcttcat ggccccgtac acccacttca cccaggccct    4260
cgctgacgcc agcctgagga acatggtgca ggcggagcag gagaacgaca cctcgggatg    4320
gtttgatgtc ctccagaaag tgtctaccca gttgaagaca aacctcacga gtgtcacaaa    4380
gaaccgtgca gataagaatg ctattcataa tcacattcgt tgtttgaac ctcttgttat    4440 aaaagcttta aacagtaca cgactacaac atgtgtgcag ttacagaagc aggttttaga    4500
tttgctggcg cagctggttc agttacgggt taattactgt cttctggatt cagatcaggt    4560
gtttattggc tttgtattga acagtttga atacattgaa gtgggccagt tcagggaatc    4620
agaggcaatc attccaaaca tcttttttctt cttggtatta ctatccttatg aacgctatca    4680
```

```
ttcaaaacag atcattggaa ttcctaaaat cattcagctc tgtgatggca tcatggccag   4740
tggaaggaag gctgtgacac atgccatacc ggctctgcag cccatagtcc acgacctctt   4800
tgtattaaga ggaacaaata aagctgatgc aggaaaagag cttgaaaccc aaaaagaggt   4860
ggtggtgtca atgttactga gactcatcca gtaccatcag gtgttggaga tgttcattct   4920
tgtcctgcag cagtgccaca aggagaatga agacaagtgg aagcgactgt ctcgacagat   4980
agctgacatc atcctcccaa tgttagccaa acagcagatg cacattgact ctcatgaagc   5040
ccttggagtg ttaaatacat tatttgagat tttggcccct tcctccctcc gtccggtaga   5100
catgctttta cggagtatgt tcgtcactcc aaacacaatg cgtccgtga gcactgttca    5160 actgtggata tcgggaattc tggccatttt gagggttctg atttcccagt caactgaaga   5220
tattgttctt tctcgtattc aggagctctc cttctctccg tatttaatct cctgtacagt   5280
aattaatagg ttaagagatg gggacagtac ttcaacgcta aagaacaca gtgaagggaa    5340 acaaataaag aatttgccag aagaaacatt ttcaaggttt ctattacaac tggttggtat   5400
tcttttagaa gacattgtta caaaacagct gaaggtggaa atgagtgagc agcaacatac   5460
tttctattgc caggaactag gcacactgct aatgtgtctg atccacatct tcaagtctgg   5520
aatgttccgg agaatcacag cagctgccac taggctgttc cgcagtgatg gctgtggcgg   5580
cagtttctac accctggaca gcttgaactt gcgggctcgt tccatgatca ccacccaccc   5640
ggccctggtc ctgctctggt gtcagatact gctgcttgtc aaccacaccg actaccgctg   5700
gtgggcagaa gtgcagcaga ccccgaaaag acacagtctg tccagcacaa agttacttag   5760
tccccagatg tctggagaag aggaggattc tgacttggca gccaaacttg gaatgtgcaa   5820
tagagaaata gtacgaagag gggctctcat tctcttctgt gattatgtct gtcagaacct   5880
ccatgactcc gagcacttaa cgtggctcat tgtaaatcac attcaagatc tgatcagcct   5940
ttcccacgag cctccagtac aggacttcat cagtgccgtt catcggaact ctgctgccag   6000
cggcctgttc atccaggcaa ttcagtctcg ttgtgaaaac cttcaactc caaccatgct    6060 gaagaaaact cttcagtgct tggaggggat ccatctcagc cagtcgggag ctgtgctcac   6120
gctgtatgtg gacaggcttc tgtgcacccc ttcgtgtg ctggctcgca tggtcgacat     6180
ccttgcttgt cgccgggtag aaatgcttct ggctgcaaat ttacagagca gcatggccca   6240
gttgccaatg gaagaactca acagaatcca ggaatacctt cagagcagcg ggctcgctca   6300
gagacaccaa aggctctatt ccctgctgga caggtttcgt ctctccacca tgcaagactc   6360
acttagtccc tctcctccag tctcttccca cccgctggac ggggatgggc acgtgtcact   6420
ggaaacagtg agtccggaca aagactggta cgttcatctt gtcaaatccc agtgttggac   6480
caggtcagat tctgcactgc tggaaggtgc agagctggtg aatcggattc ctgctgaaga   6540
tatgaatgcc ttcatgatga actcggagtt caacctaagc ctgctagctc catgcttaag   6600
cctagggatg agtgaaattt ctggtggcca aagagtgcc cttttttgaag cagcccgtga   6660 ggtgactctg gcccgtgtga gcggcaccgt gcagcagctc cctgctgtcc atcatgtctt   6720
ccagcccgag ctgcctgcag agccggcggc ctactggagc aagttgaatg atctgtttgg   6780
ggatgctgca ctgtatcagt ccctgcccac tctggcccgg gccctggcac agtacctggt   6840
ggtggtctcc aaaactgccca gtcatttgca ccttcctcct gagaaagaga aggacattgt   6900
gaaattcgtg gtggcaaccc ttgaggccct gtcctggcat ttgatccatg agcagatccc   6960
gctgagtctg gatctccagg cagggctgga ctgctgctgc ctggccctgc agctgcctgg   7020
cctctggagc gtggtctcct ccacagagtt tgtgacccac gcctgctccc tcatctactg   7080
```

```
tgtgcacttc atcctggagg ccgttgcagt gcagcctgga gagcagcttc ttagtccaga   7140
aagaaggaca ataccccaa aagccatcag cgaggaggag gaggaagtag atccaaacac    7200
acagaatcct aagtatatca ctgcagcctg tgagatggtg gcagaaatgg tggagtctct   7260
gcagtcggtg ttggccttgg gtcataaaag gaatagcggc gtgccggcgt ttctcacgcc   7320
attgctaagg aacatcatca tcagcctggc ccgcctgccc cttgtcaaca gctacacacg   7380
tgtgcccca ctggtgtgga agcttggatg gtcacccaaa ccgggagggg attttggcac    7440
agcattccct gagatccccg tggagttcct ccaggaaaag gaagtcttta aggagttcat   7500
ctaccgcatc aacacactag gctggaccag tcgtactcag tttgaagaaa cttgggccac   7560
cctccttggt gtcctggtga cgcagcccct cgtgatggag caggaggaga gcccaccaga   7620
agaagacaca gagaggaccc agatcaacgt cctggccgtg caggccatca cctcactggt   7680
gctcagtgca atgactgtgc ctgtggccgg caacccagct gtaagctgct ggagcagca   7740
gccccggaac aagcctctga aagctctcga caccaggttt ggaggaagc tgagcattat    7800
cagagggatt gtggagcaag agattcaagc aatggtttca aagagagaga atattgccac   7860
ccatcattta tatcaggcat gggatcctgt cccttctctg tctccggcta ctacaggtgc   7920
cctcatcagc cacgagaagc tgctgctaca gatcaacccc gagcgggagc tggggagcat   7980
gagctacaaa ctcggccagg tgtccataca ctccgtgtgg ctggggaaca gcatcacacc   8040
cctgagggag gaggaatggg acgaggaaga ggaggaggag gccgacgccc ctgcaccttc   8100
gtcaccaccc acgtctccag tcaactccag gaaacaccgg gctggagttg acatccactc   8160
ctgttcgcag tttttgcttg agttgtacag ccgctggatc ctgccgtcca gctcagccag   8220
gaggaccccg gccatcctga tcagtgaggt ggtcagatcc cttctagtgg tctcagactt   8280
gttcaccgag cgcaaccagt tgagctgat gtatgtgacg ctgacagaac tgcgaagggt    8340
gcacccttca gaagacgaga tcctcgctca gtacctggtg cctgccacct gcaaggcagc   8400
tgccgtcctt gggatggaca aggccgtggc ggagcctgtc agccgcctgc tggagagcac   8460
gctcaggagc agccaccctgc ccagcagggt tggagccctg cacggcgtcc tctatgtgct   8520
ggagtgcgac ctgctggacg acactgccaa gcagctcatc ccggtcatca gcgactatct   8580
cctctccaac ctgaaaggga tcgcccactg cgtgaacatt cacagccagc agcacgtact   8640
ggtcatgtgt gccactgcgt tttacctcat tgagaactat cctctggacg tagggccgga   8700
attttcagca tcaataatac agatgtgtgg ggtgatgctg tctggaagtg aggagtccac   8760
cccctccatc atttaccact gtgccctcag aggcctggag cgcctcctgc tctctgagca   8820
gctctcccgc ctggatgcag aatcgctggt caagctgagt gtggacagag tgaacgtgca   8880
cagcccgcac cgggccatgg cggctctggg cctgatgctc acctgcatgt acacaggaaa   8940
ggagaaagtc agtccgggta gaacttcaga ccctaatcct gcagccccg acagcgagtc   9000
agtgattgtt gctatggagc gggtatctgt tcttttgat aggatcagga aaggctttcc    9060
ttgtgaagcc agagtggtgg ccaggatcct gccccagttt ctagacgact tcttcccacc   9120
ccaggacatc atgaacaaag tcatcggaga gtttctgtcc aaccagcagc cataccccca   9180
gttcatggcc accgtggtgt ataaggtgtt tcagactctg cacagcaccg ggcagtcgtc   9240
catggtccgg gactgggtca tgctgtccct ctccaacttc acgcagaggg cccggtcgc    9300
catgccacg tggagcctct cctgcttctt tgtcagcgcg tccaccagcc cgtgggtcgc    9360
ggcgatcctc ccacatgtca tcagcaggat gggcaagctg gagcaggtgg acgtgaacct   9420
```

```
tttctgcctg gtcgccacag acttctacag acaccagata gaggaggagc tcgaccgcag    9480
ggccttccag tctgtgcttg aggtggttgc agcccagga agcccatatc accggctgct    9540
gacttgttta cgaaatgtcc acaaggtcac cacctgctga gcgccatggt gggagagact   9600
gtgaggcggc agctgggcc ggagcctttg gaagtctgcg ccttgtgcc ctgcctccac     9660
cgagccagct tggtccctat gggcttccgc acatgccgcg ggcggccagg caacgtgcgt   9720
gtctctgcca tgtggcagaa gtgctctttg tggcagtggc caggcaggga gtgtctgcag   9780
tcctggtggg gctgagcctg aggccttcca gaaagcagga gcagctgtgc tgcaccccat   9840
gtgggtgacc aggtcctttc tcctgatagt cacctgctgg ttgttgccag ttgcagctg    9900
ctcttgcatc tgggccagaa gtcctccctc ctgcaggctg gctgttggcc cctctgctgt   9960
cctgcagtag aaggtgccgt gagcaggctt tgggaacact ggcctgggtc tccctggtgg  10020
ggtgtgcatg ccacgccccg tgtctggatg cacagatgcc atggcctgtg ctgggccagt  10080
ggctgggggt gctagacacc cggcaccatt ctcccttctc tcttttcttc tcaggattta  10140
aaatttaatt atatcagtaa agagattaat tttaacgtaa ctctttctat gcccgtgtaa  10200
agtatgtgaa tcgcaaggcc tgtgctgcat gcgacagcgt ccggggtggt ggacagggcc  10260
cccggccacg ctccctctcc tgtagccact ggcatagccc tcctgagcac ccgctgacat  10320
ttccgttgta catgttcctg tttatgcatt cacaaggtga ctgggatgta gagaggcgtt  10380
agtgggcagg tggccacagc aggactgagg acaggccccc attatcctag ggtgcgctc   10440
acctgcagcc cctcctcctc gggcacagac gactgtcgtt ctccacccac cagtcaggga  10500
cagcagcctc cctgtcactc agctgagaag gccagccctc cctggctgtg agcagcctcc  10560
actgtgtcca gagacatggg cctcccactc ctgttccttg ctagccctgg ggtggcgtct  10620
gcctaggagc tggctggcag gtgttgggac ctgctgctcc atggatgcat gccctaagag  10680
tgtcactgag ctgtgttttg tctgagcctc tctcggtcaa cagcaaagct tggtgtcttg  10740
gcactgttag tgacagagcc cagcatccct tctgccccg ttccagctga catcttgcac   10800
ggtgacccct tttagtcagg agagtgcaga tctgtgctca tcggagactg ccccacggcc  10860
ctgtcagagc cgccactcct atccccagc caggtccctg gaccagcctc ctgtttgcag   10920
gcccagagga gccaagtcat taaaatggaa gtggattctg gatggccggg ctgctgctga  10980
tgtaggagct ggatttggga gctctgcttg ccgactggct gtgagacgag gcaggggctc  11040
tgcttcctca gccctagagg cgagccaggc aaggttggcg actgtcatgt ggcttggttt  11100
ggtcatgccc gtcgatgttt tgggtattga atgtggtaag tggaggaaat gttgaactc   11160
tgtgcaggtg ctgccttgag accccaagc ttccacctgt ccctctccta tgtggcagct   11220
ggggagcagc tgagatgtgg acttgtatgc tgcccacata cgtgaggggg agctgaaagg  11280
gagcccctcc tctgagcagc ctctgccagg cctgtatgag gcttttccca ccagctccca  11340
acagaggcct ccccagcca ggaccacctc gtcctcgtgg cggggcagca ggagcggtag   11400
aaagggtcc gatgtttgag gaggccctta agggaagcta ctgaattata acacgtaaga   11460
aaatcaccat tccgtattgg ttggggctc ctgtttctca tcctagcttt ttcctggaaa   11520
gcccgctaga aggtttggga acgagggaa agttctcaga actgttggct gctccccacc   11580
cgcctcccgc ctccccgca ggttatgtca gcagctctga cacagcagta tcacaggcca   11640
gatgttgttc ctggctagat gtttacattt gtaagaaata acactgtgaa tgtaaaacag  11700
agccattccc ttgaatgca tatcgctggg ctcaacatag agtttgtctt cctcttgttt   11760
acgacgtgat ctaaaccagt ccttagcaag gggctcagaa caccccgctc tggcagtagg  11820
```

```
tgtccccac  ccccaaagac  ctgcctgtgt  gctccggaga  tgaatatgag  ctcattagta    11880
aaaatgactt  cacccacgca  tatacataaa  gtatccatgc  atgtgcatat  agacacatct    11940
ataattttac  acacacacct  ctcaagacgg  agatgcatgg  cctctaagag  tgcccgtgtc    12000
ggttcttcct  ggaagttgac  tttccttaga  cccgccaggt  caagttagcc  gcgtgacgga    12060
catccaggcg  tgggacgtgg  tcagggcagg  gctcattcat  tgcccactag  gatcccactg    12120
gcgaagatgg  tctccatatc  agctctctgc  agaaggagg   aagactttat  catgttccta    12180
aaaatctgtg  gcaagcaccc  atcgtattat  ccaaattttg  ttgcaaatgt  gattaatttg    12240
gttgtcaagt  tttggggtg   ggctgtgggg  agattgcttt  tgttttcctg  ctggtaatat    12300
cgggaaagat  tttaatgaaa  ccagggtaga  attgtttggc  aatgcactga  agcgtgtttc    12360
tttcccaaaa  tgtgcctccc  ttccgctgcg  ggcccagctg  agtctatgta  ggtgatgttt    12420
ccagctgcca  agtgctcttt  gttactgtcc  accctcattt  ctgccagcgc  atgtgtcctt    12480
tcaaggggaa  aatgtgaagc  tgaaccccct  ccagacaccc  agaatgtagc  atctgagaag    12540
gccctgtgcc  ctaaaggaca  cccctcgccc  ccatcttcat  ggaggggtc   atttcagagc    12600 cctcggagcc  aatgaacagc  tcctcctctt  ggagctgaga  tgagcccac   gtggagctcg    12660 ggacggatag  tagacagcaa  taactcggtg  tgtggccgcc  tggcaggtgg  aacttcctcc    12720
cgttgcgggg  tggagtgagg  ttagttctgt  gtgtctggtg  ggtggagtca  ggcttctctt    12780
gctacctgtg  agcatccttc  ccagcagaca  tcctcatcgg  gctttgtccc  tcccccgctt    12840
cctccctctg  cggggaggac  ccgggaccac  agctgctggc  cagggtagac  ttggagctgt    12900
cctccagagg  ggtcacgtgt  aggagtgaga  agaaggaaga  tcttgagagc  tgctgaggga    12960
ccttggagag  ctcaggatgg  ctcagacgag  gacactcgct  tgccgggcct  gggcctcctg    13020
ggaaggaggg  agctgctcag  aatgccgcat  gacaactgaa  ggcaacctgg  aaggttcagg    13080
ggccgctctt  cccccatgtg  cctgtcacgc  tctggtgcag  tcaaaggaac  gccttcccct    13140
cagttgtttc  taagagcaga  gtctcccgct  gcaatctggg  tggtaactgc  cagccttgga    13200
ggatcgtggc  caacgtggac  ctgcctacgg  agggtgggct  ctgacccaag  tggggcctcc    13260
ttgtccaggt  ctcactgctt  tgcaccgtgg  tcagaggac   tgtcagctga  gcttgagctc    13320
ccctggagcc  agcagggctg  tgatgggcga  gtcccggagc  cccacccaga  cctgaatgct    13380
tctgagagca  aagggaagga  ctgacgagag  atgtatattt  aatttttttaa ctgctgcaaa    13440 cattgtacat  ccaaattaaa  ggaaaaaaat  ggaaaccatc  aaaaaaaaaa  aaaaaaa      13498
```

<210> SEQ ID NO 2
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 2
taaatgtgcc tgttgaaggg c                                             21

<210> SEQ ID NO 3
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 3
aagaggtgca gagtcatcat c         21

<210> SEQ ID NO 4
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 4
ttctggagga catcaaacca t         21

<210> SEQ ID NO 5
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 5
tgaactggcc cacttcaatg t         21

<210> SEQ ID NO 6
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 6
ttccattggc aactgggcca t         21

<210> SEQ ID NO 7
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 7
taagcatgga gctagcaggc t         21

<210> SEQ ID NO 8
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 8
tagcgttgaa gtactgtccc c         21

<210> SEQ ID NO 9
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 9
ttgaggcagc agcggctgtg c         21

<210> SEQ ID NO 10
<211> LENGTH: 21
<212> TYPE: DNA
<213> ORGANISM: Artificial Sequence

```
<220> FEATURE:
<223> OTHER INFORMATION: Synthetic polynucleotide

<400> SEQUENCE: 10
ttcatcagct tttccagggt c                                              21

<210> SEQ ID NO 11
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 11
tggaattctc gggtgccaag g                                              21

<210> SEQ ID NO 12
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 12
ccttggcacc cgagaattcc a                                              21

<210> SEQ ID NO 13
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 13
gcagagcaca gccgacgac                                                 19

<210> SEQ ID NO 14
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 14
aatgatacgg cgaccaccga gatctacacg ttcagagttc tacagtccga               50

<210> SEQ ID NO 15
<211> LENGTH: 63
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(30)
<223> OTHER INFORMATION: n is a, c, g, or t

<400> SEQUENCE: 15
caagcagaag acggcatacg agatnnnnnn gtgactggag ttccttggca cccgagaatt    60
cca                                                                  63

<210> SEQ ID NO 16
<211> LENGTH: 5483
<212> TYPE: DNA
<213> ORGANISM: Artificial Sequence
<220> FEATURE:
```

<223> OTHER INFORMATION: Synthetic polynucleotide

<400> SEQUENCE: 16

```
gcccaatacg caaaccgcct ctccccgcgc gttggccgat tcattaatgc agctgattct    60
aacgaggaaa gcacgttata cgtgctcgtc aaagcaacca tagtacgcgc cctgtagcgg   120
cgcattaagc gcggcgggtg tggtggttac gcgcagcgtg accgctacac ttgccagcgc   180
cctagcgccc gctcctttcg ctttcttccc ttcctttctc gccacgttcg ccggctttcc   240
ccgtcaagct ctaaatcggg ggctcccttt agggttccga tttagtgctt tacggcacct   300
cgaccccaaa aaacttgatt agggtgatgg ttcacgtagt gggccatcgc cctgatagac   360
ggttttcgc cctttgacgt tggagtccac gttctttaat agtggactct tgttccaaac   420
tggaacaaca ctcaaccta tctcggtcta ttcttttgat ttataaggga ttttgccgat   480
ttcggcctat tggttaaaaa atgagctgat ttaacaaaaa tttaacgcga atttaacaa   540
aatattaacg cttacaattt aaatatttgc ttatacaatc ttcctgtttt tggggctttt   600
ctgattatca accgggtac atatgattga catgctagtt ttacgattac cgttcatcgc   660
cctgcgcgct cgctcgctca ctgaggccgc ccgggcaaag cccgggcgtc gggcgacctt   720
tggtcgcccg gcctcagtga gcgagcgagc gcgcagagag ggagtggaat tcacgcgtgg   780
atctgaattc aattcacgcg tggtacctct ggtcgttaca taacttacgg taaatggccc   840
gcctggctga ccgcccaacg accccgccc attgacgtca ataatgacgt atgttccat   900
agtaacgcca tagggacttt ccattgacg tcaatgggtg gagtatttac ggtaaactgc   960
ccacttggca gtacatcaag tgtatcatat gccaagtacg ccccctattg acgtcaatga  1020
cggtaaatgg cccgcctggc attatgccca gtacatgacc ttatgggact ttcctacttg  1080
gcagtacatc tactcgaggc cacgttctgc ttcactctcc ccatctcccc cccctcccca  1140
cccccaattt tgtatttatt tattttttaa ttattttgtg cagcgatggg ggcgggggg  1200
ggggggggc gcgcgccagg cggggcgggg cgggcgagg ggcggggcgg ggcgaggcgg  1260
agaggtgcgg cggcagccaa tcagagcggc gcgctccgaa agtttccttt tatggcgagg  1320
cggcggcggc ggcggcccta taaaagcga agcgcgcggc gggcgggagc gggatcagcc  1380
accgcggtgg cggcctagag tcgacgagga actgaaaaac cagaaagtta actggtaagt  1440
ttagtctttt tgtcttttat ttcaggtccc ggatccggtg gtggtgcaaa tcaaagaact  1500
gctcctcagt ggatgttgcc tttacttcta ggcctgtacg gaagtgttac ttctgctcta  1560
aaagctgcgg aattgtaccc gcggccgatc caccggtcgc caccatggtg agcaagggcg  1620
aggagctgtt caccggggtg gtgcccatcc tggtcgagct ggacggcgac gtaaacggcc  1680
acaagttcag cgtgtccggc gagggcgagg gcgatgccac ctacggcaag ctgaccctga  1740
agttcatctg caccaccggc aagctgcccg tgccctggcc caccctcgtg accaccctga  1800
cctacggcgt gcagtgcttc agccgctacc ccgaccacat gaagcagcac gacttcttca  1860
agtccgccat gcccgaaggc tacgtccagg agcgcaccat cttcttcaag gacgacggca  1920
actacaagac ccgcgccgag gtgaagttcg agggcgacac cctggtgaac cgcatcgagc  1980
tgaagggcat cgacttcaag gaggacggca acatcctggg gcacaagctg gagtacaact  2040
acaacagcca caacgtctat atcatggccg acaagcagaa gaacggcatc aaggtgaact  2100
tcaagatccg ccacaacatc gaggacggca gcgtgcagct cgccgaccac taccagcaga  2160
acaccccat cggcgacggc cccgtgctgc tgcccgacaa ccactacctg agcacccagt  2220
ccgccctgag caaagacccc aacgagaagc gcgatcacat ggtcctgctg gagttcgtga  2280
```

```
ccgccgccgg gatcactctc ggcatggacg agctgtacaa gtaaagcggc cctagcgttt    2340
ccggcgacgg tgctagcgtc gaccagtgga tcctggaggc ttgctgaagg ctgtatgctg    2400
taagcatgga gctagcaggc tgttttggcc actgactgac agcctgctct ccatgcttac    2460
aggacacaag gcctgttact agcactcaca tggaacaaat ggcccagatc tggccgcact    2520
cgaaaacggg ccctctagac tcgaggacgg ggtgaactac gcctgaggat ccgatctttt    2580
tccctctgcc aaaaattatg gggacatcat gaagccccct gagcatctga cttctggcta    2640
ataaaggaaa tttattttca ttgcaatagt gtgttggaat ttttgtgtc tctcactcgg     2700 aagcaattcg ttgatctgaa tttcgaccac ccataatacc cattaccctg gtagataagt    2760
agcatggcgg gttaatcatt aactacaagg aaccctagt gatggagttg gccactccct     2820
ctctgcgcgc tcgctcgctc actgaggccg gcgaccaaa ggtcgcccga cgccgggct     2880 ttgcccgggc ggcctcagtg agcgagcgag cgcgcagcct taattaacct aattcactgg    2940
ccgtcgtttt acaacgtcgt gactgggaaa accctggcgt tacccaactt aatcgccttg    3000
cagcacatcc cctttcgcc agctggcgta atagcgaaga ggcccgcacc gatcgccctt    3060
cccaacagtt gcgcagcctg aatggcgaat gggacgcgcc ctgtagcggc gcattaagcg    3120
cggcgggtgt ggtggttacg cgcagcgtga ccgctacact gccagcgcc ctagcgcccg    3180 ctcctttcgc tttcttccct tcctttctcg ccacgttcgc cggctttccc cgtcaagctc    3240
taaatcgggg ctcccttta gggttccgat ttagtgcttt acggcacctc gaccccaaaa    3300
aacttgatta gggtgatggt tcacgtagtg gccatcgcc ctgatagacg ttttttcgcc    3360
ctttgacgtt ggagtccacg ttctttaata gtggactctt gttccaaact ggaacaacac    3420
tcaaccctat ctcggtctat tcttttgatt tataagggat tttgccgatt tcggcctatt    3480
ggttaaaaaa tgagctgatt taacaaaaat ttaacgcgaa ttttaacaaa atattaacgc    3540
ttacaattta ggtggcactt ttcggggaaa tgtgcgcgga accctatttt gtttattttt    3600
ctaaatacat tcaaatatgt atccgctcat gagacaataa ccctgataaa tgcttcaata    3660
atattgaaaa aggaagagta tgagtattca acatttccgt gtcgccctta ttcccttttt    3720
tgcggcattt tgccttcctg ttttgctca cccagaaacg ctggtgaaag taaaagatgc    3780
tgaagatcag ttgggtgcac gagtgggtta catcgaactg gatctcaaca gcggtaagat    3840
ccttgagagt tttcgccccg aagaacgttt tccaatgatg agcacttta aagttctgct    3900 atgtggcgcg gtattatccc gtattgacgc cgggcaagag caactcggtc gccgcataca    3960
ctattctcag aatgacttgg ttgagtactc accagtcaca gaaaagcatc ttacggatgg    4020
catgacagta agagaattat gcagtgctgc cataaccatg agtgataaca ctgcggccaa    4080
cttacttctg acaacgatcg gaggaccgaa ggagctaacc gcttttttgc acaacatggg    4140
ggatcatgta actcgccttg atcgttggga accggagctg aatgaagcca taccaaacga    4200
cgagcgtgac accacgatgc ctgtagcaat ggcaacaacg ttgcgcaaac tattaactgg    4260
cgaactactt actctagctt cccggcaaca attaatagac tggatggagg cggataaagt    4320
tgcaggacca cttctgcgct cggccttcc ggctggctgg tttattgctg ataaatctgg    4380
agccggtgag cgtgggtctc gcggtatcat tgcagcactg gggccagatg gtaagccctc    4440
ccgtatcgta gttatctaca cgacggggag tcaggcaact atggatgaac gaaatagaca    4500
gatcgctgag ataggtgcct cactgattaa gcattggtaa ctgtcagacc aagtttactc    4560
atatatactt tagattgatt taaaacttca ttttttaattt aaaaggatct aggtgaagat    4620
```

```
ccttttttgat aatctcatga ccaaaatccc ttaacgtgag ttttcgttcc actgagcgtc    4680
agacccgta  gaaagatca  aaggatcttc  ttgagatcct  ttttttctgc  gcgtaatctg   4740
ctgcttgcaa acaaaaaaac caccgctacc agcggtggtt tgtttgccgg atcaagagct    4800
accaactctt tttccgaagg taactggctt cagcagagcg cagataccaa atactgttct    4860
tctagtgtag ccgtagttag gccaccactt caagaactct gtagcaccgc ctacatacct    4920
cgctctgcta atcctgttac cagtggctgc tgccagtggc gataagtcgt gtcttaccgg    4980
gttggactca agacgatagt taccggataa ggcgcagcgg tcgggctgaa cggggggttc    5040
gtgcacacag cccagcttgg agcgaacgac ctacaccgaa ctgagatacc tacagcgtga    5100
gctatgagaa agcgccacgc ttcccgaagg gagaaaggcg gacaggtatc cggtaagcgg    5160
cagggtcgga acaggagagc gcacgaggga gcttccaggg ggaaacgcct ggtatcttta    5220
tagtcctgtc gggtttcgcc acctctgact tgagcgtcga ttttttgtgat gctcgtcagg    5280
ggggcggagc ctatggaaaa acgccagcaa cgcggccttt ttacggttcc tggccttttg    5340
ctggcctttt gctcacatgt tctttcctgc gttatcccct gattctgtgg ataaccgtat    5400
taccgccttt gagtgagctg ataccgctcg ccgcagccga acgaccgagc gcagcgagtc    5460
agtgagcgag gaagcggaag agc                                            5483
```

<210> SEQ ID NO 17
<211> LENGTH: 5686
<212> TYPE: DNA
<213> ORGANISM: Artificial Sequence
<220> FEATURE:
<223> OTHER INFORMATION: Synthetic polynucleotide

<400> SEQUENCE: 17

```
gcccaatacg caaaccgcct ctccccgcgc gttggccgat tcattaatgc agctgattct      60
aacgaggaaa gcacgttata cgtgctcgtc aaagcaacca tagtacgcgc cctgtagcgg     120
cgcattaagc gcggcgggtg tggtggttac gcgcagcgtg accgctacac ttgccagcgc     180
cctagcgccc gctcctttcg ctttcttccc ttcctttctc gccacgttcg ccggctttcc     240
ccgtcaagct ctaaatcggg ggctcccttt agggttccga tttagtgctt tacggcacct     300
cgaccccaaa aaacttgatt agggtgatgg ttcacgtagt gggccatcgc cctgatagac     360
ggtttttcgc cctttgacgt tggagtccac gttctttaat agtggactct gttccaaac     420
tggaacaaca ctcaacccta tctcggtcta ttcttttgat ttataaggga ttttgccgat     480
ttcggcctat tggttaaaaa atgagctgat ttaacaaaaa tttaacgcga atttttaacaa     540
aatattaacg cttacaattt aaatatttgc ttatacaatc ttcctgtttt tggggctttt     600
ctgattatca accggggtac atatgattga catgctagtt ttacgattac cgttcatcgc     660
cctgcgcgct cgctcgctca ctgaggccgc ccgggcaaag cccgggcgtc gggcgacctt     720
tggtcgcccg gcctcagtga gcgagcgagc gcgcagagag ggagtggaat tctataaagg     780
tcgggcagga agagggccta tttcccatga ttccttcata tttgcatata cgatacaagg     840
ctgttagaga gataattaga attaatttga ctgtaaacac aaagatatta gtacaaaata     900
cgtgacgtag aaagtaataa tttcttgggt agtttgcagt tttaaaatta tgttttaaaa     960
tggactatca tatgcttacc gtaacttgaa agtatttcga tttcttggct ttatatatct    1020
tgtggaaagg acgaaacacc gcctggaggc ttgctgaagg ctgtatgctg taagcatgga    1080
gctagcaggc tgttttggcc actgactgac agcctgctct ccatgcttac aggacacaag    1140
gcctgttact agcactcaca tggaacaaat ggccttttt tctagtggta cctctggtcg    1200
```

```
ttacataact tacggtaaat ggcccgcctg gctgaccgcc caacgacccc cgcccattga   1260
cgtcaataat gacgtatgtt cccatagtaa cgccaatagg gactttccat tgacgtcaat   1320
gggtggagta tttacggtaa actgcccact tggcagtaca tcaagtgtat catatgccaa   1380
gtacgccccc tattgacgtc aatgacggta aatggcccgc ctggcattat gcccagtaca   1440
tgaccttatg ggactttcct acttggcagt acatctactc gaggccacgt tctgcttcac   1500
tctccccatc tccccccct ccccaccccc aattttgtat ttatttattt tttaattatt   1560
ttgtgcagcg atggggggcgg ggggggggg gggcgcgcg ccaggcgggg cggggcgggg   1620
cgaggggcgg ggcggggcga ggcggagagg tgcggcggca gccaatcaga gcggcgcgct   1680
ccgaaagttt cctttttatgg cgaggcggcg gcggcggcgg ccctataaaa agcgaagcgc   1740
gcggcgggcg ggagcgggat cagccaccgc ggtggcggcc tagagtcgac gaggaactga   1800
aaaaccagaa agttaactgg taagtttagt cttttgtct tttatttcag gtcccggatc   1860
cggtggtggt gcaaatcaaa gaactgctcc tcagtggatg ttgcctttac ttctaggcct   1920
gtacggaagt gttacttctg ctctaaaagc tgcggaattg tacccgcggc cgatccaccg   1980
gtcgccacca tggtgagcaa gggcgaggag ctgttcaccg gggtggtgcc catcctggtc   2040
gagctggacg gcgacgtaaa cggccacaag ttcagcgtgt ccggcgaggg cgagggcgat   2100
gccacctacg gcaagctgac cctgaagttc atctgcacca ccggcaagct gcccgtgccc   2160
tggcccaccc tcgtgaccac cctgacctac ggcgtgcagt gcttcagccg ctaccccgac   2220
cacatgaagc agcacgactt cttcaagtcc gccatgcccg aaggctacgt ccaggagcgc   2280
accatcttct tcaaggacga cggcaactac aagacccgcg ccgaggtgaa gttcgagggc   2340
gacaccctgg tgaaccgcat cgagctgaag ggcatcgact tcaaggagga cggcaacatc   2400
ctggggcaca agctggagta caactacaac agccacaacg tctatatcat ggccgacaag   2460
cagaagaacg gcatcaaggt gaacttcaag atccgccaca acatcgagga cggcagcgtg   2520
cagctcgccg accactacca gcagaacacc cccatcggcg acggccccgt gctgctgccc   2580
gacaaccact acctgagcac ccagtccgcc ctgagcaaag accccaacga gaagcgcgat   2640
cacatggtcc tgctggagtt cgtgaccgcc gccgggatca ctctcggcat ggacgagctg   2700
tacaagtaaa gcggcctag cgtttccggc gacggtgcta gactcgagga cggggtgaac   2760
tacgcctgag gatccgatct ttttccctct gccaaaaatt atgggacat catgaagccc   2820 cttgagcatc tgacttctgg ctaataaagg aaatttattt tcattgcaat agtgtgttgg   2880
aattttttgt gtctctcact cggaagcaat tcgttgatct gaatttcgac cacccataat   2940
acccattacc ctggtagata agtagcatgg cgggttaatc attaactaca aggaacccct   3000
agtgatggag ttggccactc cctctctgcg cgctcgctcg ctcactgagg ccgggcgacc   3060
aaaggtcgcc cgacgcccgg gctttgcccg ggcggcctca gtgagcgagc gagcgcgcag   3120
ccttaattaa cctaattcac tggccgtcgt tttacaacgt cgtgactggg aaaaccctgg   3180
cgttacccaa cttaatcgcc ttgcagcaca tccccctttc gccagctggc gtaatagcga   3240
agaggcccgc accgatcgcc cttcccaaca gttgcgcagc ctgaatggcg aatgggacgc   3300
gccctgtagc ggcgcattaa gcgcggcggg tgtggtggtt acgcgcagcg tgaccgctac   3360
acttgccagc gccctagcgc ccgctccttt cgctttcttc ccttcctttc tcgccacgtt   3420
cgccggcttt cccccgtcaag ctctaaatcg ggggctccct ttagggttcc gatttagtgc   3480
tttacggcac ctcgacccca aaaaacttga ttagggtgat ggttcacgta gtgggccatc   3540
```

```
gccctgatag acggttttttc gcccctttgac gttggagtcc acgttcttta atagtggact   3600
cttgttccaa actggaacaa cactcaaccc tatctcggtc tattcttttg atttataagg   3660
gattttgccg atttcggcct attggttaaa aaatgagctg atttaacaaa aatttaacgc   3720
gaattttaac aaaatattaa cgcttacaat ttaggtggca ctttttcgggg aaatgtgcgc   3780
ggaacccta tttgtttatt tttctaaata cattcaaata tgtatccgct catgagacaa   3840
taaccctgat aaatgcttca ataatattga aaaggaaga gtatgagtat tcaacatttc   3900
cgtgtcgccc ttattccctt ttttgcggca ttttgccttc ctgttttttgc tcacccagaa   3960
acgctggtga agtaaaaga tgctgaagat cagttgggtg cacgagtggg ttacatcgaa   4020
ctggatctca acagcggtaa gatccttgag agttttcgcc ccgaagaacg ttttccaatg   4080
atgagcactt ttaaagttct gctatgtggc gcggtattat cccgtattga cgccgggcaa   4140
gagcaactcg gtcgccgcat acactattct cagaatgact tggttgagta ctcaccagtc   4200
acagaaaagc atcttacgga tggcatgaca gtaagagaat tatgcagtgc tgccataacc   4260
atgagtgata acactgcggc caacttactt ctgacaacga tcggaggacc gaaggagcta   4320
accgcttttt tgcacaacat gggggatcat gtaactcgcc ttgatcgttg ggaaccggag   4380
ctgaatgaag ccataccaaa cgacgagcgt gacaccacga tgcctgtagc aatggcaaca   4440
acgttgcgca aactattaac tggcgaacta cttactctag cttcccggca acaattaata   4500
gactggatgg aggcggataa agttgcagga ccacttctgc gctcggccct tccggctggc   4560
tggtttattg ctgataaatc tggagccggt gagcgtgggt ctcgcggtat cattgcagca   4620
ctggggccag atggtaagcc ctcccgtatc gtagttatct acacgacggg gagtcaggca   4680
actatggatg aacgaaatag acagatcgct gagataggtg cctcactgat taagcattgg   4740
taactgtcag accaagttta ctcatatata ctttagattg atttaaaact tcatttttaa   4800
tttaaaagga tctaggtgaa gatccttttt gataatctca tgaccaaaat cccttaacgt   4860
gagttttcgt tccactgagc gtcagacccc gtagaaaaga tcaaaggatc ttcttgagat   4920
ccttttttttc tgcgcgtaat ctgctgcttg caaacaaaaa aaccaccgct accagcggtg   4980
gtttgtttgc cggatcaaga gctaccaact cttttttccga aggtaactgg cttcagcaga   5040
gcgcagatac caaatactgt tcttctagtg tagccgtagt taggccacca cttcaagaac   5100
tctgtagcac cgcctacata cctcgctctg ctaatcctgt taccagtggc tgctgccagt   5160
ggcgataagt cgtgtcttac cgggttggac tcaagacgat agttaccgga taaggcgcag   5220
cggtcgggct gaacggggggg ttcgtgcaca cagcccagct tggagcgaac gacctacacc   5280
gaactgagat acctacagcg tgagctatga gaaagcgcca cgcttcccga agggagaaag   5340
gcggacaggt atccggtaag cggcagggtc ggaacaggag agcgcacgag ggagcttcca   5400
gggggaaacg cctggtatct ttatagtcct gtcgggtttc gccacctctg acttgagcgt   5460
cgatttttgt gatgctcgtc aggggggcgg agcctatgga aaaacgccag caacgcggcc   5520
ttttttacggt tcctggcctt ttgctggcct tttgctcaca tgttctttcc tgcgttatcc   5580
cctgattctg tggataaccg tattaccgcc tttgagtgag ctgataccgc tcgccgcagc   5640
cgaacgaccg agcgcagcga gtcagtgagc gaggaagcgg aagagc              5686
```

<210> SEQ ID NO 18
<211> LENGTH: 5155
<212> TYPE: DNA
<213> ORGANISM: Artificial Sequence
<220> FEATURE:
<223> OTHER INFORMATION: Synthetic polynucleotide

<400> SEQUENCE: 18

```
ctgcgcgctc gctcgctcac tgaggccgcc cgggcaaagc ccgggcgtcg ggcgaccttt      60
ggtcgcccgg cctcagtgag cgagcgagcg cgcagagagg gagtgtagcc atgctctagg     120
aagatcaatt caattcacgc gtcgacattg attattgact agctctggtc gttacataac     180
ttacggtaaa tggcccgcct ggctgaccgc ccaacgaccc ccgcccattg acgtcaataa     240
tgacgtatgt tcccatagta acgccaatag ggactttcca ttgacgtcaa tgggtggagt     300
atttacggta aactgcccac ttggcagtac atcaagtgta tcatatgcca agtccgcccc     360
ctattgacgt caatgacggt aaatggcccg cctggcatta tgcccagtac atgaccttac     420
gggactttcc tacttggcag tacatctacg tattagtcat cgctattacc atggtcgagg     480
tgagccccac gttctgcttc actctcccca tctcccccc ctcccaccc caattttgt       540
atttatttat tttttaatta ttttgtgcag cgatggggg gggggggggg gggggcgcg       600
cgccaggcgg ggcggggcgg ggcgagggc ggggcgggc gaggcggaga ggtgcggcgg       660
cagccaatca gagcggcgcg ctccgaaagt ttccttttat ggcgaggcgg cggcggcggc     720
ggccctataa aaagcgaagc gcgcggcggg cgggagtcgc tgcgcgctgc cttcgccccg     780
tgccccgctc cgccgccgcc tcgcgccgcc cgccccggct ctgactgacc gcgttactcc     840
cacaggtgag cgggcgggac ggcccttctc ctccgggctg taattagcgc ttggtttaat     900
gacggcttgt ttcttttctg tggctgcgtg aaagccttga ggggctccgg agggcccctt     960
tgtgcggggg ggagcggctc gggggtgcg tgcgtgtgtg tgtgcgtggg gagcgccgcg     1020
tgcggctccg cgctgcccgg cggctgtgag cgctgcgggc gcggcgcggg gctttgtgcg     1080
ctccgcagtg tgcgcgaggg gagcgcggcc ggggcggtg ccccgcggtg cggggggggc     1140
tgcgagggga acaaaggctg cgtgcgggt gtgtgcgtgg ggggtgagc aggggtgtg     1200
ggcgcgtcgg tcgggctgca accccccctg cacccccctc cccgagttgc tgagcacggc    1260
ccggcttcgg gtgcggggct ccgtacgggg cgtggcgcgg ggctcgccgt gccgggcggg    1320
gggtggcggc aggtggggt gccggcggg gcggggccgc ctcgggccgg ggagggctcg     1380
ggggaggggc gcggcggccc ccggagcgcc ggcggctgtc gaggcgcggc gagccgcagc    1440
cattgccttt tatggtaatc gtgcgagagg gcgcagggac ttcctttgtc ccaaatctgt    1500
gcggagccga atctgggag cgccgccgc accccctcta gcgggcgcgg ggcgaagcgg     1560
tgcggcgccg gcaggaagga aatgggcggg gagggccttc gtgcgtcgcc gcgccgccgt    1620
cccttctcc ctctccagcc tcgggctgt ccgcggggg acggctgcct tcgggggga       1680
cggggcaggg cggggttcgg cttctggcgt gtgaccggcg gctctagagc ctctgctaac    1740
catgttcatg ccttcttctt tttcctacag ctcctgggca acgtgctggt tattgtgctg    1800
tctcatcatt ttggcaaaga attcatcgat accgtcgacg atctagcgtc gaccagtgga    1860
tcctggaggc ttgctgaagg ctgtatgctg taagcatgga gctagcaggc tgttttggcc    1920
actgactgac agcctgctct ccatgcttac aggacacaag gcctgttact agcactcaca    1980
tggaacaaat ggcccagatc cgatcttttt ccctctgcca aaattatgg ggacatcatg    2040
aagccccttg agcatctgac ttctggctaa taaggaaat ttattttcat tgcaatagtg    2100
tgttggaatt ttttgtgtct ctcactcgat cagatctgag gaaccctag tgatggagtt    2160
ggccactccc tctctgcgcg ctcgctcgct cactgaggcc gcccgggcaa gcccgggcg    2220
tcgggcgacc tttggtcgcc cggcctcagt gagcgagcga gcgcgcagag agggagtggc    2280
```

```
cccccccccc cccccccct  gcattctaga gagctccaat tcgccctata gtgagtcgta   2340
ttacgcgcgc tcactggccg tcgttttaca acgtcgtgac tgggaaaacc ctggcgttac   2400
ccaacttaat cgccttgcag cacatccccc tttcgccagc tggcgtaata gcgaagaggc   2460
ccgcaccgat cgcccttccc aacagttgcg cagcctgaat ggcgaatgga aattgtaagc   2520
gttaatattt tgttaaaatt cgcgttaaat ttttgttaaa tcagctcatt ttttaaccaa   2580
taggccgaaa tcggcaaaat cccttataaa tcaaaagaat agaccgagat agggttgagt   2640
gttgttccag tttggaacaa gagtccacta ttaagaacg tggactccaa cgtcaaaggg   2700
cgaaaaaccg tctatcaggg cgatggccca ctacgtgaac catcacccta atcaagtttt   2760
ttggggtcga ggtgccgtaa agcactaaat cggaacccta agggagcccc cgatttaga   2820 gcttgacggg gaaagccggc gaacgtggcg agaaaggaag gaagaaagc gaaggagcg   2880 ggcgctaggg cgctggcaag tgtagcggtc acgctgcgcg taaccaccac acccgccgcg   2940
cttaatgcgc cgctacaggg cgcgtcaggt ggcacttttc ggggaaatgt gcgcggaacc   3000
cctatttgtt tattttcta aatacattca aatatgtatc cgctcatgag acaataaccc   3060
tgataaatgc ttcaataata ttgaaaaagg aagagtatga gtattcaaca tttccgtgtc   3120
gcccttattc ccttttttgc ggcattttgc cttcctgttt ttgctcaccc agaaacgctg   3180
gtgaaagtaa aagatgctga agatcagttg ggtgcacgag tgggttacat cgaactggat   3240
ctcaacagcg gtaagatcct tgagagtttt cgccccgaag aacgttttcc aatgatgagc   3300
acttttaaag ttctgctatg tggcgcggta ttatcccgta ttgacgccgg gcaagagcaa   3360
ctcggtcgcc gcatacacta ttctcagaat gacttggttg agtactcacc agtcacagaa   3420
aagcatctta cggatggcat gacagtaaga gaattatgca gtgctgccat aaccatgagt   3480
gataacactg cggccaactt acttctgaca acgatcggag gaccgaagga gctaaccgct   3540
tttttgcaca acatggggga tcatgtaact cgccttgatc gttgggaacc ggagctgaat   3600
gaagccatac caaacgacga gcgtgacacc acgatgcctg tagcaatggc aacaacgttg   3660
cgcaaactat taactggcga actacttact ctagcttccc ggcaacaatt aatagactgg   3720
atggaggcgg ataaagttgc aggaccactt ctgcgctcgg cccttccggc tggctggttt   3780
attgctgata atctggagc cggtgagcgt gggtctcgcg gtatcattgc agcactgggg   3840
ccagatggta agccctcccg tatcgtagtt atctacacga cggggagtca ggcaactatg   3900
gatgaacgaa atagacagat cgctgagata ggtgcctcac tgattaagca ttggtaactg   3960
tcagaccaag tttactcata tatactttag attgatttaa aacttcattt ttaatttaaa   4020
aggatctagg tgaagatcct ttttgataat ctcatgacca aaatccctta acgtgagttt   4080
tcgttccact gagcgtcaga ccccgtagaa aagatcaaag gatcttcttg agatcctttt   4140
tttctgcgcg taatctgctg cttgcaaaca aaaaaaccac cgctaccagc ggtggtttgt   4200
ttgccggatc aagagctacc aactctttt ccgaaggtaa ctggcttcag cagagcgcag   4260
ataccaaata ctgtccttct agtgtagccg tagttaggcc accacttcaa gaactctgta   4320
gcaccgccta catacctcgc tctgctaatc ctgttaccag tggctgctgc cagtggcgat   4380
aagtcgtgtc ttaccgggtt ggactcaaga cgatagttac cggataaggc gcagcggtcg   4440
ggctgaacgg ggggttcgtg cacacagccc agcttggagc gaacgaccta ccgaactg    4500 agatacctac agcgtgagct atgagaaagc gccacgcttc ccgaagggag aaaggcggac   4560
aggtatccgg taagcggcag ggtcggaaca ggagagcgca cgagggagct tccagggga   4620 aacgcctggt atctttatag tcctgtcggg tttcgccacc tctgacttga gcgtcgattt   4680
```

```
ttgtgatgct cgtcaggggg gcggagccta tggaaaaacg ccagcaacgc ggccttttta    4740
cggttcctgg cctttttgctg gccttttgct cacatgttct ttcctgcgtt atccctgat    4800 tctgtggata accgtattac cgcctttgag tgagctgata ccgctcgccg cagccgaacg    4860
accgagcgca gcgagtcagt gagcgaggaa gcggaagagc gcccaatacg caaaccgcct    4920
ctccccgcgc gttggccgat tcattaatgc agctggcacg acaggtttcc cgactggaaa    4980
gcgggcagtg agcgcaacgc aattaatgtg agttagctca ctcattaggc acccccaggct   5040 ttacacttta tgcttccggc tcgtatgttg tgtggaattg tgagcggata acaatttcac    5100
acaggaaaca gctatgacca tgattacgcc agatttaatt aaggccttaa ttagg         5155
```

<210> SEQ ID NO 19
<211> LENGTH: 5223
<212> TYPE: DNA
<213> ORGANISM: Artificial Sequence
<220> FEATURE:
<223> OTHER INFORMATION: Synthetic polynucleotide

<400> SEQUENCE: 19

```
gcccaatacg caaaccgcct ctccccgcgc gttggccgat tcattaatgc agctgattct      60
aacgaggaaa gcacgttata cgtgctcgtc aaagcaacca tagtacgcgc cctgtagcgg     120
cgcattaagc gcggcgggtg tggtggttac gcgcagcgtg accgctacac ttgccagcgc     180
cctagcgccc gctcctttcg ctttcttccc ttcctttctc gccacgttcg ccggctttcc     240
ccgtcaagct ctaaatcggg ggctcccttt agggttccga tttagtgctt tacggcacct     300
cgaccccaaa aaacttgatt agggtgatgg ttcacgtagt gggccatcgc cctgatagac     360 ggttttttcgc cctttgacgt tggagtccac gttctttaat agtggactct tgttccaaac     420
tggaacaaca ctcaacccta tctcggtcta ttcttttgat ttataaggga ttttgccgat     480
ttcggcctat tggttaaaaa atgagctgat ttaacaaaaa tttaacgcga atttttaacaa    540 aatattaacg cttacaattt aaatatttgc ttatacaatc ttcctgtttt tggggctttt     600
ctgattatca accggggtac atatgattga catgctagtt ttacgattac cgttcatcgc     660
cctgcgcgct cgctcgctca ctgaggccgc ccgggcaaag cccgggcgtc gggcgacctt     720
tggtcgcccg gcctcagtga gcgagcgagc gcgcagagag ggagtggaat tctataaagg     780
tcgggcagga agagggccta tttcccatga ttccttcata tttgcatata cgatacaagg     840
ctgttagaga gataattaga attaatttga ctgtaaacac aaagatatta gtacaaaata     900
cgtgacgtag aaagtaataa tttcttgggt agtttgcagt tttaaaatta tgttttaaaa    960
tggactatca tatgcttacc gtaacttgaa agtatttcga tttcttggct ttatatatct    1020
tgtggaaagc acgaaacacc gcctggaggc ttgctgaagg ctgtatgctg taagcatgga    1080
gctagcaggc tgttttggcc actgactgac agcctgctct ccatgcttac aggacacaag    1140
gcctgttact agcactcaca tggaacaaat ggccttttt tctagtggta cctctggtcg    1200
ttacataact tacggtaaat ggcccgcctg gctgaccgcc caacgacccc cgcccattga    1260
cgtcaataat gacgtatgtt cccatagtaa cgccaatagg gactttccat tgacgtcaat    1320
gggtggagta tttacggtaa actgcccact tggcagtaca tcaagtgtat catatgccaa    1380
gtacgccccc tattgacgtc aatgacggta aatggcccgc ctggcattat gcccagtaca    1440
tgaccttatg ggactttcct acttggcagt acatctactc gaggccacgt tctgcttcac    1500
tctccccatc tccccccccct ccccacccccc aattttgtat ttatttattt tttaattatt    1560
```

```
ttgtgcagcg atggggcgg ggggggggg gggcgcgcg ccaggcgggg cggggcgggg    1620 cgagggcgg gcggggcga ggcggagagg tgcggcggca gccaatcaga gcggcgcgct    1680
ccgaaagttt cctttatgg cgaggcggcg gcggcggcgg ccctataaaa agcgaagcgc    1740
gcggcgggcg ggagcgggat cagccaccgc ggtggcggcc tagagtcgac gaggaactga    1800
aaaaccagaa agttaactgg taagtttagt cttttttgtct tttatttcag gtcccggatc    1860
cggtggtggt gcaaatcaaa gaactgctcc tcagtggatg ttgcctttac ttctaggcct    1920
gtacggaagt gttacttctg ctctaaaagc tgcggaattg tacccgcggc cgcgtttaaa    1980
ccctgcaggt ctagaaagct tatcgatacc gtcgactaga gctcgctgat cagcctcgac    2040
tgtgccttct agttgccagc catctgttgt ttgcccctcc cccgtgcctt ccttgaccct    2100
ggaaggtgcc actcccactg tccttttccta taaaaatgag gaaattgcat cgcattgtct    2160
gagtaggtgt cattctattc tgggggggtgg ggtggggcag gacagcaagg gggaggattg    2220
ggaagacaat agcagggtac aagtaaagcg gccctagcgt ttccggcgac ggtgctagac    2280
tcgaggacgg ggtgaactac gcctgaggat ccgatctttt tccctctgcc aaaaattatg    2340
gggacatcat gaagccctt gagcatctga cttctggcta ataaaggaaa tttattttca    2400
ttgcaatagt gtgttggaat ttttttgtgtc tctcactcgg aagcaattcg ttgatctgaa    2460
tttcgaccac ccataatacc cattaccctg gtagataagt agcatggcgg gttaatcatt    2520
aactacaagg aaccccctagt gatggagttg gccactccct ctctgcgcgc tcgctcgctc    2580
actgaggccg ggcgaccaaa ggtcgcccga cgcccgggct tgcccgggc ggcctcagtg    2640 agcgagcgag cgcgcagcct taattaacct aattcactgg ccgtcgttttt acaacgtcgt    2700 gactgggaaa accctggcgt tacccaactt aatcgccttg cagcacatcc ccctttcgcc    2760
agctggcgta atagcgaaga ggcccgcacc gatcgccctt ccaacagtt gcgcagcctg    2820 aatggcgaat gggacgcgcc ctgtagcggc gcattaagcg cggcgggtgt ggtggttacg    2880
cgcagcgtga ccgctacact tgccagcgcc ctagcgcccg ctcctttcgc tttcttccct    2940
tcctttctcg ccacgttcgc cggctttccc cgtcaagctc taaatcgggg gctcccttta    3000
gggttccgat ttagtgcttt acggcacctc gaccccaaaa aacttgatta gggtgatggt    3060
tcacgtagtg ggccatcgcc ctgatagacg ttttttcgcc ctttgacgtt ggagtccacg    3120
ttctttaata gtggactctt gttccaaact ggaacaacac tcaaccctat ctcggtctat    3180
tcttttgatt tataagggat tttgccgatt tcggcctatt ggttaaaaaa tgagctgatt    3240
taacaaaaat ttaacgcgaa ttttaacaaa atattaacgc ttacaattta ggtggcactt    3300 ttcgggaaa tgtgcgcgga acccctattt gttttatttt ctaaatacat tcaaatatgt    3360
atccgctcat gagacaataa ccctgataaa tgcttcaata atattgaaaa aggaagagta    3420
tgagtattca acatttccgt gtcgccctta ttccctttt tgcggcattt tgccttcctg    3480 ttttttgctca cccagaaacg ctggtgaaag taaaagatgc tgaagatcag ttgggtgcac    3540
gagtgggtta catcgaactg gatctcaaca gcggtaagat ccttgagagt tttcgccccg    3600
aagaacgttt tccaatgatg agcactttta aagttctgct atgtggcgcg gtattatccc    3660
gtattgacgc cgggcaagag caactcggtc gccgcataca ctattctcag aatgacttgg    3720
ttgagtactc accagtcaca gaaaagcatc ttacggatgg catgacagta agagaattat    3780
gcagtgctgc cataaccatg agtgataaca ctgcggccaa cttacttctg acaacgatcg    3840
gaggaccgaa ggagctaacc gcttttttgc acaacatggg gatcatgta actcgccttg    3900 atcgttggga accggagctg aatgaagcca taccaaacga cgagcgtgac accacgatgc    3960
```

-continued

```
ctgtagcaat ggcaacaacg ttgcgcaaac tattaactgg cgaactactt actctagctt    4020
cccggcaaca attaatagac tggatggagg cggataaagt tgcaggacca cttctgcgct    4080
cggcccttcc ggctggctgg tttattgctg ataaatctgg agccggtgag cgtgggtctc    4140
gcggtatcat tgcagcactg gggccagatg gtaagccctc ccgtatcgta gttatctaca    4200
cgacggggag tcaggcaact atggatgaac gaaatagaca gatcgctgag ataggtgcct    4260
cactgattaa gcattggtaa ctgtcagacc aagtttactc atatatactt tagattgatt    4320
taaaacttca tttttaattt aaaaggatct aggtgaagat ccttttttgat aatctcatga    4380 ccaaaatccc ttaacgtgag ttttcgttcc actgagcgtc agaccccgta gaaaagatca    4440
aaggatcttc ttgagatcct ttttttctgc gcgtaatctg ctgcttgcaa acaaaaaaac    4500
caccgctacc agcggtggtt tgtttgccgg atcaagagct accaactctt tttccgaagg    4560
taactggctt cagcagagcg cagataccaa atactgttct tctagtgtag ccgtagttag    4620
gccaccactt caagaactct gtagcaccgc ctacatacct cgctctgcta atcctgttac    4680
cagtggctgc tgccagtggc gataagtcgt gtcttaccgg gttggactca agacgatagt    4740
taccggataa ggcgcagcgg tcgggctgaa cggggggttc gtgcacacag cccagcttgg    4800
agcgaacgac ctacaccgaa ctgagatacc tacagcgtga gctatgagaa agcgccacgc    4860
ttcccgaagg gagaaaggcg gacaggtatc cggtaagcgg cagggtcgga acaggagagc    4920
gcacgaggga gcttccaggg ggaaacgcct ggtatcttta tagtcctgtc gggtttcgcc    4980
acctctgact tgagcgtcga ttttttgtgat gctcgtcagg ggggcggagc ctatggaaaa    5040
acgccagcaa cgcggccttt ttacggttcc tggccttttg ctggcctttt gctcacatgt    5100
tctttcctgc gttatcccct gattctgtgg ataaccgtat taccgccttt gagtgagctg    5160
ataccgctcg ccgcagccga acgaccgagc gcagcgagtc agtgagcgag gaagcggaag    5220
agc                                                                  5223
```

<210> SEQ ID NO 20
<211> LENGTH: 736
<212> TYPE: PRT
<213> ORGANISM: Artificial Sequence
<220> FEATURE:
<223> OTHER INFORMATION: Synthetic polypeptide

<400> SEQUENCE: 20

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125
```

```
Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
```

```
                 545                 550                 555                 560
Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
                595                 600                 605

Asp Arg Asp Val Tyr Leu Gln Gly Pro Ile Trp Ala Lys Ile Pro His
                610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
                675                 680                 685

Lys Glu Asn Ser Lys Arg Trp Asn Pro Glu Ile Gln Tyr Thr Ser Asn
                690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 21
<211> LENGTH: 137
<212> TYPE: DNA
<213> ORGANISM: Artificial Sequence
<220> FEATURE:
<223> OTHER INFORMATION: Synthetic polynucleotide

<400> SEQUENCE: 21
gcctggaggc ttgctgaagg ctgtatgctg taagcatgga gctagcaggc tgttttggcc    60
actgactgac agcctgctct cctagcttac aggacacaag gcctgttact agcactcaca   120
taacaaatgg ccctttt                                                  137

<210> SEQ ID NO 22
<211> LENGTH: 91
<212> TYPE: DNA
<213> ORGANISM: Artificial Sequence
<220> FEATURE:
<223> OTHER INFORMATION: Synthetic polynucleotide

<400> SEQUENCE: 22
gctcgagtga gcgcagcctg ctagctccat gcttactgta aagccaccag atgggtaagc    60
atggagctag caggcttcgc ctactagttt t                                   91

<210> SEQ ID NO 23
<211> LENGTH: 139
<212> TYPE: RNA
<213> ORGANISM: Artificial Sequence
<220> FEATURE:
<223> OTHER INFORMATION: Synthetic polynucleotide

<400> SEQUENCE: 23
gccuggaggc uugcugaagg cuguaugcug uaagcaugga gcuagcaggc uguuuuggcc    60
acugacugac agccugcucu ccuagcuuac aggacacaag gccuguuacu agcacucaca   120
```

```
uggaacaaau ggcccuuuu                                                    139

<210> SEQ ID NO 24
<211> LENGTH: 91
<212> TYPE: RNA
<213> ORGANISM: Artificial Sequence
<220> FEATURE:
<223> OTHER INFORMATION: Synthetic polynucleotide

<400> SEQUENCE: 24
gcucgaguga gcgcagccug cuagcuccau gcuuacugua aagccaccag auggguaagc        60
auggagcuag caggcuucgc cuacuaguuu u                                      91

<210> SEQ ID NO 25
<211> LENGTH: 21
<212> TYPE: RNA
<213> ORGANISM: Artificial Sequence
<220> FEATURE:
<223> OTHER INFORMATION: Synthetic polynucleotide

<400> SEQUENCE: 25
uaagcaugga gcuagcaggc u                                                 21
```